US012559863B2

(12) United States Patent　　　　(10) Patent No.:　US 12,559,863 B2
Skretas　　　　　　　　　　　　　　(45) Date of Patent:　Feb. 24, 2026

(54) MACROCYCLIC MODULATORS OF DISEASE ASSOCIATED PROTEIN MISFOLDING AND AGGREGATION

(71) Applicant: RESQ BIOTECH, Patra (GR)

(72) Inventor: Georgios Skretas, Athens (GR)

(73) Assignee: RESQ BIOTECH, Patra (GR)

( * ) Notice: Subject to any disclaimer, the term of this patent is extended or adjusted under 35 U.S.C. 154(b) by 0 days.

(21) Appl. No.: 18/499,332

(22) Filed: Nov. 1, 2023

(65) Prior Publication Data

US 2024/0218034 A1　　Jul. 4, 2024

Related U.S. Application Data

(62) Division of application No. 16/613,879, filed as application No. PCT/IB2018/000622 on May 22, 2018, now Pat. No. 11,858,974.

(30) Foreign Application Priority Data

May 22, 2017　(WO) ................. PCT/EP2017/025141
Oct. 5, 2017　(WO) ................. PCT/EP2017/025298

(51) Int. Cl.
C40B 30/06　　　(2006.01)
C12N 15/10　　　(2006.01)

(52) U.S. Cl.
CPC .......... C40B 30/06 (2013.01); C12N 15/1075 (2013.01)

(58) Field of Classification Search
None
See application file for complete search history.

(56) References Cited

U.S. PATENT DOCUMENTS

2004/0034888 A1　2/2004　Liu et al.
2011/0287010 A1　11/2011　Assinder et al.
2014/0004081 A1　1/2014　Cobbold et al.

FOREIGN PATENT DOCUMENTS

EP　　　　205415　　　5/2009
WO　WO 92/10511 A1　6/1992

OTHER PUBLICATIONS

Baine et al., "Inhibition of A[beta]42 aggregation using peptides selected from combinatorial libraries," *Journal of Peptide Science*, 15(8):499-503, 2009.
Cheng et al., "Discovery of antibacterial cyclic peptides that inhibit the ClpXP protease," *Protein Science*, 16(8):1535-1545, 2007.
Gorski. D., "One reason mouse studies often don't translate to humans very well," *Science based medicine*, (2019): 1-11.

(Continued)

*Primary Examiner* — Christian C Boesen
(74) *Attorney, Agent, or Firm* — pH IP Law

(57) ABSTRACT

Aspects of the present invention disclose compounds that modulate the aggregation of amyloidogenic proteins or peptides. In some aspects, disclosed compounds modulate the aggregation of disease-associated proteins and natural β-amyloid peptides. In a preferred embodiment, the compounds can inhibit natural amyloid aggregation. Pharmaceutical compositions comprising the compounds of the embodiments, and diagnostic and treatment methods for diseases (e.g., amyloidogenic diseases) using the compounds, are also disclosed. In addition, there is provided an integrated bacterial platform for the discovery of rescuers of disease-associated protein misfolding.

11 Claims, 37 Drawing Sheets

Specification includes a Sequence Listing.

TGC
5'- GCG ATC GGC CAC AAT AGC NNS NNS ... NNS TGC TTA AGT TTT GGC -3'
ACC

Peptide sequence pSICLOPPS-NuX₁X₂X₃-Xₙ

Cyclic NuX₁X₂X₃-Xₙ oligopeptides

(56)              References Cited

OTHER PUBLICATIONS

Majmudar, S. et al., "Rehabilitation in Amyotrophic lateral sclerosis: Why it matters," *Muscle Nerve.*, 50.1 (2014): 4-13.

PCT International Search Report and Written Opinion issued in International Application No. PCT/IB2018/000622, dated Jan. 29, 2019.

PCT Invitation to Pay Additional Fees issued in International Application No. PCT/IB2018/000622, dated Dec. 7, 2018.

Qian, Z. et al., "early Endosomal Escape of a Cyclic Cell-Penetrating Peptide Allows Efefctive Cytosolic Cargo Delivery," *Biochemistry*, 53 (2014): 4034-4046.

Tavassoli et al., "SICLOPPS cyclic peptide libraries in drug discovery," *Current Opinion in Chemical Biology*, 38:30-35, 2017.

Valmori, D. et al., "Functional analysis of two tetanus toxin universal T cell epitopes in their interaction with DR1101 and DR1104 alleles," *The Journal of Immunology*, 152 (1994): 2921-2929.

Vejux, A. et al., "Biomarkers of Amyotrophic Lateral Sclerosis: Current Status and Interest of Axysterols and Phytosterols," *Frontiers in Molecular Neuroscience*, 11.12 (2018): 1-13.

Woojin Kim et al., "A High-Throughput Screen for Compounds That Inhibit Aggregation of the Alzheimer's Peptide," *ACS Chemical Biology*, 1(7):461-469, 2006.

| Peptide type | General formula[a] | Theoretical diversity | Actual library coverage |
|---|---|---|---|
| Tetrapeptides | cyclo-NuX$_1$X$_2$X$_3$ | $3 \times 20^3 = 24,000$ | |
| Pentapeptides | cyclo-NuX$_1$X$_2$X$_3$X$_4$ | $3 \times 20^4 = 480,000$ | |
| Hexapeptides | cyclo-NuX$_1$X$_2$X$_3$X$_4$X$_5$ | $3 \times 20^5 = 9,600,000$ | |
| Combined library | cyclo-NuX$_1$X$_2$X$_3$-X$_5$ | 10,104,000 | ×2 |

[a]Nu=C, S, or T; X=anyone of the twenty natural amino acids

FIG. 1B

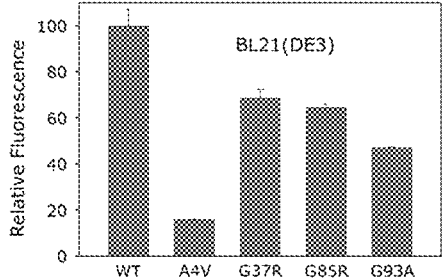
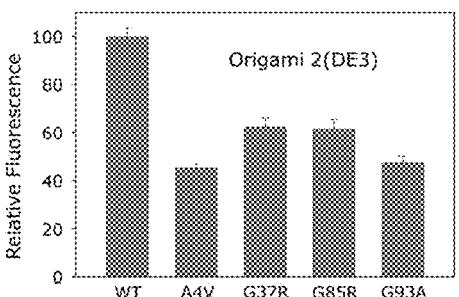
FIG. 2A
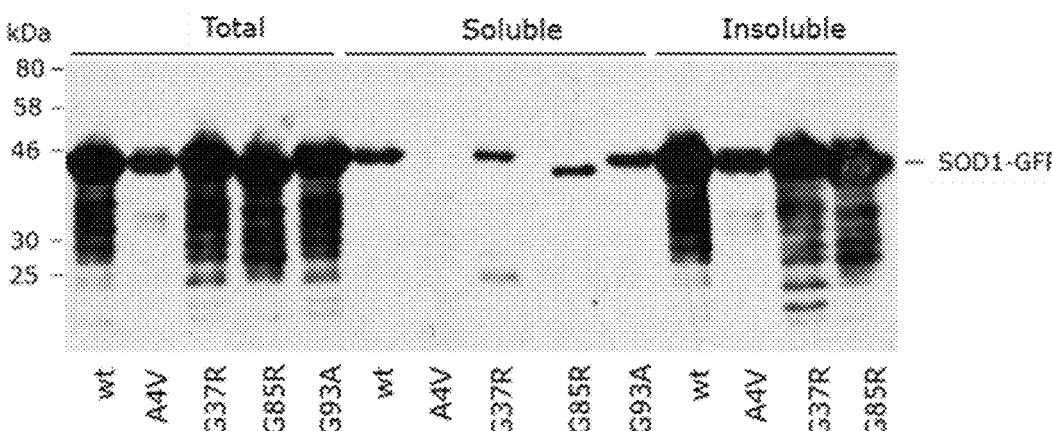
FIG. 2B

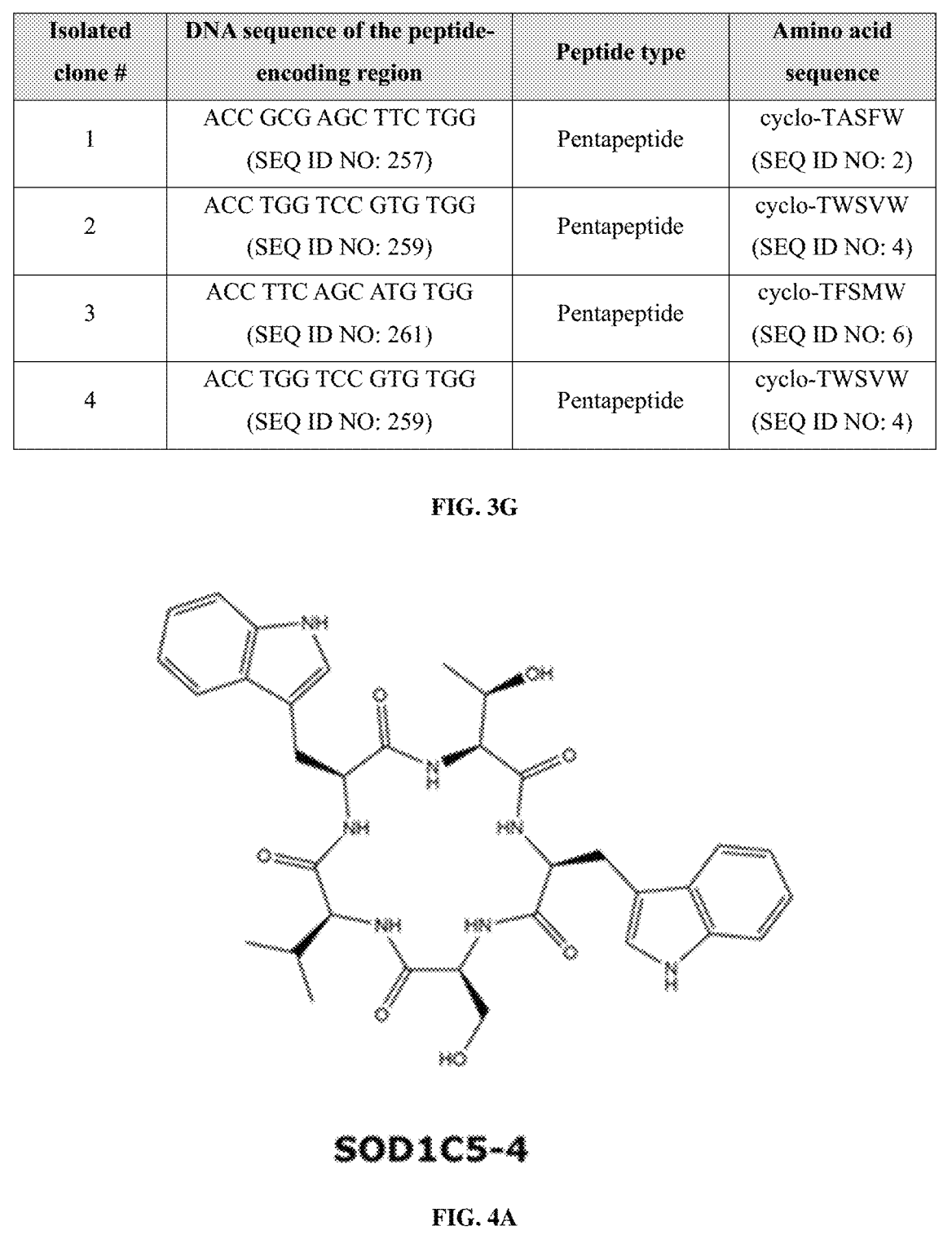

| Isolated clone # | DNA sequence of the peptide-encoding region | Peptide type | Amino acid sequence |
|---|---|---|---|
| 1 | ACC GCG AGC TTC TGG (SEQ ID NO: 257) | Pentapeptide | cyclo-TASFW (SEQ ID NO: 2) |
| 2 | ACC TGG TCC GTG TGG (SEQ ID NO: 259) | Pentapeptide | cyclo-TWSVW (SEQ ID NO: 4) |
| 3 | ACC TTC AGC ATG TGG (SEQ ID NO: 261) | Pentapeptide | cyclo-TFSMW (SEQ ID NO: 6) |
| 4 | ACC TGG TCC GTG TGG (SEQ ID NO: 259) | Pentapeptide | cyclo-TWSVW (SEQ ID NO: 4) |

FIG. 3G

SOD1C5-4

FIG. 4A

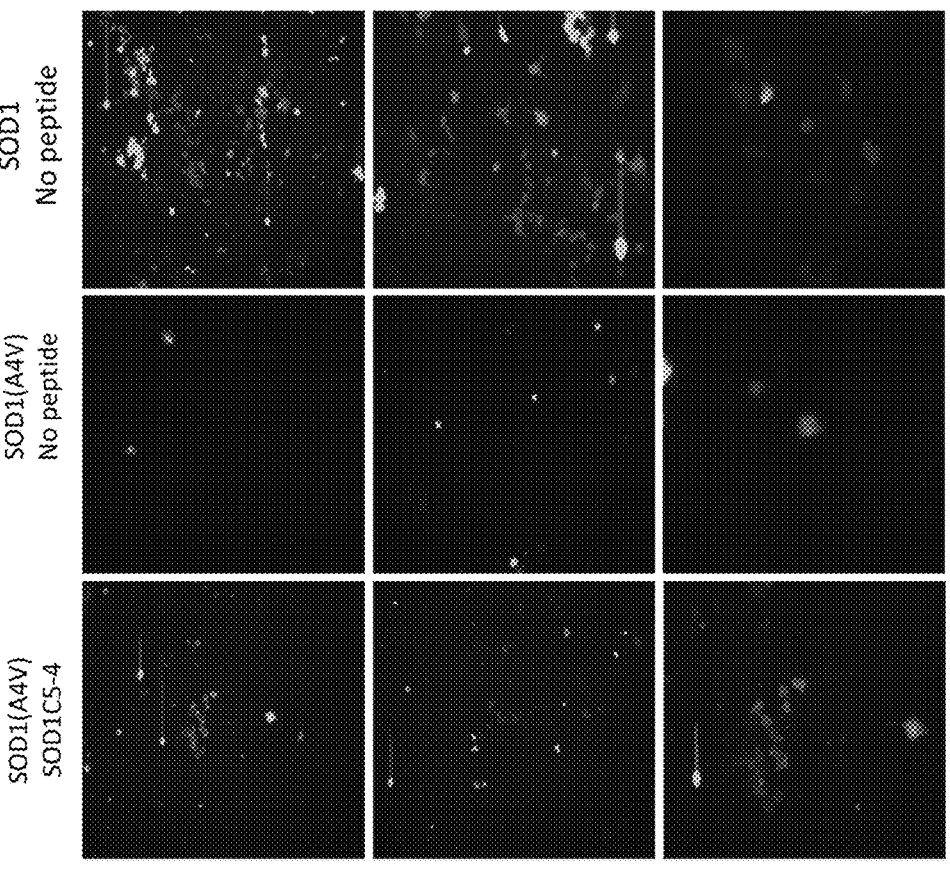
FIG. 5A
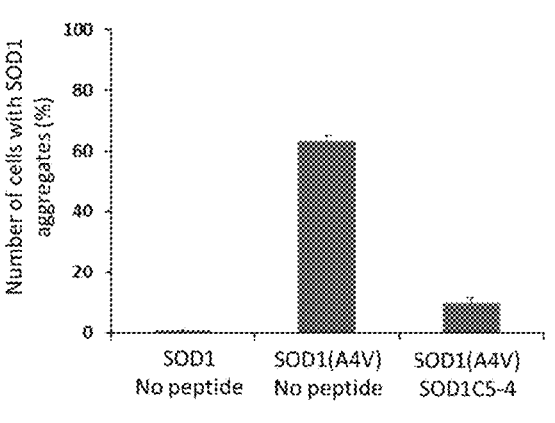
FIG. 5B
FIG. 5C

Total DNA reads corresponding to TXSXW pentapeptides

| Position | Frequency of appearance (number) | | | | | | Frequency of appearance (%) | | | | |
|---|---|---|---|---|---|---|---|---|---|---|---|
| Amino acid | 1 | 2 | 3 | 4 | 5 | | 1 | 2 | 3 | 4 | 5 |
| A | | ▓▓▓▓▓ | | 629 | | | | ▓▓▓ | | 0.02 | |
| I | | 0 | | 0 | | | | 0.00 | | 0.00 | |
| L | | 3,760 | | 2,169 | | | | 0.10 | | 0.06 | |
| V | | 31,522 | | 546,099 | | | | 0.80 | | 13.86 | |
| F | | 209,112 | | 1,479,547 | | | | 5.31 | | 37.56 | |
| W | | 545,357 | | 1,257,478 | 3,939,406 | | | 13.84 | | 31.92 | 100.00 |
| Y | | 71 | | 128 | | | | 0.00 | | 0.00 | |
| N | | 0 | | 0 | | | | 0.00 | | 0.00 | |
| Q | | 0 | | 0 | | | | 0.00 | | 0.00 | |
| C | | 268 | | 0 | | | | 0.01 | | 0.00 | |
| M | | 0 | | 318,343 | | | | 0.00 | | 8.08 | |
| S | | 702,153 | 3,939,406 | 2,484 | | | | 17.82 | 100.00 | 0.06 | |
| T | 3,939,406 | 498 | | 532 | | | 100.00 | 0.01 | | 0.01 | |
| D | | 136 | | 0 | | | | 0.00 | | 0.00 | |
| E | | 0 | | 0 | | | | 0.00 | | 0.00 | |
| R | | 797 | | 1,485 | | | | 0.02 | | 0.04 | |
| H | | 0 | | 330,416 | | | | 0.00 | | 8.39 | |
| K | | 0 | | 0 | | | | 0.00 | | 0.00 | |
| P | | 290 | | 0 | | | | 0.01 | | 0.00 | |
| G | | 1,367 | | 96 | | | | 0.03 | | 0.00 | |
| Sum | | | 3,939,406 | | | | | | 100.00 | | |

Unique TXSXW pentapeptide sequences selected

| Position | Frequency of appearance (number) | | | | | | Frequency of appearance (%) | | | | |
|---|---|---|---|---|---|---|---|---|---|---|---|
| Amino acid | 1 | 2 | 3 | 4 | 5 | | 1 | 2 | 3 | 4 | 5 |
| A | | 11 | | 2 | | | | 23.91 | | 4.35 | |
| I | | 0 | | 0 | | | | 0.00 | | 0.00 | |
| L | | 3 | | 3 | | | | 6.52 | | 6.52 | |
| V | | 3 | | 8 | | | | 6.52 | | 17.39 | |
| F | | 3 | | 7 | | | | 6.52 | | 15.22 | |
| W | | 4 | | 10 | 46 | | | 8.70 | | 21.74 | 100.00 |
| Y | | 1 | | 2 | | | | 2.17 | | 4.35 | |
| N | | 0 | | 0 | | | | 0.00 | | 0.00 | |
| Q | | 0 | | 0 | | | | 0.00 | | 0.00 | |
| C | | 2 | | 0 | | | | 4.35 | | 0.00 | |
| M | | 0 | | 5 | | | | 0.00 | | 10.87 | |
| S | | 7 | 46 | 3 | | | | 15.22 | 100.00 | 6.52 | |
| T | 46 | 2 | | 2 | | | 100.00 | 4.35 | | 4.35 | |
| D | | 1 | | 0 | | | | 2.17 | | 0.00 | |
| E | | 0 | | 0 | | | | 0.00 | | 0.00 | |
| R | | 4 | | 1 | | | | 8.70 | | 2.17 | |
| H | | 0 | | 2 | | | | 0.00 | | 4.35 | |
| K | | 0 | | 0 | | | | 0.00 | | 0.00 | |
| P | | 2 | | 0 | | | | 4.35 | | 0.00 | |
| G | | 3 | | 1 | | | | 6.52 | | 2.17 | |
| Sum | | | 46 | | | | | | 100.00 | | |

FIG. 7

| SEQ ID NO | Peptide name | Amino acid sequence | | | | | Number of reads | Reads/Total TXSXW reads (%) | Reads/Total penta-peptide reads (%) | Reads/Total peptide reads (%) | Peptide-encoding nucleotide sequence |
|---|---|---|---|---|---|---|---|---|---|---|---|
| 1 | SOD1C5-1 | T | A | S | W | W | 1,255,761 | 31.877 | 30.963 | 29.591 | ACCGCCTCGTGGTGG (SEQ ID NO: 256) |
| 2 | SOD1C5-2 | T | A | S | F | W | 744,622 | 18.902 | 18.360 | 17.547 | ACCGCGGAGCTTCTGG (SEQ ID NO: 257) |
| 3 | SOD1C5-3 | T | S | S | F | W | 700,047 | 17.770 | 17.261 | 16.496 | ACCTCGTCGTTCTGG (SEQ ID NO: 258) |
| 4 | SOD1C5-4 | T | W | S | V | W | 543,999 | 13.809 | 13.413 | 12.819 | ACCTGGTCCGTGTGG (SEQ ID NO: 259) |
| 5 | SOD1C5-5 | T | A | S | H | W | 330,358 | 8.386 | 8.146 | 7.785 | ACCGCCAGCCACTGG (SEQ ID NO: 260) |
| 6 | SOD1C5-6 | T | F | S | M | W | 208,879 | 5.302 | 5.150 | 4.922 | ACCTTCAGCATGTGG (SEQ ID NO: 261) |
| 7 | SOD1C5-7 | T | A | S | M | W | 108,582 | 2.756 | 2.677 | 2.559 | ACCGCCTCGATGTGG (SEQ ID NO: 262) |
| 8 | SOD1C5-9 | T | V | S | F | W | 31,319 | 0.795 | 0.772 | 0.738 | ACCGTCTCGTTCTGG (SEQ ID NO: 263) |
| 9 | SOD1C5-11 | T | L | S | F | W | 3,069 | 0.078 | 0.076 | 0.072 | ACCCTCTCCTTCTGG (SEQ ID NO: 264) |
| 10 | SOD1C5-13 | T | A | S | R | W | 1,485 | 0.038 | 0.037 | 0.035 | ACCGCCAGCCGGCTGG (SEQ ID NO: 265) |
| 11 | SOD1C5-14 | T | A | S | S | W | 1,459 | 0.037 | 0.036 | 0.034 | ACCGCGAGCTCGTGG (SEQ ID NO: 266) |
| 12 | SOD1C5-18 | T | A | S | L | W | 1,054 | 0.027 | 0.026 | 0.025 | ACCGCGAGCCTCTGG (SEQ ID NO: 267) |
| 13 | SOD1C5-20 | T | S | S | S | W | 966 | 0.025 | 0.024 | 0.023 | ACCTCGTCGTCCTGG (SEQ ID NO: 268) |
| 14 | SOD1C5-23 | T | G | S | V | W | 751 | 0.019 | 0.019 | 0.018 | ACCGGCTCCGTGTGG (SEQ ID NO: 269) |
| 15 | SOD1C5-25 | T | W | S | L | W | 683 | 0.017 | 0.017 | 0.016 | ACCTGGTCCCTGTGG |

| | | | | | | | | | | | (SEQ ID NO: 270) |
|---|---|---|---|---|---|---|---|---|---|---|---|
| 16 | SOD1C5-27 | T | L | S | M | W | 619 | 0.016 | 0.015 | 0.015 | ACCCTCAGCATGTGG (SEQ ID NO: 271) |
| 17 | SOD1C5-31 | T | W | S | A | W | 576 | 0.015 | 0.014 | 0.014 | ACCTGGTCCGCGTGG (SEQ ID NO: 272) |
| 18 | SOD1C5-32 | T | G | S | W | W | 563 | 0.014 | 0.014 | 0.013 | ACCGGCTCGTGGTGG (SEQ ID NO: 273) |
| 19 | SOD1C5-33 | T | R | S | V | W | 554 | 0.014 | 0.014 | 0.013 | ACCGGGTCCGTGTGG (SEQ ID NO: 274) |
| 20 | SOD1C5-39 | T | S | S | L | W | 432 | 0.011 | 0.011 | 0.010 | ACCTCGTCGCTCTGG (SEQ ID NO: 275) |
| 21 | SOD1C5-44 | T | A | S | T | W | 361 | 0.009 | 0.009 | 0.009 | ACCGCCAGCACCTGG (SEQ ID NO: 276) |
| 22 | SOD1C5-46 | T | S | S | V | W | 356 | 0.009 | 0.009 | 0.008 | ACCTCGTCCGTCTGG (SEQ ID NO: 277) |
| 23 | SOD1C5-53 | T | T | S | W | W | 295 | 0.007 | 0.007 | 0.007 | ACCACCTCGTGGTGG (SEQ ID NO: 278) |
| 24 | SOD1C5-65 | T | A | S | V | W | 245 | 0.006 | 0.006 | 0.006 | ACCGCGAGCGGTCTGG (SEQ ID NO: 279) |
| 25 | SOD1C5-74 | T | C | S | W | W | 208 | 0.005 | 0.005 | 0.005 | ACCTGCTCGTGGTGG (SEQ ID NO: 280) |
| 26 | SOD1C5-75 | T | P | S | F | W | 208 | 0.005 | 0.005 | 0.005 | ACCCCGTCGTTCTGG (SEQ ID NO: 281) |
| 27 | SOD1C5-76 | T | T | S | F | W | 203 | 0.005 | 0.005 | 0.005 | ACCACGAGCTTCTGG (SEQ ID NO: 282) |
| 28 | SOD1C5-80 | T | F | S | T | W | 171 | 0.004 | 0.004 | 0.004 | ACCTTCAGCACGTGG (SEQ ID NO: 283) |
| 29 | SOD1C5-82 | T | S | S | M | W | 164 | 0.004 | 0.004 | 0.004 | ACCTCGAGCATGTGG (SEQ ID NO: 284) |
| 30 | SOD1C5-89 | T | V | S | W | W | 144 | 0.004 | 0.004 | 0.003 | ACCGTCTCGTGGTGG (SEQ ID NO: 285) |
| 31 | SOD1C5-93 | T | D | S | W | W | 136 | 0.003 | 0.003 | 0.003 | ACCGACTCGTGGTGG (SEQ ID NO: 286) |

FIG. 7(cont.)

| # | Name | | | | | | Count | | | | Sequence |
|---|---|---|---|---|---|---|---|---|---|---|---|
| 32 | SOD1C5-105 | T | S | S | W | W | 112 | 0.003 | 0.003 | 0.003 | ACCTCGTCCTGGTGG (SEQ ID NO: 287) |
| 33 | SOD1C5-106 | T | R | S | W | W | 106 | 0.003 | 0.003 | 0.002 | ACCCGCTCGTGGTGG (SEQ ID NO: 288) |
| 34 | SOD1C5-109 | T | W | S | M | W | 99 | 0.003 | 0.002 | 0.002 | ACCTGGTCCATGTGG (SEQ ID NO: 289) |
| 35 | SOD1C5-116 | T | A | S | G | W | 96 | 0.002 | 0.002 | 0.002 | ACCGCCTCTGGGTGG (SEQ ID NO: 290) |
| 36 | SOD1C5-130 | T | P | S | W | W | 82 | 0.002 | 0.002 | 0.002 | ACGCCCTCGTGGTGG (SEQ ID NO: 291) |
| 37 | SOD1C5-135 | T | R | S | F | W | 79 | 0.002 | 0.002 | 0.002 | ACGCGGAGCTTCTGG (SEQ ID NO: 292) |
| 38 | SOD1C5-140 | T | S | S | Y | W | 76 | 0.002 | 0.002 | 0.002 | ACCTCGTCCTACTGG (SEQ ID NO: 293) |
| 39 | SOD1C5-143 | T | L | S | V | W | 72 | 0.002 | 0.002 | 0.002 | ACCTTGAGCGTGTGG (SEQ ID NO: 294) |
| 40 | SOD1C5-148 | T | Y | S | W | W | 71 | 0.002 | 0.002 | 0.002 | ACCTACTCATGGTGG (SEQ ID NO: 295) |
| 41 | SOD1C5-160 | T | F | S | V | W | 62 | 0.002 | 0.002 | 0.001 | ACCTTCAGCGTGTGG (SEQ ID NO: 296) |
| 42 | SOD1C5-164 | T | C | S | V | W | 60 | 0.002 | 0.001 | 0.001 | ACCTGCTCCGTGTGG (SEQ ID NO: 297) |
| 43 | SOD1C5-167 | T | V | S | S | W | 59 | 0.001 | 0.001 | 0.001 | ACCGTCTCGTCGTGG (SEQ ID NO: 298) |
| 44 | SOD1C5-168 | T | R | S | H | W | 58 | 0.001 | 0.001 | 0.001 | ACCCGCAGCCACTGG (SEQ ID NO: 299) |
| 45 | SOD1C5-182 | T | G | S | A | W | 53 | 0.001 | 0.001 | 0.001 | ACCGGCAGCGGCGTGG (SEQ ID NO: 300) |
| 46 | SOD1C5-188 | T | A | S | Y | W | 52 | 0.001 | 0.001 | 0.001 | ACCGCCAGCTACTGG (SEQ ID NO: 301) |
| | Sum | | | | | | 3,939,406 | 100 | 97.134 | 92.829 | |

FIG. 7(cont.)

| Isolated clone # | DNA sequence of the peptide-encoding region | Peptide type | Amino acid sequence |
|---|---|---|---|
| 1 | ACC ACC GTG GAC CGG (SEQ ID NO: 303) | Pentapeptide | cyclo-TTVDR (SEQ ID NO: 48) |
| 2 | ACC ACG TAC GCC AGG (SEQ ID NO: 302) | Pentapeptide | cyclo-TTYAR (SEQ ID NO: 47) |
| 3 | ACC ACC ACG GCC CGG (SEQ ID NO: 311) | Pentapeptide | cyclo-TTTAR (SEQ ID NO: 56) |
| 4 | ACC CCG GTC TGG TTC GAC (SEQ ID NO: 473) | Hexapeptide | cyclo-TPVWFD (SEQ ID NO: 222) |
| 5 | ACC CCG GTC TGG TTC GAC (SEQ ID NO: 473) | Hexapeptide | cyclo-TPVWFD (SEQ ID NO: 222) |
| 6 | ACC ACG TAC GCC AGG (SEQ ID NO: 302) | Pentapeptide | cyclo-TTYAR (SEQ ID NO: 47) |
| 7 | AGC GCC TCG CCG ACG (SEQ ID NO: 515) | Pentapeptide | cyclo-SASPT (SEQ ID NO: 206) |
| 8 | ACC GCG TGG TGC CGC (SEQ ID NO: 318) | Pentapeptide | cyclo-TAWCR (SEQ ID NO: 63) |
| | | | |
| | | | |
| 9 | ACC ACC TGG TGC CGG (SEQ ID NO: 315) | Pentapeptide | cyclo-TTWCR (SEQ ID NO: 60) |
| 10 | ACC GCG TTC GAC CGG (SEQ ID NO: 341) | Pentapeptide | cyclo-TAFDR (SEQ ID NO: 86) |

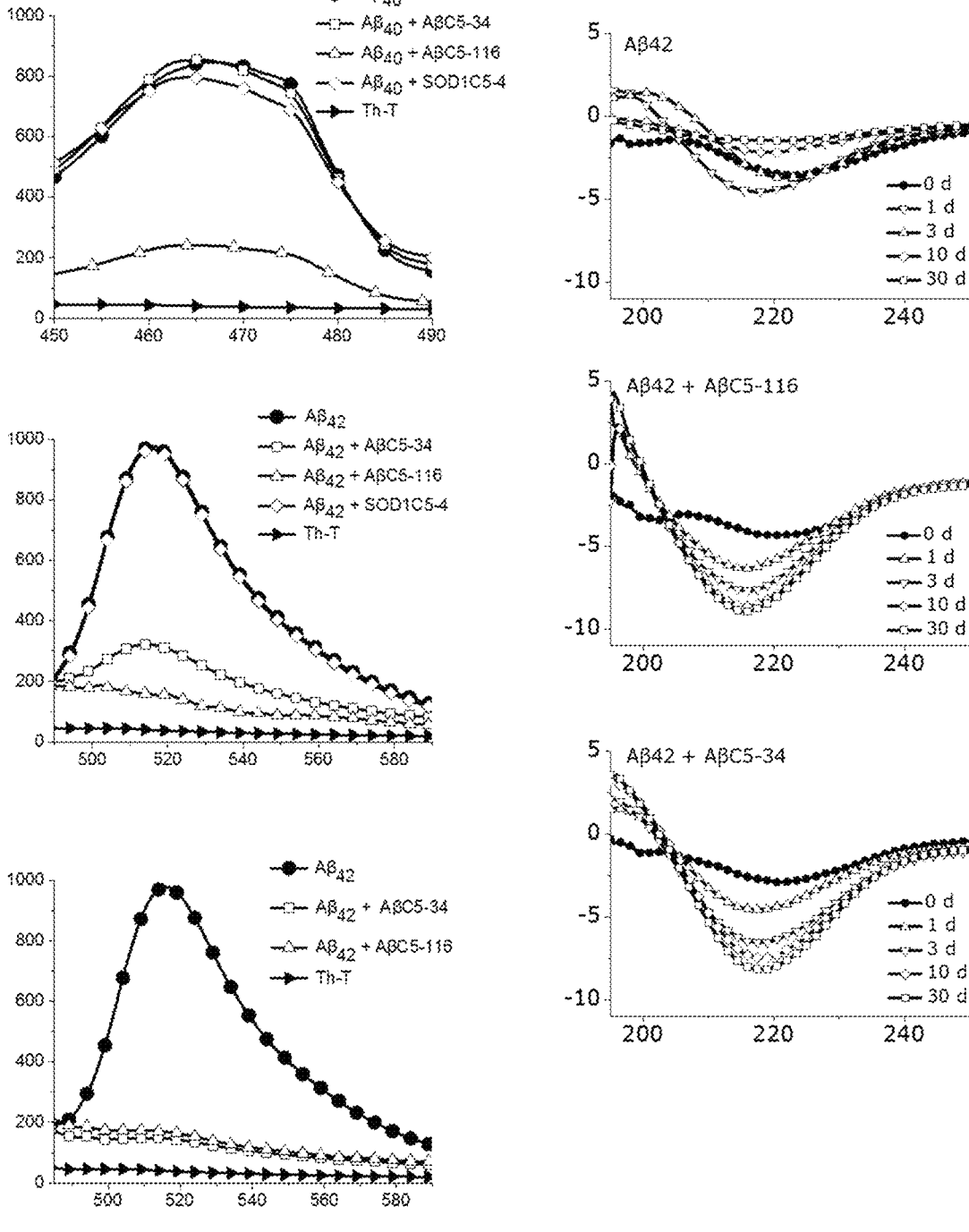
FIG. 9C                                    FIG. 9D

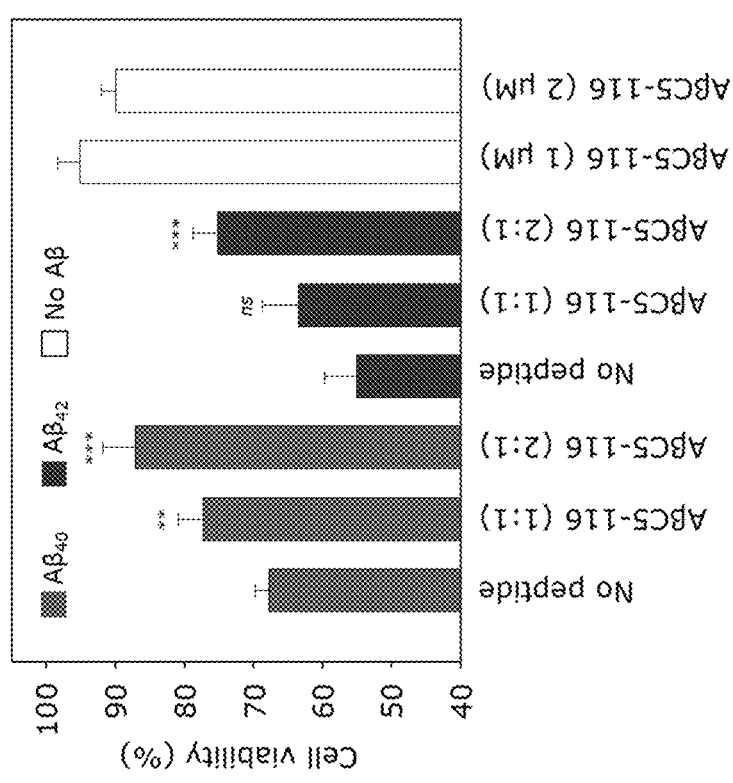
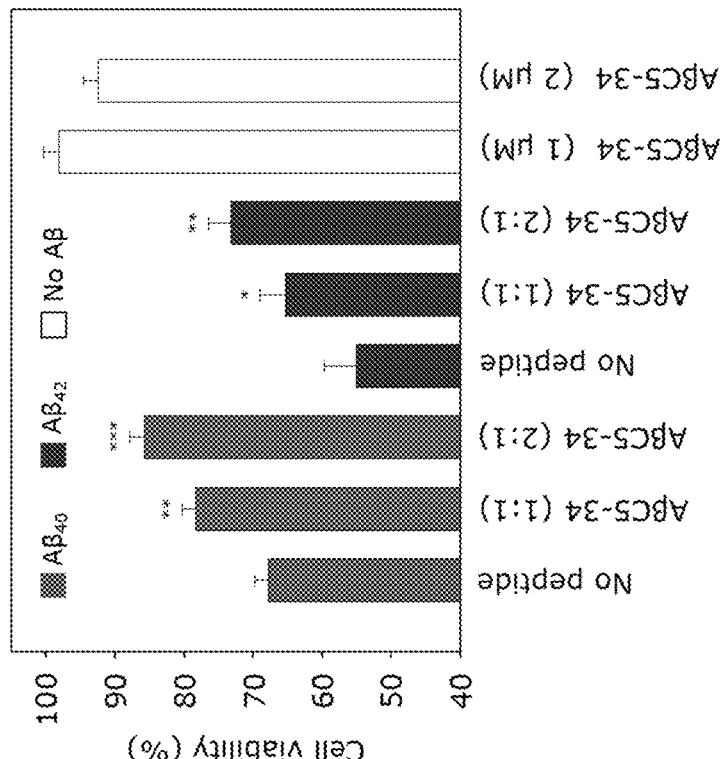
FIG. 10A

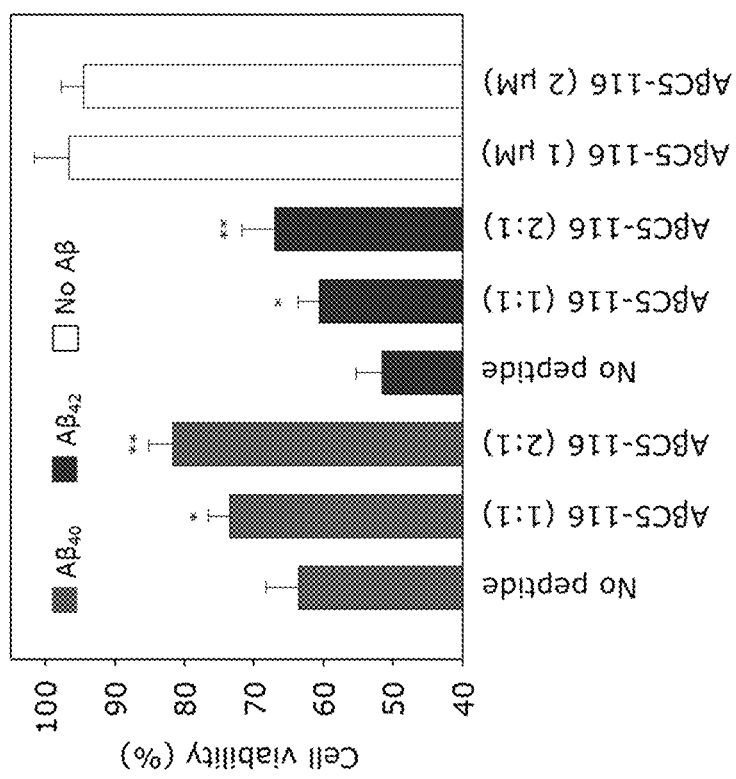
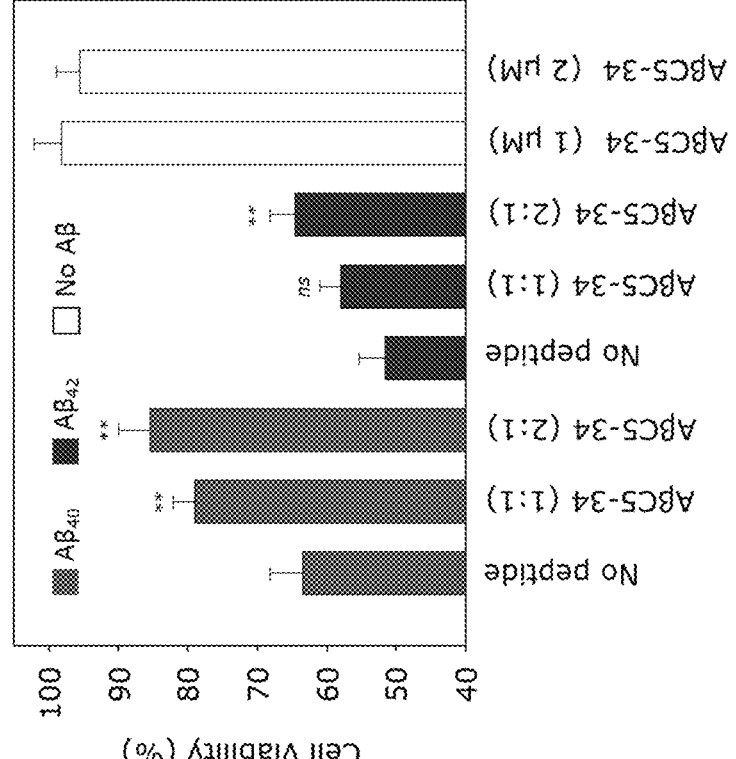
FIG. 10B

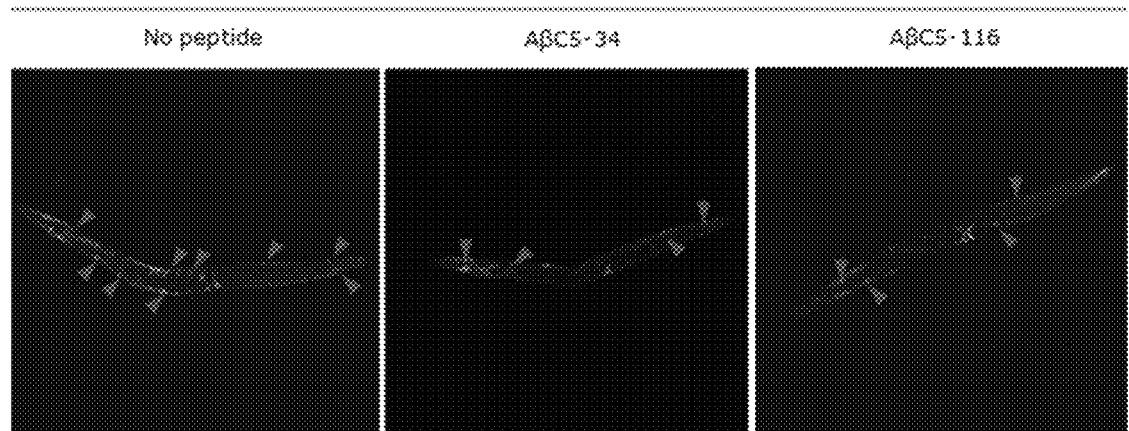
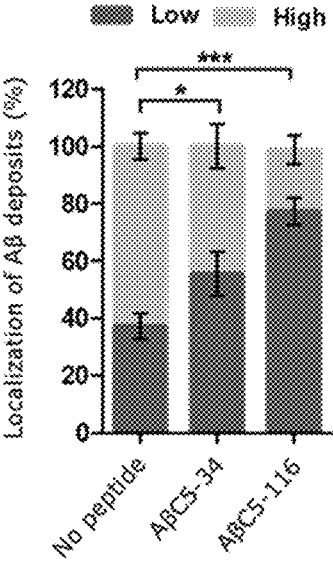
FIG. 11C

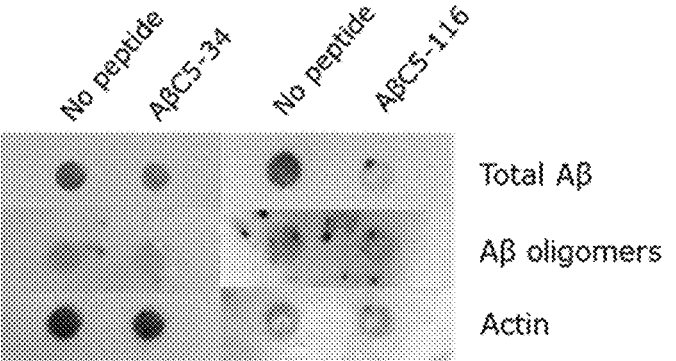
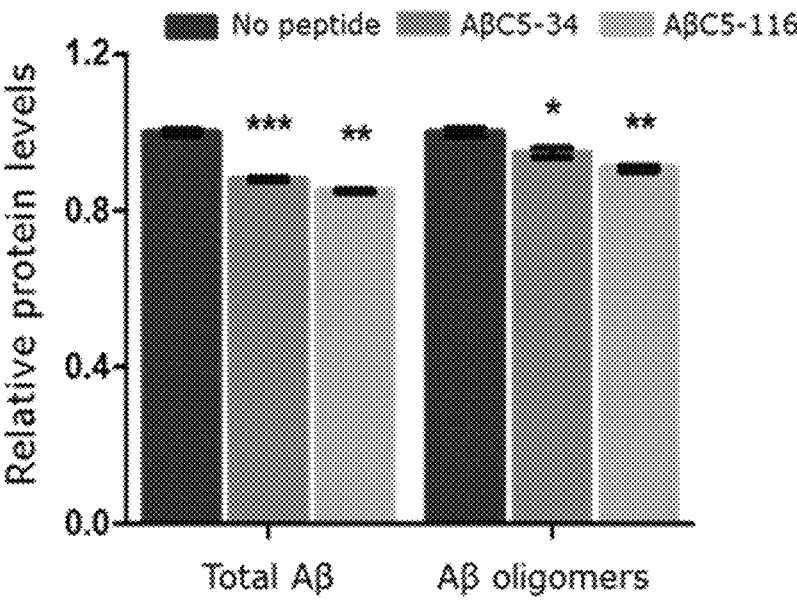
FIG. 11D

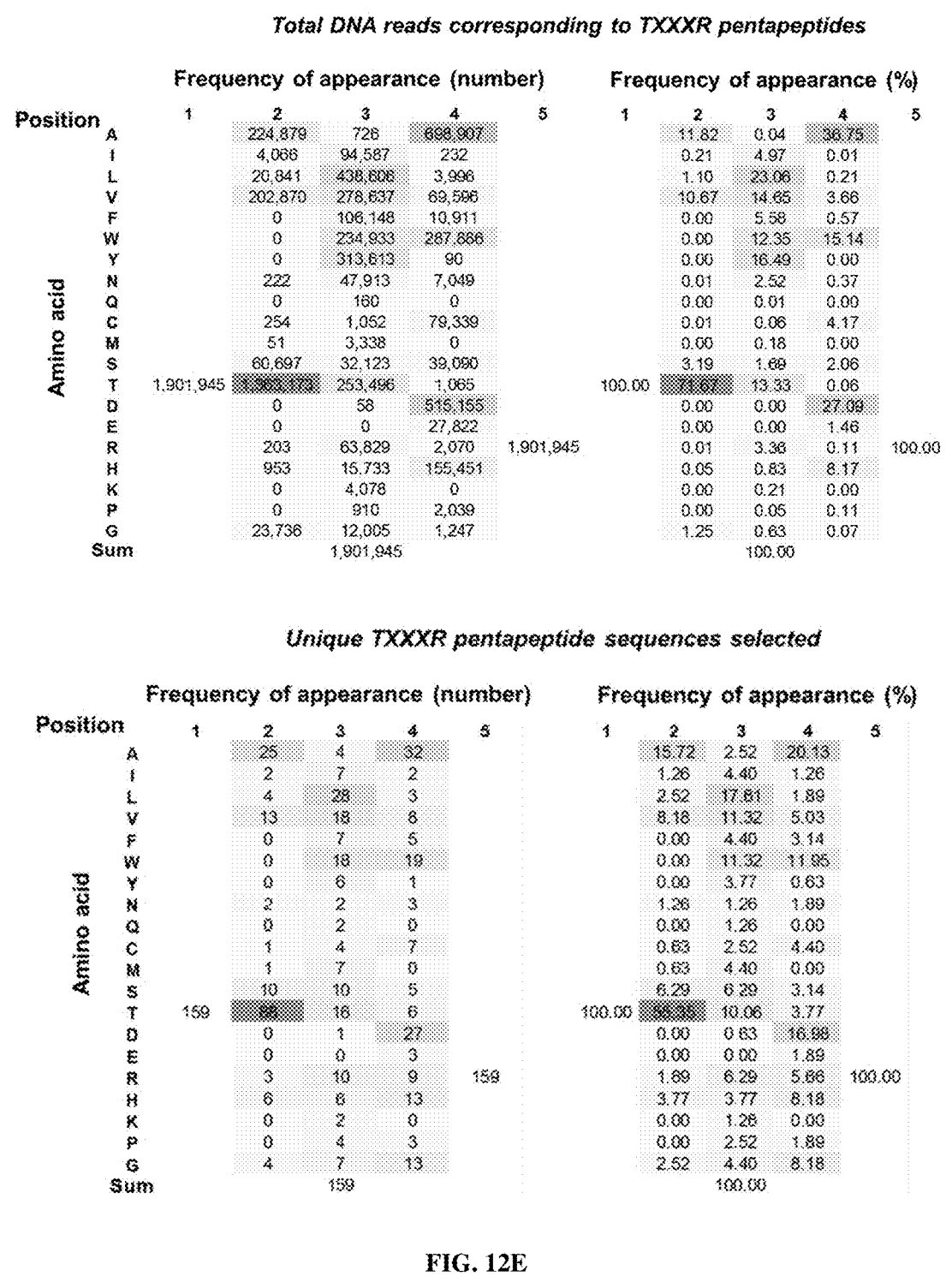

Total DNA reads corresponding to TXXXR pentapeptides

| Position | Frequency of appearance (number) | | | | | Frequency of appearance (%) | | | | |
|---|---|---|---|---|---|---|---|---|---|---|
| Amino acid | 1 | 2 | 3 | 4 | 5 | 1 | 2 | 3 | 4 | 5 |
| A | | 224,879 | 726 | 698,907 | | | 11.82 | 0.04 | 36.75 | |
| I | | 4,066 | 94,587 | 232 | | | 0.21 | 4.97 | 0.01 | |
| L | | 20,841 | 438,608 | 3,996 | | | 1.10 | 23.06 | 0.21 | |
| V | | 202,870 | 278,637 | 69,596 | | | 10.67 | 14.65 | 3.66 | |
| F | | 0 | 106,148 | 10,911 | | | 0.00 | 5.58 | 0.57 | |
| W | | 0 | 234,933 | 287,686 | | | 0.00 | 12.35 | 15.14 | |
| Y | | 0 | 313,613 | 90 | | | 0.00 | 16.49 | 0.00 | |
| N | | 222 | 47,913 | 7,049 | | | 0.01 | 2.52 | 0.37 | |
| Q | | 0 | 160 | 0 | | | 0.00 | 0.01 | 0.00 | |
| C | | 254 | 1,052 | 79,339 | | | 0.01 | 0.06 | 4.17 | |
| M | | 51 | 3,338 | 0 | | | 0.00 | 0.18 | 0.00 | |
| S | | 60,697 | 32,123 | 39,090 | | | 3.19 | 1.69 | 2.06 | |
| T | 1,901,945 | 965,773 | 253,496 | 1,065 | | 100.00 | 71.61 | 13.33 | 0.06 | |
| D | | 0 | 58 | 515,155 | | | 0.00 | 0.00 | 27.09 | |
| E | | 0 | 0 | 27,822 | | | 0.00 | 0.00 | 1.46 | |
| R | | 203 | 63,829 | 2,070 | 1,901,945 | | 0.01 | 3.36 | 0.11 | 100.00 |
| H | | 953 | 15,733 | 155,451 | | | 0.05 | 0.83 | 8.17 | |
| K | | 0 | 4,078 | 0 | | | 0.00 | 0.21 | 0.00 | |
| P | | 0 | 910 | 2,039 | | | 0.00 | 0.05 | 0.11 | |
| G | | 23,736 | 12,005 | 1,247 | | | 1.25 | 0.63 | 0.07 | |
| Sum | | | 1,901,945 | | | | | 100.00 | | |

Unique TXXXR pentapeptide sequences selected

| Position | Frequency of appearance (number) | | | | | Frequency of appearance (%) | | | | |
|---|---|---|---|---|---|---|---|---|---|---|
| Amino acid | 1 | 2 | 3 | 4 | 5 | 1 | 2 | 3 | 4 | 5 |
| A | | 25 | 4 | 32 | | | 15.72 | 2.52 | 20.13 | |
| I | | 2 | 7 | 2 | | | 1.26 | 4.40 | 1.26 | |
| L | | 4 | 28 | 3 | | | 2.52 | 17.61 | 1.89 | |
| V | | 13 | 18 | 8 | | | 8.18 | 11.32 | 5.03 | |
| F | | 0 | 7 | 5 | | | 0.00 | 4.40 | 3.14 | |
| W | | 0 | 18 | 19 | | | 0.00 | 11.32 | 11.95 | |
| Y | | 0 | 6 | 1 | | | 0.00 | 3.77 | 0.63 | |
| N | | 2 | 2 | 3 | | | 1.26 | 1.26 | 1.89 | |
| Q | | 0 | 2 | 0 | | | 0.00 | 1.26 | 0.00 | |
| C | | 1 | 4 | 7 | | | 0.63 | 2.52 | 4.40 | |
| M | | 1 | 7 | 0 | | | 0.63 | 4.40 | 0.00 | |
| S | | 10 | 10 | 5 | | | 6.29 | 6.29 | 3.14 | |
| T | 159 | 90 | 16 | 6 | | 100.00 | 56.60 | 10.06 | 3.77 | |
| D | | 0 | 1 | 27 | | | 0.00 | 0.63 | 16.98 | |
| E | | 0 | 0 | 3 | | | 0.00 | 0.00 | 1.89 | |
| R | | 3 | 10 | 9 | 159 | | 1.89 | 6.29 | 5.66 | 100.00 |
| H | | 6 | 6 | 13 | | | 3.77 | 3.77 | 8.18 | |
| K | | 0 | 2 | 0 | | | 0.00 | 1.26 | 0.00 | |
| P | | 0 | 4 | 3 | | | 0.00 | 2.52 | 1.89 | |
| G | | 4 | 7 | 13 | | | 2.52 | 4.40 | 8.18 | |
| Sum | | | 159 | | | | | 100.00 | | |

FIG. 12E

*Sequence analysis of the total cyclic hexapeptide sequences encoded by the selected bacterial clones*

| | Frequency of appearance (number) | | | | | | Frequency of appearance (%) | | | | | |
| Position | 1 | 2 | 3 | 4 | 5 | 6 | 1 | 2 | 3 | 4 | 5 | 6 |
|---|---|---|---|---|---|---|---|---|---|---|---|---|
| A | 0 | 0 | 111,637 | 0 | 0 | 0 | 0.00 | 0.00 | 34.95 | 0.00 | 0.00 | 0.00 |
| I | 0 | 227 | 384 | 13,135 | 0 | 0 | 0.00 | 0.07 | 0.12 | 4.11 | 0.00 | 0.00 |
| L | 0 | 54,431 | 13,451 | 687 | 12,121 | 0 | 0.00 | 17.04 | 4.21 | 0.22 | 3.79 | 0.00 |
| V | 0 | 17,100 | 132,533 | 915 | 586 | 0 | 0.00 | 5.35 | 41.49 | 0.29 | 0.18 | 0.00 |
| F | 0 | 0 | 227 | 27,171 | 282,676 | 0 | 0.00 | 0.00 | 0.07 | 8.51 | 88.71 | 0.00 |
| W | 0 | 0 | 355 | 275,180 | 0 | 13,368 | 0.00 | 0.00 | 0.11 | 86.14 | 0.00 | 4.18 |
| Y | 0 | 0 | 0 | 2,020 | 546 | 0 | 0.00 | 0.00 | 0.00 | 0.63 | 0.17 | 0.00 |
| N | 0 | 0 | 0 | 0 | 0 | 11,928 | 0.00 | 0.00 | 0.00 | 0.00 | 0.00 | 3.73 |
| Q | 0 | 0 | 0 | 0 | 0 | 0 | 0.00 | 0.00 | 0.00 | 0.00 | 0.00 | 0.00 |
| C | 0 | 623 | 707 | 0 | 0 | 0 | 0.00 | 0.20 | 0.22 | 0.00 | 0.00 | 0.00 |
| M | 0 | 0 | 0 | 0 | 0 | 556 | 0.00 | 0.00 | 0.00 | 0.00 | 0.00 | 0.17 |
| S | 0 | 307 | 1,284 | 0 | 86 | 0 | 0.00 | 0.10 | 0.40 | 0.00 | 0.03 | 0.00 |
| T | 319,450 | 0 | 17,100 | 0 | 0 | 0 | 100.00 | 0.00 | 5.35 | 0.00 | 0.00 | 0.00 |
| D | 0 | 0 | 114 | 0 | 0 | 292,844 | 0.00 | 0.00 | 0.04 | 0.00 | 0.00 | 91.61 |
| E | 0 | 0 | 29,077 | 307 | 0 | 954 | 0.00 | 0.00 | 9.10 | 0.10 | 0.00 | 0.30 |
| R | 0 | 0 | 0 | 55 | 13,135 | 0 | 0.00 | 0.00 | 0.00 | 0.02 | 4.11 | 0.00 |
| H | 0 | 0 | 647 | 0 | 0 | 0 | 0.00 | 0.00 | 0.20 | 0.00 | 0.00 | 0.00 |
| K | 0 | 1,231 | 11,016 | 0 | 0 | 0 | 0.00 | 0.39 | 3.45 | 0.00 | 0.00 | 0.00 |
| P | 0 | 245,531 | 289 | 0 | 0 | 0 | 0.00 | 76.86 | 0.09 | 0.00 | 0.00 | 0.00 |
| G | 0 | 0 | 629 | 0 | 0 | 0 | 0.00 | 0.00 | 0.20 | 0.00 | 0.00 | 0.00 |
| Sum | | | 319,450 | | | | | | 100.00 | | | |

Amino acid (row axis)

*Sequence analysis of the unique selected cyclic hexapeptides*

| | Frequency of appearance (number) | | | | | | Frequency of appearance (%) | | | | | |
| Position | 1 | 2 | 3 | 4 | 5 | 6 | 1 | 2 | 3 | 4 | 5 | 6 |
|---|---|---|---|---|---|---|---|---|---|---|---|---|
| A | 0 | 0 | 6 | 0 | 0 | 0 | 0.00 | 0.00 | 17.65 | 0.00 | 0.00 | 0.00 |
| I | 0 | 1 | 1 | 1 | 0 | 0 | 0.00 | 2.94 | 2.94 | 2.94 | 0.00 | 0.00 |
| L | 0 | 13 | 2 | 4 | 6 | 0 | 0.00 | 38.24 | 5.88 | 11.76 | 17.65 | 0.00 |
| V | 0 | 1 | 4 | 3 | 3 | 0 | 0.00 | 2.94 | 11.76 | 8.82 | 8.82 | 0.00 |
| F | 0 | 0 | 1 | 2 | 21 | 0 | 0.00 | 0.00 | 2.94 | 5.88 | 61.76 | 0.00 |
| W | 0 | 0 | 1 | 19 | 0 | 2 | 0.00 | 0.00 | 2.94 | 55.88 | 0.00 | 5.88 |
| Y | 0 | 0 | 0 | 3 | 2 | 0 | 0.00 | 0.00 | 0.00 | 8.82 | 5.88 | 0.00 |
| N | 0 | 0 | 0 | 0 | 0 | 4 | 0.00 | 0.00 | 0.00 | 0.00 | 0.00 | 11.76 |
| Q | 0 | 0 | 0 | 0 | 0 | 0 | 0.00 | 0.00 | 0.00 | 0.00 | 0.00 | 0.00 |
| C | 0 | 1 | 2 | 0 | 0 | 0 | 0.00 | 2.94 | 5.88 | 0.00 | 0.00 | 0.00 |
| M | 0 | 0 | 0 | 0 | 0 | 1 | 0.00 | 0.00 | 0.00 | 0.00 | 0.00 | 2.94 |
| S | 0 | 1 | 5 | 0 | 1 | 0 | 0.00 | 2.94 | 14.71 | 0.00 | 2.94 | 0.00 |
| T | 34 | 0 | 1 | 0 | 0 | 0 | 100.00 | 0.00 | 2.94 | 0.00 | 0.00 | 0.00 |
| D | 0 | 0 | 1 | 0 | 0 | 25 | 0.00 | 0.00 | 2.94 | 0.00 | 0.00 | 73.53 |
| E | 0 | 0 | 4 | 1 | 0 | 2 | 0.00 | 0.00 | 11.76 | 2.94 | 0.00 | 5.88 |
| R | 0 | 0 | 0 | 1 | 1 | 0 | 0.00 | 0.00 | 0.00 | 2.94 | 2.94 | 0.00 |
| H | 0 | 0 | 1 | 0 | 0 | 0 | 0.00 | 0.00 | 2.94 | 0.00 | 0.00 | 0.00 |
| K | 0 | 1 | 1 | 0 | 0 | 0 | 0.00 | 2.94 | 2.94 | 0.00 | 0.00 | 0.00 |
| P | 0 | 16 | 1 | 0 | 0 | 0 | 0.00 | 47.06 | 2.94 | 0.00 | 0.00 | 0.00 |
| G | 0 | 0 | 3 | 0 | 0 | 0 | 0.00 | 0.00 | 8.82 | 0.00 | 0.00 | 0.00 |
| Sum | | | 34 | | | | | | 100.00 | | | |

Amino acid (row axis)

FIG. 12H

MACROCYCLIC MODULATORS OF DISEASE ASSOCIATED PROTEIN MISFOLDING AND AGGREGATION

CROSS-REFERENCE TO RELATED APPLICATIONS

This application is a divisional of U.S. patent application Ser. No. 16/613,879, entitled, "MACROCYCLIC MODU-LATORS OF DISEASE ASSOCIATED PROTEIN MIS-FOLDING AND AGGREGATION," filed on Nov. 15, 2019, which is a national phase application under 35 U.S.C. § 371 of International Application No. PCT/IB2018/000622, entitled "MACROCYCLIC MODULATORS OF DISEASE ASSOCIATED PROTEIN MISFOLDING AND AGGRE-GATION," filed on May 22, 2018, which claims the benefit of International Patent Application No. PCT/EP2017/025141, entitled "MACROCYCLIC MODULATORS OF β-AMYLOID MISFOLDING AND AGGREGATION," filed on May 22, 2017, and of International Patent Applica-tion No. PCT/EP2017/025298, entitled "MACROCYCLIC RESCUERS FOR DISEASE-ASSOCIATED PROTEIN MISFOLDING," filed on Oct. 5, 2017, each of which is incorporated herein by reference in its entirety.

INCORPORATION OF SEQUENCE LISTING

This application contains a Sequence Listing, which has been submitted electronically and is hereby incorporated by reference in its entirety. Said Sequence Listing, created on Oct. 27, 2023, is named "SKRT.P0001US.D1_ST.26 Sequence Listing" and is 632 KB in size.

TECHNICAL FIELD OF THE INVENTION

Aspects of the present invention relate to a generalizable bacterial platform for the discovery of chemical modulators of the problematic folding and aggregation of disease-associated, misfolding-prone proteins. More particularly, studies herein demonstrate the applicability of this platform to biosynthetically produce large combinatorial libraries of macrocyclic compounds in *Escherichia coli* cells and to simultaneously screen these libraries in order to identify the bioactive compounds with the ability to rescue the problem-atic folding and aggregation of mutant Cu/Zn superoxide dismutase using a high-throughput genetic assay. Further-more, studies herein demonstrate the wider applicability of this platform to identify the bioactive compounds with the ability to rescue the problematic folding and aggregation of additional misfolding-prone polypeptides, such as the β-amyloid peptide. In some aspects, compounds of the invention preferably rescue the misfolding and modulate the aggregation of human Cu/Zn superoxide dismutase and of its variants. In further aspects, of the invention rescue misfolding and modulate the aggregation of natural β-amy-loid peptides. In a preferred embodiment, the compounds can inhibit the aggregation of Cu/Zn superoxide dismutase and of its variants. In another preferred embodiment, com-pounds of the present invention can inhibit natural β-amy-loid peptide aggregation. In another preferred embodiment, the Cu/Zn superoxide dismutase modulator compounds of the invention are head-to-tail cyclic oligopeptides, or vari-ants thereof carrying specific modifications, such that the compound alters the aggregation or inhibits the neurotoxic-ity of Cu/Zn superoxide dismutase and of its variants when contacted with the peptides. In another preferred embodi-ment, the β-amyloid modulator compounds of the invention are head-to-tail cyclic oligopeptides, or variants thereof carrying specific modifications, such that the compound alters the aggregation or inhibits the neurotoxicity of natural β-amyloid peptides when contacted with the peptides. Phar-maceutical compositions comprising the compounds of the invention, and diagnostic and treatment methods for amy-loidogenic diseases, such as amyotrophic lateral sclerosis, using the compounds of the invention, are also disclosed.

BACKGROUND OF THE INVENTION

Protein misfolding is currently linked to more than 50 diseases including Alzheimer's disease, Parkinson's disease, Huntington's disease, type 2 diabetes, cystic fibrosis, amyo-trophic lateral sclerosis, Gaucher's disease, nephrogenic diabetes insipidus, and Creutzfeldt-Jakob disease. These disorders are collectively termed "conformational diseases" or "protein misfolding diseases" (PMDs). There are two ways that misfolded prone proteins (MisPs) lead to disease; one is when they lose their ability to execute their physi-ological function (loss-of-function) and the other when they acquire a new harmful property (gain-of-function). Cellular or environmental factors such as changes in pH, oxidative stress, exposure to high concentrations of metal ions and other chemicals, as well as the presence of a mutation or mutations in amino acid sequences of particular proteins, can play a critical role in protein misfolding. Protein mis-folding diseases are becoming more common as the popu-lation ages, as many of them are age-related.

PMDs include very serious disorders with high incidence rates and a severe impact on the well-being of the human population, and anti-PMD therapeutics are in enormous demand. One of the most promising approaches for identi-fying potential anti-PMD therapeutics is the discovery of chemical rescuers of protein misfolding. Such molecules have already been identified for a number of MisPs. For example, linear peptides with homology to certain regions of the β-amyloid peptide (Aβ) and small molecules, such as scyllo-inositol, tramiprosate, methylene blue and bexaro-tene, have been found to modulate Aβ aggregation and inhibit its neurotoxicity in vitro and in vivo, and some of them have subsequently advanced to clinical studies. Simi-larly, peptides with homology to the unstructured central hydrophobic region of the PD-related protein α-synuclein (αsyn) and natural products, such as baicalein and (2)-epigallocatechin-3-gallate have exhibited similar effects on αsyn. Indeed, the small molecule tafamidis, which is capable of rescuing the misfolding of the carrier protein transthyretin, has recently been approved for the treatment of familial amyloidotic polyneuropathy in Europe and Japan and is currently marketed under the name Vyndaqel® (Pfizer). The compound and its use for the treatment tran-sthyretin amyloid disease have been disclosed in the Euro-pean patent EP1587821.

Macrocycles have been characterized as a particularly promising class of compounds of potential therapeutics, which remain underexplored (Driggers, E. M., Hale, S. P., Lee, J. & Terrett, N. K. The exploration of macrocycles for drug discovery—an underexploited structural class. Nat. Rev. Drug Discov. 7, 608-624 (2008)). Macrocycles occupy the space between small molecules and larger biologicals and often exhibit the advantages of both classes of mol-ecules i.e., the high bioavailability of small molecules com-bined with the high specificity and the fewer side-effects of biologicals. Furthermore, their typically larger size and more complex structure makes the macrocycles particularly suit-able for targeting currently undrugable targets, such as ones involved in protein-protein interactions. Since many PMDs are characterized by protein aggregation, a process that is dependent on productive protein-protein interactions, macrocycles can be expected to be particularly active modulators for this class of disorders. Their therapeutic potential is slowly beginning to rise in a wide variety of diseases and shown in U.S. Pat. No. 9,308,236 wherein macrocycles are shown to inhibit PD-1/PD-L1 (Programmed Death 1) and CD80/PD-L1 protein/protein interactions, and are thus useful in ameliorating various diseases including cancer and infectious diseases.

Amyorophic lateral sclerosis (ALS) is a neurodegenerative disorder that affects the motor neurons of the spinal cord, brain stem, and cortex of adults most frequently between 50 and 60 years of age. The disease is ultimately fatal with an average survival time of 3-5 years. Its causes remain both enigmatic and controversial. The majority of cases (90-95%) have no known genetic link and are termed sporadic. For the rest of the 5-10% of cases, there is typically a family history of ALS, the disease is inherited (familial ALS, fALS), and it is caused by genetic mutations present in specific chromosomal loci. Approximately one quarter of all cases of the familial disease are associated with missense mutations mapped onto SOD1, the gene encoding for the enzyme Cu/Zn superoxide dismutase (SOD1).

Superoxide dismutases (SODs) belong to the family of isoenzymes involved in the scavenging of $O_2$ radicals. All mammalian cells possess three isoforms of superoxide dismutase enzymes; the cytosolic copper-zinc dimeric form, known as SOD1, the mitochondrial tetrameric manganese superoxide dismutase or SOD2 and the extracellular tetrameric Cu, Zn superoxide dismutase or SOD3. All enzymes catalyze the same reaction converting the oxygen radical in molecular oxygen and hydrogen peroxide $H_2O_2$ through the alternate reduction and reoxidation of $Cu2^+$ for SOD1 and SOD3 and Mn for SOD2; the $H_2O_2$ is then enzymatically converted by catalase and glutathione peroxidase in molecular oxygen and $H_2O$. In physiological conditions, the superoxide dismutases, together with the non-enzymatic reactive oxygen species (ROS) scavengers vitamins E, A, and C, maintain a steady state between oxidant and anti-oxidant systems.

To date, more than 150 mutations in SOD1 have been found to be associated with fALS (http://alsod.iop.kcl.ac.uk/home.aspx). These result in amino acid substitutions, C-terminal truncations and other modifications in the amino acid sequence of SOD1. It is now well established that these changes in the sequence of SOD1 do not cause ALS due to loss or decrease of enzymatic activity. The main pieces of evidence supporting this are that: (i) SOD1-knockout mice do not develop ALS phenotypes, (ii) the onset and duration of motor neuron disease in transgenic mice carrying fALS-associated SOD1 alleles is similar irrespective of the presence or absence also of the wild-type allele in the animal, and (iii) many fALS-associated SOD1 variants (SOD1*) retain wild type-like levels of dismutase activity. Instead, it has been proposed that fALS-linked mutations introduce a toxic-gain-of-function property in SOD1 by causing protein misfolding and aggregation, and the formation of oligomeric/aggregated SOD1 species which are highly toxic for motor neurons. Gradual accumulation of such toxic oligomers/aggregates of mutated SOD1 initiates motor neuron degeneration and the development of fALS. Indeed, many observations support this theory: (i) biochemical studies of a variety of fALS-associated SOD1 variants have been found to be less stable, more prone to misfolding, and with higher aggregation propensity compared to wild-type SOD1,

4

(ii) prominent SOD1 aggregates have been found in the cytosolic space of cultured motors neurons, in motor neurons and in neighboring astrocytes of SOD1* transgenic mice, and of fALS patients, (iii) SOD1* aggregated species have been found to be toxic for motor neurons, (iv) SOD1*-induced motor neuron toxicity can be suppressed by up-regulating actors that assist SOD1* folding and inhibit its aggregation, such as the heat shock response regulator Hsf1, and (v) the combination of aggregation propensity and loss of stability in fALS-associated SOD1* variants has been found to be a good predictor of disease severity. The theory that SOD1*-linked fALS is a conformational disorder/protein misfolding disease is in agreement with the prevalent theories concerning the molecular origin of other major neurodegenerative diseases, such as Alzheimer's disease, Parkinson's disease and prion disorders (1. Chiti, F. & Dobson, C. M. Protein misfolding, functional amyloid, and human disease. Annu. Rev. Biochem. 75, 333-366 (2006)).

Despite the major advances in identifying genes and mechanisms contributing to ALS pathogenesis, there exist only two currently approved therapeutics: the glutamate antagonist Riluzole and the free radical scavenger that is believed to relieve the effects of oxidative stress, Radicava. However, both treatments only extend the life or the time to mechanical ventilation of the patient by two to three months. Therefore, there still remains a need for developing a novel and cost-effective treatment approach to ALS that will overcome the obstacles and side-effects of the current treatment regime that only result in a minor delay of the outcome of the disease.

Alzheimer's disease (AD) is the most common progressive neurodegenerative disease that causes dementia in aged humans. This condition affects more than 7 million people in Europe and 35 million people worldwide. In financial terms, these numbers translate to an annual AD treatment cost of $818 billion only for the United States (2015 World Alzheimer Report). Due to the aging of the human population, the incidence of AD has been rising steadily in recent years and is projected to increase by 200% within the next 20 years.

AD is neuropathologically characterized by intraneuronal neurofibrillary tangles consisting of abnormally hyperphosphorylated tau, extracellular accumulation of fibrillar amyloid-$\beta$ (A$\beta$) peptide in senile plaques, and the build-up of soluble A$\beta$ oligomers in the brain. The amyloid cascade hypothesis, which states that the formation of oligomeric and/or fibrillar A$\beta$ in the brain is neurotoxic and that their accumulation results in neuronal degeneration and death, and the development of AD is the prevalent theory regarding the molecular sources behind the pathology of AD.

A$\beta$ is produced by the cleavage of the amyloid precursor protein (APP) as a result of the action of the proteases $\beta$- and $\gamma$-secretase. Due to the broad amino acid recognition specificity of $\gamma$-secretase, its proteolytic activity on APP leads to the formation of different forms of A$\beta$ peptides. The main product of APP cleavage consists of 40 amino acids (A$\beta_{40}$), while one of the secondary products yields a 42-amino-acid-long peptide (A$\beta_{42}$). A$\beta$ is an amphipathic peptide that includes a hydrophilic (amino acids 1-16) and a hydrophobic region (amino acids 17-40/42). A$\beta_{42}$ contains two additional amino acids at its C terminus and exhibits higher hydrophobicity and higher tendency for aggregation than A$\beta_{40}$. Due to the distribution of the hydrophobic amino acids in its sequence, A$\beta$ is unable to adopt a well-defined conformation. As a result, certain hydrophobic regions of the A$\beta$ sequence remain exposed to the aqueous environment of the cell and the protein tends to form oligomers and higher-order aggregates. As mentioned above, these soluble oligomers and/or higher-order aggregates are thought to be the neurotoxic Aβ species that initiate AD. AD can thus be viewed as a proteinopathy, which is initiated due to the peculiar biochemical/biophysical properties of Aβ and its associated problematic folding (misfolding), thus categorizing AD in the large group of disorders called "conformational diseases" or "protein misfolding diseases" as described above.

Despite the huge socioeconomic impact of AD and intense research efforts for decades, preventive or therapeutic treatments against AD do not exist currently. Anti-AD therapies could be developed by identifying inhibitors of anyone step of the pathway that is initiated by the biosynthesis of Aβ and results in neuron degeneration and the development of dementia. For example, molecules with the ability to decrease the concentration of circulating Aβ could act as agents that down-regulate the formation of neurotoxic Aβ species and the onset of the disease. This could be achieved, for instance, by using antibodies against Aβ that lead to sequestration, degradation, and/or clearance of the peptide, or by using β- and γ-secretase inhibitors which inhibit APP cleavage and decrease the rate of biosynthesis of Aβ. Such compounds have already been discovered but they haven't yet demonstrated the desired therapeutic profiles, primarily due to unwanted side effects. For example, γ-secretase inhibitors have exhibited undesired actions in other physiological pathways, such as Notch signaling, which cause serious side effects in mice (gastrointestinal tract symptoms etc.).

Compounds which can bind to Aβ, correct its problematic folding, and prevent the formation of Aβ oligomers/aggregates have the potential to function as inhibitors of Aβ-induced neurotoxicity and become effective drugs against AD. Small molecules, such as scyllo-inositol, tramiprosate, methylene blue and bexarotene, have been found to modulate Aβ aggregation and inhibit its neurotoxicity in vitro and in vivo. In addition, linear peptides with homology to certain regions of Aβ have exhibited similar properties. These and other research efforts have led to the identification of a number of promising compounds which have been or are being tested in clinical trials. Until now, however, no compound has demonstrated the desired preventive or therapeutic properties against AD. Irrespective of whether it is the oligomeric or more aggregated forms of Aβ which are primarily responsible for its neurotoxicity and other pathogenic effects, the discovery of chemical modulators of the natural Aβ oligomerization/aggregation process is considered a very promising approach, since Aβ oligomerization/aggregation is viewed as a purely pathogenic process, which is not involved in other physiological functions in the cell. Such molecules are thus expected to exhibit a safer pharmacological profile.

DESCRIPTION OF FIGURES

FIGS. 1A-1B: (A) (Left) Schematic of the pSICLOPPS-NuX$_1$X$_2$X$_3$-X$_5$ vector library encoding the combinatorial oligopeptide library cyclo-NuX$_1$X$_2$X$_3$-X$_5$. Nu: Cys (C), Ser (S), or Thr (T); X: any of the 20 natural amino acids; NNS: randomized codons, where N=A, T, C or G and S=G or C; I$_C$: C-terminal fragment of the split Ssp DnaE intein; I$_N$: N-terminal fragment of the split Ssp DnaE intein; CBD: chitin-binding domain. (Right) Intein-mediated peptide cyclization using SICLOPPS. The tetra-partite fusion undergoes intein splicing upon intein fragment re-association, leading to peptide cyclization and the production of the cyclo-NuX$_1$X$_2$X$_3$-X$_5$ library. (B) Theoretical and actual diversity of the constructed combinatorial cyclo-NuX$_1$X$_2$X$_3$-X$_5$ oligopeptide library.

FIGS. 2A-2C: (A) Relative fluorescence of E. coli BL21 (DE3) (left) and Origami 2(DE3) (right) cells overexpressing chimeric SOD1-GFP fusions from the corresponding pETSOD1-GFP vectors. Mean values±s.e.m. are reported (n=3 independent experiments, each one performed in replica triplicates). (B) Solubility analysis of overexpressed SOD1-GFP fusions by SDS-PAGE/western blotting using an anti-polyHis antibody. Representative data from n=2 independent experiments are presented. (C) Solubility analysis of SOD1 variants overexpressed as in (A, right) by SDS-PAGE/western blotting using an anti-polyHis (left) or an anti-FLAG (right) antibody. Representative data from n=2 independent experiments are presented. The assay was performed using E. coli Origami 2(DE3) cells overexpressing GFP-free SOD1 from the corresponding pETSOD1 vectors by the addition of 0.01 mM IPTG at 37° C. for 2 h.

FIGS. 3A-3G: (A) Schematic representation of the utilized bacterial platform for the discovery of cyclic oligopeptide rescuers of MisP misfolding and aggregation. pMisP-GFP: plasmid encoding a MisP-GFP fusion; pSICLOPPS-NuX$_1$X$_2$X$_3$-X$_5$: vector library encoding the combinatorial oligopeptide library cyclo-NuX$_1$X$_2$X$_3$-X$_5$. Nu: Cys (C), Ser (S), or Thr (T); X: any of the twenty natural amino acids; NNS: randomized codons, where N=A, T, C or G and S=G or C; P: sorting gate. (B) FACS screening of E. coli BL21(DE3) overexpressing SOD1(A4V)-GFP and the combined cyclo-NuX$_1$X$_2$X$_3$-X$_5$ oligopeptide library. M: mean GFP fluorescence in arbitrary units. (C) Fluorescence of E. coli Origami 2(DE3) cells co-expressing SOD1(A4V)-GFP and four individual cyclic peptide sequences isolated after the fourth round of FACS sorting shown in (B) by utilizing wild-type Ssp DnaE intein or the splicing-deficient Ssp DnaE(H24L/F26A) intein. Mean values±s.e.m. are reported (n=4 independent experiments, each one performed in replica triplicates). (D) Western blot analysis using an anti-CBD antibody of the four individual selected clones investigated in (C). The upper band of ~25 kDa corresponds to the I$_C$-peptide sequence-I$_N$-CBD precursor, while the lower band of ~20 kDa corresponds to the processed I$_N$-CBD product, whose appearance is an indication of successful intein processing and cyclic peptide formation. CBD: chitin-binding domain. (E) Fluorescence of E. coli Origami 2(DE3) cells co-expressing SOD1(A4V) or Aβ$_{42}$-GFP from the vectors pETSOD1(A4V)-GFP or pETAβ$_{42}$-GFP, respectively, together with the cyclic peptides encoded by the selected clones 1-4 investigated in (C). The SOD1 (A4V)-GFP fluorescence of the cell population producing a random cyclic peptide was arbitrarily set to 100. Experiments were carried out in replica triplicates (n=1 independent experiments) and the reported data correspond to the mean value+s.e.m. (F) Solubility analysis of SOD1(A4V)-GFP overexpressed with/without the four selected cyclic peptide sequences shown in (C) by SDS-PAGE/western blotting using an anti-polyHis antibody. (G) DNA sequences of the peptide-encoding regions of the pSICLOPPS vectors contained in the selected clones tested in (C) along with the predicted amino acid sequences of the cyclic oligopeptides that they encode.

FIGS. 4A-4F: (A) Chemical structure of the selected cyclic pentapeptide SOD1C5-4. (B) Circular dichroism spectra of SOD1(A4V) incubated with/without the selected cyclic pentapeptides SOD1C5-4, AβC5-34 or AβC5-116 at room temperature for 90 d (1:1 and 5:1 indicate cyclic peptide:SOD1(A4V) molar ratios). Representative spectra from n=2 independent experiments are presented. (C)

Dynamic light scattering analysis of SOD1(A4V) incubated with/without the selected cyclic pentapeptides at room temperature for 60 d. Representative data from n=2 independent experiments are presented. (D) Thioflavin T (ThT) fluorescence of SOD1(A4V) incubated with/without the selected cyclic pentapeptides at room temperature for 90 d. Representative data from n=2 independent experiments are presented. (E) Filter retardation assay of SOD1(A4V) incubated with/without the selected cyclic pentapeptides at 37° C. for 25 d. Representative images from n=2 independent experiments performed in replica duplicates are presented. (F) Differential scanning fluorimetry analysis of isolated SOD1 (A4V) in the presence or absence of the selected cyclic pentapeptide SOD1C5-4 (5:1 peptide to protein ratio) using the conformation-sensitive dye SYPRO Orange. Data corresponding to n=2 independent experiments each one performed in three replicates±s.e.m. are presented.

FIGS. 5A-5C: (A) HEK293 cells transiently expressing SOD1-GFP (top row) or SOD1(A4V)-GFP (middle and bottom rows) in the absence and presence of the selected cyclic pentapeptide SOD1C5-4 and visualized by confocal microscopy. (B) Relative number of cells containing SOD1 aggregates in the cultures described in (A). Aggregate-positive cells are presented as percentage of the total viable and GFP-positive cells. (C) Relative viability of cells in the cultures described in (A). The viability of cells expressing wild-type SOD1 was arbitrarily set to 100.

Figure 3A:
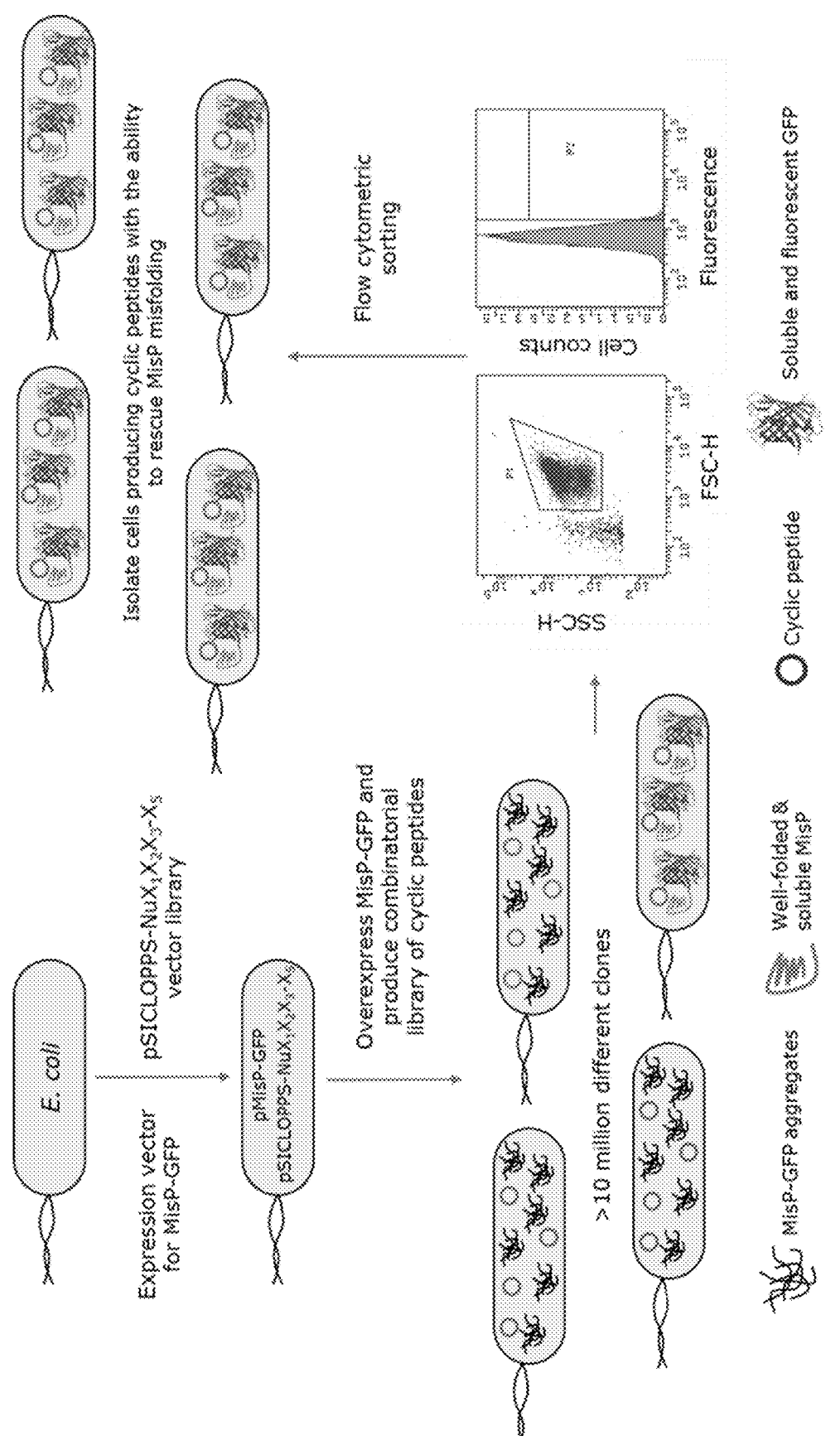
Figure 3B:
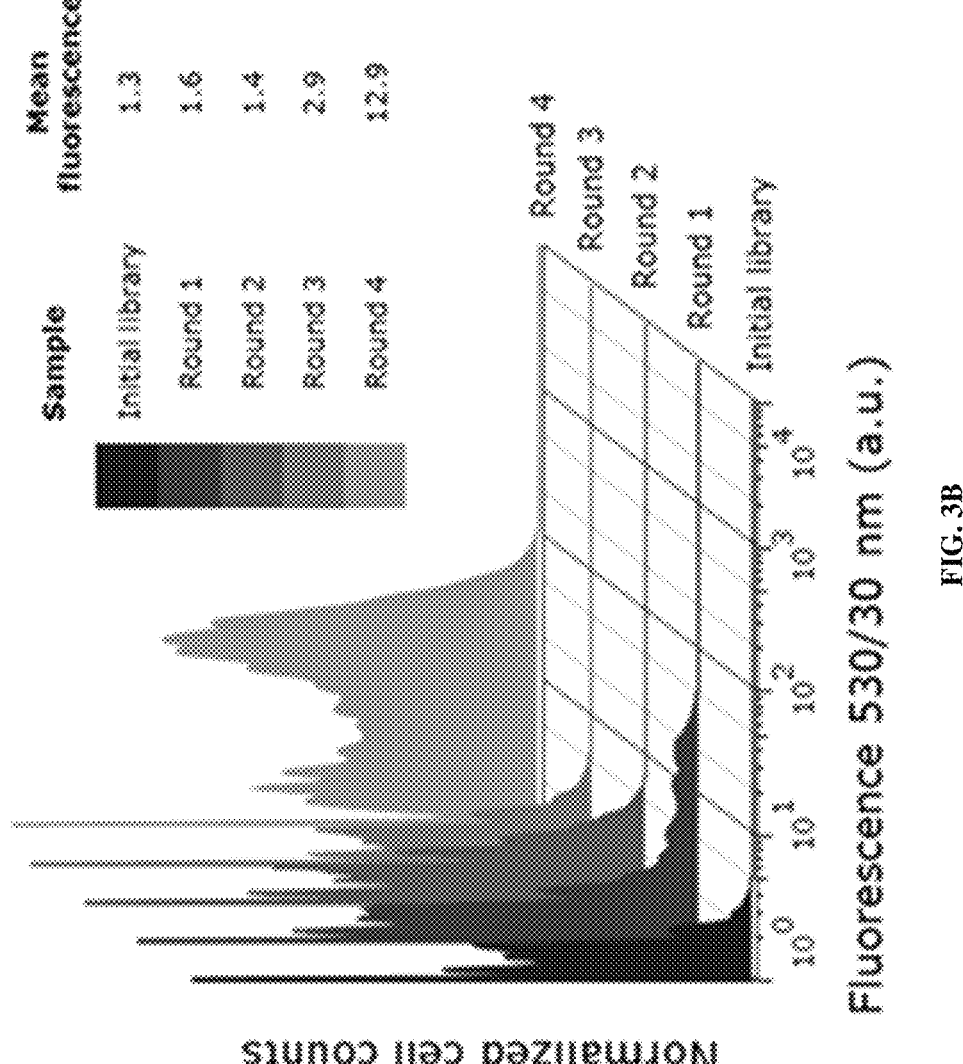

FIGS. 6A-6E: (A) Distribution of the different types of selected cyclic oligopeptides among the bacterial clones selected for enhanced SOD1(A4V)-GFP fluorescence after the fourth round of FACS sorting (FIG. 3B). (B) Heat maps depicting the amino acid distribution in the sequences of the selected TXSXW pentapeptides after the fourth round of FACS sorting (FIG. 3B) as revealed by deep sequencing analysis. (C) Frequency of appearance of codons corresponding to the twenty natural amino acids at positions 2 and 4 of the peptide-encoding region of the pSICLOPPS-NuX₁X₂X₃-X₅ vectors contained in the bacterial clones after the fourth round of FACS sorting (FIG. 3B) that encoded for TXSXW cyclic pentapeptides (3,939,406 reads corresponding to TXSXW cyclic pentapeptides out of 4,243,704 total reads that appeared more than 50 times in the sorted peptide pool). (D) Frequency of appearance of the twenty natural amino acids at positions 2 and 4 of the unique TXSXW cyclic pentapeptides encoded by the pSICLOPPS-NuX₁X₂X₃-X₅ vectors contained in the bacterial clones isolated after the fourth round of FACS sorting (FIG. 3B) (46 unique peptide sequences corresponding to TXSXW cyclic pentapeptides out of 367 total unique selected peptide sequences that appeared more than 50 times in the sorted peptide pool). (E) Fluorescence of *E. coli* Origami 2(DE3) cells co-expressing SOD1-GFP, containing either wild-type SOD1 wt) or the ALS-associated variants SOD1(G37R), G(85R) or (G93A) from the corresponding pETSOD1-GFP vectors, together with the indicated selected cyclic peptides. Experiments were carried out in replica triplicates (n=1 independent experiments) and the reported data correspond to the mean value±s.d.

FIG. 7: Sequences and frequency of appearance of the selected cyclic TXSXW pentapeptides as determined by high-throughput sequencing of the isolated pSICLOPPS-NuX₁X₂X₃-X₅ vectors after the fourth round of bacterial sorting for enhanced SOD1(A4V)-GFP fluorescence.

FIGS. 8A-8G: Depiction of the molecular evolution process with which macrocyclic rescuers of pathogenic Aβ misfolding and aggregation are identified.

FIGS. 9A-9E: Selected cyclic oligopeptides interfere with the normal Aβ aggregation process.

FIGS. 10A-10D: Selected cyclic oligopeptides inhibit Aβ-induced neurotoxicity in vitro.

FIGS. 11A-11D: Selected cyclic oligopeptides inhibit Aβ-induced neurotoxicity in vivo.

FIGS. 12A-12H: Next-generation sequencing and site-directed mutagenesis analyses may be used in order to identify all bioactive cyclic oligopeptide Aβ modulators contained in the tested cyclo-NuX₁X₂X₃-X₅ library and to facilitate structure-activity analyses of the isolated sequences.

SUMMARY OF THE INVENTION

It is an object of the present invention to provide short, drug-like peptide macrocycles with the ability to rescue the misfolding, aggregation and associated pathogenic effects of a prominent aggregation-prone and disease-associated protein target. Particularly, the object of the present invention is to identify cyclic oligopeptides that rescue the misfolding and modulate the natural aggregation process of SOD1 and of its variants, which are implicated in pathogenicity of ALS and fALS. Various tetra- and penta- and hexapeptides with these properties are described in the present invention. More particularly the inventors have identified the general formula cyclo-NuX₁X₂ ... Xₙ, wherein Nu=C, S, or T; X is any of the twenty natural amino acid and N=3-5 as a very rich source of chemical rescuers of SOD1 misfolding and modulators of its aggregation.

Another aspect of the present invention is the identification of pentapeptide macrocycles with the general formula cyclo-TXSXW, wherein the first amino acid is Threonine, the third amino acid is a Serine, the last amino acid is Tryptophan and X is any amino acid, as effective and preferred misfolding rescuers and modulators of the natural process of SOD1. More preferred misfolding rescuers and modulators of SOD1 aggregation are cyclic oligopeptide sequences exhibiting the cyclo-TΨ₁SΨ₂W motif, where Ψ₁=any amino acid excluding isoleucine (I), asparagine (N), glutamine (Q), methionine (M), glutamic acid (E), histidine (H), and lysine (K); and Ψ₂=any amino acid excluding isoleucine (I), asparagine (N), glutamine (Q), cysteine (C), aspartic acid (D), glutamic acid (E), lysine (K) and proline (P). Even more preferred misfolding rescuers and modulators of SOD1 aggregation are cyclic oligopeptide sequences exhibiting the cyclo-T(Φ₁,S)S(Φ₂,M,H)W motif, where Φ₁ is preferably one of the hydrophobic (Φ) amino acids A, W or F, while Φ₂ is preferably V, W or F. A small group of three cyclic pentapeptide rescuers with this general formula T(Φ₁,S)S(Φ₂,M,H)W are analyzed further.

In the present invention, isolated cyclic oligopeptides are also provided, which comprise the amino acid sequences set forth in SEQ ID NO:1, SEQ ID NO:2, SEQ ID NO:3, SEQ ID NO:4, up to SEQ ID NO:46. Nucleic acid sequences encoding a polypeptide of the invention are also provided. Vectors containing such nucleic acids, and cells containing such vectors, are also provided.

Another object of the present invention is to provide sufficient evidence that the selected peptide macrocycles are successful in inhibiting the misfolding and aggregation of SOD1. More particularly the inventors have studied the SOD1(A4V), a fALS-associated variant, whose misfolding and aggregation causes a very aggressive form of the disease with an average survival time of only 1.2 years after diagnosis. Indeed the effects of three selected oligopeptide macrocycles in inhibiting the misfolding and aggregation of SOD1 are shown using appropriate biochemical and/or biophysical assays.

Another object of the present invention is to provide sufficient evidence that the selected peptide macrocycles are successful in inhibiting the aggregation of SOD1* and the neurotoxicity caused by SOD1* aggregation in vitro. Indeed the effects of one selected pentapeptide macrocycle in inhibiting the aggregation and toxicity of SOD1(A4V) are shown in cultured mammalian cells.

Another objective of the present invention is to provide hybrid polypeptides that comprise a peptide motif that specifically interacts with the target polypeptide, which is then inserted into an appropriate protein scaffold. The polypeptide motif is inserted into the scaffold such that any desired function of the scaffold is retained and the inserted motif as presented retains its ability to specifically bind to the target and/or modulate the natural aggregation process of the target polypeptide. The scaffold can include, for example, neuroprotective agents to make SOD1 aggregates less toxic, aggregate-destroying molecules to eliminate amyloid SOD1 species, reagents that prevent SOD1 aggregate formation, or reagents useful for specifically imaging SOD1 aggregates in brain tissue.

It is also an object of the present invention to provide an integrated bacterial platform for the discovery of chemical/biological modulators of the problematic folding and aggregation of SOD1. In this system, large combinatorial libraries of genetically encoded macrocycles are biosynthesized in $E.$ $coli$ cells and are simultaneously screened for their ability to modulate the problematic folding and aggregation of SOD1 using a high-throughput genetic screen, which is based on the detection of enhanced fluorescence of chimeric SOD1-GFP fusions.

It is an object of the present invention to provide short, drug-like peptide macrocycles with the ability to rescue the misfolding, aggregation and associated pathogenic effects of a second prominent aggregation-prone and disease-associated protein target. Particularly, the object of the present invention is to identify cyclic oligopeptides that rescue the misfolding and modulate the natural aggregation process of the β-amyloid peptide, which is implicated in pathogenicity of Alzheimer's disease. Various tetra-, penta- and hexapeptides with these properties are described in the present invention. More particularly the inventors have identified the general formula cyclo-NuX$_1$X$_2$ . . . X$_N$, wherein Nu=C, S, or T; X is any of the twenty natural amino acid and N=3-5 as a very rich source of chemical rescuers of Aβ misfolding and modulators of its aggregation.

Another aspect of the present invention is the identification of pentapeptide macrocycles with the general formula cyclo-TXXXR, wherein the first amino acid is Threonine, the last amino acid is Arginine and X is any amino acid, as effective and preferred modulators of the natural process of Aβ aggregation. More preferred modulators of Aβ aggregation are cyclic oligopeptide sequences exhibiting the cyclo-TΦZΠR motif, where Φ=any amino acid excluding phenylalanine (F), tryptophan (W), tyrosine (Y), glutamine (Q), aspartic acid (D), glutamic acid (E), lysine (K) and proline (P); Z is any amino acid excluding E; and Π is any natural amino acid excluding Q, methionine (M) and lysine (K). Even more preferred are cyclic oligopeptide sequences exhibiting the cyclo-T(T,A,V)Ψ(A,D,W)R motif, where Ψ is a non-negatively charged amino acid. A small group of six cyclic pentapeptide rescuers with this general formula cyclo-TXXXR are analyzed further.

Another aspect of the present invention is the identification of tetrapeptide macrocycles with the general formula cyclo-TXXR, wherein the first amino acid is Threonine, the last amino acid is Arginine and X is any amino acid, as effective and preferred modulators of the natural process of Aβ aggregation. More preferred modulators of Aβ aggregation are cyclic oligopeptide sequences exhibiting the cyclo-TΘAR motif, where Θ=T, R, D, L, F or A, and Λ=C, R, S, G, Q, I, W, D, or F. A small group of two cyclic tetrapeptide rescuers with this general formula cyclo-TXXR are analyzed further.

Another aspect of the present invention is the identification of hexapeptide macrocycles as effective and preferred modulators of the natural process of Aβ aggregation. Preferred modulators of Aβ aggregation are cyclic oligopeptide sequences exhibiting the cyclo-NuX$_1$X$_2$X$_3$X$_4$X$_5$ motif for the use in rescuing Aβ misfolding and modulating aggregation, wherein Nu is T; wherein X$_1$ is any amino acid selected from I, L, V, C, S, K or P, and is more preferably P, V or L; wherein X$_2$ is selected from A, I, L, V, F, W, C, S, T, D, E, H, K, P, or G and is more preferably V or A; wherein X$_3$ is selected from I, L, V, F, W, Y, E or R, and is more preferably W; wherein X$_4$ is selected from L, V, F, Y, S or R and is more preferably F; wherein X$_5$ is selected from W, M, N, D or E and is more preferably D. The cyclic hexapeptide comprising the sequence TPVWFD is analyzed further.

In the present invention, isolated cyclic oligopeptides are also provided, which comprise the amino acid sequences set forth in SEQ ID NO:47, SEQ ID NO:48, SEQ ID NO:49, SEQ ID NO:50, up to SEQ ID NO:205. The inventors also identified the pentapeptide macrocycles cyclo-SASPT (SEQ ID NO:206), cyclo-SHSPT (SEQ ID NO:207), cyclo-SICPT (SEQ ID NO:208) and cyclo-SITPT (SEQ ID NO:209) as effective and preferred modulators of the natural process of Aβ aggregation. Furthermore the inventors also identified the tetrapeptide macrocycles cyclo-TTCR (SEQ ID NO:210), cyclo-TTRR (SEQ ID NO:211), cyclo-TTSR (SEQ ID NO:212), cyclo-TTGR (SEQ ID NO:213), cyclo-TRGR (SEQ ID NO:214), cyclo-TRRR (SEQ ID NO:215), cyclo-TDQR (SEQ ID NO:216), cyclo-TLIR (SEQ ID NO:217), cyclo-TLWR (SEQ ID NO:218), cyclo-TLGR (SEQ ID NO:219), cyclo-TFDR (SEQ ID NO:220), and cyclo-TAFR (SEQ ID NO:221) as effective and preferred modulators of the natural process of Aβ aggregation. Finally, the inventors also identified the hexapeptide macrocycles comprising the amino acid sequences set forth in SEQ ID NO:222, SEQ ID NO:223, . . . , up to SEQ ID NO:255 as effective and preferred modulators of the natural process of Aβ aggregation. Nucleic acid sequences encoding a polypeptide of the invention are also provided. Vectors containing such nucleic acids, and cells containing such vectors, are also provided.

Another object of the present invention is to provide sufficient evidence that the selected peptide macrocycles are successful in modulating Aβ aggregation. Indeed the effects of ten selected oligopeptide macrocycles in modulating Aβ aggregation are shown using appropriate biochemical and/or biophysical assays.

Another object of the present invention is to provide sufficient evidence that the selected peptide macrocycles are successful in inhibiting the neurotoxicity caused by Aβ aggregation in vitro. Indeed the effects of two selected pentapeptide macrocycles in inhibiting neurotoxicity of Aβ aggregation are shown in cultured primary hippocampal neurons.

A main objective of the present invention is to show the successful in vivo rescuing of the misfolding and aggregation of β-amyloid peptide by the selected macrocycles produced by the technique described in the present invention. The protective effects of the selected cyclic peptides against Aβ aggregation and toxicity in vivo are demonstrated in established AD animal models in the nematode *Caenorhabditis elegans* (*C. elegans*).

Another objective of the present invention is to provide hybrid polypeptides that comprise a peptide motif that specifically interacts with the target polypeptide, which is then inserted into an appropriate protein scaffold. The polypeptide motif is inserted into the scaffold such that any desired function of the scaffold is retained and the inserted motif as presented retains its ability to specifically bind to the target and/or modulate the natural aggregation process of the target polypeptide. The scaffold can include, for example, neuroprotective agents to make amyloid plaques less toxic, amyloid destroying molecules to eliminate plaques, reagents that prevent amyloid plaque formation, or reagents useful for specifically imaging amyloid plaques in brain tissue.

It is also an object of the present invention to provide an integrated bacterial platform for the discovery of chemical/biological modulators of the problematic folding and aggregation of Aβ. In this system, large combinatorial libraries of genetically encoded macrocycles are biosynthesized in *E. coli* cells and are simultaneously screened for their ability to modulate the problematic folding and aggregation of Aβ using a high-throughput genetic screen, which is based on the detection of enhanced fluorescence of chimeric Aβ-GFP fusions.

It is also an object of the present invention to provide a generalizable integrated bacterial platform for the discovery of chemical/biological modulators of the problematic folding and aggregation of disease-associated, misfolding-prone proteins (MisPs). In this system, large combinatorial libraries of genetically encoded macrocycles are biosynthesized in *E. coli* cells and are simultaneously screened for their ability to modulate the problematic folding and aggregation of the target MisP using a high-throughput genetic screen, which is based on the detection of enhanced fluorescence of chimeric MisP-GFP fusions.

In some embodiments, the present disclosure provides a method of identifying modulators of a misfolding-prone protein associated with a protein misfolding disease, comprising: (A) obtaining a population of transformed bacterial cells that co-express: (a) a nucleic acid encoding a library of peptide macrocycles, operably linked to a promoter and (b) a bipartite nucleic acid comprising a sequence for a gene encoding a misfolding-prone protein associated with a protein misfolding disease (MisP) and a sequence encoding a protein reporter; (B) identifying bacterial cells of step (A) that exhibit enhanced levels of protein reporter activity; and (C) identifying the bioactive peptide macrocycles in the library that modulate MisP misfolding. In some aspects, the protein reporter is a fluorescent protein (FP) reporter, and step (B) comprises identifying bacterial cells that exhibit enhanced levels of MisP-FP fluorescence. In some aspects, the protein reporter is an enzyme. In some aspects, the identification in step (B) comprises selection. In some aspects, step (C) comprises sequencing the nucleic acid of step (Aa). In certain aspects, the nucleic acids of (a) and (b) are encoded on the same vector. In particular aspects, the vector is a plasmid.

In aspects of the embodiments, said MisP is selected from β-amyloid peptide, SOD1, tau, α-synuclein, polyglutaminated huntingtin, polyglutaminated ataxin-1, polyglutaminated ataxin-2, polyglutaminated ataxin-3, prion protein, islet amyloid polypeptide (amylin), β2-microglbulin, fragments of immunoglobulin light chain, fragments of immunoglobulin heavy chain, serum amyloid A, ABri peptide, ADan peptide, transthyretin, apolipoprotein A1, gelsolin, transthyretin, lysozyme, phenylalanine hydroxylase, apolipoprotein A-I, calcitonin, prolactin, TDP-43, FUS/TLS; insulin, hemoglobin, α1-antitrypsin, p53, or variants thereof. In some aspects, said peptide macrocycle can be a ribosomally synthesized as a head-to-tail cyclic peptide, side-chain-to-tail cyclic peptide, bicyclic peptide, lanthipeptide, linaridin, proteusin, cyanobactin, thiopeptide, bottromycin, microcin, lasso peptide, microviridin, amatoxin, phallotoxin, θ-defensin, orbitide, or cyclotide. In some aspects, the disease is selected from amyotrophic lateral sclerosis, Alzheimer's disease, amyotrophic lateral sclerosis, Parkinson's disease, Huntington's disease, Creutzfeldt-Jakob disease, cancer, phenylketonuria, type 2 diabetes, senile systemic amyloidosis, familial amyloidotic polyneuropathy, familial amyloid cardiomyopathy, leptomeningeal amyloidosis, systemic amyloidosis, familial British dementia, familial Danish dementia, light chain amyloidosis, heavy chain amyloidosis, serum amyloid A amyloidosis, lysozyme amyloidosis, dialysis-related amyloidosis, ApoAI amyloidosis, Finnish type familial amyloidosis, hereditary cerebral hemorrhage with amyloidosis (Icelandic type), medullary carcinoma of the thyroid, pituitary prolactinoma, injection-localized amyloidosis, frontotemporal dementia, spinocerebellar ataxia 1, spinocerebellar ataxia 2, spinocerebellar ataxia 3, α1-antitrypsin deficiency, sickle-cell anemia, or transmissible spongiform encephalopathy. In further aspects, the method comprises recombinantly producing or chemically synthesizing the identified bioactive peptide macrocycle.

In some aspects, there is provided a method of treatment, prevention or diagnosis of a protein misfolding disease comprising administering to a subject a therapeutically effective amount of the bioactive peptide macrocycle identified by the embodiments and aspects of the invention provided herein. In another aspect, there is provided a pharmaceutical composition comprising the bioactive peptide macrocycle according to the embodiments or aspects of the invention provided herein, and a pharmaceutically acceptable carrier. In some aspects, the pharmaceutical composition may be used for the treatment or prevention of a protein misfolding disease.

In some aspects, there is provided a hybrid molecule comprising: a) a peptide macrocycle identified or produced according to the method of any of the embodiments or aspects of the invention provided herein, and b) a scaffold molecule linked to the peptide macrocycle. In some aspects, the scaffold molecule is a diagnostic or a therapeutic reagent. In particular aspects, the therapeutic reagent is a cytoprotective agent that renders the aggregates of the target protein less toxic or inhibits target protein aggregate formation. In some aspects, the scaffold molecule comprises all or a sufficient portion of a protein selected from the group consisting of antibodies, enzymes, chromogenic proteins, and fluorescent proteins. In specific aspects, the diagnostic reagent specifically targets protein aggregates in diseased or healthy tissue.

In some aspects, there is provided a method of treating or diagnosing a protein misfolding disease associated with aberrant aggregate formation, the method comprising administering a hybrid molecule according to the embodiments and aspects provided herein, wherein the peptide macrocycle of the hybrid molecule specifically interacts with the amyloid or non-amyloid form of the target MisP.

In some embodiments, there is provided a peptide comprising the amino acid sequence $NuX_1X_2 \ldots X_N$, wherein: Nu is T; N=4; $X_1$ is any amino acid excluding I, N, Q, M, E, H, and K; $X_2$=S; $X_3$ is any amino acid excluding I, N, Q, C, D, E, K and P; and $X_4$=W, wherein the specifically interacts with the amyloid or non-amyloid form of SOD1 and/or mutant SOD1.

In some aspects, the $X_1$ is A, L, V, F, W, Y, C, S, T, D, R, P or G. In particular aspects, the $X_1$ is is S, A, F or W. In some aspects, the $X_3$ is A, L, V, F, W, Y, M, S, T, R, H or G. In certain aspects, the $X_3$ is V, F, W, M, or H. In specific aspects, the $X_3$ is W. In some aspects, Nu is T; N=4; $X_1$ is A, L, V, F, W, Y, C, S, T, D, R, P or G; $X_2$=S; $X_3$ is A, L, V, F, W, Y, M, S, T, R, H or G; and $X_4$=W. In particular aspects, Nu is T; N=4; $X_1$ is S, A, F or W; $X_2$=S; $X_3$ is V, F, W, M, or H; and $X_4$=W.

In some embodiments, there is provided a peptide comprising the amino acid sequence set forth in any one of SEQ ID NO:1-46, wherein the peptide prevents misfolding and aggregation of SOD1 and/or mutant SOD1. In some aspects, the peptide comprises an amino acid sequence selected from TWSVW (SEQ ID NO: 4), TASFW (SEQ ID NO: 2), and TFSMW (SEQ ID NO: 6). In some aspects, said peptide prevents misfolding and aggregation of SOD1 and/or mutant SOD1. In some aspects, at least one position of the peptide is a D amino acid. In certain aspects, the peptide is a cyclic peptide. In other aspects, the peptide is a linear peptide.

In some aspects, there is provided a hybrid molecule comprising: a) a peptide set forth in the embodiments and aspects provided herein, and b) a scaffold molecule. In some aspects, the scaffolding molecule comprises a cell penetrating peptide. In specific aspects, the scaffold molecule comprises a diagnostic or therapeutic reagent. In certain aspects, the scaffold molecule comprises a polypeptide, small molecule or compound. In some aspects, the scaffold molecule comprises all or a sufficient portion of a protein selected from the group consisting of antibodies, enzymes, chromogenic proteins, fluorescent proteins and fragments thereof. In some aspects, the therapeutic agent is a neuroprotective agent that renders SOD1 aggregates less toxic or inhibits SOD1 aggregate formation. In some aspects, the diagnostic reagent specifically images SOD1 aggregates in neuronal tissue.

In some aspects of the embodiments provided herein, there is provided a peptide or a molecule to inhibit protein misfolding and aggregation wherein the peptide prevents misfolding and aggregation of SOD1 and/or mutant SOD1. In particular, there is provided a method of treatment, prevention or diagnosis of amyotrophic lateral sclerosis comprising administering to a subject a therapeutically effective amount of a peptide or hybrid molecule according to any one of the embodiments or aspects provided herein.

In some aspects, there is provided a pharmaceutical composition comprising a peptide or hybrid molecule according to any of the aspects or embodiments provided herein, and a pharmaceutically acceptable carrier. In some aspects, the pharmaceutical composition is used for the treatment or prevention of amyotrophic lateral sclerosis. In some aspects, there is provided an isolated nucleic acid sequence encoding the peptide of the aspects or embodiments provided herein. In some aspects, there is a vector comprising said nucleic acid sequence. In some aspects, the vector is an expression vector. In certain aspects, there is provided a host cell comprising said vector. In certain aspects, the host cell is a prokaryotic or eukaryotic cell.

In some embodiments, there is provided a peptide wherein the peptide comprises the amino acid sequence $NuX_1X_2 \ldots X_N$, wherein: (A) Nu=T; N=3; $X_1$ is selected from T, R, D, L, F or A; $X_2$ is selected from C, R, S, G, Q, I, W, D, or F; and $X_3$=R; (B) Nu=T; N=4; $X_1$ is any amino acid excluding F, W, Y, Q, D, E, K and P; $X_2$ is any amino acid excluding E; $X_3$ is any amino acid excluding Q, M and K; and $X_4$ is R; or (C) Nu=T; N=5; $X_1$ is I, L, V, C, S, K or P; $X_2$ is any amino acid excluding Y, N, Q, M, and R; $X_3$ is selected from I, L, V, F, W, Y, E, or R; $X_4$ is selected from L, V, F, Y, S or R; and $X_5$ is selected from W, M, N, D, or E, wherein the peptide specifically interacts with a monomeric, oligomeric and/or amyloid form of the Aβ peptide. In some aspects, Nu=T; N=3; $X_1$ is selected from T, R, D, L, F or A; $X_2$ is selected from C, R, S, G, Q, I, W, D, or F; and $X_3$=R. In certain aspects, Nu=T; N=4; $X_1$ is any amino acid excluding F, W, Y, Q, D, E, K and P; $X_2$ is any amino acid excluding E; $X_3$ is any amino acid excluding Q, M and K; and $X_4$ is R. In specific aspects, $X_1$ is selected from A, I, L, V, N, C, M, S, T, R, H, or G. In particular aspects, $X_1$ is T, V or A. In some aspects, $X_2$ is selected from A, I, L, V, F, W, Y, N, Q, C, M, S, T, D, R, H, K, P or G. In certain aspects, $X_2$ is I, L, V, F, Y or T. In specific aspects, $X_3$ is A, I, L, V, F, W, Y, N, C, S, T, D, E, R, H, P or G. In particular aspects, $X_3$ is A, W, or D. In some aspects, Nu=T; N=4; $X_1$ is selected from A, I, L, V, N, C, M, S, T, R, H, or G; $X_2$ is selected from A, I, L, V, F, W, Y, N, Q, C, M, S, T, D, R, H, K, P or G; $X_3$ is A, I, L, V, F, W, Y, N, C, S, T, D, E, R, H, P or G; and $X_4$ is R. In certain aspects, Nu=T; N=4; $X_1$ is T, V or A; $X_2$ is I, L, V, F, Y or T; $X_3$ is A, W, or D; and $X_4$ is R. In specific aspects, Nu=T; N=5; $X_1$ is I, L, V, C, S, K or P; $X_2$ is any amino acid excluding Y, N, Q, M, and R; $X_3$ is selected from I, L, V, F, W, Y, E, or R; $X_4$ is selected from L, V, F, Y, S or R; and $X_5$ is selected from W, M, N, D, or E. In particular aspects, $X_1$ is selected from I, L, V, C, S, K or P. In specific aspects, the $X_1$ is P, V or L. In some aspects, $X_2$ is selected from A, I, L, V, F, W, C, S, T, D, E, H, K, P, or G. In certain aspects, $X_2$ is V or A. In some aspects, $X_3$ is selected from I, L, V, F, W, Y, E or R. In specific aspects, $X_3$ is W. In some aspects, $X_4$ is selected from L, V, F, Y, S or R. In specific aspects, $X_4$ is F. In some aspects, $X_5$ is selected from W, M, N, D, or E. In specific aspects, $X_5$ is D. In some aspects, Nu=T; N=5; $X_1$ is P, V or L; $X_2$ is V or A; $X_3$ is selected from I, F, or W; $X_4$ is selected from L, F, or R; and $X_5$ is selected from W, N, or D. In certain aspects, Nu=T; N=5; $X_1$ is P, V or L; $X_2$ is V or A; $X_3$ is W; $X_4$ is F; and $X_5$ is D. In some aspects, the peptide comprises the sequence TTCR, TTRR, TTSR, TRGR, TTGR, TRRR, TDQR, TLIR, TLWR, TLGR, TFDR, or TAFR (SEQ ID NOs 210-221).

In some embodiments, there is provided a peptide comprising the amino acid sequence set forth in any one of SEQ ID NO:47-209, wherein, the peptide is cyclic and specifically interacts with a monomeric, oligomeric and/or amyloid form of the Aβ peptide. In some aspects, the peptide comprises an amino acid sequence selected from TAFDR (SEQ ID NO: 86), TAWCR (SEQ ID NO: 63), TTWCR (SEQ ID NO: 60), TTVDR (SEQ ID NO: 48), TTYAR (SEQ ID NO: 47), TTTAR (SEQ ID NO: 56) or SASPT (SEQ ID NO: 206). In some aspects, the the peptide comprises an amino acid sequence selected from the amino acid sequences set forth in SEQ ID NO:176-209. In some aspects, the peptide comprises an amino acid sequence of TPVWFD (SEQ ID NO:176) or TPAWFD (SEQ ID NO:177). In some aspects, at least one position of the peptide is a D amino acid. In some aspects, the peptide is a cyclic peptide. In other aspects, the peptide is a linear peptide.

In some aspects, there is provided a hybrid molecule comprising: a) a peptide set forth in any one of the embodiments or aspects, that specifically interacts with a monomeric, oligomeric and/or amyloid form of the Aβ peptide; and b) a scaffold molecule. In some aspects, the scaffolding molecule comprises a cell penetrating peptide. In certain aspects, the scaffold molecule comprises a diagnostic or therapeutic reagent. In particular aspects, the scaffold molecule comprises a polypeptide, small molecule or compound. In specific aspects, the polypeptide comprises all or a sufficient portion of a protein selected from the group consisting of antibodies, enzymes, chromogenic proteins, or a fluorescent protein. In some aspects, the therapeutic agent is a neuroprotective agent that renders amyloid plaques less toxic or inhibits plaque formation. In some aspects, the diagnostic reagent specifically images oligomers and/or amyloid aggregates in neuronal tissue.

In some aspects of the invention, there is provided methods for the use of a peptide or molecule according to any of the embodiments or aspects provided herein, to inhibit protein misfolding and aggregation. In some aspects, said peptide prevents misfolding and aggregation of the β-amyloid peptide.

In some embodiments, there is provided a method of treatment, prevention or diagnosis of a disease related to protein misfolding and aggregation, comprising administering to a subject a therapeutically effective amount of a peptide or molecule according to any of the embodiments or aspects provided herein, wherein the disease is selected from Alzheimer's disease, Parkinson's disease, Huntington's disease, amyotrophic lateral sclerosis, Creutzfeldt-Jakob disease, type 2 diabetes, familial amyloidotic polyneuropathy, systemic amyloidosis, and transmissible spongiform encephalopathy. In some aspects, there is provided a method of treatment, prevention or diagnosis of Alzheimer's disease comprising administering to a subject a therapeutically effective amount of a peptide according to any one of the aspects or embodiments provided herein. In some aspects, there is provided a pharmaceutical composition comprising a peptide according to any one of the aspects or embodiments provided herein and a pharmaceutically acceptable carrier. In some aspects, there is provided a nucleic acid encoding any of said peptides. In some aspects, there is a provided a vector comprising said nucleic acid. In some aspects, the vector is an expression vector. In some aspects, there is provided a host cell comprising said vector. In some cases, the host cell is a prokaryotic or eukaryotic cell.

Other objects and advantages of the present invention will become apparent to those skilled in the art in view of the following detailed description.

DETAILED DESCRIPTION OF THE INVENTION

I. General

It is now well established that fALS-linked amino acid substitutions in SOD1 introduce a toxic-gain-of-function property in SOD1 by causing protein misfolding and aggregation, and the formation of oligomeric/aggregated SOD1 species, which are highly toxic for motor neurons. Gradual accumulation of such toxic oligomers/aggregates of mutated SOD1 initiates motor neuron degeneration and the development of fALS. Also, the accumulation of misfolded and aggregated wild-type SOD1 has been implicated in sporadic forms of ALS. This invention pertains to compounds, and pharmaceutical compositions thereof, that can modulate the aggregation of amyloidogenic proteins and peptides, in particular compounds that can rescue the misfolding and inhibit the aggregation of SOD1 or of its fALS-associated variants and inhibit the neurotoxicity of these aggregated SOD1 species. A compound of the invention that modulates aggregation of SOD1, referred to herein interchangeably as a SOD1 modulator compound, a SOD1 modulator or simply a modulator, alters the aggregation of SOD1 or of its fALS-associated variants when the modulator is contacted with SOD1 or of its fALS-associated variants. Thus, a compound of the invention acts to alter the natural aggregation process or rate of SOD1 or of its fALS-associated variants, thereby disrupting the normal course this process. A modulator which inhibits SOD1 and/or mutant SOD1 aggregation (an "inhibitory modulator compound") can be used to prevent or delay the onset of the deposition of SOD1 and/or mutant SOD1 aggregates. Moreover, inhibitory modulator compounds of the invention inhibit the formation and/or activity of neurotoxic aggregates of SOD1 or of its fALS-associated variants (i.e., the inhibitory compounds can be used to inhibit the neurotoxicity of SOD1 or of its fALS-associated variants).

Alternatively, in another embodiment, a modulator compound of the invention promotes the aggregation of SOD1 and/or mutant SOD1. The various forms of the term "promotion" refer to an increase in the amount and/or rate of SOD1 and/or mutant SOD1 aggregation in the presence of the modulator, as compared to the amount and/or rate of SOD1 and/or mutant SOD1 aggregation in the absence of the modulator. Such a compound which promotes SOD1 and/or mutant SOD1 aggregation is referred to as a stimulatory modulator compound. Stimulatory modulator compounds may be useful, for example, in decreasing the amounts of neurotoxic SOD1 and/or mutant SOD1 oligomeric species by driving the natural SOD1 aggregation process towards the (possibly) less neurotoxic higher-order SOD1 and/or mutant SOD1 aggregates.

Compounds of the present invention may inhibit SOD1 and/or mutant SOD1 aggregation and/or oligomerization. In particular, preferred modulator compounds of the invention comprise cyclic oligopeptides with the general formula cyclo-$NuX_1X_2 \ldots X_N$, where X is any one of the twenty natural amino acids, $N=3\text{-}5$ and $Nu=$cysteine (Cys or C), serine (Ser or S) or threonine (Thr or T), which is sufficient to alter (and preferably inhibit) the natural aggregation process or rate of SOD1 and/or mutant SOD1. This SOD1 and/or mutant SOD1 modulator can comprise as few as four amino acid residues (or derivative, analogues or mimetics thereof).

According to the prevalent amyloid cascade hypothesis, the high tendency of Aβ for misfolding and aggregation results in the formation of neurotoxic Aβ oligomers/aggregates, whose accumulation ultimately leads to neuron degeneration and the development of the disease. This invention pertains to compounds, and pharmaceutical compositions thereof, that can modulate the aggregation of amyloidogenic proteins and peptides, in particular compounds that can modulate the aggregation of the β-amyloid peptide (Aβ) and inhibit the neurotoxicity of Aβ. A compound of the invention that modulates aggregation of Aβ, referred to herein interchangeably as a Aβ modulator compound, a Aβ modulator or simply a modulator, alters the aggregation of natural Aβ when the modulator is contacted with natural Aβ. Thus, a compound of the invention acts to alter the natural aggregation process or rate of Aβ, thereby disrupting the normal course this process. A modulator which inhibits Aβ aggregation (an "inhibitory modulator compound") can be used to prevent or delay the onset of β-amyloid deposition. Moreover, inhibitory modulator compounds of the invention inhibit the formation and/or activity of neurotoxic aggregates of natural Aβ peptide (i.e., the inhibitory compounds can be used to inhibit the neurotoxicity of Aβ.

Alternatively, in another embodiment, a modulator compound of the invention promotes the aggregation of natural Aβ peptides. The various forms of the term "promotion" refer to an increase in the amount and/or rate of Aβ aggregation in the presence of the modulator, as compared to the amount and/or rate of Aβ aggregation in the absence of the modulator. Such a compound which promotes Aβ aggregation is referred to as a stimulatory modulator compound. Stimulatory modulator compounds may be useful, for example, in decreasing the amounts of neurotoxic Aβ oligomeric species by driving the natural Aβ aggregation process towards the (generally) less neurotoxic higher-order Aβ aggregates.

Compounds of the present invention may inhibit Aβ aggregation and/or oligomerization. In particular, preferred modulator compounds of the invention comprise cyclic oligopeptides with the general formula cyclo-NuX$_1$X$_2$ . . . X$_N$, where X is any one of the twenty natural amino acids, N=3-5 and Nu=cysteine (Cys or C), serine (Ser or S) or threonine (Thr or T), which is sufficient to alter (and preferably inhibit) the natural aggregation process or rate Aβ. This Aβ modulator can comprise as few as four amino acid residues (or derivative, analogues or mimetics thereof).

II. Discovery of Peptide SOD1 and Aβ Modulators

The present application describes the invention of a generalizable bacterial platform for the discovery of macrocyclic peptide rescuers of the misfolding of disease-associated, misfolding-prone proteins (MisPs). The inventors demonstrate the generalizability of this integrated bacterial platform by discovering macrocyclic peptides that modulate the problematic folding and aggregation of SOD1, mutant SOD1, or Aβ.

This approach offers a number of important advantages. First, it allows the screening of molecular libraries with expanded diversities. Here, a library with diversity>10 million different macrocycles has been investigated.

In another embodiment, the present invention can be applied to construct and screen macrocyclic libraries with diversities up to $10^{10}$ different molecules. Importantly, E. coli can support the in vivo biosynthesis not only of head-to-tail cyclic peptides like the ones investigated here, but also of other macrocyclic structures, such as side-chain-to-tail cyclic peptides, bicyclic peptides, cyclotides, macrolides and other macrocyclic structures, which can accommodate not only naturally occurring amino acids, but a large variety of artificial ones as well.

In addition, the analysis of these large libraries is carried out using a very high-throughput genetic screen, which enables the identification of bioactive molecules simply by isolating compounds that enhance the fluorescence of E. coli cells expressing MisP-GFP, such as SOD1*-GFP or Aβ-GFP fusions, by flow cytometric sorting (FACS). Compared to affinity-based approaches for screening DNA-encoded chemical libraries, such as phage and mRNA display, the herein described approach does not detect mere target MisP, such as SOD1* or Aβ, binding, but selects directly the bioactive compounds with the ability to rescue MisP, such as SOD1* or Aβ, misfolding, without requiring the availability of purified MisP, such as SOD1* or Aβ.

Moreover, synthesis of the studied compounds and their screening for bioactivity are carried out in vivo as part of a single-step process, without the need for laborious organic synthesis and product isolation steps. Importantly, screening for bioactivity is carried out in a fully unbiased manner without requiring a priori knowledge of the structures of the MisP, such as SOD1* or Aβ, monomers, oligomers, or higher-order aggregates, specific assumptions about possible binding sites, or prior preparation of specific MisP, such as SOD1* or Aβ, oligomerization states.

More particularly, combinatorial libraries of random cyclic tetra-, penta-, and hexapeptides have been created and the most prominent targets have been selected to study as potential rescuers of SOD1 and Aβ misfolding. The technology described in the present invention utilizes a technique termed split intein circular ligation of peptides and proteins (SICLOPPS) for producing peptide libraries in E. coli. SICLOPPS uses split inteins, i.e. self-splicing protein elements for performing N- to C-terminal peptide cyclization and biosynthesize cyclic peptides as short as four amino acids long. The only requirement for the intein splicing reaction and peptide cyclization to occur is the presence of a nucleophilic amino acids cysteine (C), serine (S), or threonine (T) as the first amino acid of the extein following the C-terminus of the intein.

According to the present invention, peptides belonging to the general formula NuX$_1$X$_2$ . . . X$_N$, can be used for rescuing protein misfolding and modulating protein aggregation; wherein X is any one of the twenty natural amino acids, N=3-5 and Nu is selected from cysteine (Cys or C), serine (Ser or S) or threonine (Thr or T). According to the preferred embodiment of the present invention the peptide is a cyclic peptide. According to the preferred embodiment of the present invention Nu is T.

In a preferred embodiment of the present invention the peptide with the general formula cyclo-NuX$_1$ X$_2$ . . . X$_N$, for the use in protein misfolding and aggregation, has the following specifications wherein N is 3, wherein Nu is T; wherein X$_1$ is selected from T, R, D, L, F or A, wherein X$_2$ is selected form C, R, S, G, Q, I, W, D, or F; wherein X$_3$ is R. According to the above specification the preferred cyclic tetrapeptide is selected from cyclo-TTCR (SEQ ID NO:164), cyclo-TTRR (SEQ ID NO:165), cyclo-TTSR (SEQ ID NO:166), cyclo-TTGR (SEQ ID NO:167), cyclo-TRGR (SEQ ID NO:168), cyclo-TRRR (SEQ ID NO:169), cyclo-TDQR (SEQ ID NO:167), cyclo-TLIR (SEQ ID NO:171), cyclo-TLWR (SEQ ID NO:172), cyclo-TLGR (SEQ ID NO: 173), cyclo-TFDR (SEQ ID NO:174), and cyclo-TAFR (SEQ ID NO:175) as effective and preferred modulators of the natural process of Aβ aggregation.

In another preferred embodiment of the present invention the peptide with the general formula NuX$_1$X$_2$ . . . X$_N$, for the use in rescuing protein misfolding and modulating, has the following specifications wherein N is 4, wherein Nu is preferably T; wherein X$_1$ is any amino acid excluding I, N, Q, M, E, H, and K, and more preferably it is S, A, W, or F; wherein X$_2$ is preferably S; wherein X$_3$ is any amino acid excluding I, N, Q, C, D, E, K and P, and is more preferably selected from V, W, F, M, or H; wherein X$_4$ is preferably W. According to the above specification the preferred pentapeptide is selected from the amino acid sequences set forth in SEQ ID NO:1, SEQ ID NO:2, SEQ ID NO:3, SEQ ID NO:4, . . . , up to SEQ ID NO:46. According to the above specification the more preferred pentapeptide is selected from cyclo-TASFW (SEQ ID NO:2), cyclo-TWSVW (SEQ ID NO:4), and cyclo-TFSMW (SEQ ID NO:6).

In another preferred embodiment of the present invention the peptide with the general formula NuX$_1$X$_2$ . . . X$_N$, for the use in rescuing protein misfolding and modulating aggregation, has the following specifications wherein N is 4, wherein Nu is T or S; wherein X$_1$ is any amino acid excluding F, W, Y, Q, D, E, K and P, preferably it is S, H, T, V or A, and more preferably it is T, V or A; wherein $X_2$ is any amino acid excluding E, preferably a non-negatively charged amino acid, and more preferably it is selected from I, L, V, F, W, Y, M, S, T, R, H, or G; wherein $X_3$ is any amino acid excluding Q, M and K, and is more preferably selected from A, V, F, W, C, S, T, D, C, R, H, P or G; wherein $X_4$ is preferably R or T. According to the above specification the preferred pentapeptide is selected from the amino acid sequences set forth in SEQ ID NO:47, SEQ ID NO:48, SEQ ID NO:49, SEQ ID NO:50, . . . , up to SEQ ID NO: 205. According to the above specification the more preferred pentapeptide is selected from cyclo-TAFDR (SEQ ID NO:86), cyclo-TAWCR (SEQ ID NO:63), cyclo-TTWCR (SEQ ID NO:60), cyclo-TTVDR (SEQ ID NO:48), cyclo-TTYAR (SEQ ID NO:47), cyclo-TTTAR (SEQ ID NO:56), and cyclo-SASPT (SEQ ID NO:206).

In another preferred embodiment of the present invention the peptide with the general formula $NuX_1X_2 \ldots X_N$, for the use in rescuing protein misfolding and modulating aggregation, has the following specifications wherein N is 5, wherein Nu is T; wherein $X_1$ is any amino acid selected from I, L, V, C, S, K or P, and is more preferably P, V or L; wherein $X_2$ is selected from A, I, L, V, F, W, C, S, T, D, E, H, K, P, or G and is more preferably V or A; wherein $X_3$ is selected from I, L, V, F, W, Y, E or R, and is more preferably W; wherein $X_4$ is selected from L, V, F, Y, S or R and is more preferably F; wherein X5 is selected from W, M, N, D or E and is more preferably D. The hexapeptide according to the above specifications is selected from the amino acid sequences set forth in SEQ ID NO:222, SEQ ID NO: 223, . . . , up to SEQ ID NO:255, and is most preferably TPVWFD (SEQ ID NO:222) or TPAWFD (SEQ ID NO:223).

The maximum theoretical diversity of the combined cyclo-$NuX_1X_2X_3$-$X_5$ library investigated here was >10 million different sequences. The libraries of genes encoding this combinatorial library of random cyclic oligopeptides were constructed using degenerate codons. The inventors constructed the high diversity pSICLOPPS-$NuX_1X_2X_3$-$X_5$ vector library which is expected to be encoding the vast majority of the theoretically possible designed cyclic tetra-, penta-, and hexapeptide cyclo-$NuX_1X_2X_3$-$X_5$ sequences using molecular biology techniques already known and used in the art.

The invention provided herein can be used as a method of treatment, prevention or diagnosis of all diseases related to protein misfolding and aggregation, including but not limited to amyotrophic lateral sclerosis (ALS), Alzheimer's disease, Parkinson's disease, Huntington's disease, Creutzfeldt-Jakob disease, type 2 diabetes, familial amyloidotic polyneuropathy, systemic amyloidosis, and transmissible spongiform encephalopathy comprising administering to a subject a therapeutically effective amount of a peptide. Preferably the invention presented herein can be used as a method of treatment, prevention or diagnosis of amyotrophic lateral sclerosis or Alzheimer's disease.

To identify cyclic oligopeptide sequences with the ability to interfere with the problematic folding of Aβ and modulate its oligomerization/aggregation, a bacterial high-throughput genetic screen was utilized. This system monitors Aβ misfolding and aggregation by measuring the fluorescence of E. coli cells overexpressing a chimeric fusion of the human Aβ42 with GFP. It has been demonstrated previously that due to the high aggregation propensity of Aβ, E. coli cells overexpressing Aβ-GFP fusions produce misfolded fusion protein that accumulates into insoluble inclusion bodies that lack fluorescence, despite the fact that they express these fusions at high levels. Mutations in the coding sequence of Aβ or the addition of compounds that inhibit Aβ aggregation, however, result in the formation of soluble and fluorescent Aβ-GFP, and bacterial cells expressing Aβ-GFP under these conditions acquire a fluorescent phenotype. The inventors of the present invention adapted this system to perform screening for aggregation-inhibitory macrocycles in a very high-throughput fashion by isolating cyclic oligopeptide-producing bacterial clones that exhibit enhanced levels of Aβ42-GFP fluorescence using fluorescence-activated cell sorting (FACS).

Herein, the inventors describe that the integrated bacterial platform for the discovery of macrocyclic rescuers that modulate the problematic folding and aggregation of Aβ as described in the present invention, is also generalizable, i.e., it can be more generally applied for the discovery of macrocyclic peptide rescuers of the misfolding of other disease-associated, misfolding-prone proteins (MisPs) as well. To demonstrate this generalizability, the inventors have used the same system to discover macrocyclic peptides that modulate the problematic folding and aggregation of SOD1 and/or mutant SOD1.

It has been demonstrated previously that the fluorescence of E. coli cells expressing a recombinant protein whose C terminus is fused to GFP correlates well with the amount of soluble and folded protein (Waldo G S, Standish B M, Berendzen J, Terwilliger T C. Nat Biotechnol. 1999 July; 17(7):691-5). Based on this, it was reasoned that the fluorescence of MisP-GFP fusions can serve as a reliable reporter for the identification of chemical rescuers of MisP misfolding for a number of disease-associated MisPs, including SOD1. In order to test this hypothesis, the inventors generated fusions of SOD1 variants, whose misfolding and aggregation have been linked with the pathology of familial forms of ALS (fALS), with GFP. Expression of these fusions in E. coli, yielded levels of cellular fluorescence, which were significantly decreased compared to that of the generally non-pathogenic, wild-type SOD1. Western blot analysis indicated that this occurs because the accumulation of soluble SOD1-GFP is decreased in the presence of misfolding-inducing amino acid substitutions, which in turn takes place due to enhanced misfolding/aggregation of fusion-free SOD1. Thus, as in the case of Aβ, the fluorescence of E. coli cells overexpressing SOD1-GFP fusions appears to be a good indicator of SOD1 folding and misfolding.

To identify rescuers of disease-associated SOD1 misfolding, the inventors screened for cyclic oligopeptides that inhibit the aggregation of SOD1(A4V), a fALS-associated variant, whose misfolding and aggregation causes a very aggressive form of the disease with an average survival time of only 1.2 years after diagnosis.

E. coli BL21(DE3) cells producing the combined cyclo-$NuX_1X_2X_3$-$X_5$ library, while simultaneously overexpressing the SOD1(A4V)-GFP reporter, were subjected to FACS sorting for the isolation of clones exhibiting enhanced SOD1(A4V)-GFP fluorescence. This selection yielded an E. coli population with ~10-fold increased fluorescence after four rounds of sorting. Among twenty individual clones tested, four exhibited the highest levels of SOD1(A4V)-GFP fluorescence compared to cells expressing the same SOD1 (A4V)-GFP fusion in the presence of random cyclic peptide sequences picked from the initial (unselected) cyclo-$NuX_1X_2X_3$-$X_5$ library and were selected for further analyses. Furthermore, the observed phenotypic effects were dependent on the ability of the Ssp DnaE intein (utilized for peptide cyclization as part of SICLOPPS) to perform protein splicing, as the double amino acid substitution H24L/F26A in the C-terminal half of the Ssp DnaE intein, which is known to abolish asparagine cyclization at the $I_C$/extein junction, and prevent extein splicing and peptide cyclization, was found to reduce SOD1(A4V)-GFP fluorescence back to wild-type levels. Finally, the observed increases in fluorescence were found to be SOD1-specific, as the isolated pSICLOPPS-NuX$_1$X$_2$X$_3$-X$_5$ vectors from these selected clones did not enhance the levels of cellular green fluorescence when the sequence of SOD1(A4V) in the SOD1 (A4V)-GFP reporter was replaced with that of the human β-amyloid peptide (Aβ). On the contrary, the selected pSI-CLOPPS-NuX$_1$X$_2$X$_3$-X$_5$ vectors were efficient in enhancing the fluorescence of SOD1-GFP containing wild-type SOD1, as well as three additional SOD1 variants, SOD1(G37R), SOD1(G85R), and SOD1(G93A), all of which are associated with familial forms of ALS. Western blot analysis indicated that this enhanced SOD1(A4V)-GFP fluorescence phenotype occurs due to accumulation of enhanced amounts of soluble SOD1(A4V) in these clones.

The inventors further analyzed the selected peptides by DNA sequencing of the peptide-encoding regions of the four selected clones. This revealed three distinct putative SOD1 (A4V) misfolding-rescuing and aggregation-inhibitory cyclic peptide sequences, all of which encoded cyclic pentapeptides with sequences TASFW (SEQ ID NO: 2), TWSVW (SEQ ID NO: 4), and TFSMW (SEQ ID NO: 6), thus indicating a dominant TXSXW bioactive motif. Interestingly, the Ser residue at position 3, encountered among all selected pentapeptides, was encoded by two different codons in the selected pSICLOPPS plasmids, thus suggesting that its dominance among the isolated clones was not coincidental.

As depicted in Examples 4 and 5, the inventors chose the peptide cyclo-TWSVW (SEQ ID NO: 4) for further analysis. This cyclic pentapeptide is hereafter referred to as SOD1C5-4 and was produced in mg quantities by solid-phase synthesis.

Isolated SOD1(A4V) was utilized to assess the effect of the selected cyclic pentapeptide SOD1C5-4 on its aggregation process. CD spectroscopy indicated that SOD1C5-4—but not the Aβ-targeting cyclic peptides AβC5-34 or AβC5-116—interacts with SOD1(A4V), and that the time-dependent conformational transition that is indicative of SOD1(A4V) aggregation is significantly delayed in the presence of SOD1C5-4. Moreover, analysis by dynamic light scattering (DLS) revealed that SOD1C5-4 addition results in the time-dependent formation of oligomeric/aggregated SOD1(A4V) species with markedly smaller sizes. Detection of large, amyloid-like SOD1(A4V) aggregates by ThT staining and a filter retardation assay indicated that the formation of such species was dramatically decreased in the presence of SOD1C5-4. Finally, staining of SOD1(A4V) with the conformation-sensitive dye SYPRO Orange under heat-induced denaturation conditions, suggested that the aggregation-inhibitory action of SOD1C5-4 may be occurring due to its ability to decrease the propensity of SOD1 (A4V) to expose hydrophobic surfaces, a feature which has been proposed to be a molecular determinant of the pathogenesis of fALS-associated SOD1 variants. Taken together, these results demonstrate that SOD1C5-4 is an efficient and specific rescuer of SOD1(A4V) misfolding and aggregation.

The protective effects of SOD1C5-4 in mammalian cells were evaluated in human embryonic kidney 293 (HEK293) cells transiently expressing SOD1(A4V)-GFP. Cells treated with SOD1C5-4 exhibited higher fluorescence, fewer inclusions comprising aggregated SOD1(A4V)-GFP, and higher viability compared to untreated cells.

To identify all bioactive cyclic oligopeptide SOD1 modulators contained in the tested cyclo-NuX$_1$X$_2$X$_3$-X$_5$ library and to facilitate structure-activity analyses of the isolated sequences, To determine structure-activity relationships for the identified mutant SOD1-targeting cyclic oligopeptides, the sequences of the peptide-encoding regions from ~5.3 million clones selected after the fourth round of FACS sorting were determined by deep sequencing. 367 distinct oligopeptide sequences appeared more than 50 times among the selected clones and were selected for subsequent analysis, which revealed the following. First, pentapeptides were the dominant peptide species within the sorted pool, with 197 of the distinct oligopeptide sequences selected corresponding to pentapeptides (54%), 148 to hexapeptides (40%) and 22 corresponding to tetrapeptides (6%). Second, the vast majority of the selected peptides exhibited the cyclo-TXSXW motif of SOD1C5-4 (~92% of all selected clones and ~97% of the selected pentapeptide-encoding clones. Third, among the selected cyclo-TXSXW pentapeptides, I, N, Q, M, E, H, and K residues were excluded at position 2, and were preferably S, A, W or F. At position 4, I, N, Q, C, D, E, K and P residues were excluded, and were preferably V, W, F, M, or H. Taken together, these results indicate that the most bioactive macrocyclic structures against SOD1(A4V) misfolding and aggregation in the library are cyclic pentapeptides of the cyclo-T(Φ$_1$,S)S(Φ$_2$, M,H)W motif, where Φ$_1$ is preferably one of the hydrophobic (Φ) amino acids A, W or F, while Φ$_2$ is preferably V, W or F.

E. coli BL21(DE3) cells producing the combined cyclo-NuX$_1$X$_2$X$_3$-X$_5$ library, while simultaneously overexpressing the Aβ$_{42}$-GFP reporter, were subjected to FACS sorting for the isolation of clones exhibiting enhanced Aβ$_{42}$-GFP fluorescence. Increase in the mean fluorescence was measured and ten random clones were picked from the sorted population. Aβ$_{42}$-GFP fluorescence of the isolated peptide-expressing clones was found to be dramatically increased compared to cells expressing the same Aβ$_{42}$-GFP fusion in the presence of random cyclic peptide sequences picked from the initial (unselected) cyclo-NuX$_1$X$_2$X$_3$-X$_5$ library. Furthermore, the observed phenotypic effects were dependent on the ability of the Ssp DnaE intein (utilized for peptide cyclization as part of SICLOPPS) to perform protein splicing, as the double amino acid substitution H24L/F26A in the C-terminal half of the Ssp DnaE intein, which is known to abolish asparagine cyclization at the $I_C$/extein junction, and prevent extein splicing and peptide cyclization, was found to reduce Aβ$_{42}$-GFP fluorescence back to wild-type levels. Finally, the observed increases in fluorescence were found to be Aβ-specific, as the isolated pSICLOPPS-NuX$_1$X$_2$X$_3$-X$_5$ vectors from these selected clones did not enhance the levels of cellular green fluorescence when the sequence of Aβ in the Aβ$_{42}$-GFP reporter was replaced with that of each one of two unrelated disease-associated MisPs, the DNA-binding (core) domain of the human p53 containing a Tyr220Cys substitution (p53C(Y220C)) and an Ala4Val substitution of human Cu/Zn superoxide dismutase 1 (SOD1(A4V)). On the contrary, the selected pSICLOPPS-NuX$_1$X$_2$X$_3$-X$_5$ vectors were efficient in enhancing the fluorescence of Aβ-GFP containing two additional Aβ variants, Aβ$_{40}$ and the E22G (arctic) variant of Aβ$_{42}$, which is associated with familial forms of AD.

Analysis of the expressed Aβ$_{42}$-GFP fusions by sodium dodecyl sulfate polyacrylamide gel electrophoresis (SDS-PAGE) and western blotting revealed that the bacterial clones expressing the selected cyclic peptides produce markedly increased levels of soluble Aβ$_{42}$-GFP compared to random cyclic peptide sequences. Furthermore, when the same cell lysates were analyzed by native PAGE and western blotting, it was observed that co-expression of the selected cyclic peptides reduced the accumulation of higher-order $A\beta_{42}$-GFP aggregates, which could not enter the gel, and increased the abundance of species with higher electrophoretic mobility.

The inventors further analyzed the selected peptides by DNA sequencing of the peptide-encoding regions of ten isolated clones. This revealed eight distinct putative $A\beta$ aggregation-inhibitory cyclic peptide sequences: one corresponded to a hexapeptide (TPVWFD (SEQ ID NO: 222); present twice among the sequenced clones) and seven pentapeptides (TAFDR (SEQ ID NO: 86), TAWCR (SEQ ID NO: 63), TTWCR (SEQ ID NO: 60), TTVDR (SEQ ID NO: 48), TTYAR (SEQ ID NO: 47; present twice), TTTAR (SEQ ID NO: 56), and SASPT (SEQ ID NO: 206)). Interestingly, the Arg residue at position 5, frequently encountered among the selected pentapeptides, was encoded by three different codons in the selected pSICLOPPS plasmids, thus suggesting that its dominance among the isolated clones was not coincidental.

As depicted in Examples 7-10, the inventors chose two cyclic oligopeptide sequences for further analysis. These were cyclo-TAFDR (SEQ ID NO: 86) and cyclo-SASPT (SEQ ID NO: 206), hereafter referred to as $A\beta$C5-116 and $A\beta$C5-34 ($A\beta$-targeting cyclic 5-peptide number 116 and 34), and were produced by solid-phase synthesis in mg quantities. To further analyze the results the inventors of the present invention chose to focus on pentapeptides, as this was the type of peptide most frequently present among the ones selected from the genetic screen. The inventors decided to further study the sequence $A\beta$C5-116 since the TXXXR motif was particularly dominant among the selected pentapeptides, while $A\beta$C5-34 was chosen because it was the only selected pentapeptide whose sequence appeared to deviate from this motif.

Circular dichroism (CD) spectroscopy was first used to assess the effect of the selected pentapeptides on the aggregation process of $A\beta_{40}$ and $A\beta_{42}$. Addition of $A\beta$C5-116 was found to strongly inhibit the aggregation of $A\beta_{40}$, which remained at a random coil conformation for extended periods of time. The addition of $A\beta$C5-34 did not have the same effect and resulted in the appearance of a low-intensity negative peak. When the same solutions were subjected to a ThT dye-binding assay detecting amyloid fibrils, $A\beta_{40}$ fibril formation was reduced in the presence of $A\beta$C5-116, while it remained unaffected by $A\beta$C5-34. In the case of $A\beta_{42}$, both selected cyclic pentapeptides affected its normal aggregation pathway strongly and stabilized $\beta$-sheet-like structures. ThT staining of the same samples revealed that the extent of amyloid fibril formation was greatly reduced in both cases. When the cyclic peptides were added at a higher ratio, similar CD patterns were observed, however the negative peaks were much more pronounced and fibril formation was completely prevented. The addition of the control cyclic pentapeptide SOD1C5-4 targeting another protein and of randomly selected cyclic control peptides did not have any effect on $A\beta_{40}$ and $A\beta_{42}$ aggregation. Finally, the inventors also performed Transmission electron microscopy (TEM) to verify the above findings. Taken together, these results demonstrate that the selected cyclic oligopeptides interfere with the normal aggregation process of $A\beta$.

The protective effects of $A\beta$C5-34 and $A\beta$C5-116 on $A\beta$40- and $A\beta_{42}$-induced toxicity were evaluated in primary mouse hippocampal neurons and in glioblastoma cell lines. The addition of $A\beta$C5-34 and $A\beta$C5-116 was found to markedly inhibit the neurotoxicity of both $A\beta_{40}$ and $A\beta_{42}$ in a dose-responsive manner. The inventors also studied the effect of $A\beta$C5-34 and $A\beta$C5-116 on the morphology of $A\beta$-exposed neuronal cells by phase-contrast microscopy. In the presence of pre-aggregated $A\beta$, the population of attached cells was greatly reduced compared to the control, with many detached rounded-up cells floating in the supernatant, while hallmarks of degenerating neurons, such as cell shrinkage, membrane blebbings, fragmented neurites and ill-developed axons were obvious in the preparations. This phenotype was reversed with the addition of the selected cyclic peptides.

To further evaluate the protective effects of the selected cyclic peptides against $A\beta$ aggregation and toxicity in vivo, the inventors employed three established models of AD in the nematode worm *Caenorhabditis elegans*. The conservation of genetic and metabolic pathways between *C. elegans* and mammals, in combination with its completely characterized nervous and muscular system, its easy visualization and simple manipulation, has nominated *C. elegans* as an excellent model for neurodegenerative diseases including AD, while chemical screening against $A\beta$-induced toxicity in *C. elegans* is increasingly used in AD drug discovery. A paralysis assay was performed in the *C. elegans* strain CL4176, where human $A\beta_{42}$ is expressed in the animals' body wall muscle cells under the control of a heat-inducible promoter and $A\beta$ aggregate formation is accompanied by the emergence of a paralysis phenotype. When chemically synthesized $A\beta$C5-34 (10 μM) and $A\beta$C5-116 (5 μM) were supplied to CL4176 worms, the emergence of the characteristic paralysis phenotype upon temperature up-shift was significantly decelerated compared to the untreated animals. The strain CL2331, which expresses a $A\beta_{(3-42)}$-GFP fusion again in its body wall muscle cells upon temperature up-shift was also used, and treatment with either one of the selected peptides resulted in a significant reduction of $A\beta$ deposits, which was further shown with biochemical analysis of the accumulation levels of both total and oligomeric $A\beta$ levels in CL4176 animals.

To identify the functionally important residues within the isolated peptides, the inventors performed position 1 substitutions with the other two nucleophilic amino acids present in the initial libraries, as well as alanine scanning mutagenesis at positions 3-5 of the $A\beta$C5-34 and $A\beta$C5-116 pentapeptides. As judged by the ability of the generated variants to enhance the fluorescence of *E. coli* cells overexpressing $A\beta_{42}$-GFP, $A\beta$C5-116 was found to be much more tolerant to substitutions compared to $A\beta$C5-34. All tested sequence alterations within $A\beta$C5-34, apart from the S1T substitution, were found to be deleterious for its $A\beta$ aggregation-inhibitory. On the contrary, only the initial Thr and the ultimate Arg were found to be absolutely necessary for the bioactivity of $A\beta$C5-116, whereas residues at positions 3 and 4 could be substituted by Ala without significant loss of activity.

To identify all bioactive cyclic oligopeptide $A\beta$ modulators contained in the tested cyclo-Nu$X_1X_2X_3$-$X_5$ library and to facilitate structure-activity analyses of the isolated sequences, the peptide sequences isolated from the genetic screen were analyzed by next-generation sequencing. This analysis revealed the following. First, pentapeptides were the dominant peptide species within the sorted pool. Second, the most prevalent motif among the selected pentapeptide sequences were cyclo-TXXXR pentapeptides (~47% of the selected pentapeptide-encoding pSICLOPPS plasmids; ~42% of the unique selected pentapeptide sequences), in accordance with previous observations. On the contrary, only three pentapeptide sequence was found to have high similarity with AβC5-34. Third, for the selected peptides corresponding to the cyclo-TXXXR motif, residues at positions 3 and 4 were highly variable and included the majority of natural amino acids, with position 3 exhibiting the highest diversity. At position 2, Thr, Ala, and Val were preferred, while aromatic residues (Phe, Trp, Tyr) were completely excluded from the selected cyclo-TXXXR peptide pool, in full agreement with the aforementioned site-directed mutagenesis studies. At the highly variable position 3, the complete absence of the negatively charged amino acids Glu and Asp among the selected sequences was notable. In general, both negatively (Glu and Asp) and positively charged residues (Lys, His, and Arg) were found to be disfavored among the selected cyclo-TXXXR sequences at positions 2 and 3. At position 4, Ala, Asp, and Trp were found to be the preferred residues. It is noteworthy, that Lys and Gln residues were practically absent from all positions, while the β sheet-breaking amino acid Pro that is typically included in designed peptide-based inhibitors of amyloid aggregation appeared with strikingly low frequencies. Thus, preferred Aβ modulators are cyclic oligopeptide sequences exhibiting the cyclo-TXXXR motif, where X is any natural amino acid. More preferred are cyclic oligopeptide sequences exhibiting the cyclo-TΦZΠR motif, where Φ=any amino acid excluding F, W, Y, Q, D, E, K and P; Z is any amino acid excluding E; and Π is any natural amino acid excluding Q, M, K. Even more preferred are cyclic oligopeptide sequences exhibiting the cyclo-T(T,A,V)Ψ(A,D,W)R motif, where Ψ is a nonnegatively charged amino acid.

The high residue variability observed at position 3 of the selected TXXXR peptides prompted the inventors to investigate whether AβC5-116 could be further minimized. Indeed, production of truncated variants of AβC5-116, from which Ala2 or Asp4 had been deleted, resulted in a respective two- and three-fold enhancement in the fluorescence of bacterially expressed $A\beta_{42}$-GFP. In accordance with this, a total of ten distinct cyclic tetrapeptide sequences belonging to the TXXR motif were identified among the selected peptide pool. Taken together, these results indicate that the minimal bioactive entity against Aβ aggregation among this peptide family is a TXXR cyclic tetrapeptide.

The present invention describes a versatile and generally applicable method for identifying macrocyclic chemical rescuers of the misfolding of misfolding-prone proteins associated with a protein misfolding disease (MisP), wherein said MisP is selected from SOD1, β-amyloid peptide, tau, α-synuclein, polyglutaminated huntingtin, polyglutaminated ataxin-1, polyglutaminated ataxin-2, polyglutaminated ataxin-3, prion protein, islet amyloid polypeptide (amylin), β2-microglbulin, fragments of immunoglobulin light chain, fragments of immunoglobulin heavy chain, serum amyloid A, ABri peptide, ADan peptide, transthyretin, apolipoprotein A1, gelsolin, transthyretin, lysozyme, phenylalanine hydroxylase, apolipoprotein A-I, calcitonin, prolactin, TDP-43, FUS/TLS; insulin, hemoglobin, α1-antitrypsin, p53; or variants thereof.

Preferably the invention presented herein can be used as a method for the identification of chemical agents for the treatment, prevention or diagnosis of diseases related to protein misfolding and aggregation, including amyotrophic lateral sclerosis, Alzheimer's disease, Parkinson's disease, Huntington's disease, Creutzfeldt-Jakob disease, cancer, phenylketonuria, type II diabetes, senile systemic amyloidosis, familial amyloidotic polyneuropathy, familial amyloid cardiomyopathy, leptomeningeal amyloidosis, systemic amyloidosis, familial British dementia, familial Danish dementia, light chain amyloidosis, heavy chain amyloidosis, serum amyloid A amyloidosis, lysozyme amyloidosis, dialysis-related amyloidosis, ApoAI amyloidosis, Finnish type familial amyloidosis, hereditary cerebral hemorrhage with amyloidosis (Icelandic type), medullary carcinoma of the thyroid, pituitary prolactinoma, injection-localized amyloidosis, frontotemporal dementia, spinocerebellar ataxia 1, spinocerebellar ataxia 2, spinocerebellar ataxia 3, α1-antitrypsin deficiency, sickle-cell anemia, and transmissible spongiform encephalopathy. Most preferably the invention presented herein can be used as a method of treatment, prevention or diagnosis of amyotrophic lateral sclerosis or Alzheimer's disease.

TABLE 1

Sequences and frequency of appearance of the selected cyclo-TXXXR pentapeptides as determined by high-throughput sequencing of the isolated pSICLOPPS-NuX$_1$X$_2$X$_3$-X$_5$ vectors after the second round of bacterial sorting for enhanced Aβ$_{42}$-GFP fluorescence.

| SEQ ID NO | Peptide name | Aminoacid sequence | | | | | Number of reads | Reads/ Total TXXXR reads (%) | Reads/ Total pentapeptide reads (%) | Reads/ Total peptide reads (%) | Peptide-encoding nucleotide sequence |
|---|---|---|---|---|---|---|---|---|---|---|---|
| 47 | AβC5-2 | T | T | Y | A | R | 304,753 | 16.023 | 7.506 | 6.727 | ACCACGTACGCCAGG (SEQ ID NO: 302) |
| 48 | AβC5-3 | T | T | V | D | R | 214,461 | 11.276 | 5.282 | 4.734 | ACCACCGTGGACCGG (SEQ ID NO: 303) |
| 49 | AβC5-5 | T | T | T | W | R | 175,510 | 9.228 | 4.323 | 3.874 | ACCACGACCTGGAGG (SEQ ID NO: 304) |
| 50 | AβC5-7 | T | T | L | H | R | 134,018 | 7.046 | 3.301 | 2.958 | ACCACGCTGCACCGG (SEQ ID NO: 305) |
| 51 | AβC5-8 | T | T | F | A | R | 96,700 | 5.084 | 2.382 | 2.134 | ACCACCTTCGCCCGG (SEQ ID NO: 306) |
| 52 | AβC5-9 | T | V | L | D | R | 89,669 | 4.715 | 2.209 | 1.979 | ACCGTCTTGGACCGG (SEQ ID NO: 307) |

TABLE 1-continued

Sequences and frequency of appearance of the selected cyclo-TXXXR pentapeptides
as determined by high-throughput sequencing of the isolated pSICLOPPS-NuX₁X₂X₃-X₅
vectors after the second round of bacterial sorting for enhanced Aβ₄₂-GFP fluorescence.

| SEQ ID NO | Peptide name | Aminoacid sequence | | | | | Number of reads | Reads/ Total TXXXR reads (%) | Reads/ Total pentapeptide reads (%) | Reads/ Total peptide reads (%) | Peptide-encoding nucleotide sequence |
|---|---|---|---|---|---|---|---|---|---|---|---|
| 53 | AβC5-12 | T | T | W | A | R | 65,929 | 3.466 | 1.624 | 1.455 | ACCACGTGGGCCAGG (SEQ ID NO: 308) |
| 54 | AβC5-13 | T | A | L | D | R | 62,792 | 3.301 | 1.547 | 1.386 | ACCGCGCTGGACCGG (SEQ ID NO: 309) |
| 55 | AβC5-15 | T | A | N | V | R | 47,855 | 2.516 | 1.179 | 1.056 | ACCGCGAACGTGAGG (SEQ ID NO: 310) |
| 56 | AβC5-17 | T | T | T | A | R | 40,135 | 2.110 | 0.989 | 0.886 | ACCACCACGGCCCGG (SEQ ID NO: 311) |
| 57 | AβC5-18 | T | T | I | A | R | 37,150 | 1.953 | 0.915 | 0.820 | ACCACCATCGCCCGG (SEQ ID NO: 312) |
| 58 | AβC5-19 | T | V | W | D | R | 37,091 | 1.950 | 0.914 | 0.819 | ACCGTGTGGGACCGG (SEQ ID NO: 313) |
| 59 | AβC5-20 | T | T | I | S | R | 37,044 | 1.948 | 0.912 | 0.818 | ACCACCATCAGCCGG (SEQ ID NO: 314) |
| 60 | AβC5-21 | T | T | W | C | R | 36,295 | 1.908 | 0.894 | 0.801 | ACCACCTGGTGCCGG (SEQ ID NO: 315) |
| 61 | AβC5-22 | T | V | L | W | R | 35,820 | 1.883 | 0.882 | 0.791 | ACCGTCCTGTGGAGG (SEQ ID NO: 316) |
| 62 | AβC5-25 | T | T | L | A | R | 28,989 | 1.524 | 0.714 | 0.640 | ACCACCTTGGCGAGG (SEQ ID NO: 317) |
| 63 | AβC5-26 | T | A | W | C | R | 28,391 | 1.493 | 0.699 | 0.627 | ACCGCGTGGTGCCGC (SEQ ID NO: 318) |
| 64 | AβC5-27 | T | T | S | A | R | 28,188 | 1.482 | 0.694 | 0.622 | ACCACGAGCGCCCGC (SEQ ID NO: 319) |
| 65 | AβC5-29 | T | T | L | E | R | 27,514 | 1.447 | 0.678 | 0.607 | ACCACCCTCGAGAGG (SEQ ID NO: 320) |
| 66 | AβC5-30 | T | S | T | A | R | 27,456 | 1.444 | 0.676 | 0.606 | ACCTCGACGGCGCGG (SEQ ID NO: 321) |
| 67 | AβC5-35 | T | V | R | D | R | 25,428 | 1.337 | 0.626 | 0.561 | ACCGTCCGGGACCGG (SEQ ID NO: 322) |
| 68 | AβC5-41 | T | G | W | A | R | 21,784 | 1.145 | 0.537 | 0.481 | ACCGGCTGGGCGAGG (SEQ ID NO: 323) |
| 69 | AβC5-44 | T | A | W | A | R | 20,807 | 1.094 | 0.512 | 0.459 | ACCGCCTGGGCGAGG (SEQ ID NO: 324) |
| 70 | AβC5-45 | T | T | W | V | R | 20,798 | 1.094 | 0.512 | 0.459 | ACCACCTGGGTGCGG (SEQ ID NO: 325) |
| 71 | AβC5-46 | T | L | L | W | R | 19,957 | 1.049 | 0.492 | 0.440 | ACCCTATTGTGGCGG (SEQ ID NO: 326) |
| 72 | AβC5-47 | T | T | I | D | R | 19,735 | 1.038 | 0.486 | 0.436 | ACCACGATCGACAGG (SEQ ID NO: 327) |
| 73 | AβC5-50 | T | A | L | A | R | 19,433 | 1.022 | 0.479 | 0.429 | ACCGCGCTCGCGCGC (SEQ ID NO: 328) |
| 74 | AβC5-51 | T | S | V | D | R | 19,249 | 1.012 | 0.474 | 0.425 | ACCAGCGTGGACAGG (SEQ ID NO: 329) |
| 75 | AβC5-53 | T | T | V | W | R | 18,669 | 0.982 | 0.460 | 0.412 | ACCACCGTGTGGCGC (SEQ ID NO: 330) |

TABLE 1-continued

Sequences and frequency of appearance of the selected cyclo-TXXXR pentapeptides
as determined by high-throughput sequencing of the isolated pSICLOPPS-NuX₁X₂X₃-X₅
vectors after the second round of bacterial sorting for enhanced Aβ₄₂-GFP fluorescence.

| SEQ ID NO | Peptide name | Aminoacid sequence | | | | | Number of reads | Reads/ Total TXXXR reads (%) | Reads/ Total pentapeptide reads (%) | Reads/ Total peptide reads (%) | Peptide-encoding nucleotide sequence |
|---|---|---|---|---|---|---|---|---|---|---|---|
| 76 | AβC5-66 | T | T | H | W | R | 14,304 | 0.752 | 0.352 | 0.316 | ACCACGCACTGGCGG (SEQ ID NO: 331) |
| 77 | AβC5-67 | T | A | R | D | R | 14,213 | 0.747 | 0.350 | 0.314 | ACCGCGAGGGACCGG (SEQ ID NO: 332) |
| 78 | AβC5-73 | T | T | R | D | R | 12,894 | 0.678 | 0.318 | 0.285 | ACCACGCGGGACCGG (SEQ ID NO: 333) |
| 79 | AβC5-80 | T | S | V | H | R | 10,181 | 0.535 | 0.251 | 0.225 | ACCAGCGTGCACCGG (SEQ ID NO: 334) |
| 80 | AβC5-82 | T | A | V | W | R | 9,781 | 0.514 | 0.241 | 0.216 | ACCGCCGTCTGGCGG (SEQ ID NO: 335) |
| 81 | AβC5-83 | T | T | G | C | R | 9,362 | 0.492 | 0.231 | 0.207 | ACCACGGGGTGCCGG (SEQ ID NO: 336) |
| 82 | AβC5-89 | T | A | T | D | R | 7,984 | 0.420 | 0.197 | 0.176 | ACCGCCACCGACAGG (SEQ ID NO: 337) |
| 83 | AβC5-94 | T | V | L | F | R | 7,442 | 0.391 | 0.183 | 0.164 | ACCGTCTTGTTCCGC (SEQ ID NO: 338) |
| 84 | AβC5-102 | T | T | Y | N | R | 6,067 | 0.319 | 0.149 | 0.134 | ACCACCTACAACCGC (SEQ ID NO: 339) |
| 85 | AβC5-105 | T | V | R | W | R | 5,450 | 0.287 | 0.134 | 0.120 | ACCGTGCGCTGGCGC (SEQ ID NO: 340) |
| 86 | AβC5-116 | T | A | F | D | R | 4,243 | 0.223 | 0.105 | 0.094 | ACCGCGTTCGACCGG (SEQ ID NO: 341) |
| 87 | AβC5-117 | T | T | R | C | R | 4,237 | 0.223 | 0.104 | 0.094 | ACCACGCGGTGCAGG (SEQ ID NO: 342) |
| 88 | AβC5-118 | T | T | F | W | R | 4,216 | 0.222 | 0.104 | 0.093 | ACCACCTTCTGGCGG (SEQ ID NO: 343) |
| 89 | AβC5-121 | T | I | K | D | R | 3,970 | 0.209 | 0.098 | 0.088 | ACCATCAAGGACCGG (SEQ ID NO: 344) |
| 90 | AβC5-123 | T | T | V | H | R | 3,371 | 0.177 | 0.083 | 0.074 | ACCACCGTCCACCGG (SEQ ID NO: 345) |
| 91 | AβC5-126 | T | T | L | L | R | 3,016 | 0.159 | 0.074 | 0.067 | ACCACGCTCCTCAGG (SEQ ID NO: 346) |
| 92 | AβC5-129 | T | T | L | F | R | 2,630 | 0.138 | 0.065 | 0.058 | ACCACGCTCTTCCGG (SEQ ID NO: 347) |
| 93 | AβC5-130 | T | A | Y | H | R | 2,594 | 0.136 | 0.064 | 0.057 | ACCGCGTACCACCGG (SEQ ID NO: 348) |
| 94 | AβC5-136 | T | A | L | H | R | 2,026 | 0.107 | 0.050 | 0.045 | ACCGCGTTGCACCGG (SEQ ID NO: 349) |
| 95 | AβC5-139 | T | T | S | P | R | 1,904 | 0.100 | 0.047 | 0.042 | ACCACCTCGCCCCGG (SEQ ID NO: 350) |
| 96 | AβC5-146 | T | T | W | S | R | 1,612 | 0.085 | 0.040 | 0.036 | ACCACCTGGTCGCGG (SEQ ID NO: 351) |
| 97 | AβC5-147 | T | A | M | H | R | 1,611 | 0.085 | 0.040 | 0.036 | ACCGCCATGCACAGG (SEQ ID NO: 352) |
| 98 | AβC5-155 | T | S | L | D | R | 1,251 | 0.066 | 0.031 | 0.028 | ACCTCGCTCGACAGG (SEQ ID NO: 353) |

TABLE 1-continued

Sequences and frequency of appearance of the selected cyclo-TXXXR pentapeptides
as determined by high-throughput sequencing of the isolated pSICLOPPS-NuX₁X₂X₃-X₅
vectors after the second round of bacterial sorting for enhanced Aβ₄₂-GFP fluorescence.

| SEQ ID NO | Peptide name | Aminoacid sequence | | | | | Number of reads | Reads/ Total TXXXR reads (%) | Reads/ Total pentapeptide reads (%) | Reads/ Total peptide reads (%) | Peptide-encoding nucleotide sequence |
|---|---|---|---|---|---|---|---|---|---|---|---|
| 99 | AβC5-158 | T | T | G | A | R | 1,172 | 0.062 | 0.029 | 0.026 | ACCACGGGGGCGCGC (SEQ ID NO: 354) |
| 100 | AβC5-162 | T | S | V | W | R | 1,094 | 0.058 | 0.027 | 0.024 | ACCTCGGTGTGGAGG (SEQ ID NO: 355) |
| 101 | AβC5-173 | T | T | H | A | R | 953 | 0.050 | 0.023 | 0.021 | ACCACGCACGCCAGG (SEQ ID NO: 356) |
| 102 | AβC5-176 | T | A | G | W | R | 945 | 0.050 | 0.023 | 0.021 | ACCGCGGGCTGGAGG (SEQ ID NO: 357) |
| 103 | AβC5-177 | T | A | T | A | R | 925 | 0.049 | 0.023 | 0.020 | ACCGCCACCGCGAGG (SEQ ID NO: 358) |
| 104 | AβC5-184 | T | V | L | A | R | 818 | 0.043 | 0.020 | 0.018 | ACCGTGCTCGCGCGG (SEQ ID NO: 359) |
| 105 | AβC5-185 | T | T | F | N | R | 800 | 0.042 | 0.020 | 0.018 | ACCACGTTCAACAGG (SEQ ID NO: 360) |
| 106 | AβC5-188 | T | G | M | R | R | 768 | 0.040 | 0.019 | 0.017 | ACCGGGATGAGGCGG (SEQ ID NO: 361) |
| 107 | AβC5-189 | T | T | V | A | R | 757 | 0.040 | 0.019 | 0.017 | ACCACCGTCGCCAGG (SEQ ID NO: 362) |
| 108 | AβC5-190 | T | L | C | L | R | 739 | 0.039 | 0.018 | 0.016 | TGCTTGCGCACGCTG (SEQ ID NO: 363) |
| 109 | AβC5-192 | T | G | L | A | R | 720 | 0.038 | 0.018 | 0.016 | ACCGGGCTGGCGCGG (SEQ ID NO: 364) |
| 110 | AβC5-198 | T | S | W | C | R | 679 | 0.036 | 0.017 | 0.015 | ACCAGCTGGTGCAGG (SEQ ID NO: 365) |
| 111 | AβC5-209 | T | T | R | A | R | 580 | 0.030 | 0.014 | 0.013 | ACCACCAGGGCGCGG (SEQ ID NO: 366) |
| 112 | AβC5-215 | T | T | P | W | R | 524 | 0.028 | 0.013 | 0.012 | ACCACGCCCTGGAGG (SEQ ID NO: 367) |
| 113 | AβC5-218 | T | V | L | H | R | 497 | 0.026 | 0.012 | 0.011 | ACCGTCTTGCACAGG (SEQ ID NO: 368) |
| 114 | AβC5-223 | T | G | L | D | R | 464 | 0.024 | 0.011 | 0.010 | ACCGGCCTCGACAGG (SEQ ID NO: 369) |
| 115 | AβC5-230 | T | T | S | D | R | 442 | 0.023 | 0.011 | 0.010 | ACCACGTCGGACCGG (SEQ ID NO: 370) |
| 116 | AβC5-239 | T | T | M | H | R | 384 | 0.020 | 0.009 | 0.008 | ACCACGATGCACCGC (SEQ ID NO: 371) |
| 117 | AβC5-242 | T | T | S | T | R | 376 | 0.020 | 0.009 | 0.008 | ACCACCTCGACCCGG (SEQ ID NO: 372) |
| 118 | AβC5-244 | T | T | R | V | R | 366 | 0.019 | 0.009 | 0.008 | ACCACGCGCGTGAGG (SEQ ID NO: 373) |
| 119 | AβC5-245 | T | T | R | F | R | 364 | 0.019 | 0.009 | 0.008 | ACCACCCGGTTCCGG (SEQ ID NO: 374) |
| 120 | AβC5-248 | T | T | T | H | R | 339 | 0.018 | 0.008 | 0.007 | ACCACGACGCACCGG (SEQ ID NO: 375) |
| 121 | AβC5-250 | T | H | A | W | R | 334 | 0.018 | 0.008 | 0.007 | ACCCACGCCTGGAGG (SEQ ID NO: 376) |

TABLE 1-continued

Sequences and frequency of appearance of the selected cyclo-TXXXR pentapeptides
as determined by high-throughput sequencing of the isolated pSICLOPPS-NuX₁X₂X₃-X₅
vectors after the second round of bacterial sorting for enhanced Aβ₄₂-GFP fluorescence.

| SEQ ID NO | Peptide name | Aminoacid sequence | | | | | Number of reads | Reads/ Total TXXXR reads (%) | Reads/ Total pentapeptide reads (%) | Reads/ Total peptide reads (%) | Peptide-encoding nucleotide sequence |
|---|---|---|---|---|---|---|---|---|---|---|---|
| 122 | AβC5-252 | T | V | I | W | R | 331 | 0.017 | 0.008 | 0.007 | ACCGTGATCTGGCGC (SEQ ID NO: 377) |
| 123 | AβC5-253 | T | T | W | F | R | 327 | 0.017 | 0.008 | 0.007 | ACCACGTGGTTCCGG (SEQ ID NO: 378) |
| 124 | AβC5-255 | T | T | S | R | R | 325 | 0.017 | 0.008 | 0.007 | ACCACCTCGAGACGG (SEQ ID NO: 379) |
| 125 | AβC5-258 | T | T | S | C | R | 301 | 0.016 | 0.007 | 0.007 | ACCACGTCGTGCCGG (SEQ ID NO: 380) |
| 126 | AβC5-260 | T | T | W | T | R | 295 | 0.016 | 0.007 | 0.007 | ACCACCTGGACCCGG (SEQ ID NO: 381) |
| 127 | AβC5-262 | T | T | S | S | R | 286 | 0.015 | 0.007 | 0.006 | ACCACCTCGAGCCGG (SEQ ID NO: 382) |
| 128 | AβC5-263 | T | H | L | A | R | 284 | 0.015 | 0.007 | 0.006 | ACCCACCTCGCCCGG (SEQ ID NO: 383) |
| 129 | AβC5-264 | T | S | G | A | R | 282 | 0.015 | 0.007 | 0.006 | ACCAGCGGGGCCCGG (SEQ ID NO: 384) |
| 130 | AβC5-266 | T | T | L | R | R | 274 | 0.014 | 0.007 | 0.006 | ACCACGCTGCGCCGG (SEQ ID NO: 385) |
| 131 | AβC5-270 | T | A | T | W | R | 266 | 0.014 | 0.007 | 0.006 | ACCGCGACCTGGAGG (SEQ ID NO: 386) |
| 132 | AβC5-272 | T | C | M | W | R | 254 | 0.013 | 0.006 | 0.006 | ACCTGCATGTGGCGC (SEQ ID NO: 387) |
| 133 | AβC5-275 | T | A | H | V | R | 249 | 0.013 | 0.006 | 0.005 | ACCGCGCACGTGCGC (SEQ ID NO: 388) |
| 134 | AβC5-276 | T | S | W | A | R | 249 | 0.013 | 0.006 | 0.005 | ACCTCGTGGGCGCGG (SEQ ID NO: 389) |
| 135 | AβC5-278 | T | T | W | L | R | 241 | 0.013 | 0.006 | 0.005 | ACCACGTGGCTCAGG (SEQ ID NO: 390) |
| 136 | AβC5-291 | T | T | L | D | R | 213 | 0.011 | 0.005 | 0.005 | ACCACCCTGGACCGG (SEQ ID NO: 391) |
| 137 | AβC5-294 | T | T | P | H | R | 207 | 0.011 | 0.005 | 0.005 | ACCACGCCTCACCGG (SEQ ID NO: 392) |
| 138 | AβC5-298 | T | T | R | G | R | 201 | 0.011 | 0.005 | 0.004 | ACCACCCGTGGCCGG (SEQ ID NO: 393) |
| 139 | AβC5-299 | T | T | V | G | R | 200 | 0.011 | 0.005 | 0.004 | ACCACCGTGGGCCGG (SEQ ID NO: 394) |
| 140 | AβC5-301 | T | T | T | R | R | 191 | 0.010 | 0.005 | 0.004 | ACCACGACGCGCCGC (SEQ ID NO: 395) |
| 141 | AβC5-304 | T | S | I | N | R | 182 | 0.010 | 0.004 | 0.004 | ACCTCGATCAACAGG (SEQ ID NO: 396) |
| 142 | AβC5-305 | T | T | A | D | R | 181 | 0.010 | 0.004 | 0.004 | ACCACCGCGGACCGG (SEQ ID NO: 397) |
| 143 | AβC5-315 | T | T | S | E | R | 158 | 0.008 | 0.004 | 0.003 | ACCACCTCCGAGAGG (SEQ ID NO: 398) |
| 144 | AβC5-316 | T | T | C | A | R | 157 | 0.008 | 0.004 | 0.003 | ACCACGTGCGCCAGG (SEQ ID NO: 399) |

TABLE 1-continued

Sequences and frequency of appearance of the selected cyclo-TXXXR pentapeptides
as determined by high-throughput sequencing of the isolated pSICLOPPS-NuX₁X₂X₃-X₅
vectors after the second round of bacterial sorting for enhanced Aβ₄₂-GFP fluorescence.

| SEQ ID NO | Peptide name | | Aminoacid sequence | | | Number of reads | Reads/ Total TXXXR reads (%) | Reads/ Total pentapeptide reads (%) | Reads/ Total peptide reads (%) | Peptide-encoding nucleotide sequence |
|---|---|---|---|---|---|---|---|---|---|---|
| 145 | AβC5-317 | T | T | A | W | R | 156 | 0.008 | 0.004 | 0.003 | ACCACGGCCTGGAGG (SEQ ID NO: 400) |
| 146 | AβC5-320 | T | T | V | E | R | 150 | 0.008 | 0.004 | 0.003 | ACCACCGTCGAGCGG (SEQ ID NO: 401) |
| 147 | AβC5-321 | T | T | T | F | R | 148 | 0.008 | 0.004 | 0.003 | ACCACGACGTTCAGG (SEQ ID NO: 402) |
| 148 | AβC5-323 | T | A | V | D | R | 147 | 0.008 | 0.004 | 0.003 | ACCGCCGTGGACCGG (SEQ ID NO: 403) |
| 149 | AβC5-325 | T | V | W | I | R | 144 | 0.008 | 0.004 | 0.003 | ACCGTGTGGATCAGG (SEQ ID NO: 404) |
| 150 | AβC5-329 | T | T | V | R | R | 141 | 0.007 | 0.003 | 0.003 | ACCACCGTACGCAGG (SEQ ID NO: 405) |
| 151 | AβC5-333 | T | H | V | R | R | 137 | 0.007 | 0.003 | 0.003 | ACCCACGTACGCAGG (SEQ ID NO: 406) |
| 152 | AβC5-343 | T | N | L | D | R | 125 | 0.007 | 0.003 | 0.003 | ACCAACCTGGACCGG (SEQ ID NO: 407) |
| 153 | AβC5-344 | T | T | P | G | R | 125 | 0.007 | 0.003 | 0.003 | ACCACGCCTGGACGG (SEQ ID NO: 408) |
| 154 | AβC5-348 | T | T | L | T | R | 119 | 0.006 | 0.003 | 0.003 | ACCACGCTCACCCGG (SEQ ID NO: 409) |
| 155 | AβC5-355 | T | A | T | V | R | 115 | 0.006 | 0.003 | 0.003 | ACCGCGACGGTGCGC (SEQ ID NO: 410) |
| 156 | AβC5-359 | T | A | M | W | R | 110 | 0.006 | 0.003 | 0.002 | ACCGCCATGTGGCGG (SEQ ID NO: 411) |
| 157 | AβC5-361 | T | T | K | W | R | 108 | 0.006 | 0.003 | 0.002 | ACCACGAAGTGGAGG (SEQ ID NO: 412) |
| 158 | AβC5-362 | T | T | W | D | R | 107 | 0.006 | 0.003 | 0.002 | ACCACCTGGGACCGG (SEQ ID NO: 413) |
| 159 | AβC5-364 | T | T | M | A | R | 106 | 0.006 | 0.003 | 0.002 | ACCACCATGGCCCGG (SEQ ID NO: 414) |
| 160 | AβC5-365 | T | T | G | G | R | 106 | 0.006 | 0.003 | 0.002 | ACCACCGGTGGCCGG (SEQ ID NO: 415) |
| 161 | AβC5-366 | T | T | M | V | R | 105 | 0.006 | 0.003 | 0.002 | ACCACGATGGTGCGG (SEQ ID NO: 416) |
| 162 | AβC5-375 | T | N | L | A | R | 97 | 0.005 | 0.002 | 0.002 | ACCAACCTCGCCCGG (SEQ ID NO: 417) |
| 163 | AβC5-376 | T | I | R | D | R | 96 | 0.005 | 0.002 | 0.002 | ACCATCAGGGACCGG (SEQ ID NO: 418) |
| 164 | AβC5-378 | T | T | T | G | R | 96 | 0.005 | 0.002 | 0.002 | ACCACGACTGGTAGG (SEQ ID NO: 419) |
| 165 | AβC5-379 | T | R | L | G | R | 95 | 0.005 | 0.002 | 0.002 | ACCCGTCTTGGCAGG (SEQ ID NO: 420) |
| 166 | AβC5-381 | T | T | H | T | R | 93 | 0.005 | 0.002 | 0.002 | ACCACGCACACCAGG (SEQ ID NO: 421) |
| 167 | AβC5-382 | T | T | I | T | R | 92 | 0.005 | 0.002 | 0.002 | ACCACCATCACCCGG (SEQ ID NO: 422) |

TABLE 1-continued

Sequences and frequency of appearance of the selected cyclo-TXXXR pentapeptides
as determined by high-throughput sequencing of the isolated pSICLOPPS-NuX$_1$X$_2$X$_3$-X$_5$
vectors after the second round of bacterial sorting for enhanced Aβ$_{42}$-GFP fluorescence.

| SEQ ID NO | Peptide name | Aminoacid sequence | | | | | Number of reads | Reads/ Total TXXXR reads (%) | Reads/ Total pentapeptide reads (%) | Reads/ Total peptide reads (%) | Peptide-encoding nucleotide sequence |
|---|---|---|---|---|---|---|---|---|---|---|---|
| 168 | AβC5-384 | T | T | Y | T | R | 90 | 0.005 | 0.002 | 0.002 | ACCACGTACACCAGG (SEQ ID NO: 423) |
| 169 | AβC5-385 | T | T | L | Y | R | 90 | 0.005 | 0.002 | 0.002 | ACCACGCTGTACCGG (SEQ ID NO: 424) |
| 170 | AβC5-389 | T | H | L | D | R | 89 | 0.005 | 0.002 | 0.002 | ACCCACCTGGACCGG (SEQ ID NO: 425) |
| 171 | AβC5-391 | T | L | L | I | R | 88 | 0.005 | 0.002 | 0.002 | ACCTTGTTGATCAGG (SEQ ID NO: 426) |
| 172 | AβC5-392 | T | T | C | D | R | 87 | 0.005 | 0.002 | 0.002 | ACCACGTGCGACCGG (SEQ ID NO: 427) |
| 173 | AβC5-393 | T | T | G | R | R | 87 | 0.005 | 0.002 | 0.002 | ACCACGGGTCGCCGG (SEQ ID NO: 428) |
| 174 | AβC5-394 | T | T | V | S | R | 86 | 0.005 | 0.002 | 0.002 | ACCACCGTGAGCCGG (SEQ ID NO: 429) |
| 175 | AβC5-395 | T | T | Q | H | R | 85 | 0.004 | 0.002 | 0.002 | ACCACGCAGCACCGG (SEQ ID NO: 430) |
| 176 | AβC5-396 | T | T | T | P | R | 84 | 0.004 | 0.002 | 0.002 | ACCACTACGCCCAGG (SEQ ID NO: 431) |
| 177 | AβC5-399 | T | A | F | A | R | 82 | 0.004 | 0.002 | 0.002 | ACCGCCTTCGCCCGG (SEQ ID NO: 432) |
| 178 | AβC5-405 | T | T | S | H | R | 78 | 0.004 | 0.002 | 0.002 | ACCACGTCACACCGG (SEQ ID NO: 433) |
| 179 | AβC5-410 | T | V | L | G | R | 76 | 0.004 | 0.002 | 0.002 | ACCGTCTTGGGCCGG (SEQ ID NO: 434) |
| 180 | AβC5-411 | T | T | Q | R | R | 75 | 0.004 | 0.002 | 0.002 | ACCACGCAGCGCAGG (SEQ ID NO: 435) |
| 181 | AβC5-413 | T | S | H | A | R | 74 | 0.004 | 0.002 | 0.002 | ACCAGTCACGCCAGG (SEQ ID NO: 436) |
| 182 | AβC5-415 | T | T | T | C | R | 74 | 0.004 | 0.002 | 0.002 | ACCACGACGTGCCGG (SEQ ID NO: 437) |
| 183 | AβC5-422 | T | A | W | R | R | 72 | 0.004 | 0.002 | 0.002 | ACCGCGTGGCGCCGC (SEQ ID NO: 438) |
| 184 | AβC5-428 | T | T | C | G | R | 69 | 0.004 | 0.002 | 0.002 | ACCACGTGTGGCCGG (SEQ ID NO: 439) |
| 185 | AβC5-434 | T | T | S | G | R | 65 | 0.003 | 0.002 | 0.001 | ACCACCTCTGGCCGG (SEQ ID NO: 440) |
| 186 | AβC5-438 | T | T | T | S | R | 62 | 0.003 | 0.002 | 0.001 | ACCACGACGTCGAGG (SEQ ID NO: 441) |
| 187 | AβC5-440 | T | A | T | G | R | 61 | 0.003 | 0.002 | 0.001 | ACCGCGACTGGACGG (SEQ ID NO: 442) |
| 188 | AβC5-441 | T | A | W | D | R | 61 | 0.003 | 0.002 | 0.001 | ACCGCGTGGGACCGG (SEQ ID NO: 443) |
| 189 | AβC5-443 | T | T | H | H | R | 60 | 0.003 | 0.001 | 0.001 | ACCACGCATCACCGG (SEQ ID NO: 444) |
| 190 | AβC5-448 | T | A | Y | A | R | 58 | 0.003 | 0.001 | 0.001 | ACCGCGTACGCCAGG (SEQ ID NO: 445) |

TABLE 1-continued

Sequences and frequency of appearance of the selected cyclo-TXXXR pentapeptides
as determined by high-throughput sequencing of the isolated pSICLOPPS-NuX$_1$X$_2$X$_3$-X$_5$
vectors after the second round of bacterial sorting for enhanced Aβ$_{42}$-GFP fluorescence.

| SEQ ID NO | Peptide name | Aminoacid sequence | | | | Number of reads | Reads/ Total TXXXR reads (%) | Reads/ Total pentapeptide reads (%) | Reads/ Total peptide reads (%) | Peptide-encoding nucleotide sequence |
|---|---|---|---|---|---|---|---|---|---|---|
| 191 | AβC5-449 | T | A | N | A | R | 58 | 0.003 | 0.001 | 0.001 | ACCGCGAACGCGAGG (SEQ ID NO: 446) |
| 192 | AβC5-450 | T | R | D | V | R | 58 | 0.003 | 0.001 | 0.001 | ACCCGCGACGTGAGG (SEQ ID NO: 447) |
| 193 | AβC5-452 | T | H | V | D | R | 58 | 0.003 | 0.001 | 0.001 | ACCCACGTCGACAGG (SEQ ID NO: 448) |
| 194 | AβC5-453 | T | L | F | W | R | 57 | 0.003 | 0.001 | 0.001 | ACCCTATTCTGGCGG (SEQ ID NO: 449) |
| 195 | AβC5-459 | T | T | A | A | R | 55 | 0.003 | 0.001 | 0.001 | ACCACCGCGGCCCGG (SEQ ID NO: 450) |
| 196 | AβC5-463 | T | V | V | D | R | 54 | 0.003 | 0.001 | 0.001 | ACCGTCGTGGACCGG (SEQ ID NO: 451) |
| 197 | AβC5-464 | T | T | P | A | R | 54 | 0.003 | 0.001 | 0.001 | ACCACTCCGGCCCGG (SEQ ID NO: 452) |
| 198 | AβC5-469 | T | T | I | G | R | 53 | 0.003 | 0.001 | 0.001 | ACCACGATCGGCAGG (SEQ ID NO: 453) |
| 199 | AβC5-472 | T | M | Y | A | R | 51 | 0.003 | 0.001 | 0.001 | ACCATGTACGCCAGG (SEQ ID NO: 454) |
| 200 | AβC5-473 | T | H | V | A | R | 51 | 0.003 | 0.001 | 0.001 | ACCCACGTGGCCAGG (SEQ ID NO: 455) |
| 201 | AβC5-474 | T | T | W | P | R | 51 | 0.003 | 0.001 | 0.001 | ACCACCTGGCCGCGG (SEQ ID NO: 456) |
| 202 | AβC5-475 | T | T | G | D | R | 51 | 0.003 | 0.001 | 0.001 | ACCACCGGTGACCGG (SEQ ID NO: 457) |
| 203 | AβC5-479 | T | T | T | V | R | 50 | 0.003 | 0.001 | 0.001 | ACCACGACCGTGCGG (SEQ ID NO: 458) |
| 204 | AβC5-481 | T | V | F | G | R | 50 | 0.003 | 0.001 | 0.001 | ACCGTCTTTGGCAGG (SEQ ID NO: 449) |
| 205 | AβC5-483 | T | R | V | G | R | 50 | 0.003 | 0.001 | 0.001 | ACCCGTGTGGGCCGG (SEQ ID NO: 460) |
| | Sum | | | | | 1,901,945 | 100.000 | 46.847 | 41.980 | |

TABLE 2

Sequences and frequency of appearance of the selected cyclic pentapeptides
resembling AβC5-34 as determined by high-throughput sequencing of the
isolated pSICLOPPS-NuX$_1$X$_2$X$_3$-X$_5$ vectors after the second round of
bacterial sorting for enhanced Aβ$_{42}$-GFP fluorescence.

| SEQ ID NO | Peptide name | Amino acid sequence | | | | | Number of reads | Reads/ Total SASPT-like reads (%) | Reads/ Total pentapeptide reads (%) | Reads/ Total peptide reads (%) |
|---|---|---|---|---|---|---|---|---|---|---|
| 206 | AβC5-34 | S | A | S | P | T | 25673 | 97.349 | 0.632 | 0.567 |
| 207 | AβC5-216 | S | I | C | P | T | 516 | 1.957 | 0.013 | 0.011 |
| 208 | AβC5-380 | S | I | T | P | T | 94 | 0.356 | 0.002 | 0.002 |
| 209 | AβC5-387 | S | H | S | P | T | 89 | 0.337 | 0.002 | 0.002 |
| | Sum | | | | | | 26,372 | 100 | 0.645 | 0.578 |

TABLE 3

Sequences and frequency of appearance of the selected cyclo-TXXR tetrapeptides as determined by high-throughput sequencing of the isolated pSICLOPPS-Nu $X_1X_2X_3$-$X_5$ vectors for enchanced $A\beta_{42}$-GFP fluorescence.

| SEQ ID NO. | PEPTIDE NAME | CYCLIC PEPTIDE SEQUENCE | Peptide-encoding nucleotide sequence | Normalized read number (%) |
|---|---|---|---|---|
| 210 | AβC4-9 | TTCR | ACCACGTGCCGG (SEQ ID NO: 461) | 1.247884 |
| 211 | AβC4-11 | TTRR | ACCACTCGCCGG (SEQ ID NO: 462) | 1.199516 |
| 212 | AβC4-31 | TTSR | ACCACGTCGCGG (SEQ ID NO: 463) | 0.324063 |
| 213 | AβC4-34 | TRGR | ACACGTGGACGG (SEQ ID NO: 464) | 0.304716 |
| 214 | AβC4-35 | TTGR | ACCACTGGCCGG (SEQ ID NO: 465) | 0.295042 |
| 215 | AβC4-41 | TRRR | ACACGTCGCAGG (SEQ ID NO: 466) | 0.246675 |
| 216 | AβC4B-9 | TDQR | ACCGACCAGCGG (SEQ ID NO: 467) | 2.090359 |
| 217 | AβC4B-41 | TLIR | ACCCTGATCCGC (SEQ ID NO: 468) | 0.774951 |
| 218 | AβC4B-80 | TLWR | ACCCTGTGGCGG (SEQ ID NO: 469) | 0.256828 |
| 219 | AβC4B-86 | TLGR | ACCTTGGGCCGG (SEQ ID NO: 470) | 0.16973 |
| 220 | AβC5(ΔA2) | TFDR | ACCTTCGACCGG (SEQ ID NO: 471) | — |
| 221 | AβC5(ΔD4) | TAFR | ACCGCGTTCCGG (SEQ ID NO: 472) | — |

TABLE 4

Sequences and frequency of appearance of the selected cyclic hexapeptides as determined by high-throughput sequencing of the isolated pSICLOPPS-NuX$_1$X$_2$X$_3$-X$_5$ vectors after the second round of bacterial sorting for enhanced $A\beta_{42}$-GFP fluorescence.

| SEQ ID NO | Peptide name | Aminoacid sequence | | | | | | Number of reads | Reads/ Total hexapeptide reads (%) | Reads/ Total peptide reads (%) | Peptide-encoding nucleotide sequence |
|---|---|---|---|---|---|---|---|---|---|---|---|
| 222 | AβC6-1 | T | P | V | W | F | D | 131,935 | 29.151 | 2.912 | ACCCCGGTCTGGTTCGAC (SEQ ID NO: 473) |
| 223 | AβC6-2 | T | P | A | W | F | D | 111,132 | 24.555 | 2.453 | ACCCCGGCCTGGTTCGAC (SEQ ID NO: 474) |
| 224 | AβC6-4 | T | L | E | F | F | D | 27,057 | 5.978 | 0.597 | ACCTTGGAGTTCTTCGAC (SEQ ID NO: 475) |
| 225 | AβC6-6 | T | V | T | W | F | D | 17,100 | 3.778 | 0.377 | ACCGTCACGTGGTTCGAC (SEQ ID NO: 476) |
| 226 | AβC6-8 | T | L | L | I | R | W | 13,135 | 2.902 | 0.290 | ACCTTGTTGATCAGGTGG (SEQ ID NO: 477) |
| 227 | AβC6-10 | T | L | K | W | L | N | 11,016 | 2.434 | 0.243 | ACCCTCAAGTGGCTGAAC (SEQ ID NO: 478) |
| 228 | AβC6-21 | T | K | E | Y | F | D | 1,231 | 0.272 | 0.027 | ACCAAGGAGTACTTCGAC (SEQ ID NO: 479) |

TABLE 4-continued

Sequences and frequency of appearance of the selected cyclic hexapeptides as
determined by high-throughput sequencing of the isolated pSICLOPPS-
NuX$_1$X$_2$X$_3$-X$_5$ vectors after the second round of bacterial sorting
for enhanced Aβ$_{42}$-GFP fluorescence.

| SEQ ID NO | Peptide name | Aminoacid sequence | | | | | | Number of reads | Reads/ Total hexapeptide reads (%) | Reads/ Total peptide reads (%) | Peptide-encoding nucleotide sequence |
|---|---|---|---|---|---|---|---|---|---|---|---|
| 229 | AβC6-26 | T | L | H | W | F | E | 647 | 0.143 | 0.014 | ACCCTCCACTGGTTCGAG (SEQ ID NO: 480) |
| 230 | AβC6-27 | T | C | S | W | F | D | 623 | 0.138 | 0.014 | ACCTGCTCGTGGTTCGAC (SEQ ID NO: 481) |
| 231 | AβC6-28 | T | L | E | Y | F | M | 556 | 0.123 | 0.012 | ACCCTCGAGTACTTCATG (SEQ ID NO: 482) |
| 232 | AβC6-32 | T | L | C | W | L | N | 455 | 0.101 | 0.010 | ACCCTGTGCTGGCTCAAC (SEQ ID NO: 483) |
| 233 | AβC6-36 | T | P | I | V | F | D | 384 | 0.085 | 0.008 | ACCCCGATCGTGTTCGAC (SEQ ID NO: 484) |
| 234 | AβC6-37 | T | L | W | V | F | D | 355 | 0.078 | 0.008 | ACCCTGTGGGTCTTCGAC (SEQ ID NO: 485) |
| 235 | AβC6-40 | T | P | L | W | F | N | 316 | 0.070 | 0.007 | ACCCCCTTGTGGTTCAAC (SEQ ID NO: 486) |
| 236 | AβC6-41 | T | S | V | E | Y | E | 307 | 0.068 | 0.007 | ACCTCGGTCGAGTACGAG (SEQ ID NO: 487) |
| 237 | AβC6-42 | T | L | G | W | L | D | 307 | 0.068 | 0.007 | ACCCTGGGCTGGTTGGAC (SEQ ID NO: 488) |
| 238 | AβC6-44 | T | P | P | W | F | D | 289 | 0.064 | 0.006 | ACCCCGCCCTGGTTCGAC (SEQ ID NO: 489) |
| 239 | AβC6-46 | T | P | C | W | F | D | 252 | 0.056 | 0.006 | ACCCCGTGCTGGTTCGAC (SEQ ID NO: 490) |
| 240 | AβC6-47 | T | L | S | W | Y | D | 239 | 0.053 | 0.005 | ACCTTGTCCTGGTACGAC (SEQ ID NO: 491) |
| 241 | AβC6-48 | T | P | V | L | V | D | 236 | 0.052 | 0.005 | ACCCCGGTCCTGGTCGAC (SEQ ID NO: 492) |
| 242 | AβC6-49 | T | L | E | Y | L | W | 233 | 0.051 | 0.005 | ACCCTCGAGTACTTGTGG (SEQ ID NO: 493) |
| 243 | AβC6-50 | T | I | F | W | F | D | 227 | 0.050 | 0.005 | ACCATCTTCTGGTTCGAC (SEQ ID NO: 494) |
| 244 | AβC6-53 | T | P | A | L | V | D | 208 | 0.046 | 0.005 | ACCCCGGCCCTGGTCGAC (SEQ ID NO: 495) |
| 245 | AβC6-55 | T | P | G | W | F | D | 180 | 0.040 | 0.004 | ACCCCCGGCTGGTTCGAC (SEQ ID NO: 496) |
| 246 | AβC6-57 | T | L | S | V | F | D | 176 | 0.039 | 0.004 | ACCTTGTCCGTCTTCGAC (SEQ ID NO: 497) |
| 247 | AβC6-58 | T | P | G | L | V | D | 142 | 0.031 | 0.003 | ACCCCCGGTCTGGTCGAC (SEQ ID NO: 498) |
| 248 | AβC6-59 | T | L | S | W | F | N | 141 | 0.031 | 0.003 | ACCCTCTCCTGGTTCAAC (SEQ ID NO: 499) |
| 249 | AβC6-63 | T | L | D | F | F | D | 114 | 0.025 | 0.003 | ACCTTGGACTTCTTCGAC (SEQ ID NO: 500) |
| 250 | AβC6-65 | T | P | S | W | F | D | 105 | 0.023 | 0.002 | ACCCCGTCCTGGTTCGAC (SEQ ID NO: 501) |
| 251 | AβC6-68 | T | P | A | L | F | D | 101 | 0.022 | 0.002 | ACCCCGGCCCTGTTCGAC (SEQ ID NO: 502) |

TABLE 4-continued

Sequences and frequency of appearance of the selected cyclic hexapeptides as
determined by high-throughput sequencing of the isolated pSICLOPPS-
NuX₁X₂X₃-X₅ vectors after the second round of bacterial sorting
for enhanced Aβ₄₂-GFP fluorescence.

| SEQ ID NO | Peptide name | Aminoacid sequence | | | | | | Number of reads | Reads/ Total hexapeptide reads (%) | Reads/ Total peptide reads (%) | Peptide-encoding nucleotide sequence |
|---|---|---|---|---|---|---|---|---|---|---|---|
| 252 | AβC6-69 | T | P | A | W | S | D | 86 | 0.019 | 0.002 | ACCCCGGCCTGGTCCGAC (SEQ ID NO: 503) |
| 253 | AβC6-78 | T | P | A | R | F | D | 55 | 0.012 | 0.001 | ACCCCGGCCCGGTTCGAC (SEQ ID NO: 504) |
| 254 | AβC6-79 | T | P | A | W | L | D | 55 | 0.012 | 0.001 | ACCCCGGCCTGGCTCGAC (SEQ ID NO: 505) |
| 255 | AβC6-80 | T | P | V | W | L | D | 55 | 0.012 | 0.001 | ACCCCGGTCTGGCTCGAC (SEQ ID NO: 506) |
| | | Sum | | | | | | 319,553 | 70.606 | 7.053 | |

III. Peptide Modifications

Peptides and polypeptides of the invention include those corresponding to linearized versions of the described cyclic oligopeptide SOD1 modulators, i.e., sequences where a break in the amino acid backbone chain of a described cyclic oligopeptide modulator has been introduced and which thereafter contains a free N-terminal NH₂ amino group and a free C-terminal—COOH carboxyl group. For example, for the cyclic pentapeptide SOD1 modulator SOD1C5-4 with amino acid sequence cyclo-TWSVW (SEQ ID NO: 4), a preferred peptide SOD1 modulator of the present invention is also a linearized version of SOD1C5-4, namely the oligopeptide NH₂-TWSVW-COOH (SEQ ID NO: 4). In addition, since the herein described oligopeptide SOD1 modulators are cyclic in nature, they do not possess a "starting point" (e.g. N terminus) or "end point" (e.g. C terminus). Thus, all circular permutants, e.g., linear variants resulting from cleavage of an existing peptide bond to introduce new termini elsewhere in the peptide sequence, of the described cyclic oligopeptide SOD1 modulators are also preferred cyclic oligopeptide SOD1 modulators of the present invention. For example, for the cyclic pentapeptide SOD1 modulator SOD1C5-4 with amino acid sequence cyclo-TWSVW (SEQ ID NO: 4), preferred peptide SOD1 modulators of the present invention are also all equivalent circular permutants of SOD1C5-4, namely the oligopeptides cyclo-WSVWT (SEQ ID NO: 507), cyclo-SVWTW (SEQ ID NO: 508), cyclo-VWTWS (SEQ ID NO: 509), and cyclo-WTWSV (SEQ ID NO: 510). Similarly, preferred peptide SOD1 modulators of the present invention are the linearized versions of all described cyclic oligopeptide SOD1 modulators and of all of their equivalent circular permutants. For example, for SOD1C5-4, apart from the modification mentioned above, preferred peptide SOD1 modulator of the present invention are linearized versions of all circular permutants equivalent SOD1C5-4, namely the oligopeptides NH₂-WSVWT-COOH (SEQ ID NO: 507), NH₂-SVWTW-COOH (SEQ ID NO: 508), NH₂-VWTWS-COOH (SEQ ID NO: 509), and NH₂-WTWSV-COOH (SEQ ID NO: 510).

Similarly, for the cyclic pentapeptide Aβ modulator AβC5-116 with amino acid sequence cyclo-TAFDR (SEQ ID NO: 86), a preferred peptide Aβ modulator of the present invention is also a linearized version of AβC5-116, namely the oligopeptide NH₂-TAFDR-COOH. In addition, since the herein described oligopeptide Aβ modulators are cyclic in nature, they do not possess a "starting point" (e.g. N terminus) or "end point" (e.g. C terminus). Thus, all circular permutants, e.g., linear variants resulting from cleavage of an existing peptide bond to introduce new termini elsewhere in the peptide sequence, of the described cyclic oligopeptide Aβ modulators are also preferred cyclic oligopeptide Aβ modulators of the present invention. For example, for the cyclic pentapeptide Aβ modulator AβC5-116 with amino acid sequence cyclo-TAFDR (SEQ ID NO: 86), preferred peptide Aβ modulators of the present invention are also all equivalent circular permutants of AβC5-116, namely the oligopeptides cyclo-AFDRT (SEQ ID NO: 511), cyclo-FDRTA and NH₂-FDRTA-COOH (SEQ ID NO: 512), cyclo-DRTAF (SEQ ID NO: 513), and cyclo-RTAFD (SEQ ID NO: 514). Similarly, preferred peptide Aβ modulators of the present invention are the linearized versions of all described cyclic oligopeptide Aβ modulators and of all of their equivalent circular permutants. For example, for AβC5-116, apart from the modification mentioned above, preferred peptide Aβ modulator of the present invention are linearized versions of all circular permutants equivalent AβC5-116, namely the oligopeptides NH₂-AFDRT-COOH (SEQ ID NO: 511), NH₂-FDRTA-COOH (SEQ ID NO: 512), NH₂-DRTAF-COOH (SEQ ID NO: 513), and NH₂-RTAFD-COOH (SEQ ID NO: 514).

Peptides and polypeptides of the invention include those containing conservative amino acid substitutions. Such peptides and polypeptides are encompassed by the invention provided the peptide or polypeptide can bind to SOD1 or Aβ. As used herein, suitable conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p. 224). Such substitutions can be made in accordance with those set forth as follows: Ala (A) Gly; Ser Arg (R) Lys Asn (N) Gln; His Cys (C) Ser Gln (Q) Asn Glu (E) Asp Gly (G) Ala; Pro His (H) Asn; Gln Ile (I) Leu; Val Leu (L.) Ile; Val Lys (K) Arg; Gln; Glu Met (N) Leu; Tyr;

Ile Phe (F) Met; Leu; Tyr Ser (S) Thr Thr (T) Ser Trp (W) Tyr Tyr (Y) Trp; Phe Val (V) Ile; Leu. Other substitutions also are permissible and can be determined empirically or in accord with known conservative substitutions.

The peptidic compounds of the present invention can inhibit protein misfolding and aggregation, wherein said peptidic compounds can be a head-to-tail cyclic peptide, side-chain-to-tail cyclic peptide, bicyclic peptide, lanthipeptide, linaridin, proteusin, cyanobactin, thiopeptide, bottromycin, microcin, lasso peptide, microviridin, amatoxin, phallotoxin, θ-defensin, orbitide, or cyclotide.

The peptidic compounds of the present invention also serve as structural models for non-peptidic molecules or "mimetics" with similar biological activity. One can also readily modify peptides by phosphorylation, and other methods for making peptide derivatives of the compounds of the present invention are described in Hruby, et al. Biochm. J. 268(2): 249-262, 1990, incorporated herewith by reference. Thus, the peptide compounds of the invention also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan and Gainor, Ann. Rep. Med. Chem. 24:243-252, 1989, incorporated herein by reference. These techniques include replacing the peptide backbone with a backbone composed of phosphonates, amidates, carbamates, sulfonamides, and secondary amines.

The term mimetic, and in particular, peptidomimetic, is intended to include isosteres. The term "isostere" as used herein is intended to include a chemical structure that can be substituted for a second chemical structure because the steric conformation of the first structure fits a binding site specific for the second structure. The term specifically includes peptide backbone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH2S], ψ[CH2NH], ψ[CSNH2], ψ[NHCO], ψ[COCH2], and ψ[(E) or (Z) CH=CH]. In the nomenclature used above, ψ indicates the absence of an amide bond. The structure that replaces the amide group is specified within the brackets. Other examples of isosteres include peptides substituted with one or more benzodiazepine molecules (see e.g., James, G. L. et al. (1993) Science 260:1937-1942).

Other possible modifications include an N-alkyl (or aryl) substitution (ψ[CONR]), backbone crosslinking to construct lactams and other cyclic structures, substitution of all D-amino acids for all L-amino acids Within the compound ("inverso" compounds) or retro-inverso amino acid incorporation (ψ[NHCO]). By "inverso" is meant replacing L-amino acids of a sequence With D-amino acids, and by "retro-inverso" or "enantio-retro" is meant reversing the sequence of the amino acids ("retro") and replacing the L-amino acids With D-amino acids. For example, if the parent peptide is Thr-Ala-Tyr, the retro modified form is Tyr-Ala-Thr, the inverso form is thr-ala-tyr, and the retro inverso form is tyr-ala-thr (lower case letters refer to D-amino acids). Compared to the parent peptide, a retro-inverso peptide has a reversed backbone while retaining substantially the original spatial conformation of the side chains, resulting in a retro-inverso isomer with a topology that closely resembles the parent peptide. See Goodman et al. "Perspectives in Peptide Chemistry" pp. 283-294 (1981). See also U.S. Pat. No. 4,522,752 by Sisto for further description of "retro-inverso" peptides.

Preferably, the modulator compound inhibits aggregation of SOD1 or natural β-amyloid peptides when contacted with SOD1 or the natural β-amyloid peptides, and/or inhibits SOD1 or Aβ neurotoxicity. Alternatively, the modulator compound can promote aggregation of SOD1 or natural β-amyloid peptides when contacted with the SOD1 or natural β-amyloid peptides. The type and number of modifying groups coupled to the modulator are selected such that the compound alters (and preferably inhibits) aggregation of SOD1 or natural β-amyloid peptides when contacted with SOD1 or the natural β-amyloid peptides. A single modifying group can be coupled to the modulator or, alternatively, multiple modifying groups can be coupled to the modulator.

Within a modulator compound of the invention, a peptidic structure (such as a cyclic oligopeptide SOD1 or Aβ modulator or an amino acid sequence corresponding to a rearranged or modified cyclic oligopeptide SOD1 or Aβ modulator) is coupled directly or indirectly to at least one modifying group. The term "modifying group" is intended to include structures that are directly attached to the peptidic structure (e.g., by covalent coupling), as well as those that are indirectly attached to the peptidic structure (e.g., by a stable non-covalent association or by covalent coupling to additional amino acid residues, or mimetics, analogues or derivatives thereof, which may flank the cyclic oligopeptide SOD1 or Aβ modulator). For example, the modifying group can be coupled to a side chain of at least one amino acid residue of a cyclic oligopeptide SOD1 or Aβ modulator, or to a peptidic or peptidomimetic region flanking the cyclic oligopeptide SOD1 or Aβ modulator (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain). Modifying groups covalently coupled to the peptidic structure can be attached by means and using methods well known in the art for linking chemical structures, including, for example, amide, alkylamino, carbamate or urea bonds.

The modifying group(s) is selected such that the modulator compound alters, and preferably inhibits, SOD1 or β-amyloid peptides aggregation when contacted with SOD1 or the β-amyloid peptides or inhibits the neurotoxicity of SOD1 or the β-amyloid peptides when contacted by them. Although not intending to be limited by mechanism, the modifying group(s) of the modulator compounds of the invention is thought to function as a key pharmacophore which is important for conferring on the modulator the ability to disrupt SOD1 or Aβ aggregation.

In one embodiment, the modifying group is a "biotinyl structure", which includes biotinyl groups and analogues and derivatives thereof (such as a 2-iminobiotinyl group). In another embodiment, the modifying group can comprise a "fluorescein-containing group", such as a group derived from reacting a SOD1- or an Aβ-derived peptidic structure with 5-(and 6-)-carboxyfluorescein, succinimidyl ester or fluorescein isothiocyanate. In various other embodiments, the modifying group(s) can comprise an N-acetylneuraminyl group, a trans-4-cotininecarboxyl group, a 2-imino-1-imidazolidineacetyl group, an (S)-(–)-indoline-2-carboxyl group, a (–)-menthoxyacetyl group, a 2-norbornaneacetyl group, a γ-oxo-5-acenaphthenebutyryl, a (–)-2-oxo-4-thiazolidinecarboxyl group, a tetrahydro-3-furoyl group, a 2-iminobiotinyl group, a diethylenetriaminepentaacetyl group, a 4-morpholinecarbonyl group, a 2-thiopheneacetyl group or a 2-thiophenesulfonyl group.

Preferred modifying groups include groups comprising cholyl structures, biotinyl structures, fluorescein-containing groups, a diethylene-triaminepentaacetyl group, a (–)-menthoxyacetyl group, and a N-acetylneuraminyl group. More preferred modifying groups those comprising a cholyl structure or an iminiobiotinyl group. Yet another type of modifying group is a compound that contains a non-natural amino acid.

SOD1 or β-amyloid modulator compounds of the invention can be further modified to alter the specific properties of the compound while retaining the ability of the compound to alter SOD1 or Aβ aggregation and inhibit SOD1 or Aβ neurotoxicity. For example, in one embodiment, the compound is further modified to alter a pharmacokinetic property of the compound, such as in vivo stability or half-life. In another embodiment, the compound is further modified to label the compound with a detectable substance. In yet another embodiment, the compound is further modified to couple the compound to an additional therapeutic moiety. To further chemically modify the compound, such as to alter the pharmacokinetic properties of the compound, reactive groups can be derivatized.

A modulator compound can be further modified to label the compound by reacting the compound with a detectable substance. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{14}C$, $^{123}I$, $^{124}I$, $^{125}I$, $^{131}I$, $^{99m}Tc$, $^{35}S$ or $^{3}H$. In a preferred embodiment, a modulator compound is radioactively labeled with 14C, either by incorporation of $^{14}C$ into the modifying group or one or more amino acid structures in the modulator compound. Labeled modulator compounds can be used to assess the in vivo pharmacokinetics of the compounds, as well as to detect SOD1 or Aβ aggregation, for example for diagnostic purposes. SOD1 or Aβ aggregation can be detected using a labeled modulator compound either in vivo or in an in vitro sample derived from a subject.

Preferably, for use as an in vivo diagnostic agent, a modulator compound of the invention is labeled with radioactive technetium or iodine. Accordingly, in one embodiment, the invention provides a modulator compound labeled with technetium, preferably $^{99m}Tc$. Methods for labeling peptide compounds with technetium are known in the art (see e.g., U.S. Pat. Nos. 5,443,815, 5,225,180 and 5,405, 597, all by Dean et al.; Stepniak-Biniakiewicz, D., et al. (1992) J. Med. Chem. 35:274-279; Fritzberg, A. R., et al. (1988) Proc. Natl. Acad. Sci. USA 85:4025-4029; Baidoo, K. E., et al. (1990) Cancer Res. Suppl. 50:799s-803s; and Regan, L. and Smith, C. K. (1995) Science 270:980-982).

Furthermore, an additional modification of a modulator compound of the invention can serve to confer an additional therapeutic property on the compound. That is, the additional chemical modification can comprise an additional functional moiety. For example, a functional moiety which serves to break down or dissolve amyloid plaques can be coupled to the modulator compound. In this form, the modified modulator serves to target the compound to SOD1 or Aβ peptides and disrupt their polymerization, whereas the additional functional moiety serves to break down or dissolve SOD1 aggregates or amyloid plaques after the compound has been targeted to these sites.

In an alternative chemical modification, a SOD1 or β-amyloid compound of the invention is prepared in a "prodrug" form, wherein the compound itself does not modulate aggregation, but rather is capable of being transformed, upon metabolism in vivo, into a SOD1 or β-amyloid modulator compound as defined herein. For example, in this type of compound, the modulating group can be present in a prodrug form that is capable of being converted upon metabolism into the form of an active modulating group. Such a prodrug form of a modifying group is referred to herein as a "secondary modifying group." A variety of strategies are known in the art for preparing peptide prodrugs that limit metabolism in order to optimize delivery of the active form of the peptide-based drug (see e.g., Moss, J. (1995) in Peptide-Based Drug Design: Controlling Transport and Metabolism, Taylor, M. D. and Amidon, G. L. (eds), Chapter 18. Additionally strategies have been specifically tailored to achieving CNS delivery based on "sequential metabolism" (see e.g., Bodor, N., et al. (1992) Science 257:1698-1700; Prokai, L., et al. (1994) J. Am. Chem. Soc. 116:2643-2644; Bodor, N. and Prokai, L. (1995) in Peptide-Based Drug Design: Controlling Transport and Metabolism, Taylor, M. D. and Amidon, G. L. (eds), Chapter 14. In one embodiment of a prodrug form of a modulator of the invention, the modifying group comprises an alkyl ester to facilitate blood-brain barrier permeability.

Modulator compounds of the invention can be prepared by chemical synthesis using standard techniques known in the art. The peptide component of a modulator composed, at least in part, of a peptide, can be synthesized using standard techniques such as those described in Bodansky, M. Principles of Peptide Synthesis, Springer Verlag, Berlin (1993) and Grant, G. A. (ed.). Synthetic Peptides: A User's Guide, W. H. Freeman and Company, New York (1992). Automated peptide synthesizers are commercially available (e.g., Advanced ChemTech Model 396; Milligen/Biosearch 9600). Additionally, one or more modulating groups can be attached to the SOD1 or Aβ modulator (e.g., a SOD1 or an Aβ aggregation core domain) by standard methods, for example using methods for reaction through an amino group, a carboxyl group, a hydroxyl group (e.g., on a tyrosine, serine or threonine residue) or other suitable reactive group on an amino acid side chain (see e.g., Greene, T. W. and Wuts, P. G. M. Protective Groups in Organic Synthesis, John Wiley and Sons, Inc., New York (1991)).

Alternatively, modulator compounds of the invention can be prepared biosynthetically and isolated in pure or enriched form from a recombinant production host, such a bacterial, yeast, plant, or mammalian cell (see, e.g., Scott C P, Abel-Santos E, Jones A D, Benkovic S J, Structural requirements for the biosynthesis of backbone cyclic peptide libraries. Chem Biol. 2001 August; 8(8):801-15, as an example of recombinant production of cyclic oligopeptides in bacterial cells).

Alternatively, modulator compounds of the invention can be prepared biosynthetically from a recombinant production host, such a bacterial, yeast, plant, or mammalian cell, but may not be isolated in pure or enriched form, and instead be provided to the diseased organism as part of recombinant production host, such a bacterial, yeast, plant, or mammalian cell producing the specific modulator compound recombinantly in the form of a probiotic. By the term "probiotic", we mean living microorganisms or other cultured cells that may provide health benefits when administered and consumed in adequate amounts (see, e.g., O'Toole P W, Marchesi J R, Hill C, Next-generation probiotics: the spectrum from probiotics to live biotherapeutics, Nat Microbiol. 2017 Apr. 25; 2:17057).

IV. Hybrid Modulators

A hybrid molecule of the invention includes a peptide or polypeptide that binds to the amyloid or non-amyloid form of SOD1 or amyloid form of Aβ, and a scaffold molecule. The scaffold molecule can include a diagnostic or therapeutic reagent. The therapeutic or diagnostic reagent can be a polypeptide, small molecule or compound.

In particular, provided herein are hybrid molecules, such as hybrid polypeptides, that include a peptide or polypeptide provided herein, and additional amino acid residues (typically, 5, 10, 15, 20, 30, 40, 50, 100 or more) such that the resulting hybrid molecule specifically interacts with SOD1 or Aβ. The motif can be modified, such as by replacing certain amino acids or by directed and random evolution methods, to produce motifs with greater affinity. As used herein, a hybrid polypeptide refers to a polypeptide that includes regions from at least two sources, such as from an antibody or enzyme or other scaffold that can be a recipient, and a binding motif, such as a polypeptide or peptide that binds to an amyloid or non-amyloid form of SOD1 or the amyloid form of the Aβ peptide.

Thus, among the hybrid molecules provided herein are hybrid molecules, particularly hybrid polypeptides that are produced by grafting a binding motif (e.g., peptide) from one molecule into a scaffold, such as an antibody or fragment thereof or an enzyme or other reporter molecule. The hybrid polypeptides provided herein, even the hybrid immunoglobulins, are not antibodies per se, but are polypeptides that are hybrid molecules containing a selected motif (e.g., a peptide that binds to the amyloid or non-amyloid form of SOD1 or the amyloid form of the Aβ peptide) inserted into another polypeptide such that the motif retains or obtains the ability to bind to a protein involved in disease of protein aggregation. The hybrid polypeptides can include portions of antibodies or other scaffolds, but they also include a non-immunoglobulin or non-scaffold portion grafted therein. The non-immunoglobulin portion is identified by its ability to specifically bind to a targeted polypeptide isoform. The hybrid polypeptide can specifically bind to the targeted infectious or disease-related or a selected isoform of a polypeptide as monomer with sufficient affinity to detect the resulting complex or to precipitate the targeted polypeptide.

The scaffold is selected so that insertion of the motif therein does not substantially alter (i.e., retains) the desired binding specificity of the motif. The scaffold additionally can be selected for its properties, such as its ability to act as a reporter.

Methods for production of hybrid molecules that specifically interact with a one form of a conformer of a protein associated with a disease of protein conformation or involving protein aggregation are provided. In these methods a polypeptide motif from the protein is inserted into a scaffold such that the resulting molecule exhibits specific binding to one conformer compared to other conformers. In particular, the hybrid molecule can exhibit specific binding to the amyloid or non-amyloid form of SOD1 or the amyloid form of the Aβ peptide.

Peptides of the invention have been shown to bind to SOD1 or Aβ in vitro and in vivo. The peptides can be incorporated into a scaffold that comprises additional amino acid sequences and/or compounds. The hybrid molecule can then be used to label or treat the aggregates associated with SOD1 or plaques associated with Aβ amyloid. The polypeptides, nucleic acids encoding the polypeptides, and methods of using the polypeptides or nucleic acids can be used to identify, diagnose and/or treat disorders associated with plaque formation in brain tissue.

Any molecule, such as a polypeptide, into which the selected polypeptide motif is inserted (or linked) such that the resulting hybrid polypeptide has the desired binding specificity, is contemplated for use as part of the hybrid molecules herein. The polypeptides can be inserted into any sequence of amino acids that at least contains a sufficient number (10, 20, 30, 50, 100 or more amino acids) to properly present the motif for binding to the targeted amyloid plaque. The purpose of the scaffold is to present the motif to the targeted polypeptide in a form that binds thereto. The scaffold can be designed or chosen to have additional properties, such as the ability to serve as a detectable marker or label or to have additional binding specificity to permit or aid in its use in assays to detect particular isoforms of a target protein (e.g., the amyloid or non-amyloid form of SOD1 or the amyloid form of the Aβ peptide) or for screening for therapeutics or other assays and methods.

The scaffolds include reporter molecules, such as fluorescent proteins and enzymes or fragments thereof, and binding molecules, such as antibodies or fragments thereof. Selected scaffolds include all or portions of antibodies, enzymes, such as luciferases, alkaline phosphatases, β-galactosidases and other signal-generating enzymes, chemiluminescence generators, such as horseradish peroxidase; fluorescent proteins, such as red, green and blue fluorescent proteins, which are well known; and chromogenic proteins.

The peptide motif is inserted into the scaffold in a region that does not disturb any desired activity. The scaffolds can include other functional domains, such as an additional binding site, such as one specific for a second moiety for detection.

V. Nucleic Acid Molecules

Nucleic acid molecules encoding any of the peptides, polypeptides or hybrid polypeptides provided herein are provided in the general experimental procedures. Such molecules can be introduced into plasmids and vectors for expression in suitable host cells. As used herein, the term "nucleic acid" refers to single-stranded and/or double-stranded polynucleotides such as deoxyribonucleic acid (DNA), and ribonucleic acid (RNA) as well as analogs or derivatives of either RNA or DNA. Also included in the term "nucleic acid" are analogs of nucleic acids such as peptide nucleic acid (PNA), phosphorothioate DNA, and other such analogs and derivatives or combinations thereof. The term should be understood to include, as equivalents, derivatives, variants and analogs of either RNA or DNA made from nucleotide analogs, single (sense or antisense) and double-stranded polynucleotides. Deoxyribonucleotides include deoxyadenosine, deoxycytidine, deoxyguanosine and deoxythymidine. For RNA, the uracil base is uridine.

Plasmids and vectors containing the nucleic acid molecules also are provided in the general experimental procedures. Cells containing the vectors, including cells that express the encoded proteins are also provided. The cell can be a bacterial cell, a yeast cell, a fungal cell, a plant cell, an insect cell or an animal cell. Methods for producing a cyclic oligopeptide or a hybrid polypeptide, for example, growing the cell under conditions whereby the encoded polypeptide is expressed by the cell, and recovering the expressed protein, are provided herein. The cells are used for expression of the cyclic oligopeptide or the protein, which can be secreted or expressed in the cytoplasm. The hybrid poly-peptides also can be chemically synthesized using standard methods of protein synthesis known in the art.

VI. Pharmaceutical Compositions

It is envisioned that one would use the modulators of the present invention as an Alzheimer's disease or amyotrophic lateral sclerosis therapeutic. If the modulator were peptide in nature, one could use a gene therapy technique to deliver DNA constructs encoding the modulator to the affected sites. For drug formulations, one would expect that the formula-tions reach and be effective at the affected site. These modulators would more likely be carbohydrate and peptide mixtures, especially mixtures capable of overcoming the blood brain barrier. For examples, see Tamai, et al., Adv. Drug Delivery Review 19:401-424, 1996, hereby incorpo-rated by reference. In these cases, the disrupting element of the modulators would also facilitate transport across the blood-brain barrier.

Thus, the present invention encompasses methods for therapeutic treatments of amyotrophic lateral sclerosis and Alzheimer's disease, comprising administering a compound of the invention in amounts sufficient to modulate the natural course of SOD1 or Aβ aggregation. Accordingly, the present invention includes pharmaceutical compositions compris-ing, as an active ingredient, at least one of the peptides or other compounds of the invention in association with a pharmaceutical carrier or diluent. The compounds of the invention can be administered by oral, parenteral (intramus-cular, intraperitoneal, intravenous (IV) or subcutaneous injection), transdermal, nasal, vaginal, rectal, or sublingual routes of administration.

Solid dosage forms for oral administration include cap-sules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magne-sium stearate. In the case of capsules, tablets, and pills, the dosage forms may also comprise buffering agents. Tablets and pills can additionally be prepared with enteric coatings.

Liquid dosage forms for oral administration include phar-maceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solu-tions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through bacteria-retain-ing filters, by incorporating sterilizing agents into the com-positions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration area are also prepared with standard excipi-ents well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired.

The following examples illustrate aspects of the present invention including the construction and screening of a peptide macrocycle library; the identification of macrocyclic peptide rescuers of the misfolding and aggregation of the prominent PMD-associated protein target SOD1 and fALS-associated variants thereof, as well as as a second prominent PMD-associated protein target, Aβ, and finally their use in rescuing of SOD1 and Aβ aggregation and toxicity in vitro and in vivo. The Examples are not in any way limiting the scope of invention.

EXAMPLES

Example 1

Combinatorial libraries of random cyclic tetra-, penta-, and hexapeptides have been selected to be studied as poten-tial rescuers of SOD1 and mutant SOD1 misfolding and pathogenic aggregation. A technique named split intein circular ligation of peptides and proteins (SICLOPPS) (U.S. Pat. No. 7,354,756 B1 "Intein-mediated cyclization of pep-tides") for producing peptide libraries in E. coli is being used. SICLOPPS uses split inteins, i.e. self-splicing protein elements, for performing N- to C-terminal peptide cycliza-tion and biosynthesize cyclic peptides as short as four amino acids long. The only requirement for the intein splicing reaction and peptide cyclization to occur is the presence of a nucleophilic amino acids cysteine (C), serine (S), or threonine (T) as the first amino acid of the extein following the C-terminus of the intein.

Figure 1A:
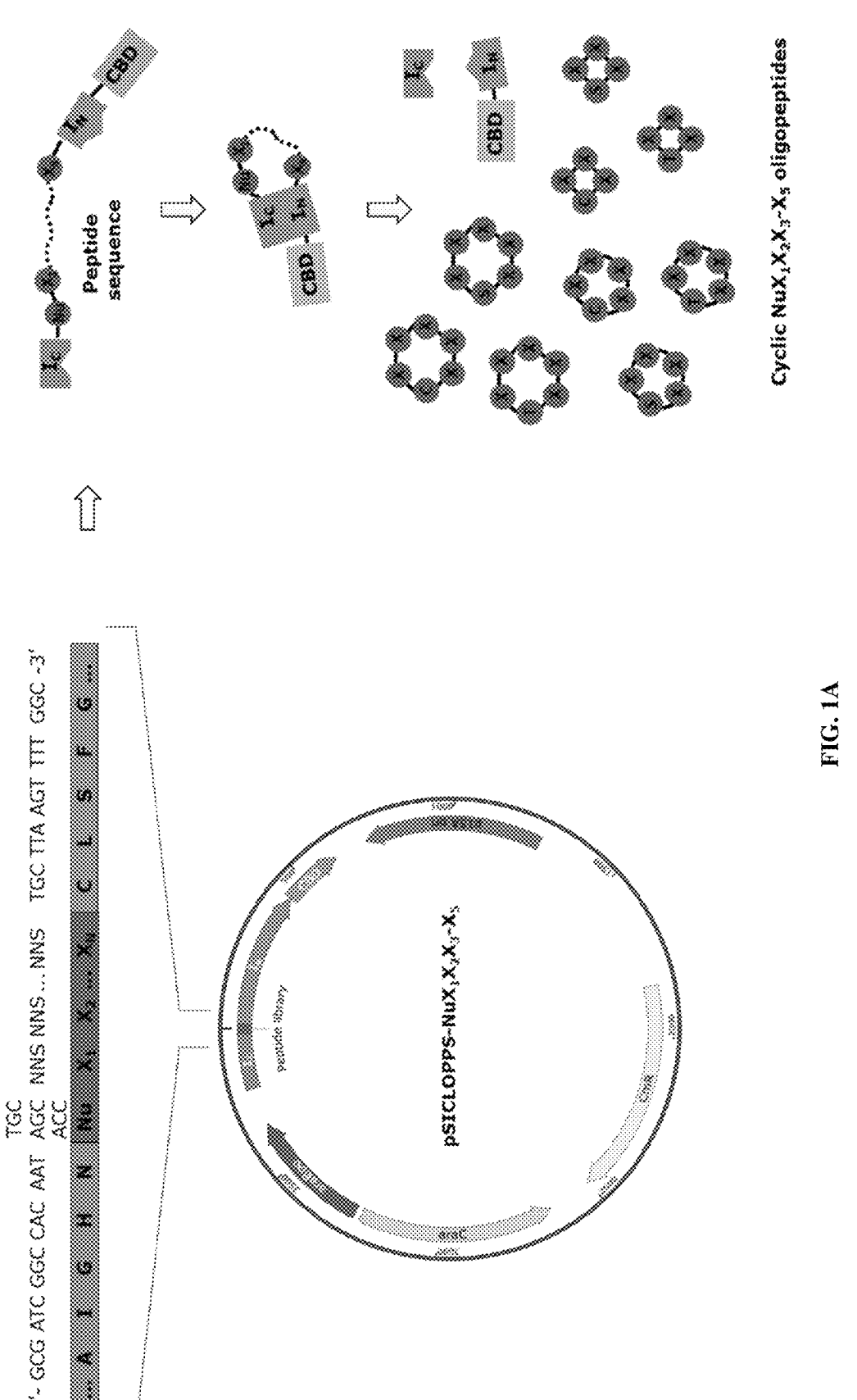

In order for the inventors to maximize the diversity of the libraries, they chose to study peptides with the general formula cyclo-NuX$_1$X$_2$ . . . X$_N$, where Nu=C, S or T; X is any one of the twenty natural amino acids and N=3-5 (FIG. 1A). The maximum theoretical diversity of the combined cyclo-NuX$_1$X$_2$X$_3$-X$_5$ library is >10 million different sequences (FIG. 1B). The libraries of genes encoding this combinatorial library of random cyclic oligopeptides were constructed using degenerate codons. The inventors con-structed the high diversity pSICLOPPS-NuX$_1$X$_2$X$_3$-X$_5$ vec-tor library which is expected to be encoding all of the theoretically possible designed cyclic tetra-, penta-, and hexapeptide NuX$_1$X$_2$X$_3$-X$_5$ sequences using molecular biol-ogy techniques already known and used in the art.

Figure 2C:
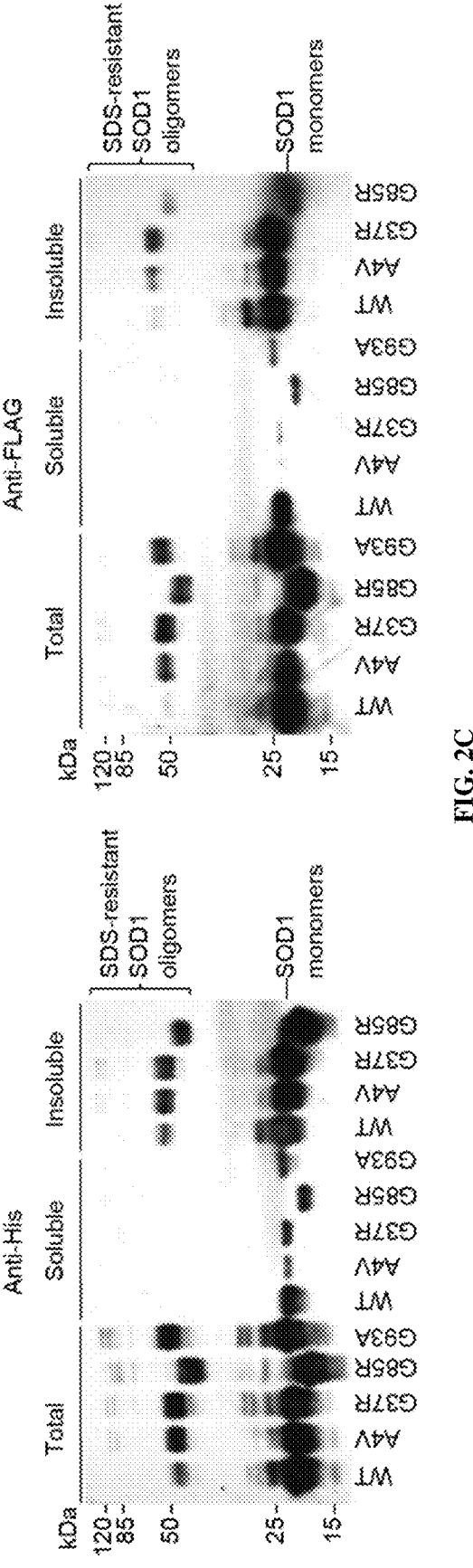

It has been demonstrated previously that the fluorescence of E. coli cells expressing a recombinant protein whose C terminus is fused to GFP correlates well with the amount of soluble and folded protein (Waldo G S, Standish B M, Berendzen J, Terwilliger T C. Nat Biotechnol. 1999 July; 17(7):691-5). Based on this, the inventors reasoned that the fluorescence of MisP-GFP fusions can serve as a reliable reporter for the identification of chemical rescuers of MisP misfolding for a number of disease-associated MisPs, including SOD1. In order to test this hypothesis, the inven-tors generated fusions of SOD1 variants, whose misfolding and aggregation have been linked with the pathology of familial forms of ALS (fALS), with GFP. Expression of these fusions in E. coli, yielded levels of cellular fluorescence, which were significantly decreased compared to that of the generally non-pathogenic, wild-type SOD1 (FIG. 2A). Western blot analysis indicated that this occurs because the accumulation of soluble SOD1-GFP is decreased in the presence of misfolding-inducing amino acid substitutions, which in turn takes place due to enhanced misfolding/aggregation of GFP-fused, as well as fusion-free SOD1 (FIG. 2B, 2C). Thus, the fluorescence of *E. coli* cells overexpressing SOD1-GFP fusions appears to be a good indicator of SOD1 folding and misfolding.

Example 2

Figure 3C:
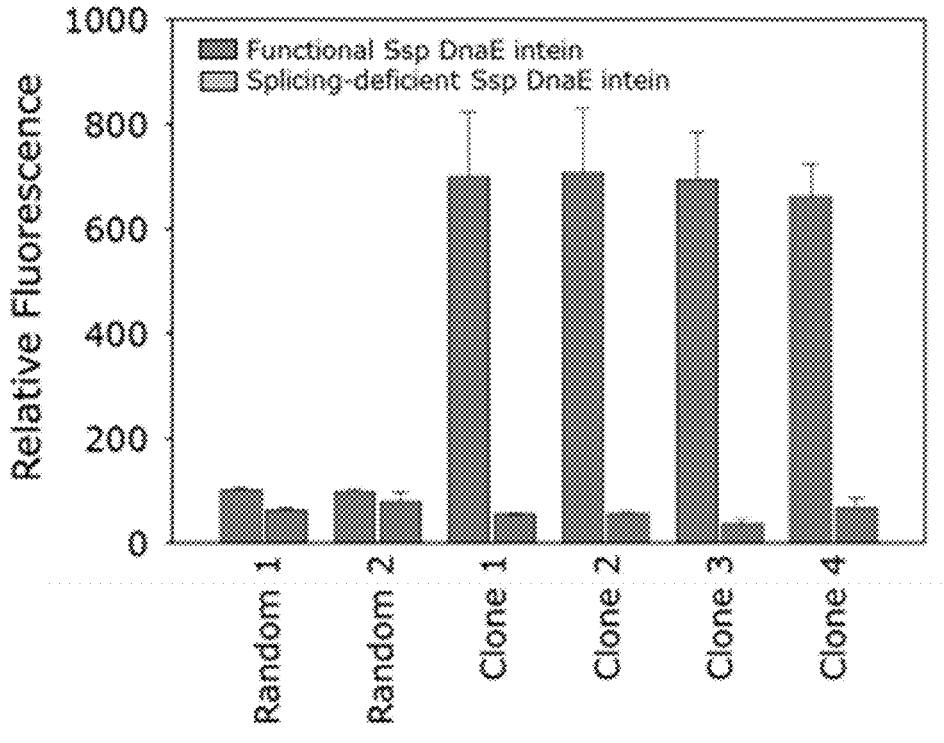
Figure 3D:
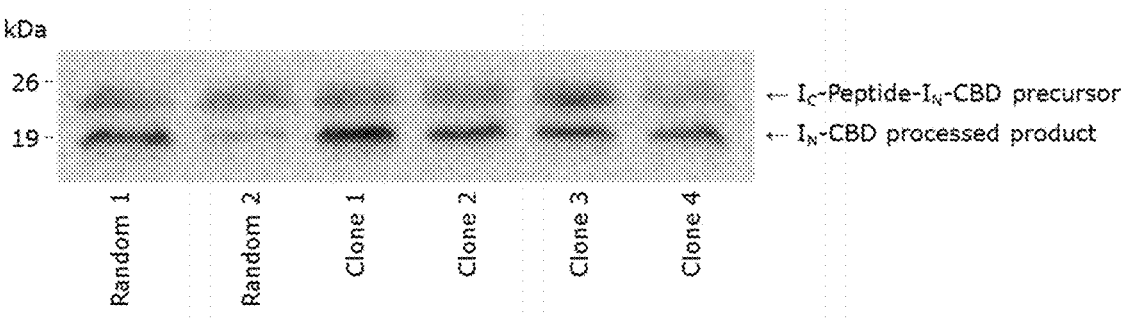
Figure 3E:
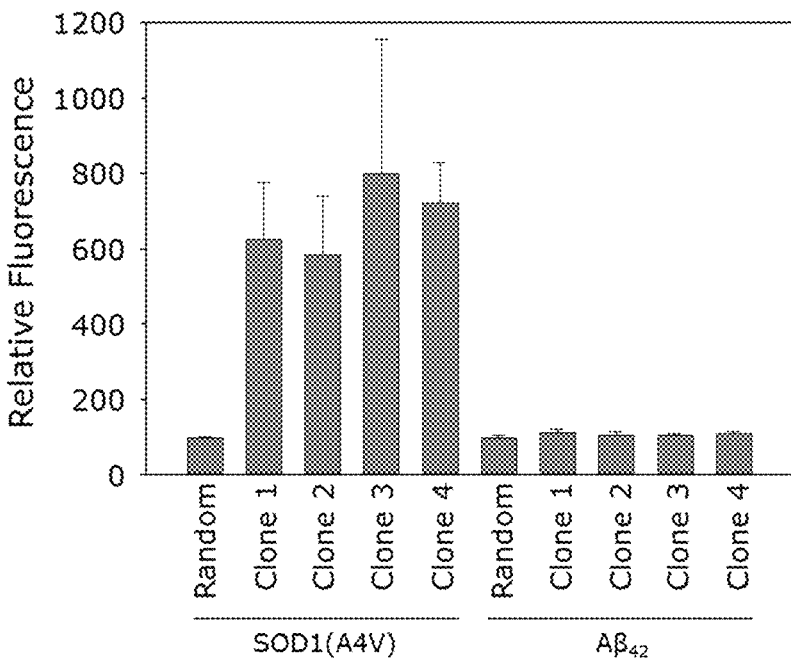
Figure 3F:
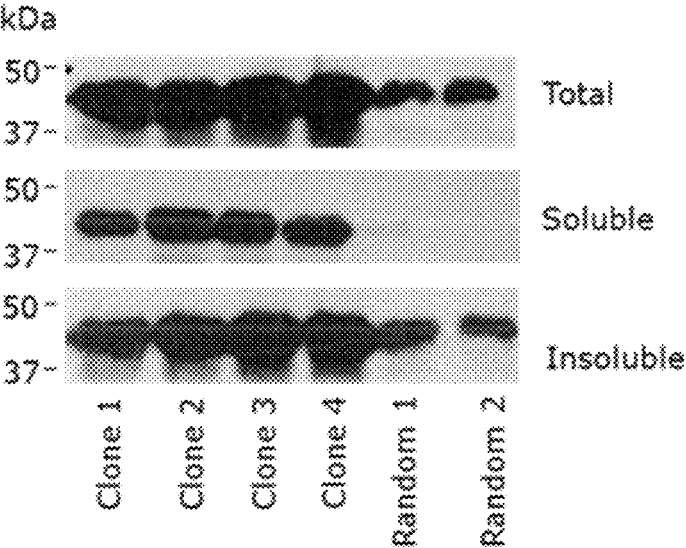

To test whether the bacterial platform can be utilized to identify chemical rescuers of disease-associated SOD1, the inventors screened for cyclic oligopeptides that inhibit the aggregation of SOD1(A4V), a fALS-associated variant, whose misfolding and aggregation causes a very aggressive form of the disease with an average survival time of only 1.2 years after diagnosis. FACS screening of the cyclo-NuX$_1$X$_2$X$_3$-X$_5$ oligopeptide library for bacterial clones exhibiting enhanced levels of SOD1(A4V)-GFP fluorescence yielded an *E. coli* population with about 10-fold increased fluorescence after four rounds of sorting (FIGS. 3A, 3B). Twenty randomly selected clones from the isolated population exhibited up to 10-fold enhanced fluorescence compared to *E. coli* cells producing randomly selected cyclic oligopeptides from the initial library. Four of the isolated clones exhibited the highest levels of cellular SOD1 (A4V)-GFP fluorescence (FIG. 3C), and were selected for further analysis. These clones (i) expressed tetra-partite I$_C$-peptide-I$_N$-CBD fusions, which could undergo splicing (FIG. 3D), (ii) exhibited splicing-activity-dependent enhanced SOD1(A4V)-GFP fluorescence (FIG. 3C), and (iii) exhibited SOD1-specific enhancement of bacterial fluorescence (FIG. 3E). Western blot analysis indicated that this enhanced SOD1(A4V)-GFP fluorescence phenotype occurs due to accumulation of enhanced amounts of soluble SOD1 (A4V) in these clones (FIG. 3F). Sequencing of the peptide-encoding region of the pSICLOPPS vector contained in these clones revealed that they all encode cyclic pentapeptides with sequences TASFW (SEQ ID NO: 2), TWSVW (SEQ ID NO: 4), and TFSMW (SEQ ID NO: 6) (FIG. 3G), thus indicating a dominant cyclo-TXSXW bioactive motif.

Example 3

Figure 4B:
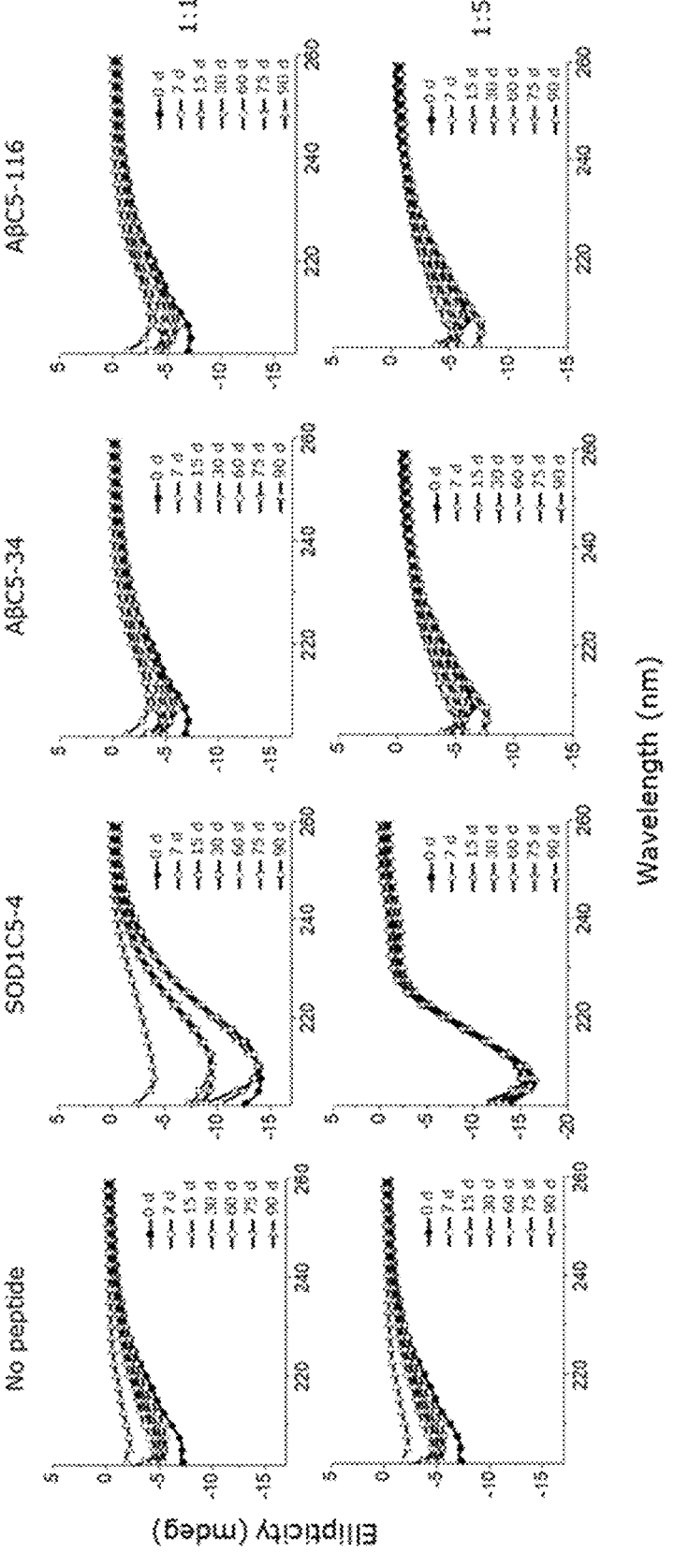
Figure 4C:
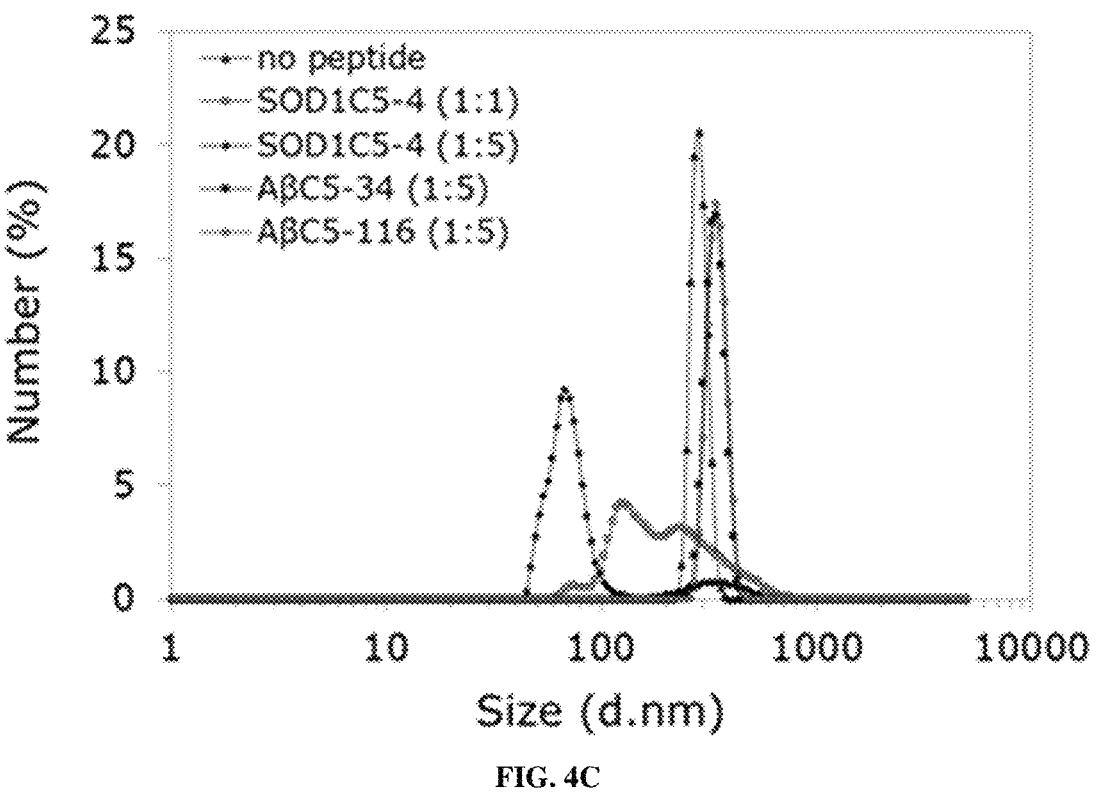
Figure 4D:
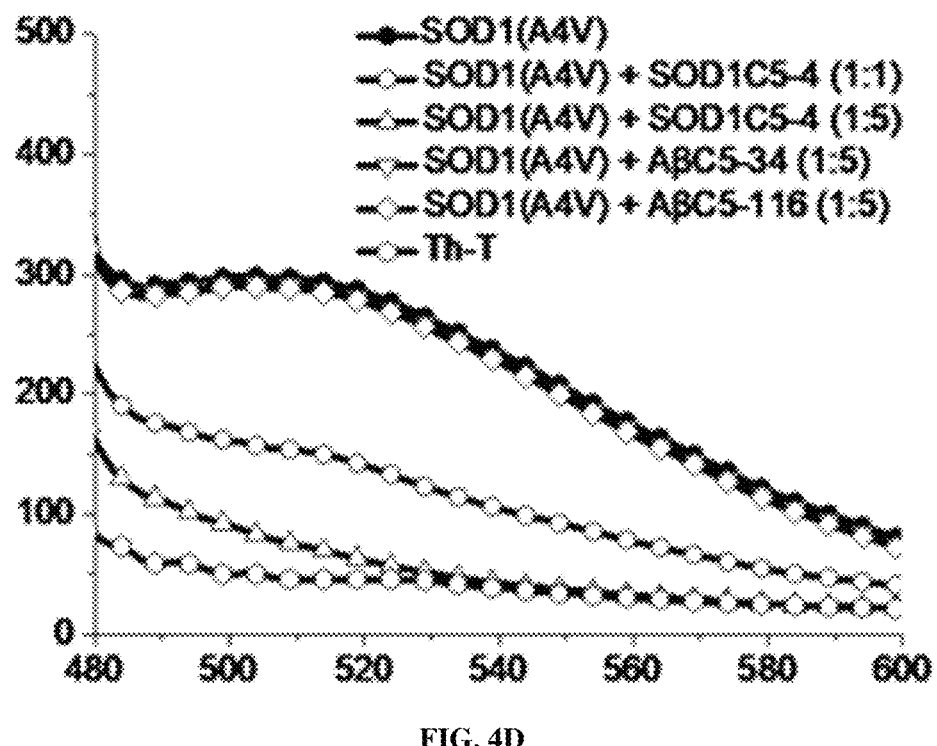
Figure 4E:
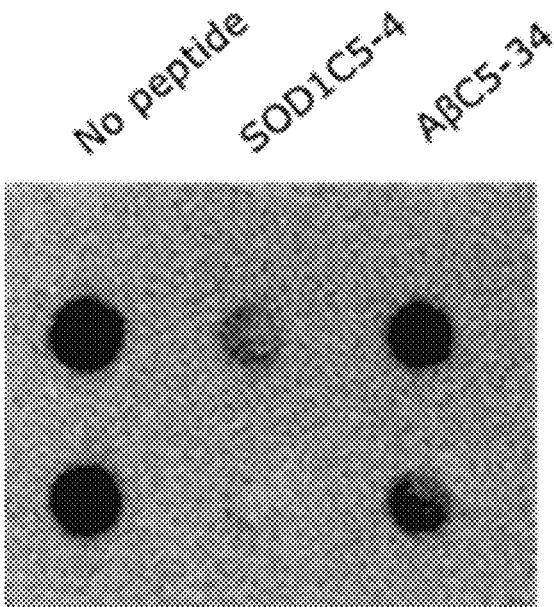

The peptide cyclo-TWSVW (SEQ ID NO: 4), hereafter referred to as SOD1C5-4 (FIG. 4A), which was present twice among the four selected clones, was selected for further analysis and was produced in mg quantities by solid-phase synthesis. Isolated SOD1(A4V) was utilized to assess the effect of the selected cyclic pentapeptide SOD1C5-4 on its aggregation process. CD spectroscopy indicated that SOD1C5-4—but not the control Aβ-targeting cyclic pentapeptides AβC5-34 or AβC5-116—interacts with SOD1(A4V), and that the time-dependent conformational transition that is indicative of SOD1(A4V) aggregation is significantly delayed in the presence of SOD1C5-4 (FIG. 4B). Moreover, dynamic light scattering (DLS) analysis revealed that SOD1C5-4 addition results in the time-dependent formation of oligomeric/aggregated SOD1(A4V) species with markedly smaller sizes (FIG. 4C). Detection of large, amyloid-like SOD1(A4V) aggregates by ThT staining and a filter retardation assay indicated that the formation of such species was dramatically decreased in the presence of SOD1C5-4 (FIGS. 4D and 4E). Finally, staining of SOD1

Figure 4F:
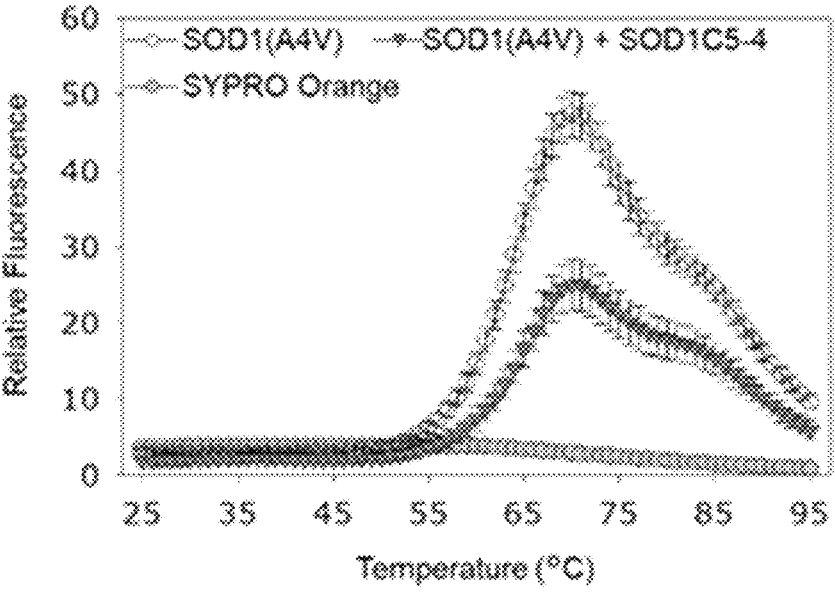

(A4V) with the conformation-sensitive dye SYPRO Orange under heat-induced denaturation conditions, suggested that the aggregation-inhibitory action of SOD1C5-4 may be occurring due to its ability to decrease the propensity of SOD1(A4V) to expose hydrophobic surfaces (FIG. 4F), a feature which has been proposed to be a molecular determinant of the pathogenesis of fALS-associated SOD1 variants (Münch C, Bertolotti A. J Mol Biol. 2010; 399(3):512-25). Taken together, these results demonstrate that SOD1C5-4 is an efficient and specific rescuer of SOD1 (A4V) misfolding and aggregation.

Example 4

The protective effects of SOD1C5-4 in mammalian cells were evaluated in human embryonic kidney 293 (HEK293) cells transiently expressing SOD1(A4V)-GFP. Cells treated with SOD1C5-4 exhibited higher fluorescence, fewer inclusions comprising aggregated SOD1(A4V)-GFP, and higher viability compared to untreated cells (FIGS. 5A-5C).

Example 5

Figure 6A:
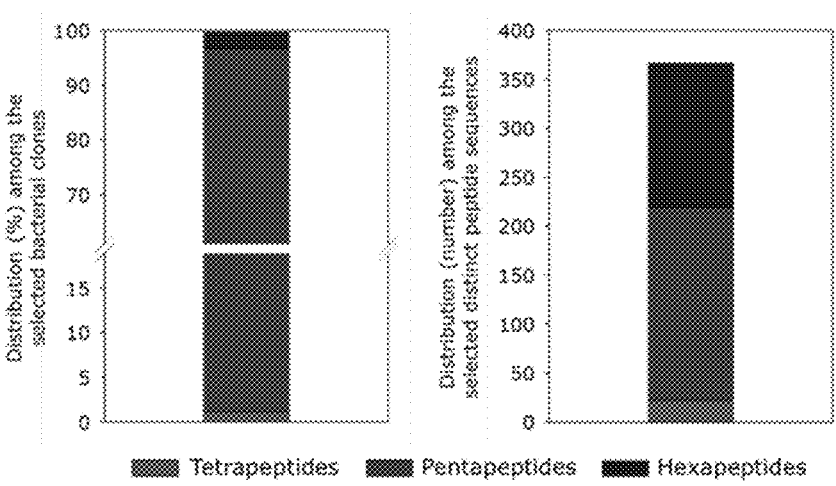
Figure 6B:
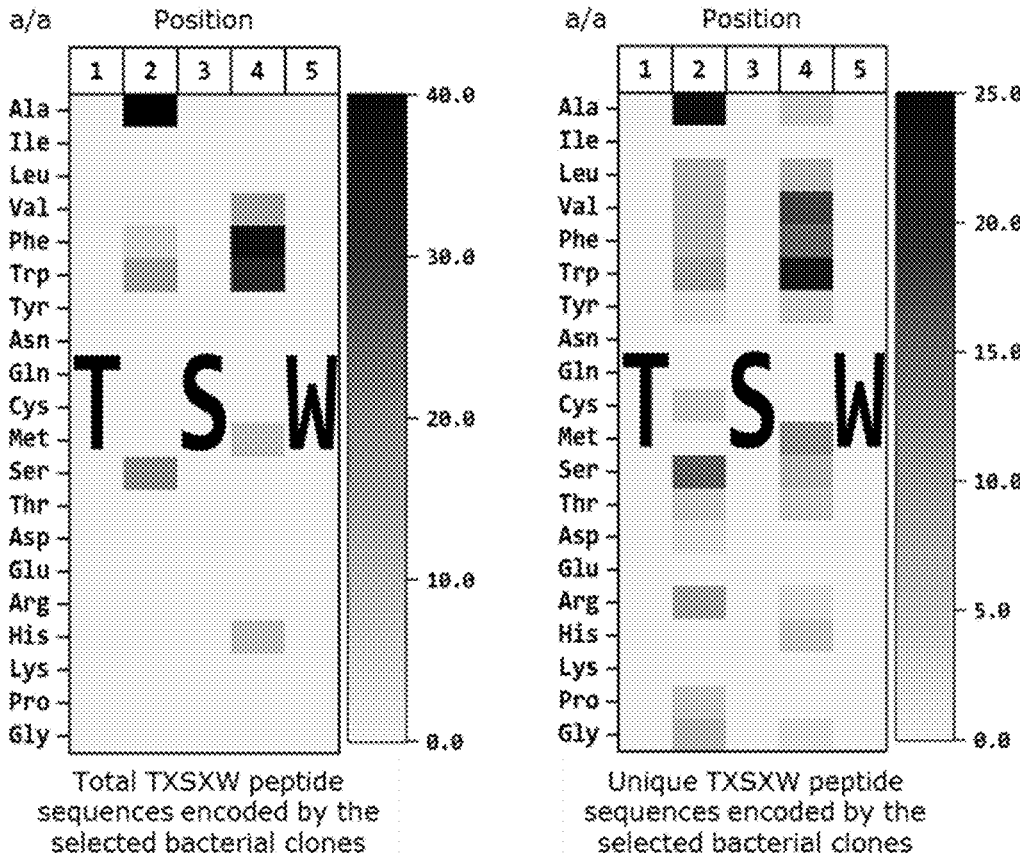
Figures 6C, 6D:
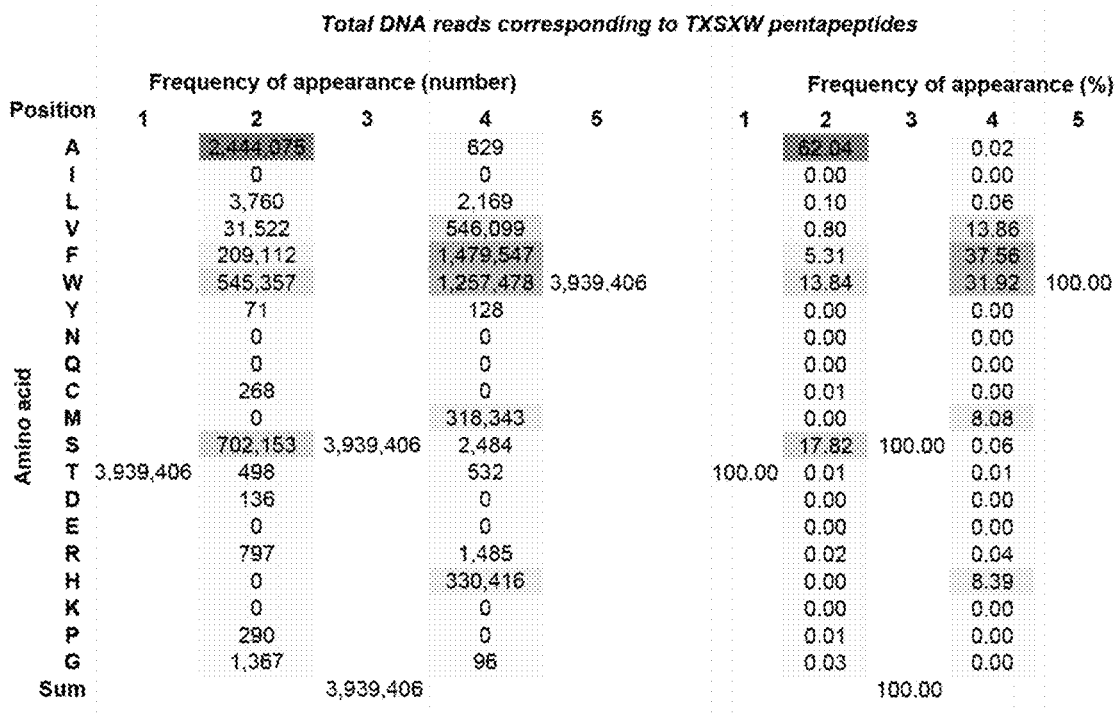
Figure 6E:
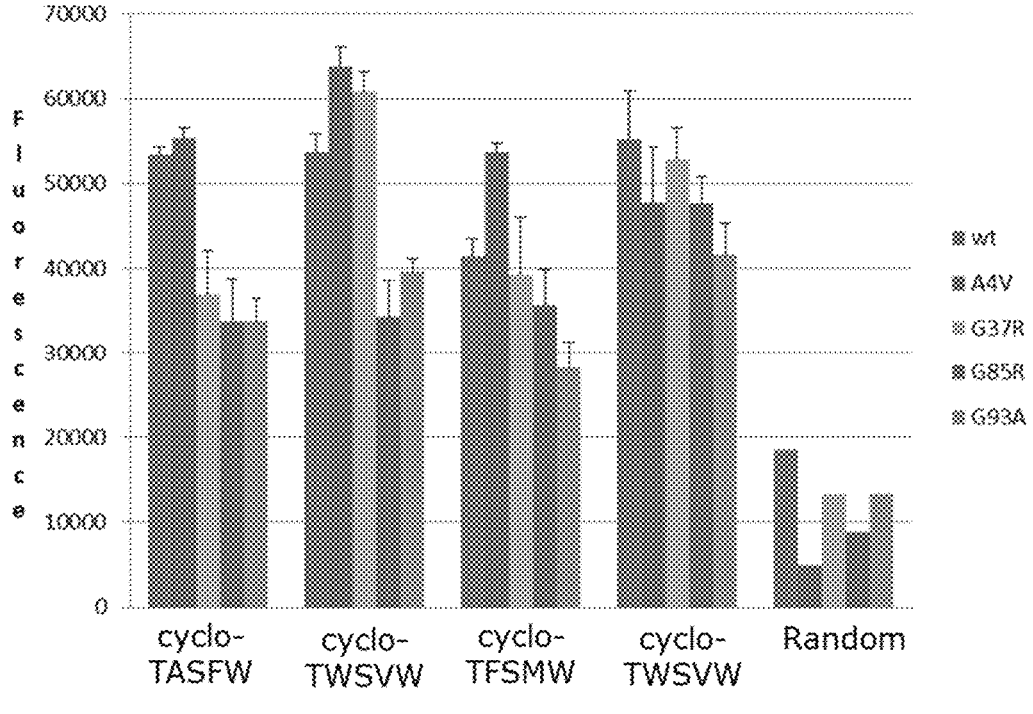

To determine structure-activity relationships for the identified mutant SOD1-targeting cyclic oligopeptides, the sequences of the peptide-encoding regions from ~5.3 million clones selected after the fourth round of FACS sorting (FIG. 3B) were determined by deep sequencing. 367 distinct oligopeptide sequences appeared more than 50 times among the selected clones and were selected for subsequent analysis, which revealed the following. First, pentapeptides were the dominant peptide species within the sorted pool, with 197 of the distinct oligopeptide sequences selected corresponding to pentapeptides (54%), 148 to hexapeptides (40%) and 22 corresponding to tetrapeptides (6%) (FIG. 6A). Second, the vast majority of the selected peptides exhibited the cyclo-TXSXW motif of SOD1C5-4 (~92% of all selected clones and ~97% of the selected pentapeptide-encoding clones (FIG. 7). Third, among the selected cyclo-TXSXW pentapeptides, I, N, Q, M, E, H, and K residues were excluded at position 2, and were preferably S, A, W or F. At position 4, I, N, Q, C, D, E, K and P residues were excluded, and were preferably V, W, F, M, or H (FIGS. 6B-6D). Taken together, these results indicate that the most bioactive macrocyclic structures against SOD1(A4V) misfolding and aggregation in the library are cyclic pentapeptides of the cyclo-T(Φ$_1$,S)S(Φ$_2$,M,H)W motif, where Φ$_1$ is preferably one of the hydrophobic (Φ) amino acids A, W or F, while Φ$_2$ is preferably V, W or F. Interestingly, selected cyclic pentapeptides belonging to this functional motif were found to be efficient in enhancing the fluorescence of SOD1-GFP containing wild-type SOD1, as well as three additional SOD1 variants, SOD1(G37R), SOD1(G85R), and SOD1 (G93A), all of which are associated with familial forms of ALS, thus indicating that these peptide macrocycles are effective rescuers of the misfolding of not only SOD1(A4V), but also of other ALS-related SOD1 variants, as well as wild-type SOD1 (FIG. 6E).

Example 6

Combinatorial libraries of random cyclic tetra-, penta-, and hexapeptides have been selected to be studied as potential rescuers of Aβ misfolding and pathogenic aggregation.

To identify cyclic oligopeptide sequences with the ability to interfere with the problematic folding of Aβ and inhibit its oligomerization/aggregation, the inventors utilized a bacterial high-throughput genetic screen. This system monitors Aβ misfolding and aggregation by measuring the fluorescence of E. coli cells overexpressing a chimeric fusion of the human Aβ(1-42) peptide (Aβ$_{42}$) with GFP (US20070077552A1 "High throughput screen for inhibitors of polypeptide aggregation"). It has been demonstrated previously that due to the high aggregation propensity of Aβ, E. coli cells overexpressing Aβ-GFP fusions produce misfolded fusion protein that accumulates into insoluble inclusion bodies that lack fluorescence, despite the fact that they express these fusions at high levels. Mutations in the coding sequence of Aβ or the addition of compounds that inhibit Aβ aggregation, however, result in the formation of soluble and fluorescent Aβ-GFP, and bacterial cells expressing Aβ-GFP under these conditions acquire a fluorescent phenotype. The inventors of the present invention adapted this system to perform screening for aggregation-inhibitory macrocycles in a very high-throughput fashion by isolating cyclic oligopeptide-producing bacterial clones that exhibit enhanced levels of Aβ$_{42}$-GFP fluorescence using fluorescence-activated cell sorting (FACS) as also performed in a similar manner and demonstrated for SOD1 in FIG. 3A.

Figure 8A:
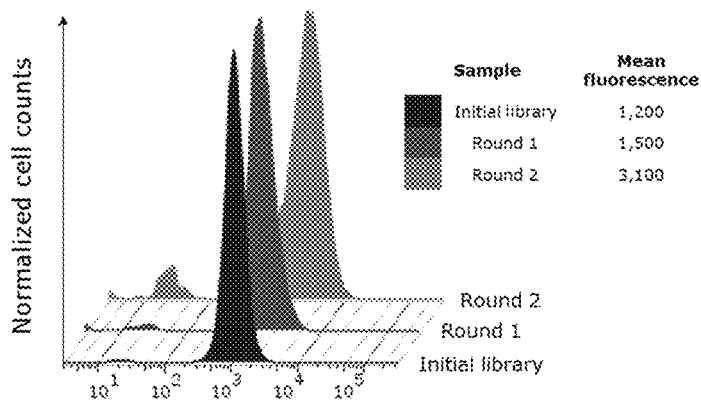
Figure 8B:
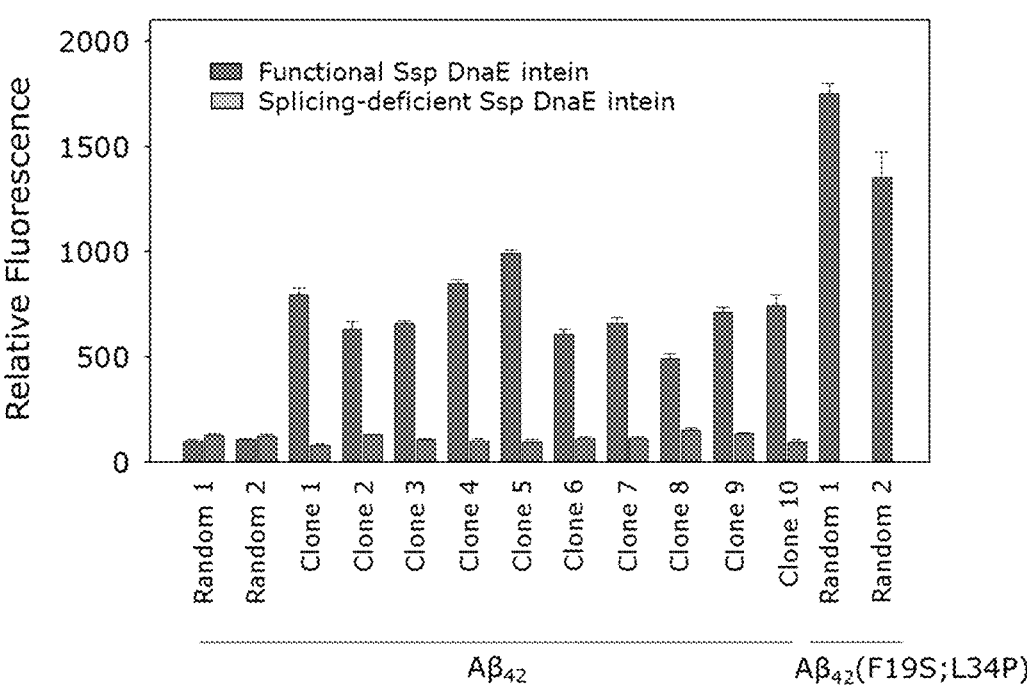
Figure 8C:
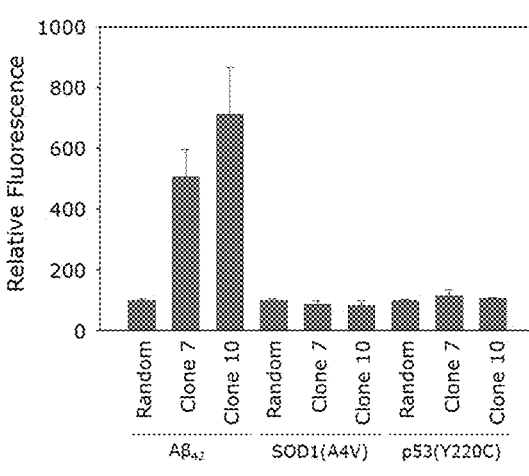
Figure 8D:
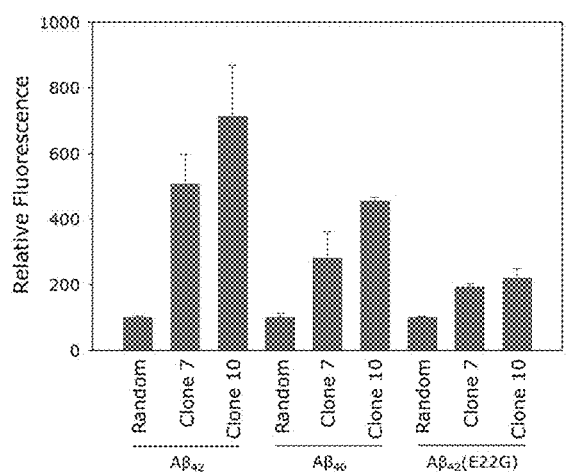

E. coli BL21(DE3) cells producing the combined cyclo-NuX$_1$X$_2$X$_3$-X$_5$ library, while simultaneously overexpressing the Aβ$_{42}$-GFP reporter, were subjected to FACS sorting for the isolation of clones exhibiting enhanced Aβ$_{42}$-GFP fluorescence. After two rounds of sorting, the mean fluorescence of the bacterial population increased by almost three-fold compared to that of the initial library (FIG. 8A). Ten individual clones were randomly picked from the sorted population and their Aβ$_{42}$-GFP fluorescence was measured using a plate reader. Aβ$_{42}$-GFP fluorescence of the isolated peptide-expressing clones was found to be dramatically increased compared to cells expressing the same Aβ$_{42}$-GFP fusion in the presence of random cyclic peptide sequences picked from the initial (unselected) cyclo-NuX$_1$X$_2$X$_3$-X$_5$ library (FIG. 8B). Furthermore, the observed phenotypic effects were dependent on the ability of the Ssp DnaE intein to perform protein splicing, as the double amino acid substitution H24L/F26A in the C-terminal half of the Ssp DnaE intein, which is known to abolish asparagine cyclization at the I$_C$/extein junction, and prevent extein splicing and peptide cyclization, was found to reduce Aβ$_{42}$-GFP fluorescence back to wild-type levels (FIG. 8B). Finally, the observed increases in fluorescence were found to be Aβ-specific, as the isolated pSICLOPPS-NuX$_1$X$_2$X$_3$-X$_5$ vectors did not enhance the levels of cellular green fluorescence when the sequence of Aβ in the Aβ$_{42}$-GFP reporter was replaced with those of two unrelated disease-associated MisPs, the DNA-binding (core) domain of the human p53 containing a tyrosine to cysteine substitution at position 220 (p53C (Y220C)) and an alanine to valine substitution at position 4 of human Cu/Zn superoxide dismutase 1 (SOD1(A4V)) (FIG. 8C). On the contrary, the selected pSICLOPPS-NuX$_1$X$_2$X$_3$-X$_5$ vectors were efficient in enhancing the fluorescence of Aβ-GFP containing two additional Aβ variants, Aβ$_{40}$ and the E22G (arctic) variant of Aβ$_{42}$, which is associated with familial forms of AD (FIG. 8D).

Figure 8E:
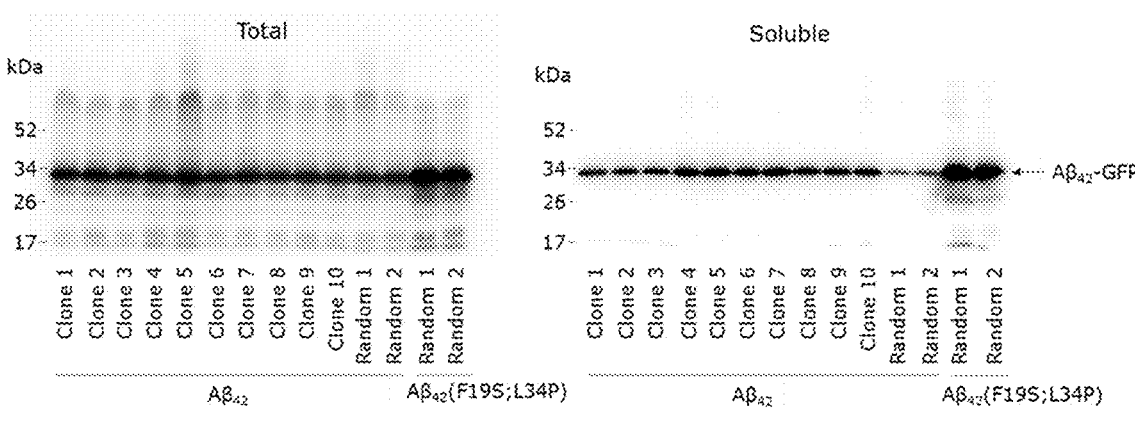
Figure 8F:
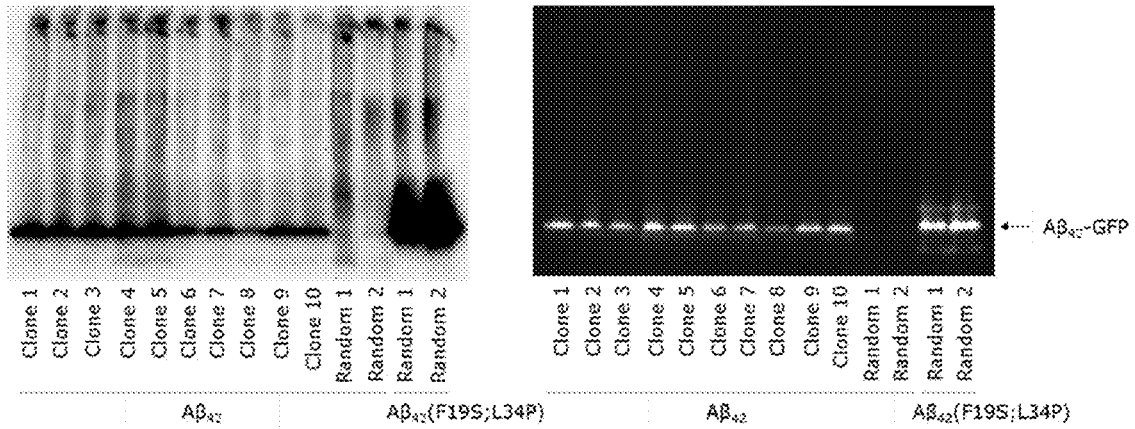

Analysis of the expressed Aβ$_{42}$-GFP fusions by sodium dodecyl sulfate polyacrylamide gel electrophoresis (SDS-PAGE) and western blotting revealed that the bacterial clones expressing the selected cyclic peptides produce markedly increased levels of soluble Aβ$_{42}$-GFP compared to random cyclic peptide sequences, despite the fact that accumulation of total Aβ$_{42}$-GFP protein remained at similar levels in all cases (FIG. 8E). Furthermore, when the same cell lysates were analyzed by native PAGE and western blotting, it was observed that co-expression of the selected cyclic peptides reduced the accumulation of higher-order Aβ$_{42}$-GFP aggregates, which could not enter the gel, and increased the abundance of species with higher electrophoretic mobility (FIG. 8F, left). As revealed by in-gel fluorescence analysis, these higher electrophoretic mobility species correspond to the fraction of the total Aβ$_{42}$-GFP that exhibits fluorescence (FIG. 8F, right). Since the solubility and fluorescence of bacterially expressed Aβ-GFP has been found to be inversely proportional to the aggregation propensity of Aβ, these results suggest that Aβ aggregation is significantly decreased in the presence of the selected cyclic peptides.

DNA sequencing of the peptide-encoding regions of ten isolated clones from the selected pool revealed eight distinct putative Aβ aggregation-inhibitory cyclic peptide sequences: one corresponded to a hexapeptide (TPVWFD (SEQ ID NO: 222); present twice among the sequenced clones) and seven pentapeptides (TAFDR (SEQ ID NO: 86), TAWCR (SEQ ID NO: 63), TTWCR (SEQ ID NO: 60), TTVDR (SEQ ID NO: 48), TTYAR (SEQ ID NO: 47; present twice), TTTAR (SEQ ID NO: 56), and SASPT (SEQ ID NO: 206)) (FIG. 8G). Interestingly, the Arg residue at position 5, frequently encountered among the selected pentapeptides, was encoded by three different codons in the selected pSICLOPPS plasmids, thus suggesting that its dominance among the isolated clones was not coincidental.

Example 7

Figure 9A:
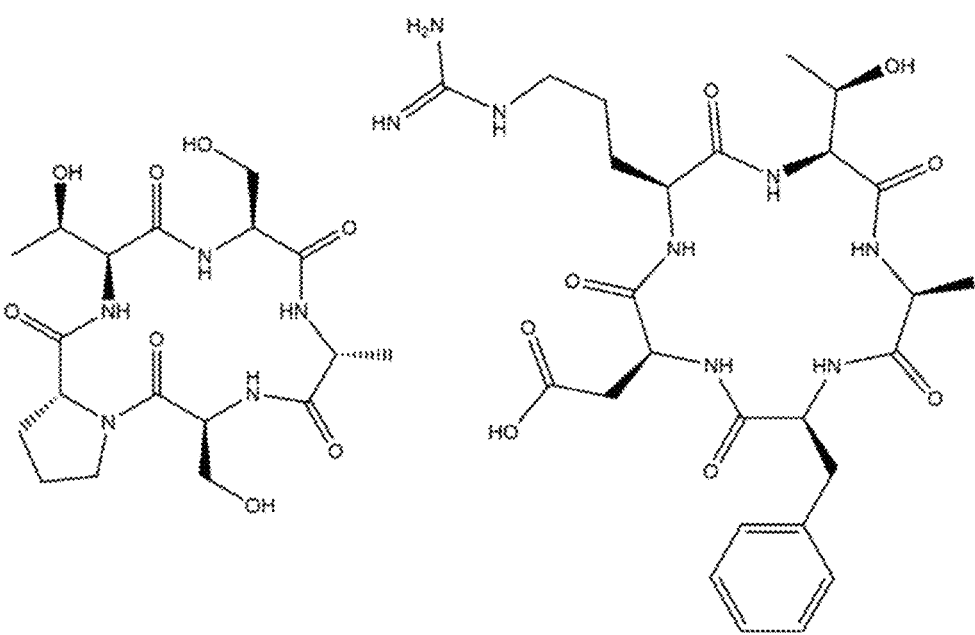

Two of the selected cyclic peptide sequences, cyclo-TAFDR (SEQ ID NO: 86) and cyclo-SASPT (SEQ ID NO: 206), hereafter referred to as AβC5-116 and AβC5-34 (Aβ-targeting cyclic 5-peptide number 116 and 34), respectively, were chosen for subsequent analysis and were produced by solid-phase synthesis in mg quantities (FIG. 9A). The inventors of the present invention chose to focus on pentapeptides, as this was the type of peptide most frequently present among the ones selected from the genetic screen. The inventors decided to further study the sequence AβC5-116 since the cyclo-TXXXR motif was particularly dominant among the selected pentapeptides, while AβC5-34 was chosen because it was the only selected pentapeptide whose sequence appeared to deviate from this motif (FIG. 8G).

Figure 9B:
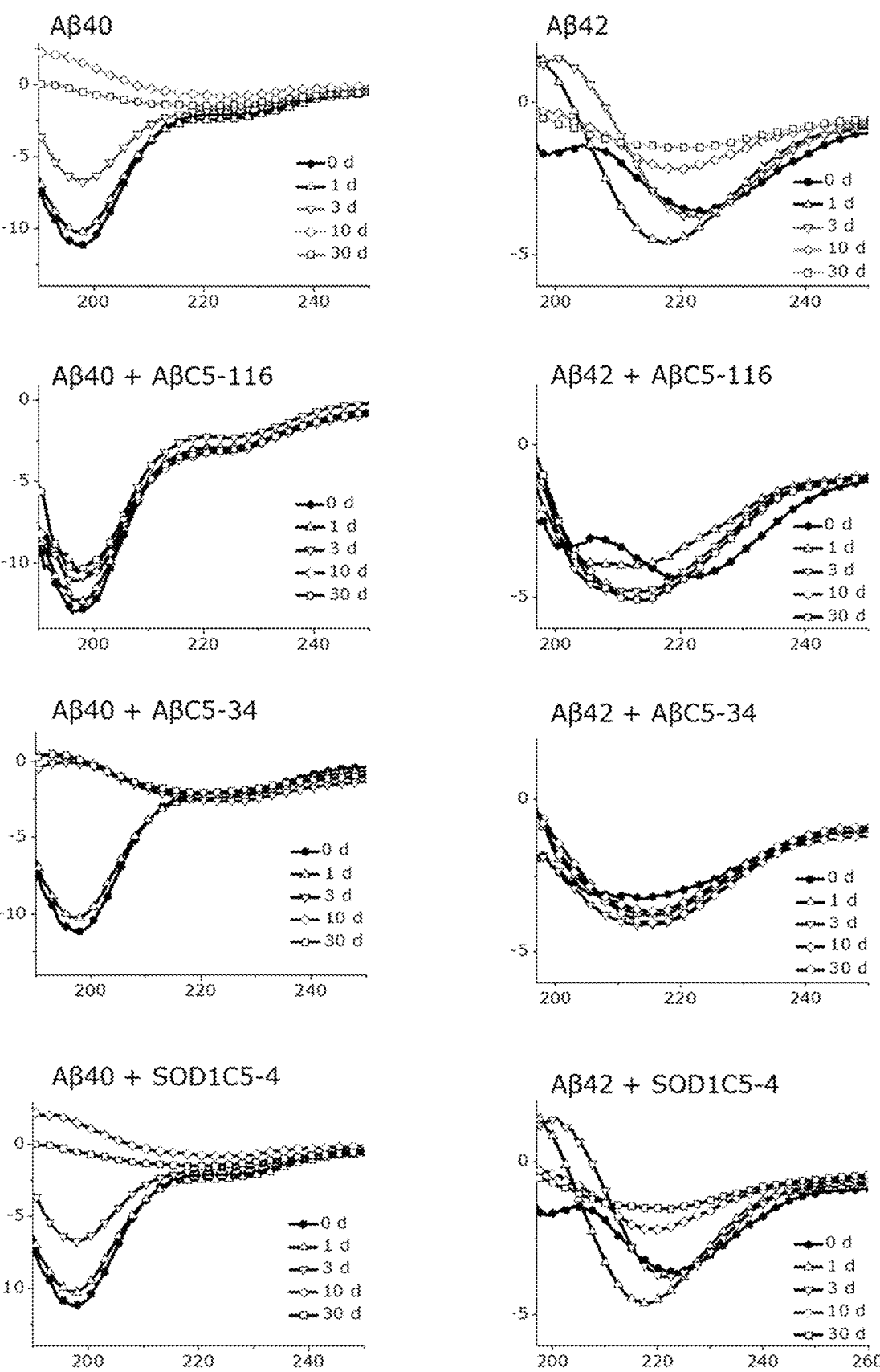

Circular dichroism (CD) spectroscopy was first used to assess the effect of the selected pentapeptides on the aggregation process of Aβ$_{40}$ and Aβ$_{42}$. Addition of AβC5-116 was found to strongly inhibit the aggregation of Aβ$_{40}$, which remained at a random coil conformation in the presence of this cyclic peptide for extended periods of time (FIG. 9B). The addition of AβC5-34 did not have the same effect and resulted in the appearance of a low-intensity negative peak (FIG. 9B). When the same CD solutions were subjected to a thioflavin T (ThT) dye-binding assay that detects amyloid fibrils, we observed that Aβ$_{40}$ fibril formation was reduced in the presence of AβC5-116, while it remained almost unaffected by AβC5-34 (FIG. 9C).

In the case of Aβ$_{42}$, both selected cyclic pentapeptides affected its normal aggregation pathway strongly and stabilized β-sheet-like structures (FIG. 9B). ThT staining of the same samples revealed that the extent of amyloid fibril formation was greatly reduced in both cases (FIG. 9C). When the cyclic peptides were added at a higher ratio, similar CD patterns were observed, however the negative peaks were much more pronounced and fibril formation was completely prevented (FIG. 9C, bottom; FIG. 9D). The addition of two control peptides, a randomly designed cyclic pentapeptide sequence and a cyclic pentapeptide (SODC5-

4) targeting a different protein did not have any effect on the aggregation process of $A\beta_{40}$ and $A\beta_{42}$ (FIGS. 9B-9C, and data not shown), thus demonstrating that cyclic peptides are not general inhibitors of $A\beta$ aggregation and that the $A\beta$ aggregation-modulating effect of the selected sequences relies on their cyclic nature.

Figure 9E:
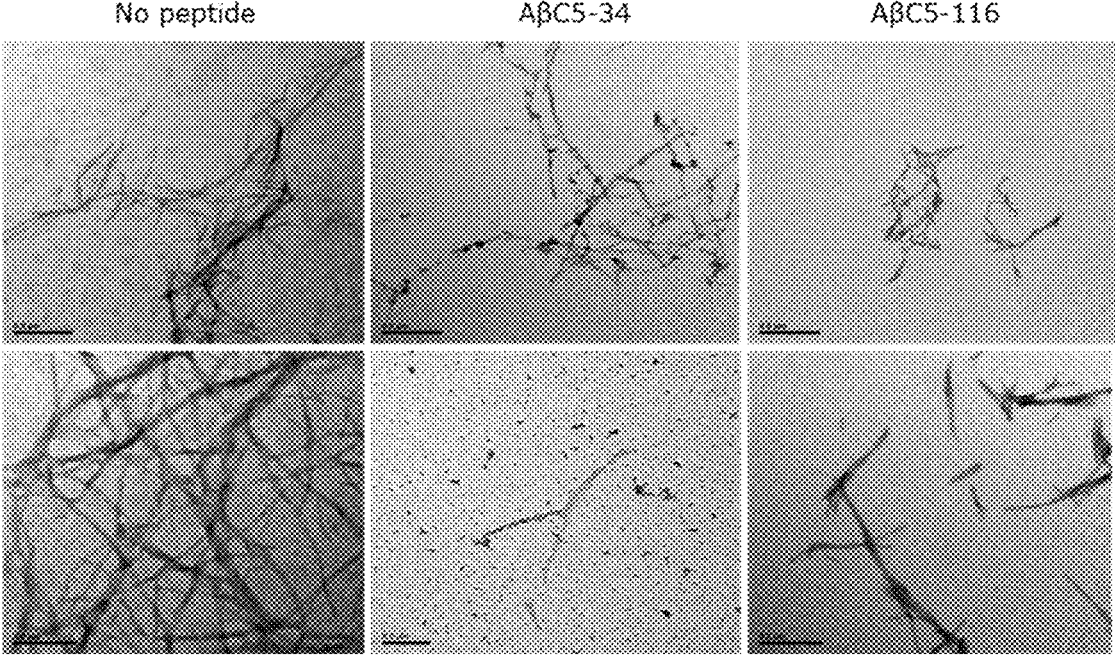

Transmission electron microscopy (TEM) images of solutions of $A\beta_{42}$ incubated without/with $A\beta$C5-34 and $A\beta$C5-116 are presented in FIG. 9E. The $A\beta_{42}$ samples were the same as those employed in the CD and ThT studies to allow for direct correlation of findings. $A\beta_{42}$ incubated alone presented the typical dense network of intertwined fibrils. In the presence of the selected cyclic peptides, however, the fibrils were notably fewer, shorter and ill-developed, and the dense fibrillary network observed in their absence was not detected anywhere on the TEM grid, in agreement with the ThT data. Taken together, these results indicate that the selected cyclic oligopeptides modulate the normal aggregation process of $A\beta$, and their presence likely stabilizes the formation of species, which cannot develop into larger fibril-like structures.

Example 8

Figure 10C:
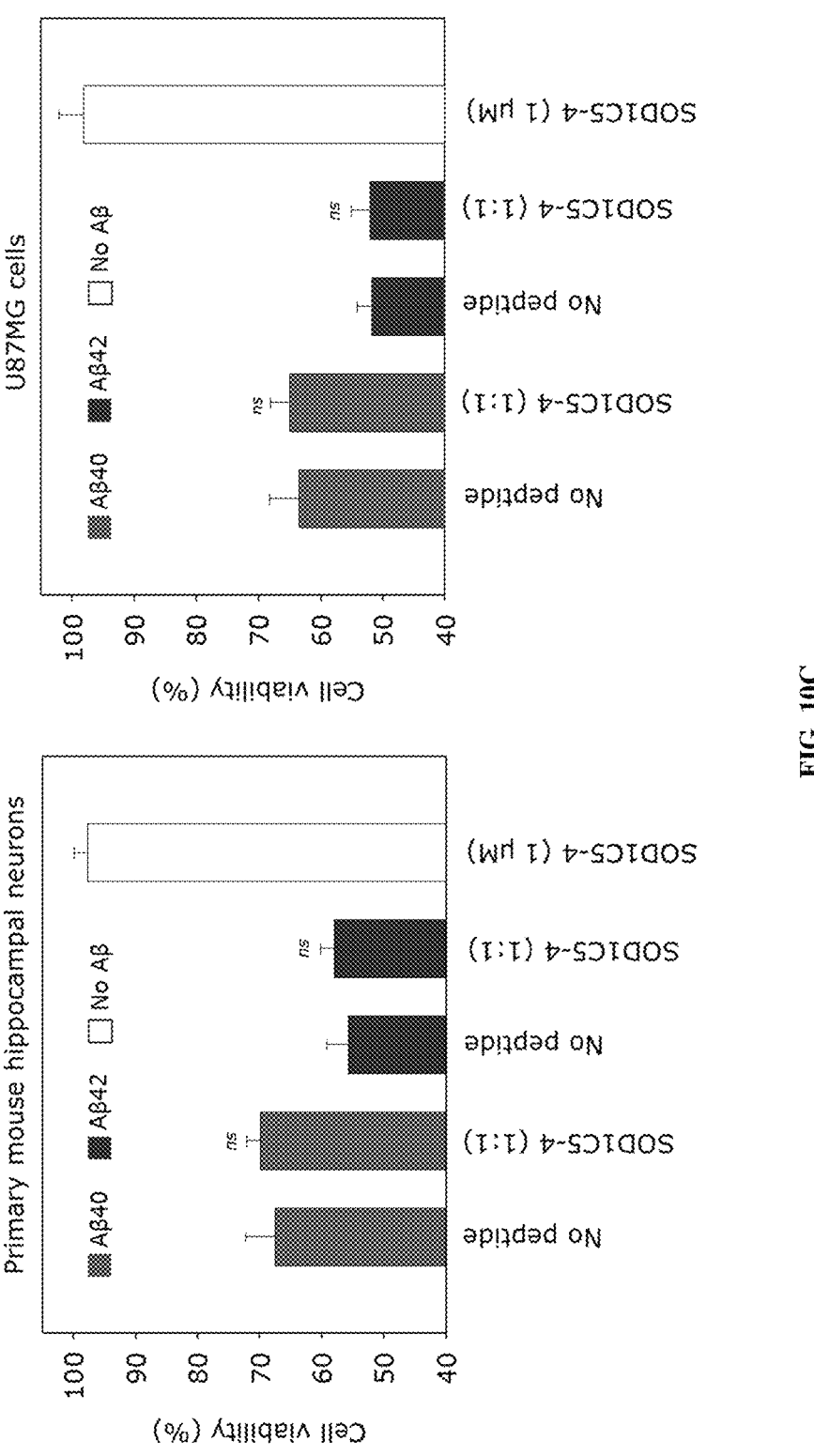

The effects of $A\beta$C5-34 and $A\beta$C5-116 on $A\beta_{40}$- and $A\beta_{42}$-induced toxicity were evaluated in primary mouse hippocampal neurons. The addition of $A\beta$C5-34 and $A\beta$C5-116 was found to markedly inhibit the neurotoxicity of both $A\beta_{40}$ and $A\beta_{42}$ in a dose-responsive manner (FIG. 10A). Similarly, $A\beta$C5-34 and $A\beta$C5-116 exhibited toxicity-suppressing effects also in the glioblastoma cell line U87MG (FIG. 10B). On their own, $A\beta$C5-34 and $A\beta$C5-116 did not exhibit general growth-promoting effects or considerable cytotoxicity (FIGS. 10A and 10B). Control SOD1-targeting cyclic peptides previously found not to interfere with $A\beta$ aggregation (FIGS. 9B and 9C and data not shown), were also found ineffective in rescuing $A\beta$-induced cytotoxicity (FIG. 10C).

Figure 10D:
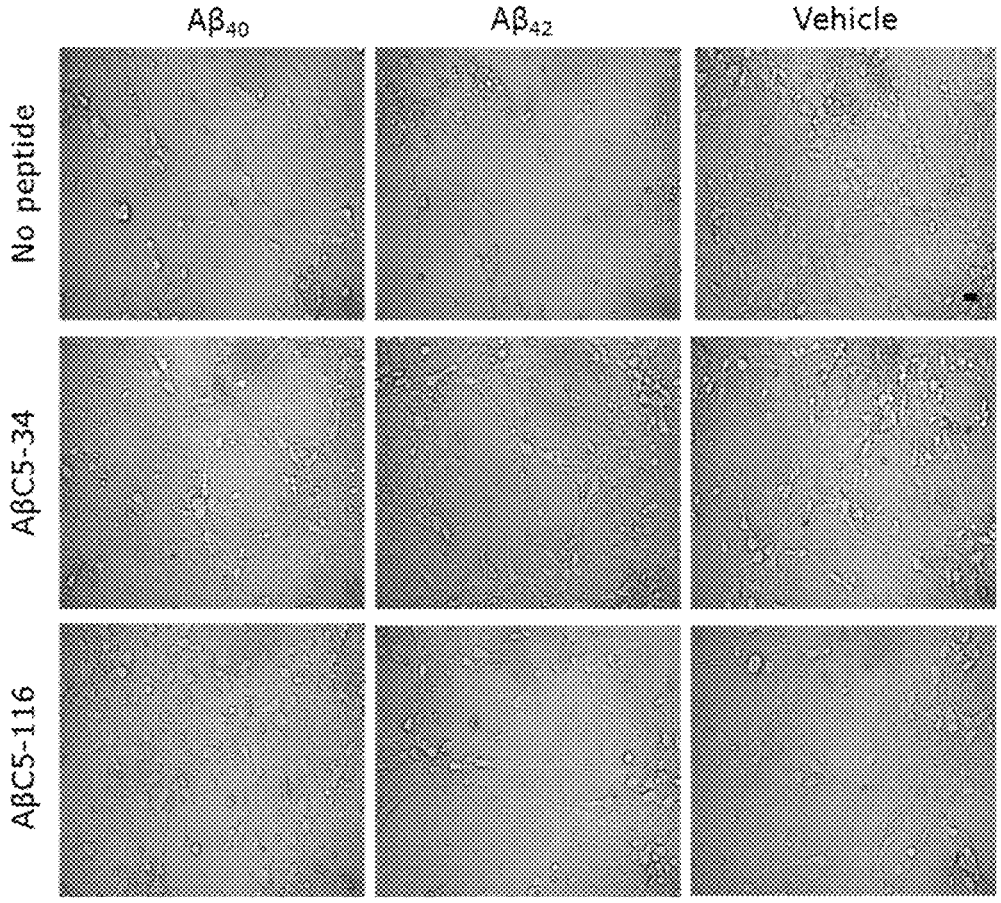

The effect of $A\beta$C5-34 and $A\beta$C5-116 on the morphology of $A\beta$-exposed neuronal cells was assessed by phase-contrast microscopy. In the presence of pre-aggregated $A\beta$, the population of attached cells was greatly reduced compared to the control, with many detached rounded-up cells floating in the supernatant, while hallmarks of degenerating neurons, such as cell shrinkage, membrane blebbings, fragmented neurites and ill-developed axons were obvious in the preparations (FIG. 10D). The addition of the selected cyclic peptides, however, mitigated the effects of $A\beta$ toxicity and a marked recovery of the $A\beta$-induced alterations was recorded (FIG. 10D).

Example 9

Figure 11A:
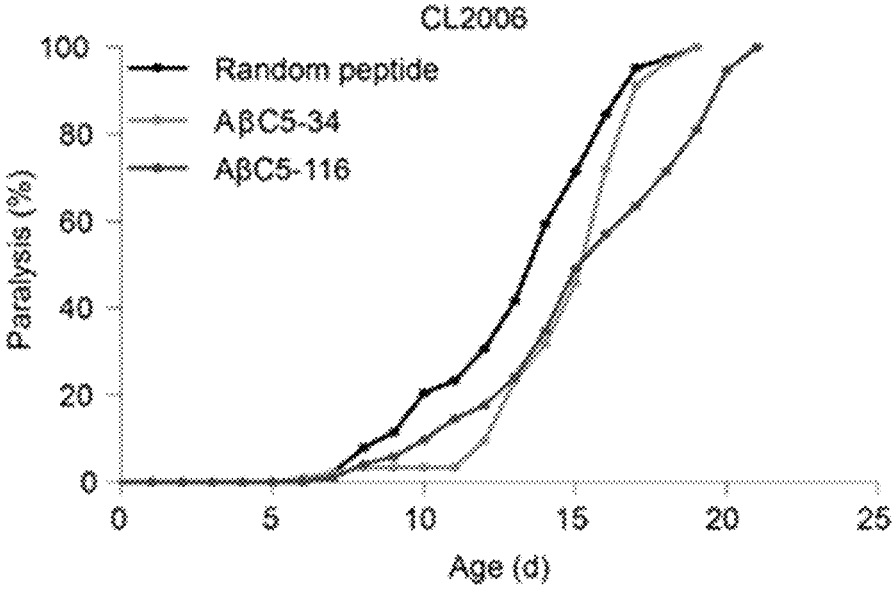
Figure 11B:
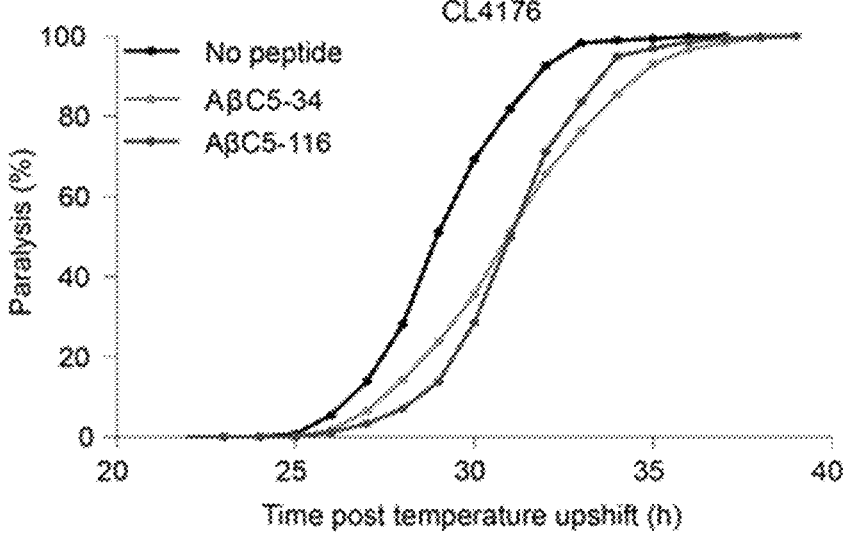

To evaluate the protective effects of the selected cyclic peptides against $A\beta$ aggregation and toxicity in vivo, the inventors employed two established models of AD in the nematode worm *Caenorhabditis elegans*. The conservation of genetic and metabolic pathways between *C. elegans* and mammals, in combination with its completely characterized nervous and muscular system, its easy visualization and simple manipulation, has nominated *C. elegans* as an excellent model for neurodegenerative diseases including AD, while chemical screening against $A\beta$-induced toxicity in *C. elegans* is increasingly used in AD drug discovery. The inventors performed initially a paralysis assay in CL2006, a strain where human $A\beta_{42}$ is constitutively expressed in the body wall muscle cells of the animals and $A\beta$ aggregate formation is accompanied by adult-onset paralysis. Animals fed throughout their lifespan with *E. coli* OP50 cells producing $A\beta$C5-34 or $A\beta$C5-116 biosynthetically from their corresponding pSICLOPPS vectors, exhibited a significant delay in the appearance of the characteristic paralysis phenotype (FIG. 11A). Similar protective effects were observed in a dose-responsive fashion when synthetic $A\beta$C5-34 or $A\beta$C5-116 were supplied to CL4176, a strain conditionally expressing human $A\beta_{42}$ under the control of a heat-inducible promoter. When chemically synthesized $A\beta$C5-34 (10 µM) and $A\beta$C5-116 (5 µM) were supplied to CL4176 animals, a significant delay in the appearance of the characteristic paralysis phenotype was recorded indicating protective effects against $A\beta$ aggregation and toxicity (FIG. 11B). To evaluate the state of $A\beta$ aggregation in vivo, we utilized the strain CL2331, which expresses an $A\beta_{3-42}$-GFP fusion in its body wall muscle cells upon temperature up-shift. Treatment with either one of the selected peptides resulted in a significant reduction of $A\beta$ deposits (FIG. 11C). Biochemical analysis of the accumulation levels of total and oligomeric $A\beta$ levels in CL4176 worms, revealed a significant reduction of both $A\beta$ species upon treatment with $A\beta$C5-34 and $A\beta$C5-116 (FIG. 11D), an effect coinciding with the observed decelerated paralysis. Taken together, our results demonstrate that $A\beta$C5-34 and $A\beta$C5-116 exert a protective role against $A\beta$

Example 10

Figure 12A:
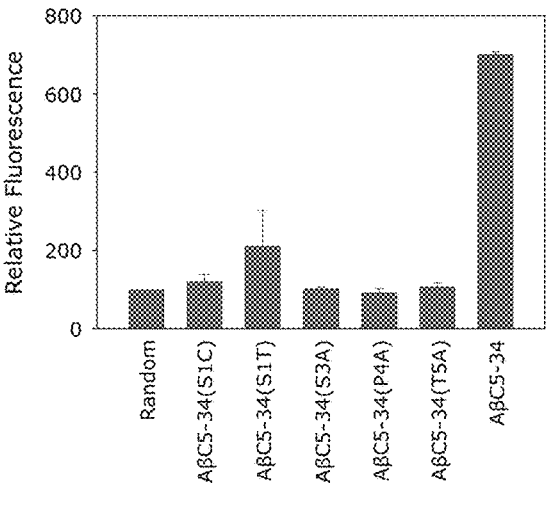
Figure 12B:
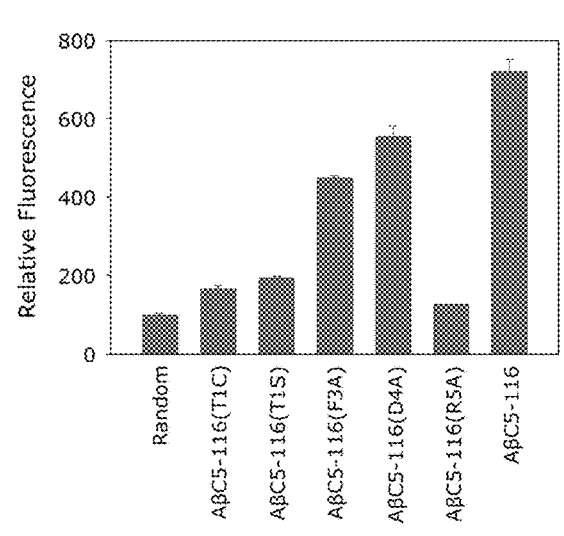
Figure 12C:
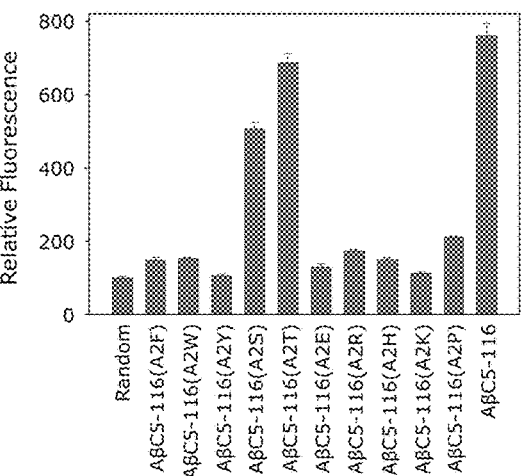
Figure 12D:
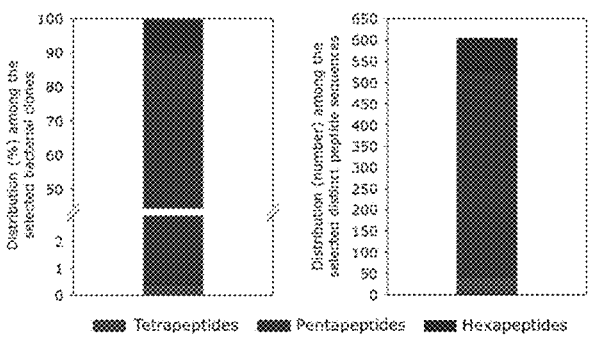
Figure 12F:
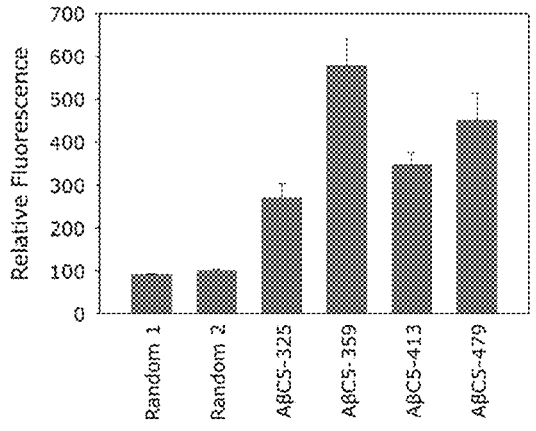

To identify the functionally important residues within the isolated peptides, the inventors performed position 1 substitutions with the other two nucleophilic amino acids present in the initial libraries, as well as alanine scanning mutagenesis at positions 3-5 of the $A\beta$C5-34 and $A\beta$C5-116 pentapeptides. As judged by the ability of the generated variants to enhance the fluorescence of *E. coli* cells overexpressing $A\beta_{42}$-GFP, $A\beta$C5-116 was found to be much more tolerant to substitutions compared to $A\beta$C5-34. All tested sequence alterations within $A\beta$C5-34 were found to be deleterious for its $A\beta$ aggregation-inhibitory effects (FIG. 12A). On the contrary, only the initial Thr and the ultimate Arg were found to be absolutely necessary for the bioactivity of $A\beta$C5-116, whereas residues at positions 3 and 4 could be substituted by Ala without significant loss of activity (FIG. 12B). These observations are in line with the high frequency of initial Thr and ultimate Arg residues in the sequences of the isolated pentapeptides, as well as with the high amino acid variabilities at the corresponding positions 3 and 4, and indicates that all isolated sequences with this pattern may belong to the same consensus motif. In order to investigate this hypothesis, the inventors performed semi-saturation mutagenesis of the Ala residue of $A\beta$C5-116 with representative amino acids from all categories. Among the tested amino acids, only Thr and Ser could be tolerated at position 2 (FIG. 12C), in agreement with the fact that four out of six identified pentapeptides containing the cyclo-TXXXR motif included a Thr at position 2.

The results presented in the invention indicated that there should be a significant number of pentapeptide sequences with the ability to modulate $A\beta$ aggregation that resemble $A\beta$C5-116. On the other hand, very few bioactive sequences resembling $A\beta$C5-34 should exist. To test this hypothesis and to identify all the additional bioactive cyclic oligopeptide sequences with the ability to modulate $A\beta$ oligomerization/aggregation, the inventors turned back to the selected bacterial population exhibiting high $A\beta_{42}$-GFP fluorescence (FIG. 8A). The peptide-encoding vectors contained in these clones were isolated and the peptide-encoding region of approximately 5.6 million of these plasmids was sequenced using an Ion Torrent high-throughput sequencing platform. 605 distinct oligopeptide sequences appeared more than 50 times within the analyzed population, suggesting that their presence in the isolated pool is not coincidental. Indeed, cloning of four randomly chosen sequences appearing in the sorted pool only with very low frequencies, revealed that they are also efficient in increasing the fluorescence of bacterially expressed $A\beta_{42}$-GFP (FIG. 12F; Table 1). Analysis of the peptide sequences isolated from the genetic screen, and after considering all circular permutants thereof, revealed the following. First, pentapeptides were the dominant peptide species within the sorted pool (FIG. 12D), in agreement with previous observations (FIG. 8G). Second, the most prevalent motif among the selected pentapeptide sequences were TXXXR pentapeptides (~47% of the selected pentapeptide-encoding pSICLOPPS plasmids; ~42% of the unique selected pentapeptide sequences) (Table 1), in accordance with previous observations (FIG. 8G). On the contrary, only three pentapeptide sequences were found to have high similarity with $A\beta$C5-34 (Table 2). Third, for the selected peptides corresponding to the TXXXR motif, residues at positions 3 and 4 were highly variable and included the majority of natural amino acids, with position 3 exhibiting the highest diversity (FIG. 12E). At position 2, Thr, Ala, and Val were preferred, while aromatic residues (Phe, Trp, Tyr) were completely excluded from the selected TXXXR peptide pool, in full agreement with our site-directed mutagenesis studies. At the highly variable position 3, the complete absence of the negatively charged amino acids Glu and Asp among the selected sequences was notable (FIG. 12E). In general, both negatively (Glu and Asp) and positively charged residues (Lys, His, and Arg) were found to be strongly disfavored among the selected TXXXR sequences at positions 2 and 3. At position 4, Ala, Asp, and Trp were found to be the preferred residues. It is noteworthy, that Lys and Gln residues were practically absent from all positions, while the β sheet-breaking amino acid Pro that is typically included in designed peptide-based inhibitors of amyloid aggregation appeared with strikingly low frequencies (FIG. 12E). The motif cyclo-T(T,A,V)Ψ(A, D,W)R, where Ψ is anyone of the twenty natural amino acids excluding negatively charged ones, was found to be the most bioactive motif against $A\beta$ in the investigated macrocycle library.

Figure 12G:
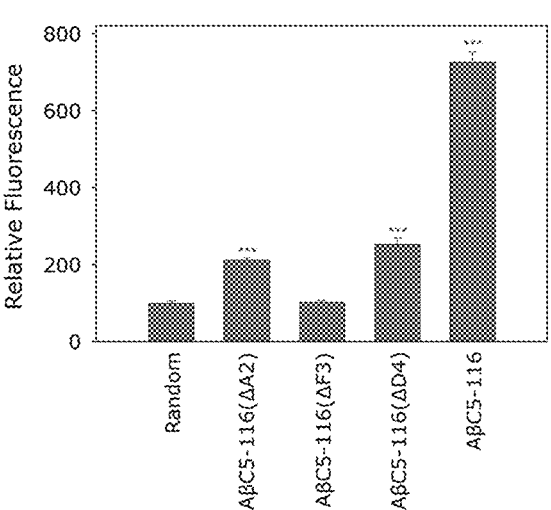

The high residue variability observed at position 3 of the selected TXXXR peptides prompted the inventors to investigate whether $A\beta$C5-116 could be further minimized. Indeed, production of truncated variants of $A\beta$C5-116, from which Ala2 or Asp4 had been deleted, resulted in a respective two- and three-fold enhancement in the fluorescence of bacterially expressed $A\beta_{42}$-GFP (FIG. 12G). In accordance with this, a total of ten distinct cyclic tetrapeptide sequences belonging to the TXXR motif were identified among the selected peptide pool (Table 3). Taken together, our results indicate that the minimal bioactive entity against $A\beta$ aggregation among this peptide family is a TXXR cyclic tetrapeptide, albeit with significantly reduced efficiency compared to the more privileged cyclic pentapeptide scaffold.

In terms of the selected cyclic hexapeptides, sequences with an initial Threonine (T) and an ultimate Aspartic acid (D) were highly dominant among the selected pool (FIG. 12H; Table 4). As in the case of the selected $A\beta$-targeting pentapeptides, charged amino acids were strongly disfavored among the selected sequences, with the exception of the dominant ultimate D residue. It is striking that aromatic amino acids were completely (or almost completely) absent at positions 2 and 3 of the selected hexapeptides, but highly dominant at positions 4 and 5. This sequence analysis revealed the motif cyclo-T(P,L)(V,A)WFD as the most bioactive hexapeptide motif against $A\beta$ in the investigated macrocycle library.

Example 13

Materials

Synthetic human amyloid peptides $A\beta_{40}$ and $A\beta_{42}$ were purchased from Eurogentec, Belgium (>95% pure). $A\beta$C5-34 and $A\beta$C5-116 were synthesized by and purchased from Genscript (USA), while SOD1C5-4 was synthesized and purchased from CPC Scientific (USA). All DNA-processing enzymes were purchased from New England Biolabs (USA) apart from alkaline phosphatase FastAP, which was purchased from ThermoFisher Scientific (USA). Recombinant plasmids were purified using NucleoSpin Plasmid from Macherey-Nagel (Germany) or Plasmid Midi kits from Qiagen (Germany). PCR products and DNA extracted from agarose gels were purified using Nucleospin Gel and PCR Clean-up kits from Macherey-Nagel (Germany), respectively. All chemicals were purchased from Sigma-Aldrich (USA), unless otherwise stated. Isopropyl-β-D-thiogalactoside (IPTG) was purchased from MP Biomedicals (Germany). Stock solutions of the synthetic cyclic peptides were as follows: 32.5 mM in water for $A\beta$C5-34, 10 mM in 40% DMSO for $A\beta$C5-116 and 30 mM in 40% DMSO for SOD1C5-4.

Cyclic Oligopeptide Library Construction and Initial Characterization

Initially, nine distinct combinatorial cyclic peptide sub-libraries were constructed: the cyclo-$CysX_1X_2X_3$, cyclo-$SerX_1X_2X_3$, and cyclo-$ThrX_1X_2X_3$ tetrapeptide sub-libraries (pSICLOPPS-$CysX_1X_2X_3$, pSICLOPPS-$SerX_1X_2X_3$, and pSICLOPPS-$ThrX_1X_2X_3$ vector sub-libraries), the cyclo-$CysX_1X_2X_3X_4$, cyclo-$SerX_1X_2X_3X_4$, and cyclo-$ThrX_1X_2X_3X_4$ cyclic pentapeptide sub-libraries (pSICLOPPS-$CysX_1X_2X_3X_4$, pSICLOPPS-$SerX_1X_2X_3X_4$, and pSICLOPPS-$ThrX_1X_2X_3X_4$ vector sub-libraries) and the cyclo-$CysX_1X_2X_3X_4X_5$, cyclo-$SerX_1X_2X_3X_4X_5$, and cyclo-$ThrX_1X_2X_3X_4X_5$ cyclic hexapeptide sub-libraries (pSICLOPPS-$CysX_1X_2X_3X_4X_5$, pSICLOPPS-$SerX_1X_2X_3X_4X_5$, and pSICLOPPS-$ThrX_1X_2X_3X_4X_5$ vector sub-libraries). These vectors express libraries of fusion proteins comprising four parts: (i) the C-terminal domain of the split Ssp DnaE intein ($I_C$), (ii) a tetra-, penta-, or hexapeptide sequence, (iii) the N-terminal domain of the split Ssp DnaE intein ($I_N$), and (iv) a chitin-binding domain (CBD) under the control of the $P_{BAD}$ promoter and its inducer L(+)-arabinose (FIG. 1A). The libraries of genes encoding these combinatorial libraries of random cyclic oligopeptides were constructed using degenerate primers. Cys, Ser, and Thr were encoded in these primers by the codons UGC, AGC, and ACC, respectively, which are the most frequently utilized ones for these amino acids in *E. coli*, while the randomized amino acids (X) were encoded using random NNS codons, where N=A, T, G, or C and S=G or C. A second PCR reaction was conducted in each case to eliminate mismatches. The resulting PCR products were digested with BglI and HindIII for 5 h and inserted into the similarly digested and dephosphorylated auxiliary vector pSICLOPPSKanR (see below). The ligation reactions were optimised at a 12:1 insert:vector molar ratio and performed for 4 h at 16° C. Approximately 0.35, 0.7 and 3.5 μg of the pSICLOPPSKanR vector were used for each one of the tetra-, penta- and hexapeptide libraries, respectively. The ligated DNA was then purified using spin columns (Macherey-Nagel, Germany), transformed into electro-competent MC1061 cells prepared in-house, plated onto LB agar plates containing 25 µg/mL chloramphenicol and incubated at 37 °C. for 14-16 h. This procedure resulted in the construction of the combined pSICLOPPS-NuX$_1$X$_2$X$_3$-X$_5$ library with a total diversity of about 31,240,000 independent transformants, as judged by plating experiments after serial dilutions.

Colony PCR of 124 randomly selected clones with intein-specific primers revealed that 88 of them (~71%) contained the correct insert. Overexpression of the tetra-partite fusion in 150 randomly selected clones using 0.002% arabinose and monitoring of the production of this fusion protein by western blotting using a mouse anti-CBD primary antibody (New England Biolabs, USA; 1:100,000 dilution) and a goat anti-mouse HRP-conjugated secondary antibody (Bio-Rad, USA; 1:4,000 dilution), showed that 99 of them (~66%) produced high yields of the tetra-partite fusion protein. Among these 99 clones that produced precursor fusion protein (molecular mass ~25 kDa), 82 clones (~55% of total clones tested) also yielded a lower molecular weight band (molecular mass ~20 kDa), which corresponds to one of the splicing reaction products, the N-terminal domain of the Ssp DnaE intein fused to CBD (I$_N$-CBD), after intein splicing and cyclic peptide formation takes place. Therefore, according to these results, the generated bacterial libraries encoding for cyclic tetra-, penta- and hexapeptide contain approximately 20,760,000 clones, which express tetra-partite peptide fusions at high levels and which are capable of undergoing splicing and potentially yielding cyclic peptide products. This diversity covers fully the theoretical diversity of our combined cyclo-NuX$_1$X$_2$X$_3$, NuX$_1$X$_2$X$_3$X$_4$ and NuX$_1$X$_2$X$_3$X$_4$X$_5$ libraries (3×20$^3$+3×20$^4$+3×20$^5$=10,104, 000) by more than two-fold (FIG. 1B).

Expression Vector Construction

For the construction of pETSOD1-GFP, the human SOD1 cDNA was generated by PCR-mediated gene assembly. The assembled gene was further amplified by PCR and the resulting product was digested with NdeI and BamHI, and inserted into similarly digested pAβ$_{42}$-GFP vector GFP (Wurth C, Guimard N K, Hecht M H., J Mol Biol. 2002; 319(5): 1279-90), in the place of Aβ$_{42}$. For pETSOD1 (A4V)-GFP, SOD1 was amplified by PCR from the pET-SOD1-GFP vector using the mutagenic forward primer GS059 and the reverse primer GS060. The resulting PCR product was then digested with NdeI and BamHI, and inserted into similarly digested pETAβ$_{42}$-GFP. For pET-SOD1(G37R)-GFP, pETSOD1(G85R)-GFP and pETSOD1 (G93A)-GFP construction, SOD1 was mutated by overlap extension PCR starting from pETSOD1-GFP as a template. All SOD1 PCR products were then digested with NdeI and BamHI, and inserted into similarly digested pETAβ$_{42}$-GFP vector. For the construction of pETSOD1, pETSOD1 (G37R), pETSOD1(G85R) and pETSOD1(G93A), the corresponding SOD1 genes were amplified by PCR from pET-SOD1-GFP, pETSOD1(G37R)-GFP, pETSOD1(G85R)-GFP and pETSOD1(G93A)-GFP, respectively. For the construction of pETSOD1(A4V), SOD1 was amplified from pETSOD1(A4V)-GFP. All SOD1 PCR products were digested with XbaI and BamHI, and cloned into similarly digested pET28a(+) (Novagen).

For the construction of the pSICLOPPS vectors encoding for variants of the selected AβC5-34 and AβC5-116 peptides, the auxiliary pSICLOPPSKanR vector was generated initially. pSICLOPPSKanR was constructed by PCR amplification of the gene encoding aminoglycoside 3'-phospho-transferase (KanR—the enzyme conferring resistance to the antibiotic kanamycin) from pET28a(+), digestion with BglI and HindIII and insertion into similarly digested pSI-CLOPPS. For the construction of the vectors pSICLOPPS-AβC5-34(S1C), pSICLOPPS-AβC5-34(S1T), pSICLOPPS-AβC5-34(S3A), pSICLOPPS-AβC5-34(P4A) and pSICLOPPS-AβC5-34(T5A), mutagenic PCR was carried out starting from pSICLOPPS-AβC5-34, followed by digestion of the generated product with BglI and HindIII and insertion into similarly digested pSICLOPPSKanR. The vectors pSICLOPPS-AβC5-116(T1C), pSICLOPPS-AβC5-116(T1S), pSICLOPPS-AβC5-116(F3A), pSICLOPPS-AβC5-116(D4A), pSICLOPPS-AβC5-116(R5A), pSI-CLOPPS-AβC5-116(A2F), pSICLOPPS-AβC5-116(A2S), pSICLOPPS-AβC5-116(A2P), pSICLOPPS-AβC5-116 (A2T), pSICLOPPS-AβC5-116(A2Y), pSICLOPPS-AβC5-116(A2H), pSICLOPPS-AβC5-116(A2K), pSICLOPPS-AβC5-116(A2E), pSICLOPPS-AβC5-116(A2W), pSICLOPPS-AβC5-116(A2R), pSICLOPPS-AβC5-116 (A2del), pSICLOPPS-AβC5-116(F3del) and pSICLOPPS-AβC5-116(D4del) were generated in a similar fashion.

Cyclic Oligopeptide Library Screening

Electrocompetent E. coli BL21(DE3) cells (Novagen, USA) carrying either the expression vector pETSOD1 (A4V)-GFP, which produces SOD1(A4V)-GFP under control of the strong bacteriophage T7 promoter, or pETAβ42-GFP, which produces Aβ$_{42}$-GFP under control of the T7 promoter, were co-transformed with the combined pSI-CLOPPS-NuX$_1$X$_2$X$_3$-X$_5$ vector library. Approximately 10$^8$ transformants carrying both the vector library and either pETSOD1(A4V)-GFP or pETAβ$_{42}$-GFP vectors were harvested, pooled together, and grown in Luria-Bertani (LB) liquid medium containing either 0.005% (pETSOD1(A4F)-GFP) or 0.002% (pETAβ$_{42}$-GFP) L-arabinose—the inducer of cyclic peptide production—at 37° C. with shaking. When the optical density at 600 nm (OD$_{600}$) of the bacterial culture was about 0.5, 0.01 (pETSOD1(A4F)-GFP) or 0.1 (pETAβ$_{42}$-GFP) mM isopropyl-β-D-thiogalactoside (IPTG) was added to the medium to induce overexpression of the reporter. After about two hours at 37° C., ~10$^8$ cells were screened and the population exhibiting the top 1-3% fluorescence was isolated using FACS (BD FACSAria, BD Biosciences, USA). The isolated cells were re-grown and screened for additional rounds in an identical manner until the desired enrichment in high-fluorescence clones was achieved.

Protein/Cyclic Peptide Production in Liquid Cultures

E. coli cells freshly transformed with the appropriate expression vector(s) were used for protein production experiments in all cases. Single bacterial colonies were used to inoculate overnight liquid LB cultures containing the appropriate antibiotics for plasmid maintenance (100 µg/mL ampicillin, 40 µg/mL chloramphenicol (Sigma, USA)) at 37° C. These cultures were used with a 1:100 dilution to inoculate fresh LB cultures in all cases.

For SOD1 or SOD1-GFP production, BL21(DE3) (Novagen, USA) or Origami 2(DE3) cells (Novagen, USA) were transformed with the corresponding SOD1- or SOD1-GFP-encoding vector, either with the appropriate pSICLOPPS vector or alone. Cells were grown in 5 mL liquid LB cultures containing 50 µg/mL kanamycin (or 100 µg/mL ampicillin for PASK75-based vectors), 40 µg/mL chloramphenicol (for cell cultures carrying also a pSICLOPPS vector), 200 µM CuCl$_2$, 200 µM ZnCl$_2$ and 0.005% arabinose (for cell cultures carrying also a pSICLOPPS vector) at 37° C. to an OD$_{600}$ of ~0.3-0.5 with shaking, at which point SOD1 or SOD1-GFP production was induced by the addition of 0.01 mM IPTG (0.2 μg/mL anhydrotetracycline (aTc) for pASK-based vectors) for 2-3 h.

For $A\beta_{42}$-GFP production, BL21(DE3) cells were transformed with pETA$\beta_{42}$-GFP and the appropriate pSICLOPPS vector. Cells were grown in 5 mL liquid LB cultures containing 50 μg/mL kanamycin, 40 μg/mL chloramphenicol and 0.02% arabinose at 37° C. to an $OD_{600}$ of ~0.3-0.5 with shaking, at which point $A\beta_{42}$-GFP production was induced by the addition of 0.1 mM IPTG for 2-3 h.

Bacterial Cell Fluorescence

Bacterial cells corresponding to 1 mL culture with $OD_{600}$=1 were harvested by centrifugation and re-suspended in 100 μL phosphate-buffered saline (PBS), transferred to a 96-well FLUOTRAC 200 plate (Greiner Bio One International, Austria), and their fluorescence was measured using a TECAN Safire II-Basic plate reader (Tecan, Austria). Excitation was set at 488 nm and emission was measured at 510 nm.

High-Throughput Sequencing Analysis

For the characterization of the initial libraries, a combined pSICLOPPS-NuX$_1$X$_2$X$_3$-X$_5$ vector library was prepared containing approximately equal amounts of each one of the tetra-, penta- and hexapeptide sub-libraries. These samples were digested with NcoI and BsrGI and the resulting ~250 bp product that contained the variable peptide-encoding region was isolated. High-throughput sequencing analysis was performed using an Ion Torrent high-throughput sequencing platform. From the obtained data, all the sequences with mismatches outside of the variable peptide-encoding region were removed, and only the 12-, 15- or 18-bp-long peptide-encoding sequences were subjected to further analysis. The libraries of the selected cyclic peptides that enhance either SOD1(A4V)-GFP or $A\beta_{42}$-GFP fluorescence were sequenced in a similar manner, with the only exception being that all sequences including stop codons were discarded from subsequent analysis.

Protein Electrophoresis and Western Blot Analysis

Bacterial cells corresponding to 1 mL culture with $OD_{600}$=1 were harvested by centrifugation and re-suspended in 200 μL PBS. Samples were lysed by brief sonication for 10 s on ice twice. These lysates (total lysate fraction) were then centrifuged at 13,000×g for 10 min, the supernatant was collected (soluble fraction) and the pellet was re-suspended in 200 μL PBS (insoluble fraction). For analysis by SDS-PAGE, samples were boiled for 5 min and 10 μL of each sample were loaded onto 12% or 15% gels. For analysis by native PAGE, 10-20 μL of each sample were loaded onto SDS-free 10% gels without prior boiling. In-gel fluorescence was analyzed on a ChemiDoc-It$^2$ Imaging System equipped with a CCD camera and a GFP filter (UVP, UK), after exposure for 3-5 sec. For western blotting, proteins were transferred to polyvinylidene fluoride (PVDF) membranes (Merck, Germany) for 50 min at 12 V on a semi-dry blotter (Thermo Fisher, USA). Membranes were blocked with 5% non-fat dry milk in Tris-buffered saline containing 0.1% Tween-20 (TBST) for 1 h at room temperature. After washing with TBST three times, membranes were incubated with the appropriate antibody dilution in TBST containing 0.5% non-fat dried milk at room temperature for 1 h. The utilized antibodies are described in SI Materials and Methods. The proteins were visualized using a ChemiDoc-It$^2$ Imaging System (UVP, UK). The utilized antibodies were a mouse monoclonal, horseradish peroxidase (HRP)-conjugated anti-polyhistidine antibody (Sigma, USA) at 1:2,500 dilution, a mouse monoclonal anti-FLAG (Sigma, USA) at 1:1,000 dilution, a mouse anti-GFP at 1:20,000 dilution (Clontech, USA), a mouse anti-Aβ (6E10) (Covance, USA) at 1:2,000 dilution, a mouse anti-CBD (New England Biolabs, USA) at 1:25,000 or 1:100,000 dilution, and a HRP-conjugated goat anti-mouse antibody (Bio-Rad, USA) at 1:4,000.

Preparation of SOD1 Stocks and Solutions

SOD1 or mutants thereof were overexpressed from the appropriate pET-SOD1 or PASK-SOD1 vectors in *E. coli* Origami 2(DE3) cells in LB medium containing 50 μg/mL kanamycin (for pET-SOD1) or 100 μg/mL ampicillin (for pASK-SOD1), 200 μM CuCl$_2$, and 200 μM ZnCl$_2$ by the addition of 0.01 mM IPTG (for pET-SOD1) or 0.2 μg/mL anhydrotetracycline (aTc) (for pASK-SOD1), either at 37° C. for 2-3 h or at 18° C. for about 16 h. Origami 2(DE3) cells were utilized in order to provide an oxidizing cytoplasmic environment in order to promote correct formation of disulfide bonds, which are required for proper SOD1 folding and function. Under these conditions, bacterially produced SOD1 is produced in dimeric and enzymatically active form, while it simultaneously co-exists with misfolded, soluble and insoluble SOD1 oligomeric/aggregated species (FIG. 3C). Thus, the acquired protein is found in a state that resembles the conditions encountered in human cells under stressful or pathogenic conditions. The appearance of misfolded SOD1 oligomers/aggregates is enhanced with increasing incubation temperatures. Thus, for assays that are more appropriate for monitoring the early steps of SOD1 oligomerization/aggregation, such as dynamic light scattering (DLS), we utilized SOD1 produced at 18° C., whereas for assays that are more appropriate for monitoring the later steps of SOD1 aggregation, such as filter retardation, ThT staining and CD spectroscopy, we utilized SOD1 produced at 37° C.

Preparation of Aβ Stocks and Solutions

Synthetic $A\beta_{40}$ and $A\beta_{42}$ peptides were gently dissolved without vortexing in doubly deionized water to a final concentration of 100 μM. These solutions were then diluted by PBS addition (10 mM, pH 7.33) to achieve a final Aβ concentration of 50 μM.

Circular Dichroism

Appropriate amounts of synthetic cyclic peptides were added to either 40 μM SOD1(A4V) or 50 μM Aβ solutions at the desired cyclic peptide:target protein molar ratio. SOD1(A4V) structural changes were monitored for 90 d at 25° C., under quiescent conditions. Aβ structural changes were monitored for 30 d at 33° C. under quiescent conditions. CD spectra in the range 190-260 nm were recorded on a JASCO J-715 spectropolarimeter (Jasco Co., Japan) using quartz cuvettes with 1 mm path length. Each reported spectrum is the average of three scans at a rate of 100 nm·min$^{-1}$ and a resolution of 0.5 nm.

Dynamic Light Scattering

The sizes of the SOD1 particles were measured using a Zetasizer NanoZS90 (Malvern) instrument. After a 2-min temperature-equilibration step at 37° C., eighteen consecutive 10-s measurements, per sample, were averaged to produce the particle size (Z average) distributions.

Thioflavin T Staining

40 μM SOD1(A4V) solutions, aged for 90 d at 25° C., with or without the selected synthetic peptides, were diluted to 10 μM with PBS. 5 μL from a stock solution of ThT (Sigma-Aldrich, USA) in PBS (10 mM, pH 7.33) was added to these SOD1(A4V) solutions to achieve a final ThT concentration of 10 μM. The mixture was agitated adequately by pipetting and immediately thereafter, fluorescence was monitored with excitation at 440 nm (EM slit=2.5 nm, PMT Voltage 700 V, response 0.4 s) using a HITACHI F-2500 (Japan) spectrofluorometer.

For $A\beta$ ThT staining, 100 μL of the 30-d aged 50 μM CD solutions were diluted in PBS (10 mM, pH 7.33) to form a 25 μM $A\beta$ solution with 200 μL final volume. 2.5 μL from a stock solution of ThT (Sigma-Aldrich, USA) in PBS (10 mM, pH 7.33) was added to the prepared $A\beta$ solutions to achieve a final ThT concentration of 5 μM. The mixture was agitated adequately by pipetting and immediately thereafter, fluorescence was monitored with excitation at 440 nm (EM slit=2.5 nm, PMT Voltage 700 V, response 0.4 s) using a HITACHI F-2500 (Japan) spectrofluorometer.

Filter Retardation Assay

SOD1(A4V) solutions (10 μM), incubated in the presence or absence of the selected cyclic peptides for 25 d at 37° C., were mixed with a stock solution of SDS to achieve a final SDS concentration of 2% and then boiled for 10 min. These samples were subsequently applied under vacuum on a 0.2 μm-pore size PVDF membrane (Merck), which had been previously equilibrated with transfer buffer containing 0.1% SDS, and then washed twice with 100 μl TBS under vacuum. The membrane was blocked with 5% non-fat dry milk in TBST for 1 h at room temperature and then stained with a HRP-conjugated anti-polyHis antibody at a 1:2,500 dilution (Sigma-Aldrich) overnight at 4° C.

SOD1 Aggregation and Viability Measurements in HEK293 Cells

Human embryonic kidney (HEK) 293 cells were transfected using a Nucleofector (Amaxa) following the manufacturer's protocol. 6 ug DNA (SOD1 or SOD1(A4V) cloned into the pEGFP-N3 plasmid vector) were used per $2\times106$ cells and 5 μM synthetic SOD1C5-4 was added, where appropriate, before plating. Transfected cells were sorted 18 h later on a FACSAria to isolate GFP-positive clones. 4',6-Diamidino-2-phenylindole dihydrochloride (DAPI) dye was used to exclude dead cells. ~28% of the SOD1 and ~15% of the SOD1(A4V) total cells were found to be GFP-positive. Collected cells were plated onto a 24-well plate at a density of 50,000 cells/well. Microscopy analysis was performed under an inverted microscope on day 1 and day 5 in culture after sorting. Cell counts are the average number of viable GFP-fluorescing cells of two areas per triplicate of wells of 24-well plates (magnification 20×). Cell counts are presented as percentage of viability of SOD1-overxoressing cell. As aggregate-positive cells are counted the fluorescing inclusion body-positive cells. Again, two areas per triplicate of wells of 24-well plate are averaged (magnification 20×). Aggregate-positive cells are presented as percentage of the total viable GFP-fluorescing cells.

Transmission Electron Microscopy (TEM)

For TEM analysis, the 30-d aged 50 μM CD solutions of $A\beta_{42}$ (with 100 μM of the selected peptides or without) was mixed well by pipetting. 2 μL of this solution were placed in a carbon-coated film on 200-mesh copper grids (Agar Scientific, UK) for 5 min. After adsorption, grids were washed in deionized water and negatively stained by applying a 2-μl drop of freshly prepared 1% (w/v) uranyl acetate (Sigma-Aldrich, USA) in Milli-Q water for 5 min. Excess fluid was blotted off, and grids were washed in deionized water and dried in air. Images were recorded using a FEI CM20 electron microscope (FEI, USA) with a Gatan GIF200 imaging filter (Gatan, USA), equipped with a Peltier-cooled slow-scan CCD camera.

Neuronal Cell Cultures

The media/agents for primary neuronal cell cultures were purchased from Thermo Fisher Scientific (USA). Hippocampal neuronal cultures were obtained from postnatal day 1 female pups of C57BL/6 mice. Briefly, after being dissected, the hippocampus was incubated with 0.25% trypsin for 15 min at 37° C. The hippocampi were then rinsed in 10 mL of Hibernate containing 10% (v/v) heat-inactivated fetal bovine serum (FBS). Cultures were maintained in Neurobasal-A medium containing 2% B-27 supplement, 0.5 mM Gluta-MAX and 1% penicillin/streptomycin at 37° C. and 5% $CO_2$. Half of the medium was replaced twice a week. Neuronal hippocampal cells were plated at a density of approximately $2\times10^4$ per well in 96-well plates and $5\times10^5$ per well in 24-well plates for MTT and induced cell death assays, respectively. After seven days of incubation in culture well plates, the primary hippocampal neurons were used for the cell viability measurements.

The utilized U87MG cells (human glioblastoma-astrocytoma, epithelial-like cell line) were kind a gift from Dr. Maria Paravatou-Petsotas, Radiobiology Laboratory, Institute of Nuclear & Radiological Sciences & Technology, Energy & Safety, NCSR "Demokritos". The utilized media/agents for U87MG cell cultures were obtained from Biochrom AG (Germany) and PAA Laboratories (USA). U87MG cells were grown in Dulbecco's modified Eagle medium (DMEM), supplemented with 10% fetal bovine serum (FBS), 2.5 mM L-glutamine, 1% penicillin/streptomycin at 37° C. and 5% $CO_2$. For MTT cytotoxicity studies, cells were plated at a density of $2\times10^4$ cells per well in 96-well plates and incubated at 37° C. for 24 h to allow cells to attach. The medium was subsequently removed and cells were rendered quiescent by incubation in serum-free medium for 24 h. For cell viability measurements cells were subsequently treated with the indicated concentrations of $A\beta$ in the presence or absence of synthetic peptides, as described in Materials and Methods.

Cell Viability Measurements

Solutions of synthetic $A\beta_{40}$ or $A\beta_{42}$ (10 μM) in PBS, preincubated at 37° C. (3 d for $A\beta_{40}$ solutions and 1 d for $A\beta_{42}$ solutions) in the presence or absence of synthetic cyclic peptides (1:1 and 2:1 ratio of peptides:$A\beta$), were diluted with fresh medium and transferred into wells at a 1 μM final $A\beta$ concentration. Cell viability was determined using the MTT assay. MTT (3-[4,5-dimethylthiazol-2-yl]-2, 5-diphenyl tetrazolium bromide) was purchased from Applichem (Germany). After 24 h of exposure to $A\beta$ solutions, 100 μL of a 0.5 mg/mL stock solution of MTT in Neurobasal-A was added to each well of primary hippocampal neurons followed by a 3 h incubation at 37° C., while 100 μL of a 1 mg/mL stock solution of MTT in DMEM complete medium was added to each well of U87MG cells followed by a 4 h incubation at 37° C. The medium was then removed and the cells were diluted in DMSO. The relative formazan concentration was measured by determination of the absorbance at 540 nm using a plate reader (Tecan, Austria). Results were expressed as the percentage of MTT reduction, assuming that the absorbance of control (untreated) cells was 100%, and represent the mean of three independent experiments with six replicate wells for each condition. Induced cell death was also qualitatively examined by phase-contrast microscopy (Carl Zeiss, Axiovert 25 CFL, Germany) using the above solutions. In each run, the effect of solutions of plain synthetic peptides and plain $A\beta_{40}$ or $A\beta_{42}$ was independently checked to serve as internal control.

In Vivo Assays in *C. elegans*

Strains

We followed standard procedures for *C. elegans* strains maintenance at 16° C. The following strains were used: CL2179: dvIs179 [myo-3p::GFP::3'UTR(long)+rol-6 (su1006)] (available on the world wide web at: cgc.cbs.umn- .edu/strain.php?id=26134); CL2331: dvIs37 [myo-3p::GFP::Aβ(3-42)+rol-6(su1006)] (available on the world wide web at: cgc.cbs.umn.edu/strain.php?id=26135); CL4176: smg-1(cc546) I; dvIs27 [myo-3::Aβ(1-42)-let 3'UTR (pAF29); pRF4 (rol-6(su1006)] (available on the world wide web at: cgc.cbs.umn.edu/strain.php?id=7663).

Treatment with Cyclic Peptides

For treatments with synthetic cyclic peptides, nematodes were exposed to the indicated AβC5-34 and AβC5-116 concentrations per NGM plate. Stock solutions of the two chemically synthesized pure peptides were obtained after dissolution in DMSO and stored at −20° C. The appropriate amount of compound or DMSO (control cultures) was added onto an *E. coli* OP50 bacterial lawn. Synchronized offspring were randomly distributed to treatment plates to avoid systematic differences in egg lay batches. Treatment and control plates were handled, scored and assayed in parallel.

Paralysis Assay

Synchronized CL4176 animals (150-300 animals per condition) were transferred to NGM plates containing synthetic AβC5-34, AβC5-116 or 0.26% DMSO at 16° C. for 48 h before transgene induction via temperature up-shift to 25° C. Synchronized offspring were randomly distributed to treatment plates to avoid systematic differences in egg lay batches. Treatment and control plates were handled, scored and assayed in parallel. Scoring of paralyzed animals was initiated 24 h after temperature up-shift for the CL4176 strain. Nematodes were scored as paralyzed upon failure to move their half end-body upon prodding. Animals that died were excluded. Plates were indexed as 1, 2, 3 etc by an independent person and were given to the observer for scoring in random order. The index was revealed only after scoring.

Dot Blot Analysis

CL4176 animals were allowed to lay eggs for 3 h on NGM plates containing either synthetic peptides or 0.26%

DMSO. Paralysis was induced upon temperature up-shift and the progeny were exposed to either pure peptides or 0.26% DMSO until 50% of the control population was paralyzed. The animals were then collected and boiled in non-reducing Laemmli buffer. For dot blot analysis, 1-5 µg of protein lysates were spotted onto 0.2 µm nitrocellulose membranes (Bio-Rad, USA) after soaking into TBS pre-heated at 80° C. Immunoblotting was performed using the anti-Aβ antibody 6E10 (recognizes total Aβ) and the anti-amyloid protein, oligomer-specific antibody AB9234 (Merck Millipore, Germany). Actin was used as a loading control. Blots were developed with chemiluminescence by using the Clarity™ Western ECL substrate (Bio-Rad, USA). Quantification of the ratio of each detected protein to actin using the anti-actin antibody sc-1615 (Santa Cruz, Germany), and normalization to control appears next to each representative blot.

Confocal Microscopy Analysis

For Aβ$_{3-42}$ deposit measurements, synchronized (at the L4 larval stage) CL2331 and CL2179 (control strain) animals exposed to solvent (0.26% DMSO), 10 µM AβC5-34 or 5 µM AβC5-116 and grown at 20° C. (to induce aggregation) until day 2 of adulthood were collected. Animals were mounted onto 2% agarose pads on glass slides, anesthetized with 10 mM levamisole and observed at RT using a Leica TCS SPE confocal laser scanning microscope (Leica Lasertechnik GmbH, Germany). The LAS AF software was used for image acquisition. At least twenty animals/condition in three independent experiments were processed. Images of whole worms and focused images in the posterior area of nematodes were acquired with 10×0.45 and 20×0.70 numerical aperture, respectively.

While the invention has been described with respect to specific embodiments, it is apparent that modifications are possible without departing from the scope of the invention.

---

What is claimed is:

1. A method of identifying modulators of a misfolding-prone protein associated with a protein misfolding disease, comprising:

(A) obtaining a population of transformed bacterial cells that co-express:

(a) a nucleic acid encoding a library of peptide macrocycles, operably linked to a promoter and;

(b) a bipartite nucleic acid comprising a sequence for a gene encoding a misfolding-prone protein associated with a protein misfolding disease (MisP) and a sequence encoding a protein reporter;

(B) identifying bacterial cells of step (A) that exhibit enhanced levels of protein reporter activity, as measured by a detectable output indicative of reporter function; and (C) identifying the bioactive peptide macrocycles in the library that modulate MisP misfolding.

2. The method of claim 1, wherein the protein reporter is a fluorescent protein (FP) reporter, and step (B) comprises identifying bacterial cells that exhibit enhanced levels of MisP-FP fluorescence.

3. The method of claim 1, wherein the protein reporter is an enzyme.

4. The method of claim 1, wherein the identification of step (B) comprises selection.

5. The method of claim 1, wherein step (C) comprises sequencing the nucleic acid of step (Aa).

6. The method of claim 1, wherein the nucleic acids of (a) and (b) are encoded on the same vector.

7. The method of claim 1, wherein the vector is a plasmid.

8. The method of claim 1, wherein said MisP is selected from β-amyloid peptide, SOD1, tau, α-synuclein, polyglutaminated huntingtin, polyglutaminated ataxin-1, polyglutaminated ataxin-2, polyglutaminated ataxin-3, prion protein, islet amyloid polypeptide (amylin), β2-microglbulin, frag-ments of immunoglobulin light chain, fragments of immunoglobulin heavy chain, serum amyloid A, ABri peptide, ADan peptide, transthyretin, apolipoprotein A1, gelsolin, transthyretin, lysozyme, phenylalanine hydroxylase, apolipoprotein A-I, calcitonin, prolactin, TDP-43, FUS/TLS; insulin, hemoglobin, α1-antitrypsin, p53 or variants thereof.

9. The method of claim 1, wherein said peptide macrocycle can be a ribosomally synthesized as a head-to-tail cyclic peptide, side-chain-to-tail cyclic peptide, bicyclic peptide, lanthipeptide, linaridin, proteusin, cyanobactin, thiopeptide, bottromycin, microcin, lasso peptide, microviridin, amatoxin, phallotoxin, θ-defensin, orbitide, or cyclotide.

10. The method of claim 1, wherein the disease is selected from amyotrophic lateral sclerosis, Alzheimer's disease, amyotrophic lateral sclerosis, Parkinson's disease, Huntington's disease, Creutzfeldt-Jakob disease, cancer, phenylketonuria, type 2 diabetes, senile systemic amyloidosis, familial amyloidotic polyneuropathy, familial amyloid cardiomyopathy, leptomeningeal amyloidosis, systemic amyloidosis, familial British dementia, familial Danish dementia, light chain amyloidosis, heavy chain amyloidosis, serum amyloid A amyloidosis, lysozyme amyloidosis, dialysis-related amyloidosis, ApoAI amyloidosis, Finnish type familial amyloidosis, hereditary cerebral hemorrhage with amyloidosis (Icelandic type), medullary carcinoma of the thyroid, pituitary prolactinoma, injection-localized amyloidosis, frontotemporal dementia, spinocerebellar ataxia 1, spinocerebellar ataxia 2, spinocerebellar ataxia 3, α1-antitrypsin deficiency, sickle-cell anemia, or transmissible spongiform encephalopathy.

11. The method of claim 1, further comprising recombinantly producing or chemically synthesizing the identified bioactive peptide macrocycle.

*     *     *     *     *

SEQUENCE LISTING

```
Sequence total quantity: 515
SEQ ID NO: 1              moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 1
TASWW                                                              5

SEQ ID NO: 2              moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 2
TASFW                                                              5

SEQ ID NO: 3              moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 3
TSSFW                                                              5

SEQ ID NO: 4              moltype = AA   length = 5
```

-continued

```
FEATURE            Location/Qualifiers
REGION             1..5
                   note = Synthetic polypeptide
source             1..5
                   mol_type = protein
                   organism = synthetic construct
SEQUENCE: 4
TWSVW                                                                  5

SEQ ID NO: 5       moltype = AA   length = 5
FEATURE            Location/Qualifiers
REGION             1..5
                   note = Synthetic polypeptide
source             1..5
                   mol_type = protein
                   organism = synthetic construct
SEQUENCE: 5
TASHW                                                                  5

SEQ ID NO: 6       moltype = AA   length = 5
FEATURE            Location/Qualifiers
REGION             1..5
                   note = Synthetic polypeptide
source             1..5
                   mol_type = protein
                   organism = synthetic construct
SEQUENCE: 6
TFSMW                                                                  5

SEQ ID NO: 7       moltype = AA   length = 5
FEATURE            Location/Qualifiers
REGION             1..5
                   note = Synthetic polypeptide
source             1..5
                   mol_type = protein
                   organism = synthetic construct
SEQUENCE: 7
TASMW                                                                  5

SEQ ID NO: 8       moltype = AA   length = 5
FEATURE            Location/Qualifiers
REGION             1..5
                   note = Synthetic polypeptide
source             1..5
                   mol_type = protein
                   organism = synthetic construct
SEQUENCE: 8
TVSFW                                                                  5

SEQ ID NO: 9       moltype = AA   length = 5
FEATURE            Location/Qualifiers
REGION             1..5
                   note = Synthetic polypeptide
source             1..5
                   mol_type = protein
                   organism = synthetic construct
SEQUENCE: 9
TLSFW                                                                  5

SEQ ID NO: 10      moltype = AA   length = 5
FEATURE            Location/Qualifiers
REGION             1..5
                   note = Synthetic polypeptide
source             1..5
                   mol_type = protein
                   organism = synthetic construct
SEQUENCE: 10
TASRW                                                                  5

SEQ ID NO: 11      moltype = AA   length = 5
FEATURE            Location/Qualifiers
REGION             1..5
                   note = Synthetic polypeptide
source             1..5
                   mol_type = protein
                   organism = synthetic construct
SEQUENCE: 11
TASSW                                                                  5
```

-continued

```
SEQ ID NO: 12          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 12
TASLW                                                          5

SEQ ID NO: 13          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 13
TSSSW                                                          5

SEQ ID NO: 14          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 14
TGSVW                                                          5

SEQ ID NO: 15          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 15
TWSLW                                                          5

SEQ ID NO: 16          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 16
TLSMW                                                          5

SEQ ID NO: 17          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 17
TWSAW                                                          5

SEQ ID NO: 18          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 18
TGSWW                                                          5

SEQ ID NO: 19          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 19
TRSVW                                                          5
```

```
SEQ ID NO: 20        moltype = AA   length = 5
FEATURE              Location/Qualifiers
REGION               1..5
                     note = Synthetic polypeptide
source               1..5
                     mol_type = protein
                     organism = synthetic construct
SEQUENCE: 20
TSSLW                                                                5

SEQ ID NO: 21        moltype = AA   length = 5
FEATURE              Location/Qualifiers
REGION               1..5
                     note = Synthetic polypeptide
source               1..5
                     mol_type = protein
                     organism = synthetic construct
SEQUENCE: 21
TASTW                                                                5

SEQ ID NO: 22        moltype = AA   length = 5
FEATURE              Location/Qualifiers
REGION               1..5
                     note = Synthetic polypeptide
source               1..5
                     mol_type = protein
                     organism = synthetic construct
SEQUENCE: 22
TSSVW                                                                5

SEQ ID NO: 23        moltype = AA   length = 5
FEATURE              Location/Qualifiers
REGION               1..5
                     note = Synthetic polypeptide
source               1..5
                     mol_type = protein
                     organism = synthetic construct
SEQUENCE: 23
TTSWW                                                                5

SEQ ID NO: 24        moltype = AA   length = 5
FEATURE              Location/Qualifiers
REGION               1..5
                     note = Synthetic polypeptide
source               1..5
                     mol_type = protein
                     organism = synthetic construct
SEQUENCE: 24
TASVW                                                                5

SEQ ID NO: 25        moltype = AA   length = 5
FEATURE              Location/Qualifiers
REGION               1..5
                     note = Synthetic polypeptide
source               1..5
                     mol_type = protein
                     organism = synthetic construct
SEQUENCE: 25
TCSWW                                                                5

SEQ ID NO: 26        moltype = AA   length = 5
FEATURE              Location/Qualifiers
REGION               1..5
                     note = Synthetic polypeptide
source               1..5
                     mol_type = protein
                     organism = synthetic construct
SEQUENCE: 26
TPSFW                                                                5

SEQ ID NO: 27        moltype = AA   length = 5
FEATURE              Location/Qualifiers
REGION               1..5
                     note = Synthetic polypeptide
source               1..5
                     mol_type = protein
                     organism = synthetic construct
```

-continued

```
SEQUENCE: 27
TTSFW                                                                              5

SEQ ID NO: 28          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 28
TFSTW                                                                              5

SEQ ID NO: 29          moltype = AA   length = 5
FEATURE                Location/Qualifiers
REGION                 1..5
                       note = Synthetic polypeptide
source                 1..5
                       mol_type = protein
                       organism = synthetic construct SEQUENCE: 29
TSSMW                                                                              5

SEQ ID NO: 30          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 30
TVSWW                                                                              5

SEQ ID NO: 31          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 31
TDSWW                                                                              5

SEQ ID NO: 32          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 32
TSSWW                                                                              5

SEQ ID NO: 33          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 33
TRSWW                                                                              5

SEQ ID NO: 34          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 34
TWSMW                                                                              5

SEQ ID NO: 35          moltype = AA   length = 5
FEATURE                Location/Qualifiers
REGION                 1..5
                       note = Synthetic polypeptide
```

-continued

```
source                    1..5
                          mol_type = protein
                          organism = synthetic construct
SEQUENCE: 35
TASGW                                                            5

SEQ ID NO: 36             moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 36
TPSWW                                                            5

SEQ ID NO: 37             moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 37
TRSFW                                                            5

SEQ ID NO: 38             moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 38
TSSYW                                                            5

SEQ ID NO: 39             moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 39
TLSVW                                                            5

SEQ ID NO: 40             moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 40
TYSWW                                                            5

SEQ ID NO: 41             moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 41
TFSVW                                                            5

SEQ ID NO: 42             moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 42
TCSVW                                                            5

SEQ ID NO: 43             moltype = AA   length = 5
FEATURE                   Location/Qualifiers
```

```
REGION                    1..5
                          note = Synthetic polypeptide
source                    1..5
                          mol_type = protein
                          organism = synthetic construct
SEQUENCE: 43
TVSSW                                                                          5

SEQ ID NO: 44             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 44
TRSHW                                                                          5

SEQ ID NO: 45             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 45
TGSAW                                                                          5

SEQ ID NO: 46             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 46
TASYW                                                                          5

SEQ ID NO: 47             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 47
TTYAR                                                                          5

SEQ ID NO: 48             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 48
TTVDR                                                                          5

SEQ ID NO: 49             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 49
TTTWR                                                                          5

SEQ ID NO: 50             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 50
TTLHR                                                                          5

SEQ ID NO: 51             moltype = AA  length = 5
```

-continued

```
FEATURE           Location/Qualifiers
REGION            1..5
                  note = Synthetic polypeptide
source            1..5
                  mol_type = protein
                  organism = synthetic construct
SEQUENCE: 51
TTFAR                                                              5

SEQ ID NO: 52     moltype = AA   length = 5
FEATURE           Location/Qualifiers
REGION            1..5
                  note = Synthetic polypeptide
source            1..5
                  mol_type = protein
                  organism = synthetic construct
SEQUENCE: 52
TVLDR                                                             5

SEQ ID NO: 53     moltype = AA   length = 5
FEATURE           Location/Qualifiers
REGION            1..5
                  note = Synthetic polypeptide
source            1..5
                  mol_type = protein
                  organism = synthetic construct
SEQUENCE: 53
TTWAR                                                             5

SEQ ID NO: 54     moltype = AA   length = 5
FEATURE           Location/Qualifiers
REGION            1..5
                  note = Synthetic polypeptide
source            1..5
                  mol_type = protein
                  organism = synthetic construct
SEQUENCE: 54
TALDR                                                             5

SEQ ID NO: 55     moltype = AA   length = 5
FEATURE           Location/Qualifiers
REGION            1..5
                  note = Synthetic polypeptide
source            1..5
                  mol_type = protein
                  organism = synthetic construct
SEQUENCE: 55
TANVR                                                             5

SEQ ID NO: 56     moltype = AA   length = 5
FEATURE           Location/Qualifiers
REGION            1..5
                  note = Synthetic polypeptide
source            1..5
                  mol_type = protein
                  organism = synthetic construct
SEQUENCE: 56
TTTAR                                                             5

SEQ ID NO: 57     moltype = AA   length = 5
FEATURE           Location/Qualifiers
REGION            1..5
                  note = Synthetic polypeptide
source            1..5
                  mol_type = protein
                  organism = synthetic construct
SEQUENCE: 57
TTIAR                                                             5

SEQ ID NO: 58     moltype = AA   length = 5
FEATURE           Location/Qualifiers
REGION            1..5
                  note = Synthetic polypeptide
source            1..5
                  mol_type = protein
                  organism = synthetic construct
SEQUENCE: 58
TVWDR                                                             5
```

-continued

```
SEQ ID NO: 59            moltype = AA   length = 5
FEATURE                  Location/Qualifiers
REGION                   1..5
                         note = Synthetic polypeptide
source                   1..5
                         mol_type = protein
                         organism = synthetic construct
SEQUENCE: 59
TTISR                                                            5

SEQ ID NO: 60            moltype = AA   length = 5
FEATURE                  Location/Qualifiers
REGION                   1..5
                         note = Synthetic polypeptide
source                   1..5
                         mol_type = protein
                         organism = synthetic construct
SEQUENCE: 60
TTWCR                                                            5

SEQ ID NO: 61            moltype = AA   length = 5
FEATURE                  Location/Qualifiers
REGION                   1..5
                         note = Synthetic polypeptide
source                   1..5
                         mol_type = protein
                         organism = synthetic construct
SEQUENCE: 61
TVLWR                                                            5

SEQ ID NO: 62            moltype = AA   length = 5
FEATURE                  Location/Qualifiers
REGION                   1..5
                         note = Synthetic polypeptide
source                   1..5
                         mol_type = protein
                         organism = synthetic construct
SEQUENCE: 62
TTLAR                                                            5

SEQ ID NO: 63            moltype = AA   length = 5
FEATURE                  Location/Qualifiers
REGION                   1..5
                         note = Synthetic polypeptide
source                   1..5
                         mol_type = protein
                         organism = synthetic construct
SEQUENCE: 63
TAWCR                                                            5

SEQ ID NO: 64            moltype = AA   length = 5
FEATURE                  Location/Qualifiers
REGION                   1..5
                         note = Synthetic polypeptide
source                   1..5
                         mol_type = protein
                         organism = synthetic construct
SEQUENCE: 64
TTSAR                                                            5

SEQ ID NO: 65            moltype = AA   length = 5
FEATURE                  Location/Qualifiers
REGION                   1..5
                         note = Synthetic polypeptide
source                   1..5
                         mol_type = protein
                         organism = synthetic construct
SEQUENCE: 65
TTLER                                                            5

SEQ ID NO: 66            moltype = AA   length = 5
FEATURE                  Location/Qualifiers
REGION                   1..5
                         note = Synthetic polypeptide
source                   1..5
                         mol_type = protein
                         organism = synthetic construct
SEQUENCE: 66
TSTAR                                                            5
```

```
SEQ ID NO: 67          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 67
TVRDR                                                                  5

SEQ ID NO: 68          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 68
TGWAR                                                                  5

SEQ ID NO: 69          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 69
TAWAR                                                                  5

SEQ ID NO: 70          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 70
TTWVR                                                                  5

SEQ ID NO: 71          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 71
TLLWR                                                                  5

SEQ ID NO: 72          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 72
TTIDR                                                                  5

SEQ ID NO: 73          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 73
TALAR                                                                  5

SEQ ID NO: 74          moltype = AA   length = 5
FEATURE                Location/Qualifiers
REGION                 1..5
                       note = Synthetic polypeptide
source                 1..5
                       mol_type = protein
                       organism = synthetic construct
```

-continued

```
SEQUENCE: 74
TSVDR                                                              5

SEQ ID NO: 75          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 75
TTVWR                                                              5

SEQ ID NO: 76          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 76
TTHWR                                                              5

SEQ ID NO: 77          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 77
TARDR                                                              5

SEQ ID NO: 78          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 78
TTRDR                                                              5

SEQ ID NO: 79          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 79
TSVHR                                                              5

SEQ ID NO: 80          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 80
TAVWR                                                              5

SEQ ID NO: 81          moltype = AA   length = 5
FEATURE                Location/Qualifiers
REGION                 1..5
                       note = Synthetic polypeptide
source                 1..5
                       mol_type = protein
                       organism = synthetic construct
SEQUENCE: 81
TTGCR                                                              5

SEQ ID NO: 82          moltype = AA   length = 5
FEATURE                Location/Qualifiers
REGION                 1..5
                       note = Synthetic polypeptide
```

```
source                    1..5
                          mol_type = protein
                          organism = synthetic construct
SEQUENCE: 82
TATDR                                                                     5

SEQ ID NO: 83             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 83
TVLFR                                                                     5

SEQ ID NO: 84             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 84
TTYNR                                                                     5

SEQ ID NO: 85             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 85
TVRWR                                                                     5

SEQ ID NO: 86             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 86
TAFDR                                                                     5

SEQ ID NO: 87             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 87
TTRCR                                                                     5

SEQ ID NO: 88             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 88
TTFWR                                                                     5

SEQ ID NO: 89             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 89
TIKDR                                                                     5

SEQ ID NO: 90             moltype = AA  length = 5
FEATURE                   Location/Qualifiers
```

-continued

```
REGION                    1..5
                          note = Synthetic polypeptide
source                    1..5
                          mol_type = protein
                          organism = synthetic construct
SEQUENCE: 90
TTVHR                                                                          5

SEQ ID NO: 91             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 91
TTLLR                                                                          5

SEQ ID NO: 92             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 92
TTLFR                                                                          5

SEQ ID NO: 93             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 93
TAYHR                                                                          5

SEQ ID NO: 94             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 94
TALHR                                                                          5

SEQ ID NO: 95             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 95
TTSPR                                                                          5

SEQ ID NO: 96             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 96
TTWSR                                                                          5

SEQ ID NO: 97             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 97
TAMHR                                                                          5

SEQ ID NO: 98             moltype = AA  length = 5
```

-continued

```
FEATURE           Location/Qualifiers
REGION            1..5
                  note = Synthetic polypeptide
source            1..5
                  mol_type = protein
                  organism = synthetic construct
SEQUENCE: 98
TSLDR                                                       5

SEQ ID NO: 99      moltype = AA  length = 5
FEATURE            Location/Qualifiers
REGION             1..5
                   note = Synthetic polypeptide
source             1..5
                   mol_type = protein
                   organism = synthetic construct
SEQUENCE: 99
TTGAR                                                       5

SEQ ID NO: 100     moltype = AA  length = 5
FEATURE            Location/Qualifiers
REGION             1..5
                   note = Synthetic polypeptide
source             1..5
                   mol_type = protein
                   organism = synthetic construct
SEQUENCE: 100
TSVWR                                                       5

SEQ ID NO: 101     moltype = AA  length = 5
FEATURE            Location/Qualifiers
REGION             1..5
                   note = Synthetic polypeptide
source             1..5
                   mol_type = protein
                   organism = synthetic construct
SEQUENCE: 101
TTHAR                                                       5

SEQ ID NO: 102     moltype = AA  length = 5
FEATURE            Location/Qualifiers
REGION             1..5
                   note = Synthetic polypeptide
source             1..5
                   mol_type = protein
                   organism = synthetic construct
SEQUENCE: 102
TAGWR                                                       5

SEQ ID NO: 103     moltype = AA  length = 5
FEATURE            Location/Qualifiers
REGION             1..5
                   note = Synthetic polypeptide
source             1..5
                   mol_type = protein
                   organism = synthetic construct
SEQUENCE: 103
TATAR                                                       5

SEQ ID NO: 104     moltype = AA  length = 5
FEATURE            Location/Qualifiers
REGION             1..5
                   note = Synthetic polypeptide
source             1..5
                   mol_type = protein
                   organism = synthetic construct
SEQUENCE: 104
TVLAR                                                       5

SEQ ID NO: 105     moltype = AA  length = 5
FEATURE            Location/Qualifiers
REGION             1..5
                   note = Synthetic polypeptide
source             1..5
                   mol_type = protein
                   organism = synthetic construct
SEQUENCE: 105
TTFNR                                                       5
```

-continued

```
SEQ ID NO: 106            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 106
TGMRR                                                                  5

SEQ ID NO: 107            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 107
TTVAR                                                                  5

SEQ ID NO: 108            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 108
TLCLR                                                                  5

SEQ ID NO: 109            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 109
TGLAR                                                                  5

SEQ ID NO: 110            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 110
TSWCR                                                                  5

SEQ ID NO: 111            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 111
TTRAR                                                                  5

SEQ ID NO: 112            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 112
TTPWR                                                                  5

SEQ ID NO: 113            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 113
TVLHR                                                                  5
```

```
SEQ ID NO: 114          moltype = AA   length = 5
FEATURE                 Location/Qualifiers
REGION                  1..5
                        note = Synthetic polypeptide
source                  1..5
                        mol_type = protein
                        organism = synthetic construct
SEQUENCE: 114
TGLDR                                                                       5

SEQ ID NO: 115          moltype = AA   length = 5
FEATURE                 Location/Qualifiers
REGION                  1..5
                        note = Synthetic polypeptide
source                  1..5
                        mol_type = protein
                        organism = synthetic construct
SEQUENCE: 115
TTSDR                                                                       5

SEQ ID NO: 116          moltype = AA   length = 5
FEATURE                 Location/Qualifiers
REGION                  1..5
                        note = Synthetic polypeptide
source                  1..5
                        mol_type = protein
                        organism = synthetic construct
SEQUENCE: 116
TTMHR                                                                       5

SEQ ID NO: 117          moltype = AA   length = 5
FEATURE                 Location/Qualifiers
REGION                  1..5
                        note = Synthetic polypeptide
source                  1..5
                        mol_type = protein
                        organism = synthetic construct
SEQUENCE: 117
TTSTR                                                                       5

SEQ ID NO: 118          moltype = AA   length = 5
FEATURE                 Location/Qualifiers
REGION                  1..5
                        note = Synthetic polypeptide
source                  1..5
                        mol_type = protein
                        organism = synthetic construct
SEQUENCE: 118
TTRVR                                                                       5

SEQ ID NO: 119          moltype = AA   length = 5
FEATURE                 Location/Qualifiers
REGION                  1..5
                        note = Synthetic polypeptide
source                  1..5
                        mol_type = protein
                        organism = synthetic construct
SEQUENCE: 119
TTRFR                                                                       5

SEQ ID NO: 120          moltype = AA   length = 5
FEATURE                 Location/Qualifiers
REGION                  1..5
                        note = Synthetic polypeptide
source                  1..5
                        mol_type = protein
                        organism = synthetic construct
SEQUENCE: 120
TTTHR                                                                       5

SEQ ID NO: 121          moltype = AA   length = 5
FEATURE                 Location/Qualifiers
REGION                  1..5
                        note = Synthetic polypeptide
source                  1..5
                        mol_type = protein
                        organism = synthetic construct
```

```
SEQUENCE: 121
THAWR                                                                    5

SEQ ID NO: 122            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 122
TVIWR                                                                    5

SEQ ID NO: 123            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 123
TTWFR                                                                    5

SEQ ID NO: 124            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 124
TTSRR                                                                    5

SEQ ID NO: 125            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 125
TTSCR                                                                    5

SEQ ID NO: 126            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 126
TTWTR                                                                    5

SEQ ID NO: 127            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 127
TTSSR                                                                    5

SEQ ID NO: 128            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 128
THLAR                                                                    5

SEQ ID NO: 129            moltype = AA  length = 5
FEATURE                   Location/Qualifiers
REGION                    1..5
                          note = Synthetic polypeptide
```

-continued

```
source                     1..5
                           mol_type = protein
                           organism = synthetic construct
SEQUENCE: 129
TSGAR                                                                                5

SEQ ID NO: 130             moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 130
TTLRR                                                                                5

SEQ ID NO: 131             moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 131
TATWR                                                                                5

SEQ ID NO: 132             moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 132
TCMWR                                                                               5

SEQ ID NO: 133             moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 133
TAHVR                                                                               5

SEQ ID NO: 134             moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 134
TSWAR                                                                               5

SEQ ID NO: 135             moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 135
TTWLR                                                                               5

SEQ ID NO: 136             moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 136
TTLDR                                                                               5

SEQ ID NO: 137             moltype = AA  length = 5
FEATURE                    Location/Qualifiers
```

-continued

```
REGION                  1..5
                        note = Synthetic polypeptide
source                  1..5
                        mol_type = protein
                        organism = synthetic construct
SEQUENCE: 137
TTPHR                                                                              5

SEQ ID NO: 138          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 138
TTRGR                                                                              5

SEQ ID NO: 139          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 139
TTVGR                                                                              5

SEQ ID NO: 140          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 140
TTTRR                                                                              5

SEQ ID NO: 141          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 141
TSINR                                                                              5

SEQ ID NO: 142          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 142
TTADR                                                                              5

SEQ ID NO: 143          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 143
TTSER                                                                              5

SEQ ID NO: 144          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 144
TTCAR                                                                              5

SEQ ID NO: 145          moltype = AA  length = 5
```

-continued

| FEATURE | Location/Qualifiers |
|---|---|
| REGION | 1..5 |
| | note = Synthetic polypeptide |
| source | 1..5 |
| | mol_type = protein |
| | organism = synthetic construct |

SEQUENCE: 145
TTAWR                                                                    5

| SEQ ID NO: 146 | moltype = AA  length = 5 |
|---|---|
| FEATURE | Location/Qualifiers |
| REGION | 1..5 |
| | note = Synthetic polypeptide |
| source | 1..5 |
| | mol_type = protein |
| | organism = synthetic construct |

SEQUENCE: 146
TTVER                                                                    5

| SEQ ID NO: 147 | moltype = AA  length = 5 |
|---|---|
| FEATURE | Location/Qualifiers |
| REGION | 1..5 |
| | note = Synthetic polypeptide |
| source | 1..5 |
| | mol_type = protein |
| | organism = synthetic construct |

SEQUENCE: 147
TTTFR                                                                    5

| SEQ ID NO: 148 | moltype = AA  length = 5 |
|---|---|
| FEATURE | Location/Qualifiers |
| REGION | 1..5 |
| | note = Synthetic polypeptide |
| source | 1..5 |
| | mol_type = protein |
| | organism = synthetic construct |

SEQUENCE: 148
TAVDR                                                                    5

| SEQ ID NO: 149 | moltype = AA  length = 5 |
|---|---|
| FEATURE | Location/Qualifiers |
| REGION | 1..5 |
| | note = Synthetic polypeptide |
| source | 1..5 |
| | mol_type = protein |
| | organism = synthetic construct |

SEQUENCE: 149
TVWIR                                                                    5

| SEQ ID NO: 150 | moltype = AA  length = 5 |
|---|---|
| FEATURE | Location/Qualifiers |
| REGION | 1..5 |
| | note = Synthetic polypeptide |
| source | 1..5 |
| | mol_type = protein |
| | organism = synthetic construct |

SEQUENCE: 150
TTVRR                                                                    5

| SEQ ID NO: 151 | moltype = AA  length = 5 |
|---|---|
| FEATURE | Location/Qualifiers |
| REGION | 1..5 |
| | note = Synthetic polypeptide |
| source | 1..5 |
| | mol_type = protein |
| | organism = synthetic construct |

SEQUENCE: 151
THVRR                                                                    5

| SEQ ID NO: 152 | moltype = AA  length = 5 |
|---|---|
| FEATURE | Location/Qualifiers |
| REGION | 1..5 |
| | note = Synthetic polypeptide |
| source | 1..5 |
| | mol_type = protein |
| | organism = synthetic construct |

SEQUENCE: 152
TNLDR                                                                    5

-continued

```
SEQ ID NO: 153            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 153
TTPGR                                                          5

SEQ ID NO: 154            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 154
TTLTR                                                          5

SEQ ID NO: 155            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 155
TATVR                                                          5

SEQ ID NO: 156            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 156
TAMWR                                                         5

SEQ ID NO: 157            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 157
TTKWR                                                         5

SEQ ID NO: 158            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 158
TTWDR                                                         5

SEQ ID NO: 159            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 159
TTMAR                                                         5

SEQ ID NO: 160            moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 160
TTGGR                                                         5
```

-continued

```
SEQ ID NO: 161            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 161
TTMVR                                                                          5

SEQ ID NO: 162            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 162
TNLAR                                                                          5

SEQ ID NO: 163            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 163
TIRDR                                                                          5

SEQ ID NO: 164            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 164
TTTGR                                                                          5

SEQ ID NO: 165            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 165
TRLGR                                                                          5

SEQ ID NO: 166            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 166
TTHTR                                                                          5

SEQ ID NO: 167            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 167
TTITR                                                                          5

SEQ ID NO: 168            moltype = AA   length = 5
FEATURE                   Location/Qualifiers
REGION                    1..5
                          note = Synthetic polypeptide
source                    1..5
                          mol_type = protein
                          organism = synthetic construct
```

-continued

```
SEQUENCE: 168
TTYTR                                                                    5

SEQ ID NO: 169          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 169
TTLYR                                                                    5

SEQ ID NO: 170          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 170
THLDR                                                                    5

SEQ ID NO: 171          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 171
TLLIR                                                                    5

SEQ ID NO: 172          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 172
TTCDR                                                                    5

SEQ ID NO: 173          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 173
TTGRR                                                                    5

SEQ ID NO: 174          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 174
TTVSR                                                                    5

SEQ ID NO: 175          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 175
TTQHR                                                                    5

SEQ ID NO: 176          moltype = AA  length = 5
FEATURE                 Location/Qualifiers
REGION                  1..5
                        note = Synthetic polypeptide
```

-continued

```
source                    1..5
                          mol_type = protein
                          organism = synthetic construct
SEQUENCE: 176
TTTPR                                                                              5

SEQ ID NO: 177            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 177
TAFAR                                                                              5

SEQ ID NO: 178            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 178
TTSHR                                                                              5

SEQ ID NO: 179            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 179
TVLGR                                                                              5

SEQ ID NO: 180            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 180
TTQRR                                                                              5

SEQ ID NO: 181            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 181
TSHAR                                                                              5

SEQ ID NO: 182            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 182
TTTCR                                                                              5

SEQ ID NO: 183            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 183
TAWRR                                                                              5

SEQ ID NO: 184            moltype = AA   length = 5
FEATURE                   Location/Qualifiers
```

-continued

```
REGION                  1..5
                        note = Synthetic polypeptide
source                  1..5
                        mol_type = protein
                        organism = synthetic construct
SEQUENCE: 184
TTCGR                                                                          5

SEQ ID NO: 185          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 185
TTSGR                                                                          5

SEQ ID NO: 186          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 186
TTTSR                                                                          5

SEQ ID NO: 187          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 187
TATGR                                                                          5

SEQ ID NO: 188          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 188
TAWDR                                                                          5

SEQ ID NO: 189          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 189
TTHHR                                                                          5

SEQ ID NO: 190          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 190
TAYAR                                                                          5

SEQ ID NO: 191          moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 191
TANAR                                                                          5

SEQ ID NO: 192          moltype = AA  length = 5
```

-continued

```
FEATURE              Location/Qualifiers
REGION               1..5
                     note = Synthetic polypeptide
source               1..5
                     mol_type = protein
                     organism = synthetic construct
SEQUENCE: 192
TRDVR                                                            5

SEQ ID NO: 193       moltype = AA   length = 5
FEATURE              Location/Qualifiers
REGION               1..5
                     note = Synthetic polypeptide
source               1..5
                     mol_type = protein
                     organism = synthetic construct
SEQUENCE: 193
THVDR                                                            5

SEQ ID NO: 194       moltype = AA   length = 5
FEATURE              Location/Qualifiers
REGION               1..5
                     note = Synthetic polypeptide
source               1..5
                     mol_type = protein
                     organism = synthetic construct
SEQUENCE: 194
TLFWR                                                            5

SEQ ID NO: 195       moltype = AA   length = 5
FEATURE              Location/Qualifiers
REGION               1..5
                     note = Synthetic polypeptide
source               1..5
                     mol_type = protein
                     organism = synthetic construct
SEQUENCE: 195
TTAAR                                                            5

SEQ ID NO: 196       moltype = AA   length = 5
FEATURE              Location/Qualifiers
REGION               1..5
                     note = Synthetic polypeptide
source               1..5
                     mol_type = protein
                     organism = synthetic construct
SEQUENCE: 196
TVVDR                                                            5

SEQ ID NO: 197       moltype = AA   length = 5
FEATURE              Location/Qualifiers
REGION               1..5
                     note = Synthetic polypeptide
source               1..5
                     mol_type = protein
                     organism = synthetic construct
SEQUENCE: 197
TTPAR                                                            5

SEQ ID NO: 198       moltype = AA   length = 5
FEATURE              Location/Qualifiers
REGION               1..5
                     note = Synthetic polypeptide
source               1..5
                     mol_type = protein
                     organism = synthetic construct
SEQUENCE: 198
TTIGR                                                            5

SEQ ID NO: 199       moltype = AA   length = 5
FEATURE              Location/Qualifiers
REGION               1..5
                     note = Synthetic polypeptide
source               1..5
                     mol_type = protein
                     organism = synthetic construct
SEQUENCE: 199
TMYAR                                                            5
```

-continued

```
SEQ ID NO: 200            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 200
THVAR                                                              5

SEQ ID NO: 201            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 201
TTWPR                                                              5

SEQ ID NO: 202            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 202
TTGDR                                                              5

SEQ ID NO: 203            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 203
TTTVR                                                              5

SEQ ID NO: 204            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 204
TVFGR                                                             5

SEQ ID NO: 205            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 205
TRVGR                                                             5

SEQ ID NO: 206            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 206
SASPT                                                             5

SEQ ID NO: 207            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 207
SICPT                                                             5
```

-continued

```
SEQ ID NO: 208          moltype = AA   length = 5
FEATURE                 Location/Qualifiers
REGION                  1..5
                        note = Synthetic polypeptide
source                  1..5
                        mol_type = protein
                        organism = synthetic construct
SEQUENCE: 208
SITPT                                                          5

SEQ ID NO: 209          moltype = AA   length = 5
FEATURE                 Location/Qualifiers
REGION                  1..5
                        note = Synthetic polypeptide
source                  1..5
                        mol_type = protein
                        organism = synthetic construct
SEQUENCE: 209
SHSPT                                                          5

SEQ ID NO: 210          moltype = AA   length = 4
FEATURE                 Location/Qualifiers
REGION                  1..4
                        note = Synthetic polypeptide
source                  1..4
                        mol_type = protein
                        organism = synthetic construct
SEQUENCE: 210
TTCR                                                           4

SEQ ID NO: 211          moltype = AA   length = 4
FEATURE                 Location/Qualifiers
REGION                  1..4
                        note = Synthetic polypeptide
source                  1..4
                        mol_type = protein
                        organism = synthetic construct
SEQUENCE: 211
TTRR                                                           4

SEQ ID NO: 212          moltype = AA   length = 4
FEATURE                 Location/Qualifiers
REGION                  1..4
                        note = Synthetic polypeptide
source                  1..4
                        mol_type = protein
                        organism = synthetic construct
SEQUENCE: 212
TTSR                                                           4

SEQ ID NO: 213          moltype = AA   length = 4
FEATURE                 Location/Qualifiers
REGION                  1..4
                        note = Synthetic polypeptide
source                  1..4
                        mol_type = protein
                        organism = synthetic construct
SEQUENCE: 213
TRGR                                                           4

SEQ ID NO: 214          moltype = AA   length = 4
FEATURE                 Location/Qualifiers
REGION                  1..4
                        note = Synthetic polypeptide
source                  1..4
                        mol_type = protein
                        organism = synthetic construct
SEQUENCE: 214
TTGR                                                           4

SEQ ID NO: 215          moltype = AA   length = 4
FEATURE                 Location/Qualifiers
REGION                  1..4
                        note = Synthetic polypeptide
source                  1..4
                        mol_type = protein
                        organism = synthetic construct
```

```
SEQUENCE: 215
TRRR                                                                          4

SEQ ID NO: 216            moltype = AA   length = 4
FEATURE                   Location/Qualifiers
REGION                    1..4
                          note = Synthetic polypeptide
source                    1..4
                          mol_type = protein
                          organism = synthetic construct
SEQUENCE: 216
TDQR                                                                          4

SEQ ID NO: 217            moltype = AA   length = 4
FEATURE                   Location/Qualifiers
REGION                    1..4
                          note = Synthetic polypeptide
source                    1..4
                          mol_type = protein
                          organism = synthetic construct
SEQUENCE: 217
TLIR                                                                          4

SEQ ID NO: 218            moltype = AA   length = 4
FEATURE                   Location/Qualifiers
REGION                    1..4
                          note = Synthetic polypeptide
source                    1..4
                          mol_type = protein
                          organism = synthetic construct
SEQUENCE: 218
TLWR                                                                          4

SEQ ID NO: 219            moltype = AA   length = 4
FEATURE                   Location/Qualifiers
REGION                    1..4
                          note = Synthetic polypeptide
source                    1..4
                          mol_type = protein
                          organism = synthetic construct
SEQUENCE: 219
TLGR                                                                          4

SEQ ID NO: 220            moltype = AA   length = 4
FEATURE                   Location/Qualifiers
REGION                    1..4
                          note = Synthetic polypeptide
source                    1..4
                          mol_type = protein
                          organism = synthetic construct
SEQUENCE: 220
TFDR                                                                          4

SEQ ID NO: 221            moltype = AA   length = 4
FEATURE                   Location/Qualifiers
REGION                    1..4
                          note = Synthetic polypeptide
source                    1..4
                          mol_type = protein
                          organism = synthetic construct
SEQUENCE: 221
TAFR                                                                          4

SEQ ID NO: 222            moltype = AA   length = 6
FEATURE                   Location/Qualifiers
REGION                    1..6
                          note = Synthetic polypeptide
source                    1..6
                          mol_type = protein
                          organism = synthetic construct
SEQUENCE: 222
TPVWFD                                                                        6

SEQ ID NO: 223            moltype = AA   length = 6
FEATURE                   Location/Qualifiers
REGION                    1..6
                          note = Synthetic polypeptide
```

-continued

```
source                    1..6
                          mol_type = protein
                          organism = synthetic construct
SEQUENCE: 223
TPAWFD                                                                    6

SEQ ID NO: 224            moltype = AA  length = 6
FEATURE                   Location/Qualifiers
REGION                    1..6
                          note = Synthetic polypeptide
source                    1..6
                          mol_type = protein
                          organism = synthetic construct
SEQUENCE: 224
TLEFFD                                                                    6

SEQ ID NO: 225            moltype = AA  length = 6
FEATURE                   Location/Qualifiers
REGION                    1..6
                          note = Synthetic polypeptide
source                    1..6
                          mol_type = protein
                          organism = synthetic construct
SEQUENCE: 225
TVTWFD                                                                    6

SEQ ID NO: 226            moltype = AA  length = 6
FEATURE                   Location/Qualifiers
REGION                    1..6
                          note = Synthetic polypeptide
source                    1..6
                          mol_type = protein
                          organism = synthetic construct
SEQUENCE: 226
TLLIRW                                                                    6

SEQ ID NO: 227            moltype = AA  length = 6
FEATURE                   Location/Qualifiers
REGION                    1..6
                          note = Synthetic polypeptide
source                    1..6
                          mol_type = protein
                          organism = synthetic construct
SEQUENCE: 227
TLKWLN                                                                    6

SEQ ID NO: 228            moltype = AA  length = 6
FEATURE                   Location/Qualifiers
REGION                    1..6
                          note = Synthetic polypeptide
source                    1..6
                          mol_type = protein
                          organism = synthetic construct
SEQUENCE: 228
TKEYFD                                                                    6

SEQ ID NO: 229            moltype = AA  length = 6
FEATURE                   Location/Qualifiers
REGION                    1..6
                          note = Synthetic polypeptide
source                    1..6
                          mol_type = protein
                          organism = synthetic construct
SEQUENCE: 229
TLHWFE                                                                    6

SEQ ID NO: 230            moltype = AA  length = 6
FEATURE                   Location/Qualifiers
REGION                    1..6
                          note = Synthetic polypeptide
source                    1..6
                          mol_type = protein
                          organism = synthetic construct
SEQUENCE: 230
TCSWFD                                                                    6

SEQ ID NO: 231            moltype = AA  length = 6
FEATURE                   Location/Qualifiers
```

-continued

```
REGION                   1..6
                         note = Synthetic polypeptide
source                   1..6
                         mol_type = protein
                         organism = synthetic construct
SEQUENCE: 231
TLEYFM                                                                    6

SEQ ID NO: 232           moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 232
TLCWLN                                                                    6

SEQ ID NO: 233           moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 233
TPIVFD                                                                    6

SEQ ID NO: 234           moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 234
TLWVFD                                                                    6

SEQ ID NO: 235           moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 235
TPLWFN                                                                    6

SEQ ID NO: 236           moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 236
TSVEYE                                                                    6

SEQ ID NO: 237           moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 237
TLGWLD                                                                    6

SEQ ID NO: 238           moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 238
TPPWFD                                                                    6

SEQ ID NO: 239           moltype = AA  length = 6
```

-continued

```
FEATURE            Location/Qualifiers
REGION             1..6
                   note = Synthetic polypeptide
source             1..6
                   mol_type = protein
                   organism = synthetic construct
SEQUENCE: 239
TPCWFD                                                              6

SEQ ID NO: 240     moltype = AA   length = 6
FEATURE            Location/Qualifiers
REGION             1..6
                   note = Synthetic polypeptide
source             1..6
                   mol_type = protein
                   organism = synthetic construct
SEQUENCE: 240
TLSWYD                                                              6

SEQ ID NO: 241     moltype = AA   length = 6
FEATURE            Location/Qualifiers
REGION             1..6
                   note = Synthetic polypeptide
source             1..6
                   mol_type = protein
                   organism = synthetic construct
SEQUENCE: 241
TPVLVD                                                              6

SEQ ID NO: 242     moltype = AA   length = 6
FEATURE            Location/Qualifiers
REGION             1..6
                   note = Synthetic polypeptide
source             1..6
                   mol_type = protein
                   organism = synthetic construct
SEQUENCE: 242
TLEYLW                                                              6

SEQ ID NO: 243     moltype = AA   length = 6
FEATURE            Location/Qualifiers
REGION             1..6
                   note = Synthetic polypeptide
source             1..6
                   mol_type = protein
                   organism = synthetic construct
SEQUENCE: 243
TIFWFD                                                              6

SEQ ID NO: 244     moltype = AA   length = 6
FEATURE            Location/Qualifiers
REGION             1..6
                   note = Synthetic polypeptide
source             1..6
                   mol_type = protein
                   organism = synthetic construct
SEQUENCE: 244
TPALVD                                                             6

SEQ ID NO: 245     moltype = AA   length = 6
FEATURE            Location/Qualifiers
REGION             1..6
                   note = Synthetic polypeptide
source             1..6
                   mol_type = protein
                   organism = synthetic construct
SEQUENCE: 245
TPGWFD                                                             6

SEQ ID NO: 246     moltype = AA   length = 6
FEATURE            Location/Qualifiers
REGION             1..6
                   note = Synthetic polypeptide
source             1..6
                   mol_type = protein
                   organism = synthetic construct
SEQUENCE: 246
TLSVFD                                                             6
```

-continued

```
SEQ ID NO: 247            moltype = AA   length = 6
FEATURE                   Location/Qualifiers
REGION                    1..6
                          note = Synthetic polypeptide
source                    1..6
                          mol_type = protein
                          organism = synthetic construct
SEQUENCE: 247
TPGLVD                                                              6

SEQ ID NO: 248            moltype = AA   length = 6
FEATURE                   Location/Qualifiers
REGION                    1..6
                          note = Synthetic polypeptide
source                    1..6
                          mol_type = protein
                          organism = synthetic construct
SEQUENCE: 248
TLSWFN                                                              6

SEQ ID NO: 249            moltype = AA   length = 6
FEATURE                   Location/Qualifiers
REGION                    1..6
                          note = Synthetic polypeptide
source                    1..6
                          mol_type = protein
                          organism = synthetic construct
SEQUENCE: 249
TLDFFD                                                              6

SEQ ID NO: 250            moltype = AA   length = 6
FEATURE                   Location/Qualifiers
REGION                    1..6
                          note = Synthetic polypeptide
source                    1..6
                          mol_type = protein
                          organism = synthetic construct
SEQUENCE: 250
TPSWFD                                                              6

SEQ ID NO: 251            moltype = AA   length = 6
FEATURE                   Location/Qualifiers
REGION                    1..6
                          note = Synthetic polypeptide
source                    1..6
                          mol_type = protein
                          organism = synthetic construct
SEQUENCE: 251
TPALFD                                                              6

SEQ ID NO: 252            moltype = AA   length = 6
FEATURE                   Location/Qualifiers
REGION                    1..6
                          note = Synthetic polypeptide
source                    1..6
                          mol_type = protein
                          organism = synthetic construct
SEQUENCE: 252
TPAWSD                                                              6

SEQ ID NO: 253            moltype = AA   length = 6
FEATURE                   Location/Qualifiers
REGION                    1..6
                          note = Synthetic polypeptide
source                    1..6
                          mol_type = protein
                          organism = synthetic construct
SEQUENCE: 253
TPARFD                                                              6

SEQ ID NO: 254            moltype = AA   length = 6
FEATURE                   Location/Qualifiers
REGION                    1..6
                          note = Synthetic polypeptide
source                    1..6
                          mol_type = protein
                          organism = synthetic construct
SEQUENCE: 254
TPAWLD                                                              6
```

-continued

```
SEQ ID NO: 255            moltype = AA   length = 6
FEATURE                   Location/Qualifiers
REGION                    1..6
                          note = Synthetic polypeptide
source                    1..6
                          mol_type = protein
                          organism = synthetic construct
SEQUENCE: 255
TPVWLD                                                                        6

SEQ ID NO: 256            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 256
accgcctcgt ggtgg                                                             15

SEQ ID NO: 257            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 257
accgcgagct tctgg                                                             15

SEQ ID NO: 258            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 258
acctcgtcgt tctgg                                                             15

SEQ ID NO: 259            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 259
acctggtccg tgtgg                                                             15

SEQ ID NO: 260            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 260
accgccagcc actgg                                                             15

SEQ ID NO: 261            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 261
accttcagca tgtgg                                                             15

SEQ ID NO: 262            moltype = DNA   length = 15
FEATURE                   Location/Qualifiers
misc_feature              1..15
                          note = Synthetic polynucleotide
source                    1..15
                          mol_type = other DNA
                          organism = synthetic construct
```

-continued

```
SEQUENCE: 262
accgcctcga tgtgg                                                    15

SEQ ID NO: 263          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 263
accgtctcgt tctgg                                                    15

SEQ ID NO: 264          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 264
accctctcct tctgg                                                    15

SEQ ID NO: 265          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 265
accgccagcc gctgg                                                    15

SEQ ID NO: 266          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 266
accgcgagct cgtgg                                                    15

SEQ ID NO: 267          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 267
accgcgagcc tctgg                                                    15

SEQ ID NO: 268          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 268
acctcgtcgt cctgg                                                    15

SEQ ID NO: 269          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 269
accggctccg tgtgg                                                    15

SEQ ID NO: 270          moltype = DNA   length = 15
FEATURE                 Location/Qualifiers
misc_feature            1..15
                        note = Synthetic polynucleotide
```

-continued

```
source                    1..15
                          mol_type = other DNA
                          organism = synthetic construct
SEQUENCE: 270
acctggtccc tgtgg                                                        15

SEQ ID NO: 271            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 271
accctcagca tgtgg                                                        15

SEQ ID NO: 272            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 272
acctggtccg cgtgg                                                        15

SEQ ID NO: 273            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 273
accggctcgt ggtgg                                                        15

SEQ ID NO: 274            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 274
acccggtccg tgtgg                                                        15

SEQ ID NO: 275            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 275
acctcgtcgc tctgg                                                        15

SEQ ID NO: 276            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 276
accgccagca cctgg                                                        15

SEQ ID NO: 277            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 277
acctcgtccg tctgg                                                        15

SEQ ID NO: 278            moltype = DNA   length = 15
FEATURE                   Location/Qualifiers
```

-continued

```
misc_feature         1..15
                     note = Synthetic polynucleotide
source               1..15
                     mol_type = other DNA
                     organism = synthetic construct
SEQUENCE: 278
accacctcgt ggtgg                                                        15

SEQ ID NO: 279       moltype = DNA  length = 15
FEATURE              Location/Qualifiers
misc_feature         1..15
                     note = Synthetic polynucleotide
source               1..15
                     mol_type = other DNA
                     organism = synthetic construct
SEQUENCE: 279
accgcgagcg tctgg                                                        15

SEQ ID NO: 280       moltype = DNA  length = 15
FEATURE              Location/Qualifiers
misc_feature         1..15
                     note = Synthetic polynucleotide
source               1..15
                     mol_type = other DNA
                     organism = synthetic construct
SEQUENCE: 280
acctgctcgt ggtgg                                                        15

SEQ ID NO: 281       moltype = DNA  length = 15
FEATURE              Location/Qualifiers
misc_feature         1..15
                     note = Synthetic polynucleotide
source               1..15
                     mol_type = other DNA
                     organism = synthetic construct
SEQUENCE: 281
accccgtcgt tctgg                                                        15

SEQ ID NO: 282       moltype = DNA  length = 15
FEATURE              Location/Qualifiers
misc_feature         1..15
                     note = Synthetic polynucleotide
source               1..15
                     mol_type = other DNA
                     organism = synthetic construct
SEQUENCE: 282
accacgagct tctgg                                                        15

SEQ ID NO: 283       moltype = DNA  length = 15
FEATURE              Location/Qualifiers
misc_feature         1..15
                     note = Synthetic polynucleotide
source               1..15
                     mol_type = other DNA
                     organism = synthetic construct
SEQUENCE: 283
accttcagca cgtgg                                                        15

SEQ ID NO: 284       moltype = DNA  length = 15
FEATURE              Location/Qualifiers
misc_feature         1..15
                     note = Synthetic polynucleotide
source               1..15
                     mol_type = other DNA
                     organism = synthetic construct
SEQUENCE: 284
acctcgagca tgtgg                                                        15

SEQ ID NO: 285       moltype = DNA  length = 15
FEATURE              Location/Qualifiers
misc_feature         1..15
                     note = Synthetic polynucleotide
source               1..15
                     mol_type = other DNA
                     organism = synthetic construct
SEQUENCE: 285
accgtctcgt ggtgg                                                        15

SEQ ID NO: 286       moltype = DNA  length = 15
```

-continued

| FEATURE | Location/Qualifiers |
|---|---|
| misc_feature | 1..15 |
| | note = Synthetic polynucleotide |
| source | 1..15 |
| | mol_type = other DNA |
| | organism = synthetic construct |

SEQUENCE: 286
accgactcgt ggtgg                                                                    15

SEQ ID NO: 287        moltype = DNA   length = 15
FEATURE               Location/Qualifiers
misc_feature          1..15
                      note = Synthetic polynucleotide
source                1..15
                      mol_type = other DNA
                      organism = synthetic construct
SEQUENCE: 287
acctcgtcct ggtgg                                                                    15

SEQ ID NO: 288        moltype = DNA   length = 15
FEATURE               Location/Qualifiers
misc_feature          1..15
                      note = Synthetic polynucleotide
source                1..15
                      mol_type = other DNA
                      organism = synthetic construct
SEQUENCE: 288
acccgctcgt ggtgg                                                                    15

SEQ ID NO: 289        moltype = DNA   length = 15
FEATURE               Location/Qualifiers
misc_feature          1..15
                      note = Synthetic polynucleotide
source                1..15
                      mol_type = other DNA
                      organism = synthetic construct
SEQUENCE: 289
acctggtcca tgtgg                                                                    15

SEQ ID NO: 290        moltype = DNA   length = 15
FEATURE               Location/Qualifiers
misc_feature          1..15
                      note = Synthetic polynucleotide
source                1..15
                      mol_type = other DNA
                      organism = synthetic construct
SEQUENCE: 290
accgcctctg ggtgg                                                                    15

SEQ ID NO: 291        moltype = DNA   length = 15
FEATURE               Location/Qualifiers
misc_feature          1..15
                      note = Synthetic polynucleotide
source                1..15
                      mol_type = other DNA
                      organism = synthetic construct
SEQUENCE: 291
acgccctcgt ggtgg                                                                    15

SEQ ID NO: 292        moltype = DNA   length = 15
FEATURE               Location/Qualifiers
misc_feature          1..15
                      note = Synthetic polynucleotide
source                1..15
                      mol_type = other DNA
                      organism = synthetic construct
SEQUENCE: 292
acgcggagct tctgg                                                                    15

SEQ ID NO: 293        moltype = DNA   length = 15
FEATURE               Location/Qualifiers
misc_feature          1..15
                      note = Synthetic polynucleotide
source                1..15
                      mol_type = other DNA
                      organism = synthetic construct
SEQUENCE: 293
acctcgtcct actgg                                                                    15

-continued

```
SEQ ID NO: 294         moltype = DNA   length = 15
FEATURE                Location/Qualifiers
misc_feature           1..15
                       note = Synthetic polynucleotide
source                 1..15
                       mol_type = other DNA
                       organism = synthetic construct SEQUENCE: 294
accttgagcg tgtgg                                                    15

SEQ ID NO: 295         moltype = DNA   length = 15
FEATURE                Location/Qualifiers
misc_feature           1..15
                       note = Synthetic polynucleotide
source                 1..15
                       mol_type = other DNA
                       organism = synthetic construct SEQUENCE: 295
acctactcat ggtgg                                                    15

SEQ ID NO: 296         moltype = DNA   length = 15
FEATURE                Location/Qualifiers
misc_feature           1..15
                       note = Synthetic polynucleotide
source                 1..15
                       mol_type = other DNA
                       organism = synthetic construct SEQUENCE: 296
accttcagcg tgtgg                                                    15

SEQ ID NO: 297         moltype = DNA   length = 15
FEATURE                Location/Qualifiers
misc_feature           1..15
                       note = Synthetic polynucleotide
source                 1..15
                       mol_type = other DNA
                       organism = synthetic construct SEQUENCE: 297
acctgctccg tgtgg                                                    15

SEQ ID NO: 298         moltype = DNA   length = 15
FEATURE                Location/Qualifiers
misc_feature           1..15
                       note = Synthetic polynucleotide
source                 1..15
                       mol_type = other DNA
                       organism = synthetic construct SEQUENCE: 298
accgtctcgt cgtgg                                                    15

SEQ ID NO: 299         moltype = DNA   length = 15
FEATURE                Location/Qualifiers
misc_feature           1..15
                       note = Synthetic polynucleotide
source                 1..15
                       mol_type = other DNA
                       organism = synthetic construct SEQUENCE: 299
acccgcagcc actgg                                                    15

SEQ ID NO: 300         moltype = DNA   length = 15
FEATURE                Location/Qualifiers
misc_feature           1..15
                       note = Synthetic polynucleotide
source                 1..15
                       mol_type = other DNA
                       organism = synthetic construct SEQUENCE: 300
accggcagcg cgtgg                                                    15

SEQ ID NO: 301         moltype = DNA   length = 15
FEATURE                Location/Qualifiers
misc_feature           1..15
                       note = Synthetic polynucleotide
source                 1..15
                       mol_type = other DNA
                       organism = synthetic construct SEQUENCE: 301
accgccagct actgg                                                    15
```

-continued

```
SEQ ID NO: 302          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 302
accacgtacg ccagg                                                    15

SEQ ID NO: 303          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 303
accaccgtgg accgg                                                    15

SEQ ID NO: 304          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 304
accacgacct ggagg                                                    15

SEQ ID NO: 305          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 305
accacgctgc accgg                                                    15

SEQ ID NO: 306          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 306
accaccttcg cccgg                                                    15

SEQ ID NO: 307          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 307
accgtcttgg accgg                                                    15

SEQ ID NO: 308          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 308
accacgtggg ccagg                                                    15

SEQ ID NO: 309          moltype = DNA   length = 15
FEATURE                 Location/Qualifiers
misc_feature            1..15
                        note = Synthetic polynucleotide
source                  1..15
                        mol_type = other DNA
                        organism = synthetic construct
```

```
SEQUENCE: 309
accgcgctgg accgg                                                          15

SEQ ID NO: 310            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 310
accgcgaacg tgagg                                                          15

SEQ ID NO: 311            moltype = DNA   length = 15
FEATURE                   Location/Qualifiers
misc_feature              1..15
                          note = Synthetic polynucleotide
source                    1..15
                          mol_type = other DNA
                          organism = synthetic construct SEQUENCE: 311
accaccacgg cccgg                                                          15

SEQ ID NO: 312            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 312
accaccatcg cccgg                                                          15

SEQ ID NO: 313            moltype = DNA   length = 15
FEATURE                   Location/Qualifiers
misc_feature              1..15
                          note = Synthetic polynucleotide
source                    1..15
                          mol_type = other DNA
                          organism = synthetic construct SEQUENCE: 313
accgtgtggg accgg                                                          15

SEQ ID NO: 314            moltype = DNA   length = 15
FEATURE                   Location/Qualifiers
misc_feature              1..15
                          note = Synthetic polynucleotide
source                    1..15
                          mol_type = other DNA
                          organism = synthetic construct SEQUENCE: 314
accaccatca gccgg                                                          15

SEQ ID NO: 315            moltype = DNA   length = 15
FEATURE                   Location/Qualifiers
misc_feature              1..15
                          note = Synthetic polynucleotide
source                    1..15
                          mol_type = other DNA
                          organism = synthetic construct SEQUENCE: 315
accacctggt gccgg                                                          15

SEQ ID NO: 316            moltype = DNA   length = 15
FEATURE                   Location/Qualifiers
misc_feature              1..15
                          note = Synthetic polynucleotide
source                    1..15
                          mol_type = other DNA
                          organism = synthetic construct SEQUENCE: 316
accgtcctgt ggagg                                                          15

SEQ ID NO: 317            moltype = DNA   length = 15
FEATURE                   Location/Qualifiers
misc_feature              1..15
                          note = Synthetic polynucleotide
```

-continued

```
source                    1..15
                          mol_type = other DNA
                          organism = synthetic construct
SEQUENCE: 317
accaccttgg cgagg                                                            15

SEQ ID NO: 318            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 318
accgcgtggt gccgc                                                            15

SEQ ID NO: 319            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 319
accacgagcg cccgc                                                            15

SEQ ID NO: 320            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 320
accaccctcg agagg                                                            15

SEQ ID NO: 321            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 321
acctcgacgg cgcgg                                                            15

SEQ ID NO: 322            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 322
accgtccggg accgg                                                            15

SEQ ID NO: 323            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 323
accggctggg cgagg                                                            15

SEQ ID NO: 324            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 324
accgcctggg cgagg                                                            15

SEQ ID NO: 325            moltype = DNA   length = 15
FEATURE                   Location/Qualifiers
```

-continued

```
misc_feature              1..15
                          note = Synthetic polynucleotide
source                    1..15
                          mol_type = other DNA
                          organism = synthetic construct
SEQUENCE: 325
accacctggg tgcgg                                                          15

SEQ ID NO: 326            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 326
accctattgt ggcgg                                                          15

SEQ ID NO: 327            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 327
accacgatcg acagg                                                          15

SEQ ID NO: 328            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 328
accgcgctcg cgcgc                                                          15

SEQ ID NO: 329            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 329
accagcgtgg acagg                                                          15

SEQ ID NO: 330            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 330
accaccgtgt ggcgc                                                          15

SEQ ID NO: 331            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 331
accacgcact ggcgg                                                          15

SEQ ID NO: 332            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 332
accgcgaggg accgg                                                          15

SEQ ID NO: 333            moltype = DNA   length = 15
```

-continued

```
FEATURE                 Location/Qualifiers
misc_feature            1..15
                        note = Synthetic polynucleotide
source                  1..15
                        mol_type = other DNA
                        organism = synthetic construct SEQUENCE: 333
accacgcggg accgg                                              15

SEQ ID NO: 334          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 334
accagcgtgc accgg                                              15

SEQ ID NO: 335          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 335
accgccgtct ggcgg                                              15

SEQ ID NO: 336          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 336
accacggggt gccgg                                              15

SEQ ID NO: 337          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 337
accgccaccg acagg                                              15

SEQ ID NO: 338          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 338
accgtcttgt tccgc                                              15

SEQ ID NO: 339          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 339
accacctaca accgc                                              15

SEQ ID NO: 340          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 340
accgtgcgct ggcgc                                              15
```

```
SEQ ID NO: 341              moltype = DNA   length = 15
FEATURE                     Location/Qualifiers
misc_feature                1..15
                            note = Synthetic polynucleotide
source                      1..15
                            mol_type = other DNA
                            organism = synthetic construct
SEQUENCE: 341
accgcgttcg accgg                                                    15

SEQ ID NO: 342              moltype = DNA   length = 15
FEATURE                     Location/Qualifiers
misc_feature                1..15
                            note = Synthetic polynucleotide
source                      1..15
                            mol_type = other DNA
                            organism = synthetic construct
SEQUENCE: 342
accacgcggt gcagg                                                    15

SEQ ID NO: 343              moltype = DNA   length = 15
FEATURE                     Location/Qualifiers
misc_feature                1..15
                            note = Synthetic polynucleotide
source                      1..15
                            mol_type = other DNA
                            organism = synthetic construct
SEQUENCE: 343
accaccttct ggcgg                                                    15

SEQ ID NO: 344              moltype = DNA   length = 15
FEATURE                     Location/Qualifiers
misc_feature                1..15
                            note = Synthetic polynucleotide
source                      1..15
                            mol_type = other DNA
                            organism = synthetic construct
SEQUENCE: 344
accatcaagg accgg                                                    15

SEQ ID NO: 345              moltype = DNA   length = 15
FEATURE                     Location/Qualifiers
misc_feature                1..15
                            note = Synthetic polynucleotide
source                      1..15
                            mol_type = other DNA
                            organism = synthetic construct
SEQUENCE: 345
accaccgtcc accgg                                                    15

SEQ ID NO: 346              moltype = DNA   length = 15
FEATURE                     Location/Qualifiers
misc_feature                1..15
                            note = Synthetic polynucleotide
source                      1..15
                            mol_type = other DNA
                            organism = synthetic construct
SEQUENCE: 346
accacgctcc tcagg                                                    15

SEQ ID NO: 347              moltype = DNA   length = 15
FEATURE                     Location/Qualifiers
misc_feature                1..15
                            note = Synthetic polynucleotide
source                      1..15
                            mol_type = other DNA
                            organism = synthetic construct
SEQUENCE: 347
accacgctct tccgg                                                    15

SEQ ID NO: 348              moltype = DNA   length = 15
FEATURE                     Location/Qualifiers
misc_feature                1..15
                            note = Synthetic polynucleotide
source                      1..15
                            mol_type = other DNA
                            organism = synthetic construct
SEQUENCE: 348
accgcgtacc accgg                                                    15
```

```
SEQ ID NO: 349          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 349
accgcgttgc accgg                                                    15

SEQ ID NO: 350          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 350
accacctcgc cccgg                                                    15

SEQ ID NO: 351          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 351
accacctggt cgcgg                                                    15

SEQ ID NO: 352          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 352
accgccatgc acagg                                                    15

SEQ ID NO: 353          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 353
acctcgctcg acagg                                                    15

SEQ ID NO: 354          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 354
accacggggg cgcgc                                                    15

SEQ ID NO: 355          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 355
acctcggtgt ggagg                                                    15

SEQ ID NO: 356          moltype = DNA   length = 15
FEATURE                 Location/Qualifiers
misc_feature            1..15
                        note = Synthetic polynucleotide
source                  1..15
                        mol_type = other DNA
                        organism = synthetic construct
```

```
SEQUENCE: 356
accacgcacg ccagg                                                        15

SEQ ID NO: 357         moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 357
accgcgggct ggagg                                                        15

SEQ ID NO: 358         moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 358
accgccaccg cgagg                                                        15

SEQ ID NO: 359         moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 359
accgtgctcg cgcgg                                                        15

SEQ ID NO: 360         moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 360
accacgttca acagg                                                        15

SEQ ID NO: 361         moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 361
accgggatga ggcgg                                                        15

SEQ ID NO: 362         moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 362
accaccgtcg ccagg                                                        15

SEQ ID NO: 363         moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 363
tgcttgcgca cgctg                                                        15

SEQ ID NO: 364         moltype = DNA  length = 15
FEATURE                Location/Qualifiers
misc_feature           1..15
                       note = Synthetic polynucleotide
```

-continued

```
source                    1..15
                          mol_type = other DNA
                          organism = synthetic construct
SEQUENCE: 364
accgggctgg cgcgg                                                       15

SEQ ID NO: 365            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 365
accagctggt gcagg                                                       15

SEQ ID NO: 366            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 366
accaccaggg cgcgg                                                       15

SEQ ID NO: 367            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 367
accacgccct ggagg                                                       15

SEQ ID NO: 368            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 368
accgtcttgc acagg                                                       15

SEQ ID NO: 369            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 369
accggcctcg acagg                                                       15

SEQ ID NO: 370            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 370
accacgtcgg accgg                                                       15

SEQ ID NO: 371            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 371
accacgatgc accgc                                                       15

SEQ ID NO: 372            moltype = DNA  length = 15
FEATURE                   Location/Qualifiers
```

-continued

```
misc_feature                1..15
                            note = Synthetic polynucleotide
source                      1..15
                            mol_type = other DNA
                            organism = synthetic construct
SEQUENCE: 372
accacctcga cccgg                                                    15

SEQ ID NO: 373              moltype = DNA  length = 15
FEATURE                     Location/Qualifiers
misc_feature                1..15
                            note = Synthetic polynucleotide
source                      1..15
                            mol_type = other DNA
                            organism = synthetic construct
SEQUENCE: 373
accacgcgcg tgagg                                                    15

SEQ ID NO: 374              moltype = DNA  length = 15
FEATURE                     Location/Qualifiers
misc_feature                1..15
                            note = Synthetic polynucleotide
source                      1..15
                            mol_type = other DNA
                            organism = synthetic construct
SEQUENCE: 374
accacccggt tccgg                                                    15

SEQ ID NO: 375              moltype = DNA  length = 15
FEATURE                     Location/Qualifiers
misc_feature                1..15
                            note = Synthetic polynucleotide
source                      1..15
                            mol_type = other DNA
                            organism = synthetic construct
SEQUENCE: 375
accacgacgc accgg                                                    15

SEQ ID NO: 376              moltype = DNA  length = 15
FEATURE                     Location/Qualifiers
misc_feature                1..15
                            note = Synthetic polynucleotide
source                      1..15
                            mol_type = other DNA
                            organism = synthetic construct
SEQUENCE: 376
acccacgcct ggagg                                                    15

SEQ ID NO: 377              moltype = DNA  length = 15
FEATURE                     Location/Qualifiers
misc_feature                1..15
                            note = Synthetic polynucleotide
source                      1..15
                            mol_type = other DNA
                            organism = synthetic construct
SEQUENCE: 377
accgtgatct ggcgc                                                    15

SEQ ID NO: 378              moltype = DNA  length = 15
FEATURE                     Location/Qualifiers
misc_feature                1..15
                            note = Synthetic polynucleotide
source                      1..15
                            mol_type = other DNA
                            organism = synthetic construct
SEQUENCE: 378
accacgtggt tccgg                                                    15

SEQ ID NO: 379              moltype = DNA  length = 15
FEATURE                     Location/Qualifiers
misc_feature                1..15
                            note = Synthetic polynucleotide
source                      1..15
                            mol_type = other DNA
                            organism = synthetic construct
SEQUENCE: 379
accacctcga gacgg                                                    15

SEQ ID NO: 380              moltype = DNA  length = 15
```

| FEATURE | Location/Qualifiers |
| --- | --- |
| misc_feature | 1..15 |
| | note = Synthetic polynucleotide |
| source | 1..15 |
| | mol_type = other DNA |
| | organism = synthetic construct |

SEQUENCE: 380
accacgtcgt gccgg                                                              15

SEQ ID NO: 381        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 381
accacctgga cccgg                                                              15

SEQ ID NO: 382        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 382
accacctcga gccgg                                                              15

SEQ ID NO: 383        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 383
acccacctcg cccgg                                                              15

SEQ ID NO: 384        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 384
accagcgggg cccgg                                                              15

SEQ ID NO: 385        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 385
accacgctgc gccgg                                                              15

SEQ ID NO: 386        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 386
accgcgacct ggagg                                                             15

SEQ ID NO: 387        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 387
acctgcatgt ggcgc                                                             15

```
SEQ ID NO: 388            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 388
accgcgcacg tgcgc                                              15

SEQ ID NO: 389            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 389
acctcgtggg cgcgg                                              15

SEQ ID NO: 390            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 390
accacgtggc tcagg                                              15

SEQ ID NO: 391            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 391
accaccctgg accgg                                              15

SEQ ID NO: 392            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 392
accacgcctc accgg                                              15

SEQ ID NO: 393            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 393
accacccgtg gccgg                                              15

SEQ ID NO: 394            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 394
accaccgtgg gccgg                                              15

SEQ ID NO: 395            moltype = DNA  length = 15
FEATURE                   Location/Qualifiers
misc_feature              1..15
                          note = Synthetic polynucleotide
source                    1..15
                          mol_type = other DNA
                          organism = synthetic construct
SEQUENCE: 395
accacgacgc gccgc                                              15
```

-continued

```
SEQ ID NO: 396        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 396
acctcgatca acagg                                                    15

SEQ ID NO: 397        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 397
accaccgcgg accgg                                                    15

SEQ ID NO: 398        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 398
accacctccg agagg                                                    15

SEQ ID NO: 399        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 399
accacgtgcg ccagg                                                    15

SEQ ID NO: 400        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 400
accacggcct ggagg                                                    15

SEQ ID NO: 401        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 401
accaccgtcg agcgg                                                    15

SEQ ID NO: 402        moltype = DNA   length = 15
FEATURE               Location/Qualifiers
misc_feature          1..15
                      note = Synthetic polynucleotide
source                1..15
                      mol_type = other DNA
                      organism = synthetic construct SEQUENCE: 402
accacgacgt tcagg                                                    15

SEQ ID NO: 403        moltype = DNA   length = 15
FEATURE               Location/Qualifiers
misc_feature          1..15
                      note = Synthetic polynucleotide
source                1..15
                      mol_type = other DNA
                      organism = synthetic construct
```

-continued

```
SEQUENCE: 403
accgccgtgg accgg                                                    15

SEQ ID NO: 404          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 404
accgtgtgga tcagg                                                    15

SEQ ID NO: 405          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 405
accaccgtac gcagg                                                    15

SEQ ID NO: 406          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 406
acccacgtac gcagg                                                    15

SEQ ID NO: 407          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 407
accaacctgg accgg                                                    15

SEQ ID NO: 408          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 408
accacgcctg gacgg                                                    15

SEQ ID NO: 409          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 409
accacgctca cccgg                                                    15

SEQ ID NO: 410          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 410
accgcgacgg tgcgc                                                    15

SEQ ID NO: 411          moltype = DNA   length = 15
FEATURE                 Location/Qualifiers
misc_feature            1..15
                        note = Synthetic polynucleotide
```

-continued

```
source                    1..15
                          mol_type = other DNA
                          organism = synthetic construct
SEQUENCE: 411
accgccatgt ggcgg                                                    15

SEQ ID NO: 412           moltype = DNA   length = 15
FEATURE                  Location/Qualifiers
misc_feature             1..15
                         note = Synthetic polynucleotide
source                   1..15
                         mol_type = other DNA
                         organism = synthetic construct
SEQUENCE: 412
accacgaagt ggagg                                                    15

SEQ ID NO: 413           moltype = DNA   length = 15
FEATURE                  Location/Qualifiers
misc_feature             1..15
                         note = Synthetic polynucleotide
source                   1..15
                         mol_type = other DNA
                         organism = synthetic construct
SEQUENCE: 413
accacctggg accgg                                                    15

SEQ ID NO: 414           moltype = DNA   length = 15
FEATURE                  Location/Qualifiers
misc_feature             1..15
                         note = Synthetic polynucleotide
source                   1..15
                         mol_type = other DNA
                         organism = synthetic construct
SEQUENCE: 414
accaccatgg cccgg                                                    15

SEQ ID NO: 415           moltype = DNA   length = 15
FEATURE                  Location/Qualifiers
misc_feature             1..15
                         note = Synthetic polynucleotide
source                   1..15
                         mol_type = other DNA
                         organism = synthetic construct
SEQUENCE: 415
accaccggtg gccgg                                                    15

SEQ ID NO: 416           moltype = DNA   length = 15
FEATURE                  Location/Qualifiers
misc_feature             1..15
                         note = Synthetic polynucleotide
source                   1..15
                         mol_type = other DNA
                         organism = synthetic construct
SEQUENCE: 416
accacgatgg tgcgg                                                    15

SEQ ID NO: 417           moltype = DNA   length = 15
FEATURE                  Location/Qualifiers
misc_feature             1..15
                         note = Synthetic polynucleotide
source                   1..15
                         mol_type = other DNA
                         organism = synthetic construct
SEQUENCE: 417
accaacctcg cccgg                                                    15

SEQ ID NO: 418           moltype = DNA   length = 15
FEATURE                  Location/Qualifiers
misc_feature             1..15
                         note = Synthetic polynucleotide
source                   1..15
                         mol_type = other DNA
                         organism = synthetic construct
SEQUENCE: 418
accatcaggg accgg                                                    15

SEQ ID NO: 419           moltype = DNA   length = 15
FEATURE                  Location/Qualifiers
```

```
misc_feature          1..15
                      note = Synthetic polynucleotide
source                1..15
                      mol_type = other DNA
                      organism = synthetic construct
SEQUENCE: 419
accacgactg gtagg                                                              15

SEQ ID NO: 420        moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 420
acccgtcttg gcagg                                                              15

SEQ ID NO: 421        moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 421
accacgcaca ccagg                                                              15

SEQ ID NO: 422        moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 422
accaccatca cccgg                                                              15

SEQ ID NO: 423        moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 423
accacgtaca ccagg                                                              15

SEQ ID NO: 424        moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 424
accacgctgt accgg                                                              15

SEQ ID NO: 425        moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 425
acccacctgg accgg                                                              15

SEQ ID NO: 426        moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 426
accttgttga tcagg                                                              15

SEQ ID NO: 427        moltype = DNA  length = 15
```

-continued

| FEATURE | Location/Qualifiers |
| --- | --- |
| misc_feature | 1..15 |
| | note = Synthetic polynucleotide |
| source | 1..15 |
| | mol_type = other DNA |
| | organism = synthetic construct |

SEQUENCE: 427
accacgtgcg accgg                                                                                                              15

SEQ ID NO: 428          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 428
accacgggtc gccgg                                                                                                              15

SEQ ID NO: 429          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 429
accaccgtga gccgg                                                                                                              15

SEQ ID NO: 430          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 430
accacgcagc accgg                                                                                                              15

SEQ ID NO: 431          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 431
accactacgc ccagg                                                                                                              15

SEQ ID NO: 432          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 432
accgccttcg cccgg                                                                                                              15

SEQ ID NO: 433          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 433
accacgtcac accgg                                                                                                              15

SEQ ID NO: 434          moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 434
accgtcttgg gccgg                                                                                                              15

-continued

```
SEQ ID NO: 435           moltype = DNA   length = 15
FEATURE                  Location/Qualifiers
misc_feature             1..15
                         note = Synthetic polynucleotide
source                   1..15
                         mol_type = other DNA
                         organism = synthetic construct SEQUENCE: 435
accacgcagc gcagg                                                    15

SEQ ID NO: 436           moltype = DNA   length = 15
FEATURE                  Location/Qualifiers
misc_feature             1..15
                         note = Synthetic polynucleotide
source                   1..15
                         mol_type = other DNA
                         organism = synthetic construct SEQUENCE: 436
accagtcacg ccagg                                                    15

SEQ ID NO: 437           moltype = DNA   length = 15
FEATURE                  Location/Qualifiers
misc_feature             1..15
                         note = Synthetic polynucleotide
source                   1..15
                         mol_type = other DNA
                         organism = synthetic construct SEQUENCE: 437
accacgacgt gccgg                                                    15

SEQ ID NO: 438           moltype = DNA   length = 15
FEATURE                  Location/Qualifiers
misc_feature             1..15
                         note = Synthetic polynucleotide
source                   1..15
                         mol_type = other DNA
                         organism = synthetic construct SEQUENCE: 438
accgcgtggc gccgc                                                    15

SEQ ID NO: 439           moltype = DNA   length = 15
FEATURE                  Location/Qualifiers
misc_feature             1..15
                         note = Synthetic polynucleotide
source                   1..15
                         mol_type = other DNA
                         organism = synthetic construct SEQUENCE: 439
accacgtgtg gccgg                                                    15

SEQ ID NO: 440           moltype = DNA   length = 15
FEATURE                  Location/Qualifiers
misc_feature             1..15
                         note = Synthetic polynucleotide
source                   1..15
                         mol_type = other DNA
                         organism = synthetic construct SEQUENCE: 440
accacctctg gccgg                                                    15

SEQ ID NO: 441           moltype = DNA   length = 15
FEATURE                  Location/Qualifiers
misc_feature             1..15
                         note = Synthetic polynucleotide
source                   1..15
                         mol_type = other DNA
                         organism = synthetic construct SEQUENCE: 441
accacgacgt cgagg                                                    15

SEQ ID NO: 442           moltype = DNA   length = 15
FEATURE                  Location/Qualifiers
misc_feature             1..15
                         note = Synthetic polynucleotide
source                   1..15
                         mol_type = other DNA
                         organism = synthetic construct SEQUENCE: 442
accgcgactg gacgg                                                    15
```

-continued

```
SEQ ID NO: 443          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 443
accgcgtggg accgg                                                    15

SEQ ID NO: 444          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 444
accacgcatc accgg                                                    15

SEQ ID NO: 445          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 445
accgcgtacg ccagg                                                    15

SEQ ID NO: 446          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 446
accgcgaacg cgagg                                                    15

SEQ ID NO: 447          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 447
acccgcgacg tgagg                                                    15

SEQ ID NO: 448          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 448
acccacgtcg acagg                                                    15

SEQ ID NO: 449          moltype = DNA   length = 15
FEATURE                 Location/Qualifiers
misc_feature            1..15
                        note = Synthetic polynucleotide
source                  1..15
                        mol_type = other DNA
                        organism = synthetic construct SEQUENCE: 449
accctattct ggcgg                                                    15

SEQ ID NO: 450          moltype = DNA   length = 15
FEATURE                 Location/Qualifiers
misc_feature            1..15
                        note = Synthetic polynucleotide
source                  1..15
                        mol_type = other DNA
                        organism = synthetic construct
```

-continued

```
SEQUENCE: 450
accaccgcgg cccgg                                                             15

SEQ ID NO: 451              moltype = DNA   length = 15
FEATURE                    Location/Qualifiers
misc_feature               1..15
                           note = Synthetic polynucleotide
source                     1..15
                           mol_type = other DNA
                           organism = synthetic construct
SEQUENCE: 451
accgtcgtgg accgg                                                             15

SEQ ID NO: 452              moltype = DNA   length = 15
FEATURE                    Location/Qualifiers
misc_feature               1..15
                           note = Synthetic polynucleotide
source                     1..15
                           mol_type = other DNA
                           organism = synthetic construct
SEQUENCE: 452
accactccgg cccgg                                                             15

SEQ ID NO: 453              moltype = DNA   length = 15
FEATURE                    Location/Qualifiers
misc_feature               1..15
                           note = Synthetic polynucleotide
source                     1..15
                           mol_type = other DNA
                           organism = synthetic construct
SEQUENCE: 453
accacgatcg gcagg                                                             15

SEQ ID NO: 454              moltype = DNA   length = 15
FEATURE                    Location/Qualifiers
misc_feature               1..15
                           note = Synthetic polynucleotide
source                     1..15
                           mol_type = other DNA
                           organism = synthetic construct
SEQUENCE: 454
accatgtacg ccagg                                                             15

SEQ ID NO: 455              moltype = DNA   length = 15
FEATURE                    Location/Qualifiers
misc_feature               1..15
                           note = Synthetic polynucleotide
source                     1..15
                           mol_type = other DNA
                           organism = synthetic construct
SEQUENCE: 455
acccacgtgg ccagg                                                             15

SEQ ID NO: 456              moltype = DNA   length = 15
FEATURE                    Location/Qualifiers
misc_feature               1..15
                           note = Synthetic polynucleotide
source                     1..15
                           mol_type = other DNA
                           organism = synthetic construct
SEQUENCE: 456
accacctggc cgcgg                                                             15

SEQ ID NO: 457              moltype = DNA   length = 15
FEATURE                    Location/Qualifiers
misc_feature               1..15
                           note = Synthetic polynucleotide
source                     1..15
                           mol_type = other DNA
                           organism = synthetic construct
SEQUENCE: 457
accaccggtg accgg                                                             15

SEQ ID NO: 458              moltype = DNA   length = 15
FEATURE                    Location/Qualifiers
misc_feature               1..15
                           note = Synthetic polynucleotide
```

-continued

```
source                    1..15
                          mol_type = other DNA
                          organism = synthetic construct
SEQUENCE: 458
accacgaccg tgcgg                                                                    15

SEQ ID NO: 459            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 459
accgtctttg gcagg                                                                    15

SEQ ID NO: 460            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 460
acccgtgtgg gccgg                                                                    15

SEQ ID NO: 461            moltype = DNA   length = 12
FEATURE                   Location/Qualifiers
misc_feature              1..12
                          note = Synthetic polynucleotide
source                    1..12
                          mol_type = other DNA
                          organism = synthetic construct
SEQUENCE: 461
accacgtgcc gg                                                                       12

SEQ ID NO: 462            moltype = DNA   length = 12
FEATURE                   Location/Qualifiers
misc_feature              1..12
                          note = Synthetic polynucleotide
source                    1..12
                          mol_type = other DNA
                          organism = synthetic construct
SEQUENCE: 462
accactcgcc gg                                                                       12

SEQ ID NO: 463            moltype = DNA   length = 12
FEATURE                   Location/Qualifiers
misc_feature              1..12
                          note = Synthetic polynucleotide
source                    1..12
                          mol_type = other DNA
                          organism = synthetic construct
SEQUENCE: 463
accacgtcgc gg                                                                       12

SEQ ID NO: 464            moltype = DNA   length = 12
FEATURE                   Location/Qualifiers
misc_feature              1..12
                          note = Synthetic polynucleotide
source                    1..12
                          mol_type = other DNA
                          organism = synthetic construct
SEQUENCE: 464
acacgtggac gg                                                                       12

SEQ ID NO: 465            moltype = DNA   length = 12
FEATURE                   Location/Qualifiers
misc_feature              1..12
                          note = Synthetic polynucleotide
source                    1..12
                          mol_type = other DNA
                          organism = synthetic construct
SEQUENCE: 465
accactggcc gg                                                                       12

SEQ ID NO: 466            moltype = DNA   length = 12
FEATURE                   Location/Qualifiers
```

```
misc_feature                1..12
                            note = Synthetic polynucleotide
source                      1..12
                            mol_type = other DNA
                            organism = synthetic construct
SEQUENCE: 466
acacgtcgca gg                                                              12

SEQ ID NO: 467              moltype = DNA  length = 12
FEATURE                     Location/Qualifiers
misc_feature                1..12
                            note = Synthetic polynucleotide
source                      1..12
                            mol_type = other DNA
                            organism = synthetic construct
SEQUENCE: 467
accgaccagc gg                                                              12

SEQ ID NO: 468              moltype = DNA  length = 12
FEATURE                     Location/Qualifiers
misc_feature                1..12
                            note = Synthetic polynucleotide
source                      1..12
                            mol_type = other DNA
                            organism = synthetic construct
SEQUENCE: 468
accctgatcc gc                                                              12

SEQ ID NO: 469              moltype = DNA  length = 12
FEATURE                     Location/Qualifiers
misc_feature                1..12
                            note = Synthetic polynucleotide
source                      1..12
                            mol_type = other DNA
                            organism = synthetic construct
SEQUENCE: 469
accctgtggc gg                                                              12

SEQ ID NO: 470              moltype = DNA  length = 12
FEATURE                     Location/Qualifiers
misc_feature                1..12
                            note = Synthetic polynucleotide
source                      1..12
                            mol_type = other DNA
                            organism = synthetic construct
SEQUENCE: 470
accttgggcc gg                                                              12

SEQ ID NO: 471              moltype = DNA  length = 12
FEATURE                     Location/Qualifiers
misc_feature                1..12
                            note = Synthetic polynucleotide
source                      1..12
                            mol_type = other DNA
                            organism = synthetic construct
SEQUENCE: 471
accttcgacc gg                                                              12

SEQ ID NO: 472              moltype = DNA  length = 12
FEATURE                     Location/Qualifiers
misc_feature                1..12
                            note = Synthetic polynucleotide
source                      1..12
                            mol_type = other DNA
                            organism = synthetic construct
SEQUENCE: 472
accgcgttcc gg                                                              12

SEQ ID NO: 473              moltype = DNA  length = 18
FEATURE                     Location/Qualifiers
misc_feature                1..18
                            note = Synthetic polynucleotide
source                      1..18
                            mol_type = other DNA
                            organism = synthetic construct
SEQUENCE: 473
accccggtct ggttcgac                                                       18

SEQ ID NO: 474              moltype = DNA  length = 18
```

-continued

```
FEATURE            Location/Qualifiers
misc_feature       1..18
                   note = Synthetic polynucleotide
source             1..18
                   mol_type = other DNA
                   organism = synthetic construct
SEQUENCE: 474
accccggcct ggttcgac                                                          18

SEQ ID NO: 475     moltype = DNA   length = 18
FEATURE            Location/Qualifiers
misc_feature       1..18
                   note = Synthetic polynucleotide
source             1..18
                   mol_type = other DNA
                   organism = synthetic construct
SEQUENCE: 475
accttggagt tcttcgac                                                          18

SEQ ID NO: 476     moltype = DNA   length = 18
FEATURE            Location/Qualifiers
misc_feature       1..18
                   note = Synthetic polynucleotide
source             1..18
                   mol_type = other DNA
                   organism = synthetic construct
SEQUENCE: 476
accgtcacgt ggttcgac                                                          18

SEQ ID NO: 477     moltype = DNA   length = 18
FEATURE            Location/Qualifiers
misc_feature       1..18
                   note = Synthetic polynucleotide
source             1..18
                   mol_type = other DNA
                   organism = synthetic construct
SEQUENCE: 477
accttgttga tcaggtgg                                                          18

SEQ ID NO: 478     moltype = DNA   length = 18
FEATURE            Location/Qualifiers
misc_feature       1..18
                   note = Synthetic polynucleotide
source             1..18
                   mol_type = other DNA
                   organism = synthetic construct
SEQUENCE: 478
accctcaagt ggctgaac                                                          18

SEQ ID NO: 479     moltype = DNA   length = 18
FEATURE            Location/Qualifiers
misc_feature       1..18
                   note = Synthetic polynucleotide
source             1..18
                   mol_type = other DNA
                   organism = synthetic construct
SEQUENCE: 479
accaaggagt acttcgac                                                          18

SEQ ID NO: 480     moltype = DNA   length = 18
FEATURE            Location/Qualifiers
misc_feature       1..18
                   note = Synthetic polynucleotide
source             1..18
                   mol_type = other DNA
                   organism = synthetic construct
SEQUENCE: 480
accctccact ggttcgag                                                          18

SEQ ID NO: 481     moltype = DNA   length = 18
FEATURE            Location/Qualifiers
misc_feature       1..18
                   note = Synthetic polynucleotide
source             1..18
                   mol_type = other DNA
                   organism = synthetic construct
SEQUENCE: 481
acctgctcgt ggttcgac                                                          18
```

```
SEQ ID NO: 482          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 482
accctcgagt acttcatg                                                   18

SEQ ID NO: 483          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 483
accctgtgct ggctcaac                                                   18

SEQ ID NO: 484          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 484
accccgatcg tgttcgac                                                   18

SEQ ID NO: 485          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 485
accctgtggg tcttcgac                                                   18

SEQ ID NO: 486          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 486
acccccttgt ggttcaac                                                   18

SEQ ID NO: 487          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 487
acctcggtcg agtacgag                                                   18

SEQ ID NO: 488          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 488
accctgggct ggttggac                                                   18

SEQ ID NO: 489          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 489
accccgccct ggttcgac                                                   18
```

-continued

```
SEQ ID NO: 490            moltype = DNA  length = 18
FEATURE                   Location/Qualifiers
misc_feature              1..18
                          note = Synthetic polynucleotide
source                    1..18
                          mol_type = other DNA
                          organism = synthetic construct
SEQUENCE: 490
accccgtgct ggttcgac                                                        18

SEQ ID NO: 491            moltype = DNA  length = 18
FEATURE                   Location/Qualifiers
misc_feature              1..18
                          note = Synthetic polynucleotide
source                    1..18
                          mol_type = other DNA
                          organism = synthetic construct
SEQUENCE: 491
accttgtcct ggtacgac                                                        18

SEQ ID NO: 492            moltype = DNA  length = 18
FEATURE                   Location/Qualifiers
misc_feature              1..18
                          note = Synthetic polynucleotide
source                    1..18
                          mol_type = other DNA
                          organism = synthetic construct
SEQUENCE: 492
accccggtcc tggtcgac                                                        18

SEQ ID NO: 493            moltype = DNA  length = 18
FEATURE                   Location/Qualifiers
misc_feature              1..18
                          note = Synthetic polynucleotide
source                    1..18
                          mol_type = other DNA
                          organism = synthetic construct
SEQUENCE: 493
accctcgagt acttgtgg                                                        18

SEQ ID NO: 494            moltype = DNA  length = 18
FEATURE                   Location/Qualifiers
misc_feature              1..18
                          note = Synthetic polynucleotide
source                    1..18
                          mol_type = other DNA
                          organism = synthetic construct
SEQUENCE: 494
accatcttct ggttcgac                                                        18

SEQ ID NO: 495            moltype = DNA  length = 18
FEATURE                   Location/Qualifiers
misc_feature              1..18
                          note = Synthetic polynucleotide
source                    1..18
                          mol_type = other DNA
                          organism = synthetic construct
SEQUENCE: 495
accccggccc tggtcgac                                                        18

SEQ ID NO: 496            moltype = DNA  length = 18
FEATURE                   Location/Qualifiers
misc_feature              1..18
                          note = Synthetic polynucleotide
source                    1..18
                          mol_type = other DNA
                          organism = synthetic construct
SEQUENCE: 496
acccccggct ggttcgac                                                        18

SEQ ID NO: 497            moltype = DNA  length = 18
FEATURE                   Location/Qualifiers
misc_feature              1..18
                          note = Synthetic polynucleotide
source                    1..18
                          mol_type = other DNA
                          organism = synthetic construct
```

-continued

```
SEQUENCE: 497
accttgtccg tcttcgac                                                    18

SEQ ID NO: 498          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 498
accccggtc tggtcgac                                                     18

SEQ ID NO: 499          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 499
accctctcct ggttcaac                                                    18

SEQ ID NO: 500          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 500
accttggact tcttcgac                                                    18

SEQ ID NO: 501          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 501
accccgtcct ggttcgac                                                    18

SEQ ID NO: 502          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 502
accccggccc tgttcgac                                                    18

SEQ ID NO: 503          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 503
accccggcct ggtccgac                                                    18

SEQ ID NO: 504          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 504
accccggccc ggttcgac                                                    18

SEQ ID NO: 505          moltype = DNA   length = 18
FEATURE                 Location/Qualifiers
misc_feature            1..18
                        note = Synthetic polynucleotide
```

-continued

```
source                     1..18
                           mol_type = other DNA
                           organism = synthetic construct
SEQUENCE: 505
accccggcct ggctcgac                                                    18

SEQ ID NO: 506             moltype = DNA  length = 18
FEATURE                    Location/Qualifiers
misc_feature               1..18
                           note = Synthetic polynucleotide
source                     1..18
                           mol_type = other DNA
                           organism = synthetic construct
SEQUENCE: 506
accccggtct ggctcgac                                                    18

SEQ ID NO: 507             moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 507
WSVWT                                                                    5

SEQ ID NO: 508             moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 508
SVWTW                                                                    5

SEQ ID NO: 509             moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 509
VWTWS                                                                    5

SEQ ID NO: 510             moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 510
WTWSV                                                                    5

SEQ ID NO: 511             moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 511
AFDRT                                                                    5

SEQ ID NO: 512             moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 512
FDRTA                                                                    5

SEQ ID NO: 513             moltype = AA  length = 5
FEATURE                    Location/Qualifiers
```

-continued

```
REGION                    1..5
                          note = Synthetic polypeptide
source                    1..5
                          mol_type = protein
                          organism = synthetic construct
SEQUENCE: 513
DRTAF                                                                     5

SEQ ID NO: 514            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 514
RTAFD                                                                     5

SEQ ID NO: 515            moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 515
agcgcctcgc cgacg                                                         15
```